(12) United States Patent
Seo et al.

(10) Patent No.: US 12,029,057 B2
(45) Date of Patent: *Jul. 2, 2024

(54) LIGHT-EMITTING DEVICE, LIGHT-EMITTING APPARATUS, ELECTRONIC DEVICE, AND LIGHTING DEVICE

(71) Applicant: Semiconductor Energy Laboratory Co., Ltd., Kanagawa-ken (JP)

(72) Inventors: Satoshi Seo, Kanagawa (JP); Tsunenori Suzuki, Kanagawa (JP); Yusuke Takita, Kanagawa (JP); Takumu Okuyama, Kanagawa (JP); Anna Tada, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/134,847

(22) Filed: Apr. 14, 2023

(65) Prior Publication Data
US 2023/0301126 A1    Sep. 21, 2023

Related U.S. Application Data

(63) Continuation of application No. 16/981,793, filed as application No. PCT/IB2019/052020 on Mar. 13, 2019, now Pat. No. 11,647,642.

(30) Foreign Application Priority Data

Mar. 20, 2018 (JP) .................. 2018-053135

(51) Int. Cl.
*H10K 50/11* (2023.01)
*H10K 50/15* (2023.01)
(Continued)

(52) U.S. Cl.
CPC ............. *H10K 50/11* (2023.02); *H10K 50/15* (2023.02); *H10K 2101/30* (2023.02); *H10K 2101/40* (2023.02)

(58) Field of Classification Search
CPC .... H10K 50/11; H10K 50/15; H10K 2101/30; H10K 2101/40; H10K 50/155;
(Continued)

(56) References Cited

U.S. PATENT DOCUMENTS 10,270,041 B2   4/2019  Suzuki et al.
10,388,900 B2   8/2019  Seo et al.
(Continued)

FOREIGN PATENT DOCUMENTS

CN    105529406 A    4/2016
CN    106687444 A    5/2017
(Continued)

OTHER PUBLICATIONS

International Search Report (Application No. PCT/IB2019/052020) dated Jun. 18, 2019.
(Continued)

*Primary Examiner* — Mohammad A Rahman
(74) *Attorney, Agent, or Firm* — Husch Blackwell LLP

(57) ABSTRACT

A novel light-emitting device is provided. Alternatively, a light-emitting device with favorable emission efficiency is provided. Alternatively, a light-emitting device with a favorable lifetime is provided. Alternatively, a light-emitting device with a low driving voltage is provided. Provided is a light-emitting device including an anode, a cathode, and a layer including an organic compound that is positioned between the anode and the cathode, in which the layer including the organic compound includes a first layer, a second layer, and a light-emitting layer in this order from the anode side, the first layer includes a first substance and a
(Continued)

second substance, the second layer includes a third substance, the first substance is an organic compound a HOMO level of which is higher than or equal to −5.8 eV and lower than or equal to −5.4 eV, the second substance is a substance that has an electron-acceptor property with respect to the first substance, and the third substance is an organic compound having a structure in which at least two substituents comprising carbazole rings are bonded to a naphthalene ring.

20 Claims, 55 Drawing Sheets

(51) Int. Cl.
*H10K 101/30* (2023.01)
*H10K 101/40* (2023.01)

(58) Field of Classification Search
CPC .... H10K 50/156; H10K 50/17; H10K 85/615; H10K 85/631; H10K 85/6572; H10K 59/00; H10K 2101/00; H10K 10/10; H10K 19/00; H10K 30/00; H10K 39/00; H10K 50/00; H10K 65/00; H10K 71/00; H10K 77/00; H10K 85/00; H10K 99/10; H10K 2102/00; C07D 209/86; H05B 33/14

See application file for complete search history.

(56) References Cited

U.S. PATENT DOCUMENTS

| | | |
|---|---|---|
| 10,411,193 B2 | 9/2019 | Kawakami et al. |
| 2016/0111663 A1 | 4/2016 | Kim et al. |
| 2017/0062734 A1 | 3/2017 | Suzuki et al. |
| 2017/0222156 A1* | 8/2017 | Kawakami ............ H10K 85/633 |
| 2017/0256722 A1 | 9/2017 | Shim et al. |
| 2018/0033993 A1 | 2/2018 | Seo et al. |
| 2019/0363259 A1 | 11/2019 | Kawakami et al. |
| 2019/0372045 A1 | 12/2019 | Seo et al. |

FOREIGN PATENT DOCUMENTS

| | | |
|---|---|---|
| CN | 107665955 A | 2/2018 |
| CN | 107925009 A | 4/2018 |
| CN | 108604641 A | 9/2018 |
| EP | 3 010 067 A1 | 4/2016 |
| EP | 3 189 035 A0 | 7/2017 |
| JP | 2015-133493 A | 7/2015 |
| JP | 2017-076780 A | 4/2017 |
| JP | 2017-139457 A | 8/2017 |
| JP | 2017-532772 | 11/2017 |
| JP | 2017-222714 A | 12/2017 |
| JP | 2018-026552 A | 2/2018 |
| KR | 2016-0029399 A | 3/2016 |
| KR | 2016-0046296 A | 4/2016 |
| KR | 2018-0013773 A | 2/2018 |
| KR | 2018-0044985 A | 5/2018 |
| KR | 2018-0107159 A | 10/2018 |
| TW | 201724611 | 7/2017 |
| TW | 201736357 | 10/2017 |
| WO | WO 2011/065136 A1 | 6/2011 |
| WO | WO 2016/036207 A1 | 3/2016 |
| WO | WO 2017/037559 A1 | 3/2017 |
| WO | WO 2017/130079 A1 | 8/2017 |

OTHER PUBLICATIONS

Written Opinion (Application No. PCT/IB2019/052020) dated Jun. 18, 2019.

* cited by examiner

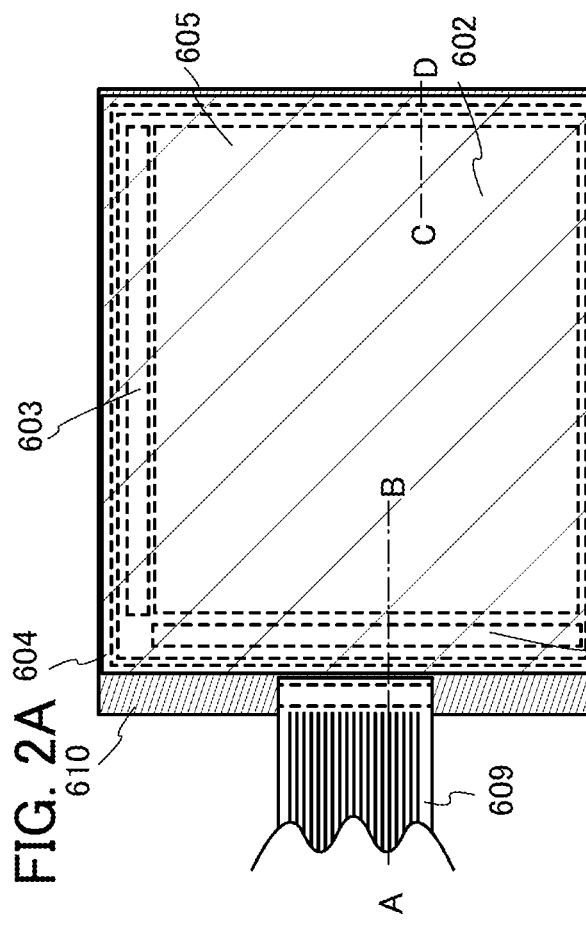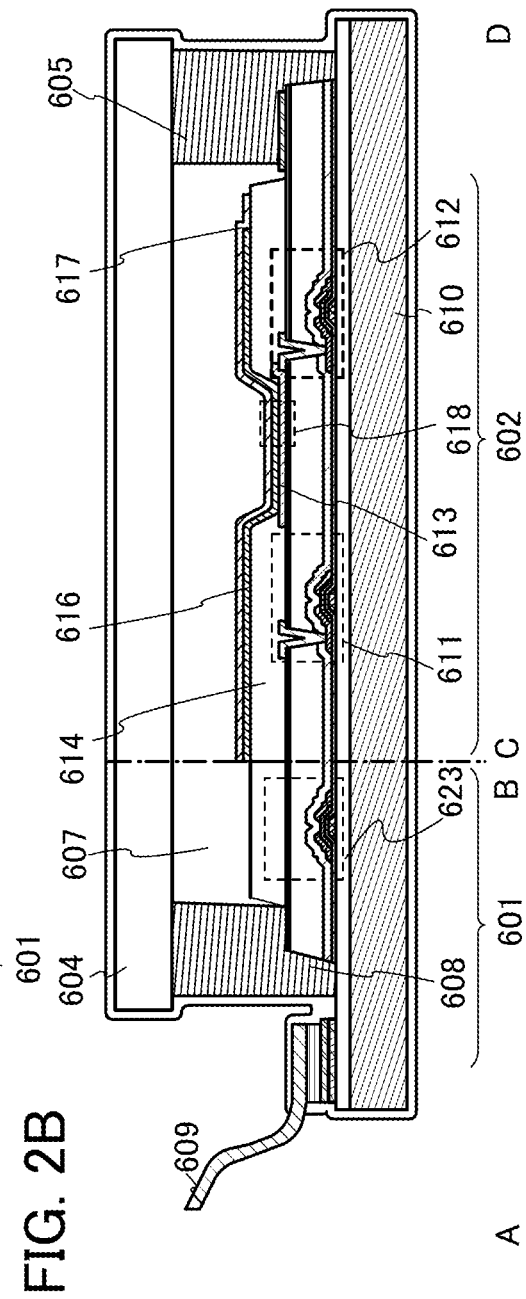

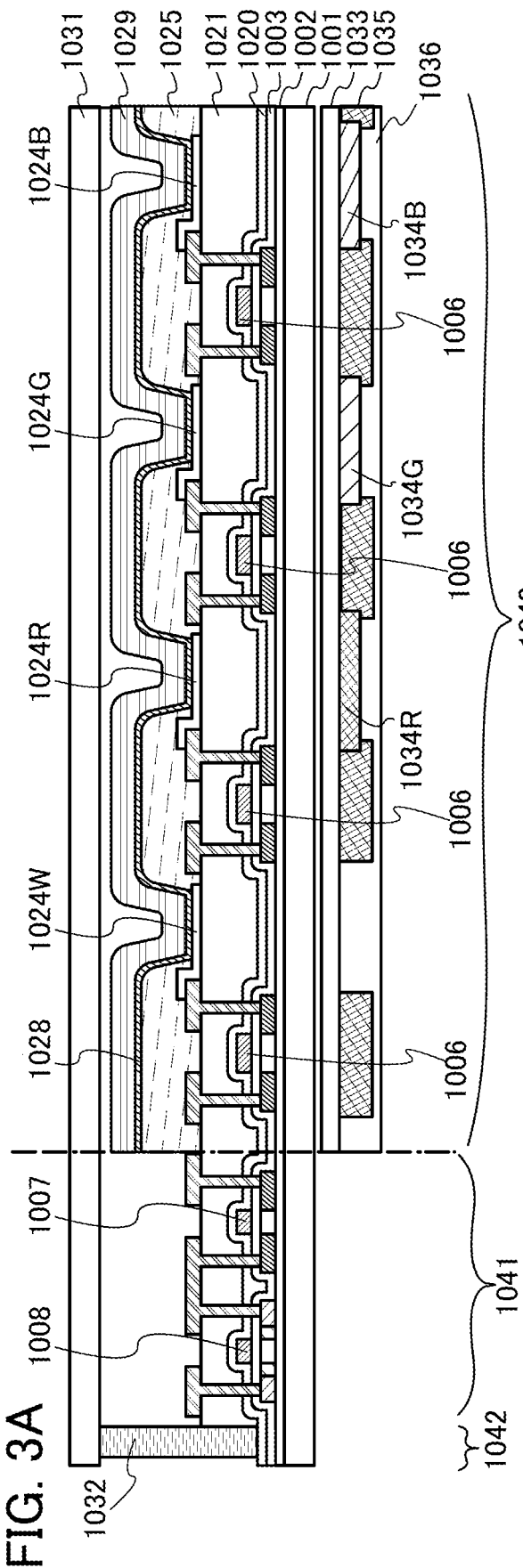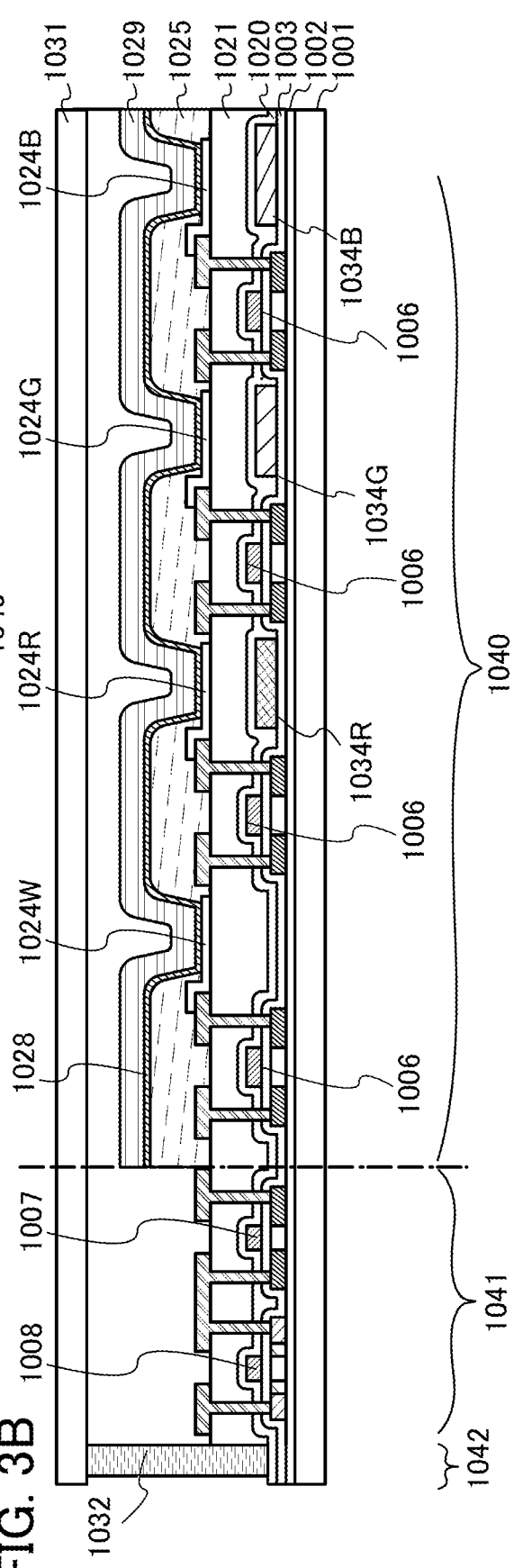

FIG. 7A
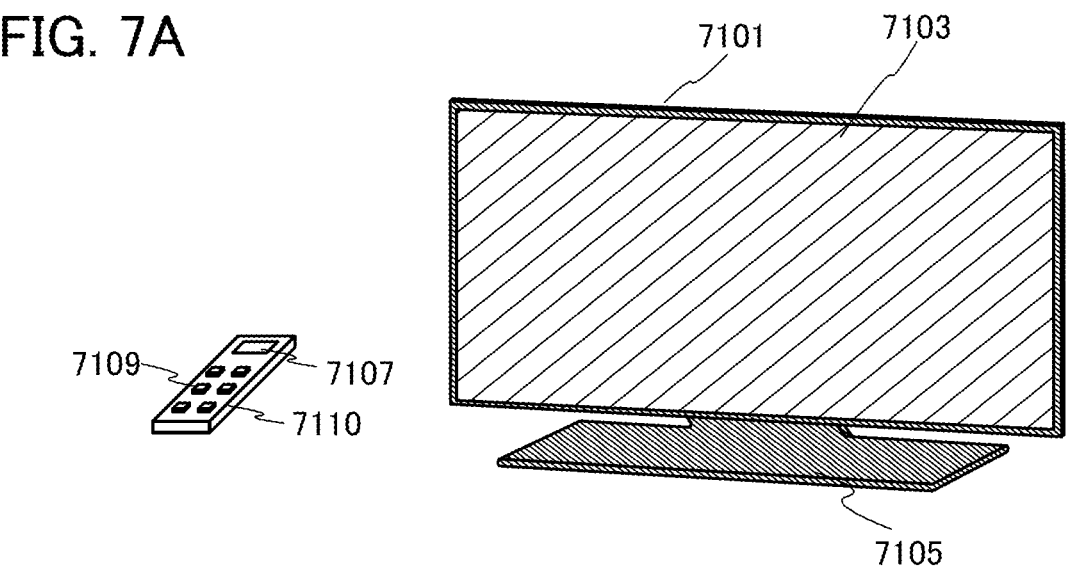
FIG. 7B1
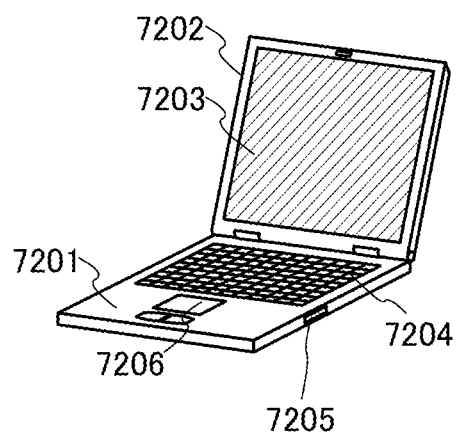
FIG. 7B2
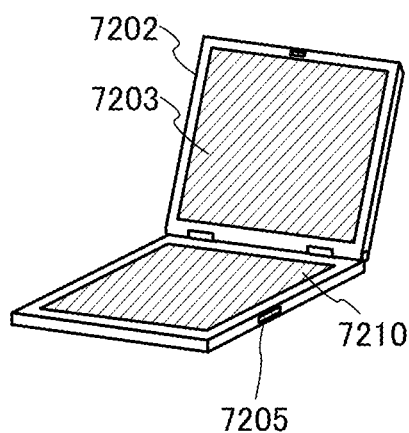
FIG. 7C
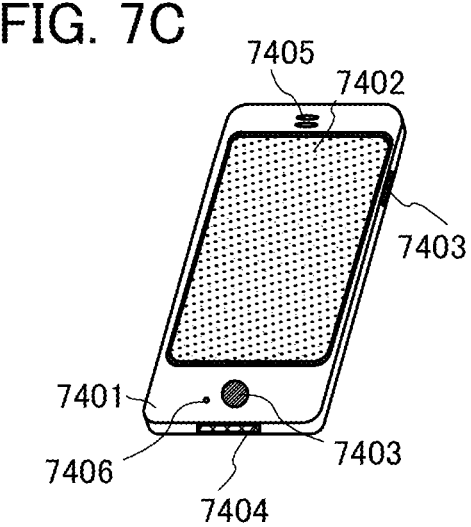

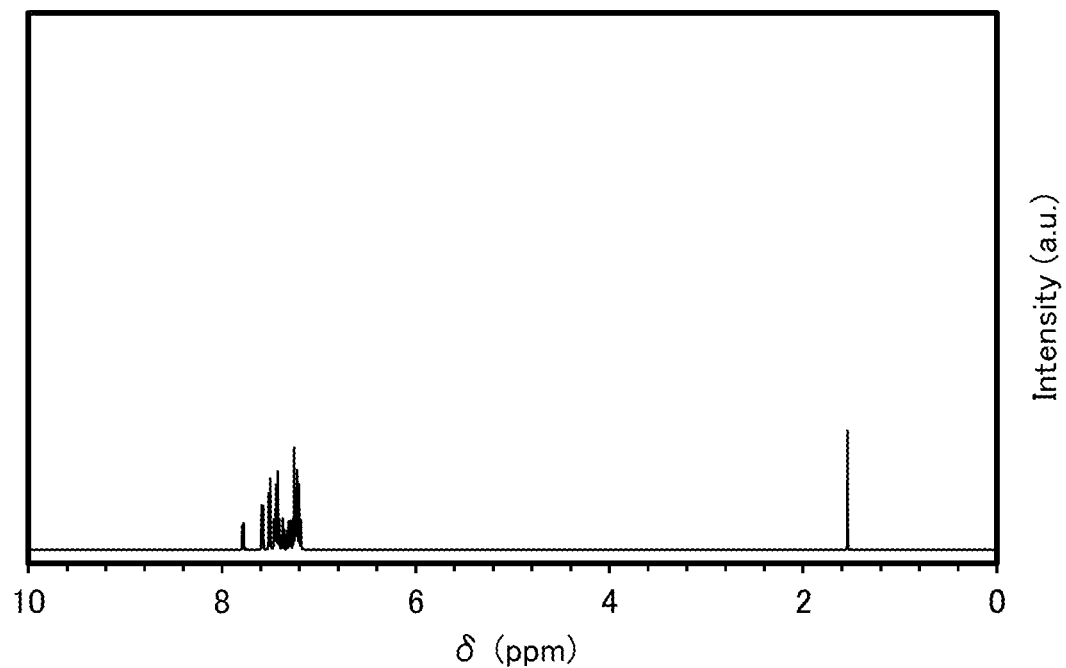
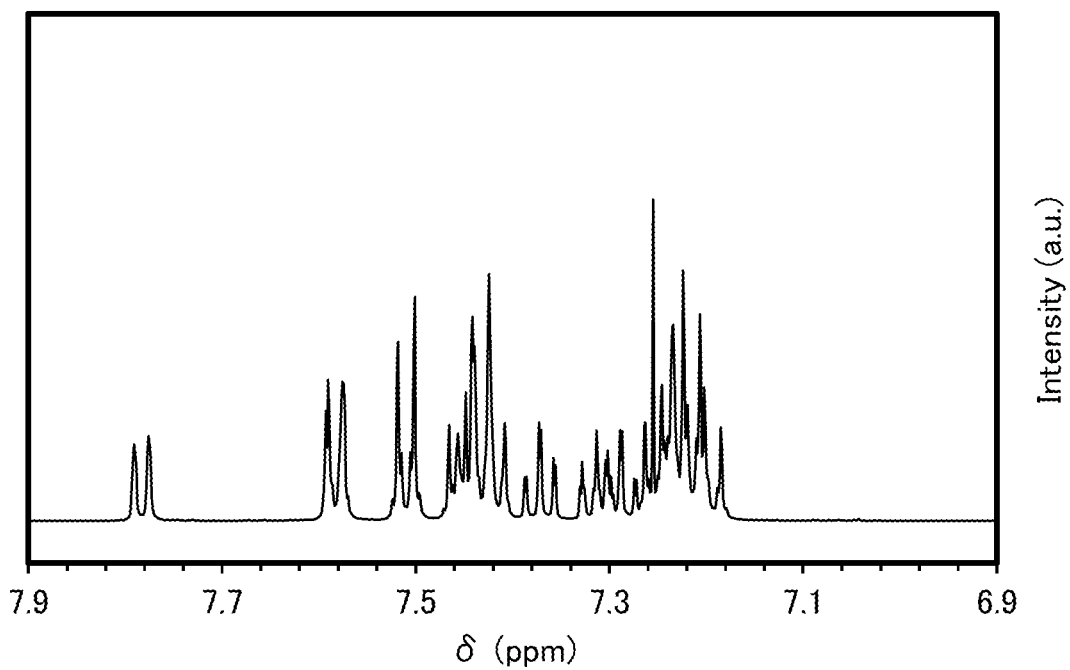

LIGHT-EMITTING DEVICE, LIGHT-EMITTING APPARATUS, ELECTRONIC DEVICE, AND LIGHTING DEVICE

This application is a continuation of copending U.S. application Ser. No. 16/981,793, filed on Sep. 17, 2020 which is a 371 of international application PCT/IB2019/052020 filed on Mar. 13, 2019 which are all incorporated herein by reference.

TECHNICAL FIELD

One embodiment of the present invention relates to a light-emitting device, a display module, a lighting module, a display device, a light-emitting apparatus, an electronic device, and a lighting device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition (composition of matter). Specifically, examples of the technical field of one embodiment of the present invention disclosed in this specification include a semiconductor device, a display device, a liquid crystal display device, a light-emitting apparatus, a lighting device, a power storage device, a memory device, an imaging device, a driving method thereof, and a manufacturing method thereof.

BACKGROUND ART

Light-emitting devices (organic EL devices) that use organic compounds and utilize electroluminescence (EL) have been put into practical use. In the basic structure of such light-emitting devices, an organic compound layer (EL layer) containing a light-emitting material is interposed between a pair of electrodes. Carriers are injected by application of voltage to this device, and recombination energy of the carriers is used, whereby light emission can be obtained from the light-emitting material.

Such light-emitting devices are of self-light-emitting type, and have advantages over liquid crystal such as high visibility and no need for backlight when used for pixels of a display; accordingly, the light-emitting devices are suitable as flat panel display devices. Displays using such light-emitting devices are also highly advantageous in that they can be fabricated thin and lightweight. Moreover, an extremely fast response speed is also a feature.

Since light-emitting layers of such light-emitting devices can be successively formed two-dimensionally, planar light emission can be obtained. This feature is difficult to obtain with point light sources typified by incandescent lamps and LEDs or linear light sources typified by fluorescent lamps. Thus, light-emitting devices are also of great utility value as planar light sources, which can be applied to lighting and the like.

Displays or lighting devices using light-emitting devices can be suitably used for a variety of electronic devices as described above, and research and development of light-emitting devices have progressed for more favorable efficiency or lifetimes.

Patent Document 1 discloses a structure in which a hole-transport material, which has a HOMO level between the HOMO level of a first hole-injection layer and the HOMO level of a host material, is provided between a light-emitting layer and a first hole-transport layer in contact with the hole-injection layer.

The characteristics of light-emitting devices have been improved remarkably, but are still insufficient to satisfy advanced requirements for various characteristics including efficiency and durability.

REFERENCE

Patent Document

[Patent Document 1] PCT International Publication No. WO2011/065136

SUMMARY OF THE INVENTION

Problems to be Solved by the Invention

Thus, an object of one embodiment of the present invention is to provide a novel light-emitting device. Alternatively, an object is to provide a light-emitting element with favorable emission efficiency. Another object is to provide a light-emitting device with a favorable lifetime. Another object is to provide a light-emitting device with a low driving voltage.

Alternatively, an object of another embodiment of the present invention is to provide each of a light-emitting apparatus, an electronic device, and a display device with high reliability. An object of another embodiment of the present invention is to provide a light-emitting apparatus, an electronic device, and a display device each having low power consumption.

It is only necessary that at least one of the above-described objects be achieved in the present invention.

Means for Solving the Problems

One embodiment of the present invention is a light-emitting device including an anode, a cathode, and a layer including an organic compound positioned between the anode and the cathode. The layer including the organic compound comprises a first layer, a second layer, and a light-emitting layer in this order from the anode side, the first layer includes a first substance and a second substance, the second layer includes a third substance, the first substance is an organic compound a HOMO level of which is higher than or equal to $-5.8$ eV and lower than or equal to $-5.4$ eV, the second substance is a substance that has an electron-acceptor property with respect to the first substance, and the third substance is an organic compound having a structure in which at least two substituents including carbazole rings are bonded to a naphthalene ring.

Another embodiment of the present invention is a light-emitting device including an anode, a cathode, and a layer including an organic compound positioned between the anode and the cathode. The layer including the organic compound includes a first layer, a second layer, and a light-emitting layer in this order from the anode side, the first layer includes a first substance and a second substance, the second layer includes a third substance, the first substance is aromatic amine including a substituent including a dibenzofuran ring or a dibenzothiophene ring, the second substance is a substance that has an electron-acceptor property with respect to the first substance, and the third substance is an organic compound having a structure in which at least two substituents including carbazole rings are bonded to a naphthalene ring.

Another embodiment of the present invention is a light-emitting device including an anode, a cathode, and a layer including an organic compound positioned between the anode and the cathode. The layer including the organic compound includes a first layer, a second layer, and a light-emitting layer in this order from the anode side, the first layer includes a first substance and a second substance, the second layer includes a third substance, the first substance is aromatic monoamine including a naphthalene ring, the second substance is a substance that has an electron-acceptor property with respect to the first substance, and the third substance is an organic compound having a structure in which at least two substituents including carbazole rings are bonded to a naphthalene ring.

Another embodiment of the present invention is a light-emitting device including an anode, a cathode, and a layer including an organic compound positioned between the anode and the cathode. The layer including the organic compound includes a first layer, a second layer, and a light-emitting layer in this order from the anode side, the first layer includes a first substance and a second substance, the second layer includes a third substance, the first substance is aromatic monoamine in which a 9-fluorenyl group is bonded to nitrogen through an arylene group, the second substance is a substance that has an electron-acceptor property with respect to the first substance, and the third substance is an organic compound having a structure in which at least two substituents including carbazole rings are bonded to a naphthalene ring.

Another embodiment of the present invention is the light-emitting device having the above structure in which the first substance is an organic compound including an N,N-bis(4-biphenyl)amino group.

Another embodiment of the present invention is the light-emitting device having the above structure in which a third layer is provided between the first layer and the second layer, and the third layer includes a fourth substance, and the fourth substance is an organic compound having a hole-transport property.

Another embodiment of the present invention is the light-emitting device having the above structure in which a third layer is provided between the first layer and the second layer, and the third layer includes a fourth substance, and the fourth substance is an organic compound a HOMO level of which is higher than or equal to −5.8 eV and lower than or equal to −5.4 eV.

Another embodiment of the present invention is the light-emitting device having the above structure in which the fourth substance is the same substance as the first substance.

Another embodiment of the present invention is a light-emitting device including an anode, a cathode, and a layer including an organic compound positioned between the anode and the cathode. The layer including the organic compound includes a first layer and a light-emitting layer in this order from the anode side, the first layer includes a third substance and a second substance, the second substance is a substance that has an electron-acceptor property with respect to the third substance, and the third substance is an organic compound having a structure in which at least two substituents including carbazole rings are bonded to a naphthalene ring.

Another embodiment of the present invention is the light-emitting device having the above structure in which the HOMO level of the third substance is higher than or equal to −5.8 eV and lower than or equal to −5.6 eV.

Another embodiment of the present invention is the light-emitting device having the above structure in which the third substance is an organic compound represented by a general formula (G1) shown below.

[Chemical formulae 1]

Note that in the general formula (G1), L represents a substituted or unsubstituted naphthalene-1,4-diyl group or a substituted or unsubstituted naphthalene-1,5-diyl group. In addition, A represents a group represented by a general formula (gA) shown below, and B represents a group represented by a general formula (gB) shown below.

[Chemical formulae 2]

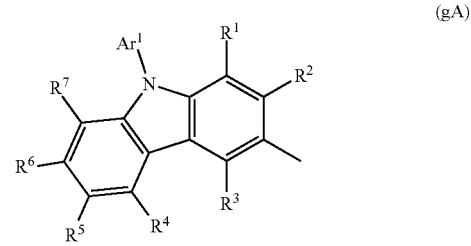

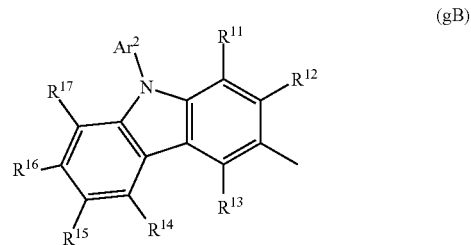

Note that in the general formula (gA), $Ar^1$ represents a substituted or unsubstituted aryl group having 6 to 13 carbon atoms in a ring. In addition, $R^1$ to $R^7$ each independently represent any of hydrogen, an alkyl group having 1 to 6 carbon atoms, a cycloalkyl group having 3 to 6 carbon atoms, and a substituted or unsubstituted aryl group having 6 to 25 carbon atoms. Note that, among them, $R^1$ and $R^2$, $R^4$ and $R^5$, $R^5$ and $R^6$, and $R^6$ and $R^7$ may be condensed to form benzene rings.

In the general formula (gB), $Ar^2$ represents a substituted or unsubstituted aryl group having 6 to 13 carbon atoms in a ring. In addition, $R^{11}$ to $R^{17}$ each independently represent any of hydrogen, an alkyl group having 1 to 6 carbon atoms, a cycloalkyl group having 3 to 6 carbon atoms, and a substituted or unsubstituted aryl group having 6 to 25 carbon atoms. Note that $R^{11}$ and $R^{12}$, $R^{14}$ and $R^{15}$, $R^{15}$ and $R^{16}$, and $R^{16}$ and $R^{17}$ may be condensed to form benzene rings.

Another embodiment of the present invention is the organic compound having the above structure in which the third substance is represented by a general formula (G1) shown below.

[Chemical formulae 3]

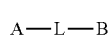

(G1)

Note that in the general formula (G1), L represents a group represented by a general formula (gL-1) shown below or a general formula (gL-2) shown below, A represents a group represented by a general formula (gA) shown below, and B represents a group represented by a general formula (gB) shown below.

[Chemical formulae 4]

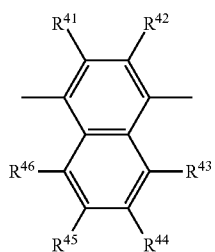

(gL-1)

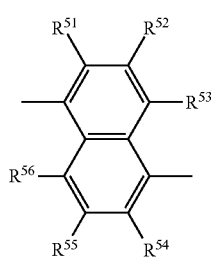

(gL-2)

Note that in the general formula (gL-1), $R^{41}$ to $R^{46}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms in a ring.

In the general formula (gL-2), $R^{51}$ to $R^{56}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms in a ring.

[Chemical formulae 5]

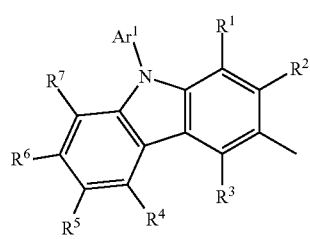

(gA)

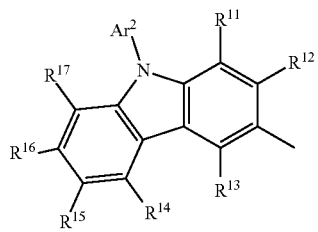

(gB)

Note that in the general formula (gA), $Ar^1$ represents a substituted or unsubstituted aryl group having 6 to 13 carbon atoms in a ring. In addition, $R^1$ to $R^7$ each independently represent any of hydrogen, an alkyl group having 1 to 6 carbon atoms, a cycloalkyl group having 3 to 6 carbon atoms, and a substituted or unsubstituted aryl group having 6 to 25 carbon atoms. Note that, among them, $R^1$ and $R^2$, $R^4$ and $R^5$, $R^5$ and $R^6$, and $R^6$ and $R^7$ may be condensed to form benzene rings.

In the general formula (gB), $Ar^2$ represents a substituted or unsubstituted aryl group having 6 to 13 carbon atoms in a ring. Furthermore, $R^{11}$ to $R^{17}$ each independently represent any of hydrogen, an alkyl group having 1 to 6 carbon atoms, a cycloalkyl group having 3 to 6 carbon atoms, and a substituted or unsubstituted aryl group having 6 to 25 carbon atoms. Note that $R^{11}$ and $R^{12}$, $R^{14}$ and $R^{15}$, $R^{15}$ and $R^{16}$, and $R^{16}$ and $R^{17}$ may be condensed to form benzene rings.

Another embodiment of the present invention is the light-emitting device having the above structure in which the third substance is 3,3'-(naphthalene-1,4-diyl)bis(9-phenyl-9H-carbazole) or 3,3'-(naphthalene-1,5-diyl)bis(9-phenyl-9H-carbazole).

Another embodiment of the present invention is the light-emitting device having the above structure in which the second substance is an organic compound.

Another embodiment of the present invention is an electronic device having the above structure, which includes a sensor, an operation button, a speaker, or a microphone.

Another embodiment of the present invention is a light-emitting apparatus having the above structure, which includes a transistor or a substrate.

Another embodiment of the present invention is a lighting device having the above structure, which includes a housing.

Note that the light-emitting apparatus in this specification includes an image display device using a light-emitting device. The light-emitting apparatus includes, in some cases, a module in which a light-emitting device is provided with a connector such as an anisotropic conductive film or a TCP (Tape Carrier Package), a module in which a printed wiring board is provided at the end of a TCP, or a module in which an IC (integrated circuit) is directly mounted on a light-emitting device by a COG (Chip On Glass) method. Furthermore, in some cases, lighting equipment or the like includes the light-emitting apparatus.

Effect of the Invention

In one embodiment of the present invention, a novel light-emitting device can be provided. Alternatively, a light-emitting device with a favorable lifetime can be provided. Alternatively, a light-emitting device with favorable emission efficiency can be provided.

Alternatively, in another embodiment of the present invention, a light-emitting apparatus, an electronic device, and a display device with high reliability can each be provided. In another embodiment of the present invention, a light-emitting apparatus, an electronic device, and a display device each having low power consumption can be provided.

Note that the descriptions of the effects do not disturb the existence of other effects. Note that one embodiment of the present invention does not need to have all these effects. Effects other than these will be apparent from and can be derived from the description of the specification, the drawings, the claims, and the like.

BRIEF DESCRIPTION OF THE DRAWINGS

FIGS. 2A and 2B are conceptual diagrams of an active matrix light-emitting apparatus.

FIGS. 3A and 3B are conceptual diagrams of active matrix light-emitting apparatuses.

FIGS. 7A-7C are diagrams illustrating electronic devices.

FIGS. 51A and 51B are $^1$H NMR charts of BBAFLBi.

Figure 1A:
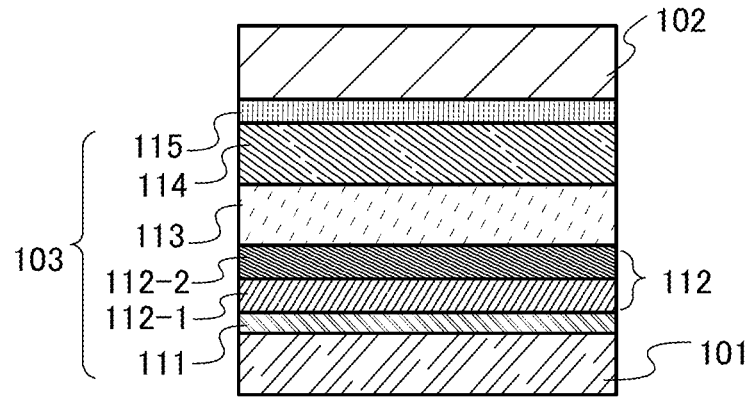
FIGS. 1A-1C are schematic diagrams of light-emitting devices.

Embodiments of the present invention are described in detail below with reference to drawings. Note that the present invention is not limited to the following description, and it will be readily appreciated by those skilled in the art that modes and details of the present invention can be modified in various ways without departing from the spirit and scope of the present invention. Thus, the present invention should not be construed as being limited to the descriptions in the following embodiments.

Embodiment 1

FIG. 1 shows diagrams illustrating light-emitting devices of one embodiment of the present invention. The light-emitting devices of one embodiment of the present invention each include a first electrode 101, a second electrode 102, and an EL layer 103, and the EL layer includes a hole-injection layer 111, a hole-transport layer 112, and a light-emitting layer 113.

Figure 1B:
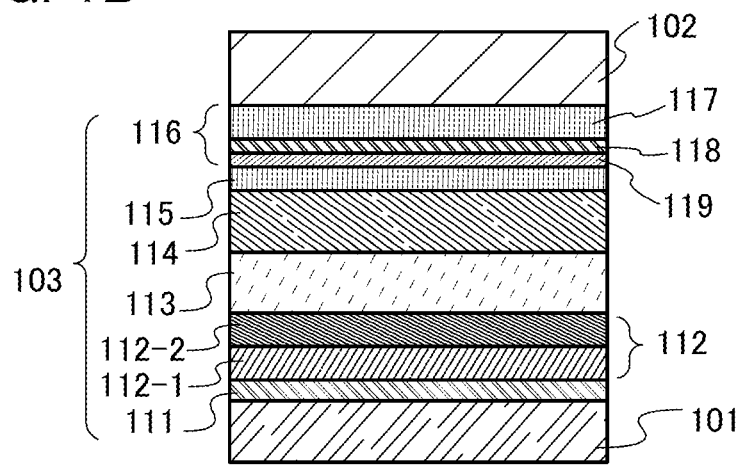

In addition to them an electron-transport layer 114 and an electron-injection layer 115 are shown in the EL layer 103 in FIG. 1(A) and FIG. 1(B); however, the structure of the light-emitting device is not limited thereto.

The hole-injection layer 111 contains a first substance and a second substance. The first substance is a substance the HOMO level of which is higher than or equal to −5.8 eV and lower than or equal to −5.4 eV The second substance is a substance exhibiting an electron-acceptor property with respect to the first substance.

A third substance contained in the hole-transport layer 112 is an organic compound having a structure in which at least two substituents including carbazole rings are bonded to a naphthalene ring.

The light-emitting device of the present invention, which has the above-described structure, can be a light-emitting device that has favorable emission efficiency and a long lifetime.

The first substance is preferably an organic compound having a hole-transport property. Alternatively, aromatic amine having a substituent that includes a dibenzofuran ring or a dibenzothiophene ring, aromatic monoamine that includes a naphthalene ring, or aromatic monoamine in which a 9-fluorenyl group is bonded to nitrogen of amine through an arylene group may be used. Note that it is preferable that the first substance be a substance including an N,N-bis(4-biphenyl)amino group because a light-emitting device with a favorable lifetime can be manufactured. As specific examples of the above-described first substance, N-(4-biphenyl)-6,N-diphenylbenzo[b]naphtho[1,2-d]furan-8-amine (abbreviation: BnfABP), N,N-bis(4-biphenyl)-6-phenylbenzo[b]naphtho[1,2-d]furan-8-amine (abbreviation: BBABnf), 4,4'-bis(6-phenylbenzo[b]naphtho[1,2-d]furan-8-yl)-4''-phenyltriphenylamine (abbreviation: BnfBB1BP), N,N-bis(4-biphenyl)benzo[b]naphtho[1,2-d]furan-6-amine (abbreviation: BBABnf(6)), N,N-bis(4-biphenyl)benzo[b]naphtho[1,2-d]furan-8-amine (abbreviation: BBABnf(8)), N,N-bis(4-biphenyl)benzo[b]naphtho[2,3-d]furan-4-amine (abbreviation: BBABnf(II)(4)), N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4''-diphenyltriphenylamine (abbreviation: BBAβNB), 4-[4-(2-naphthyl)phenyl]-4',4''-diphenyltriphenylamine (abbreviation: BBAβNBi), 4,4'-diphenyl-4''-(6; 1'-binaphthyl-2-yl)triphenylamine (abbreviation: BBAαNβNB), 4,4'-diphenyl-4''-(7; 1'-binaphthyl-2-yl)triphenylamine (abbreviation: BBAαNβNB-03), 4,4'-diphenyl-4''-(7-phenyl)naphthyl-2-yltriphenylamine (abbreviation: BBAPβNB-03), 4,4'-diphenyl-4''-(6; 2'-binaphthyl-2-yl)triphenylamine (abbreviation: BBA(βN2)B), 4,4'-diphenyl-4''-(7; 2'-binaphthyl-2-yl)triphenylamine (abbreviation: BBA(βN2)B-03), 4,4'-diphenyl-4''-(4;2'-binaphthyl-1-yl)triphenylamine (abbreviation: BBAβNαNB), 4,4'-diphenyl-4''-(5;2'-binaphthyl-1-yl)triphenylamine (abbreviation: BBAβNαNB-02), 4-(4-biphenylyl)-4'-(2-naphthyl)-4''-phenyltriphenylamine (abbreviation: TPBiAβNB), 4-(3-biphenylyl)-4'-[4-(2-naphthyl)phenyl]-4''-phenyltriphenylamine (abbreviation: mTPBiAβNBi), 4-(4-biphenylyl)-4'-[4-(2-naphthyl)phenyl]-4''-phenyltriphenylamine (abbreviation: TPBiAβNBi), 4-phenyl-4'-(1-naphthyl)triphenylamine (abbreviation: αNBA1BP), 4,4'-bis(1-naphthyl)triphenylamine (abbreviation: αNBB1BP), 4,4'-diphenyl-4''-[4'-(carbazol-9-yl)biphenyl-4-yl]triphenylamine (abbreviation: YGTBi1BP), 4'-[4-(3-phenyl-9H-carbazol-9-yl)phenyl]tris(1,1'-biphenyl-4-yl)amine (abbreviation: YGTBi1BP-02), 4-diphenyl-4'-(2-naphthyl)-4''-{9-(4-biphenylyl)carbazol}triphenylamine (abbreviation: YGTBiβNB), N-[4-(9-phenyl-9H-carbazol-3-yl)phenyl]-N-[4-(1-naphthyl)phenyl]-9,9'-spirobi(9H-fluoren)-2-amine (abbreviation: PCBNBSF), N,N-bis(4-biphenylyl)-9,9'-spirobi[9H-fluoren]-2-amine (abbreviation: BBASF), N,N-bis(1,1'-biphenyl-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spiro-bi(9H-fluoren)-4-amine (abbreviation: oFBiSF), N-(4-biphenyl)-N-(dibenzofuran-4-yl)-9,9-dimethyl-9H-fluoren-2-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-[4-(9-phenylfluoren-9-yl)phenyl]triphenylamine (abbreviation: BPAFLBi), 4-phenyl-4'-(9-phenyl-9H-carbazol-3-yl)triphenylamine (abbreviation: PCBA1BP), 4,4'-diphenyl-4''-(9-phenyl-9-H-carbazol-3-yl)triphenylamine (abbreviation: PCBBi1BP), 4-(1-naphthyl)-4'-(9-phenyl-9H-carbazol-3-yl)-triphenylamine (abbreviation:PCBANB), 4,4'-di(1-naphthyl)-4''-(9-phenyl-9H-carbazol-3-yl)triphenylamine (abbreviation: PCBNBB), N-phenyl-N-[4-(9-phenyl-9H-carbazol-3-yl)phenyl]-spiro-9,9'-bifluoren-2-amine (abbreviation: PCBASF), and the like can be given.

The second substance may be an inorganic compound or an organic compound. As the second substance, transition metal oxide, oxide of metal that belongs to Group 4 to Group 8 of the periodic table, or an organic compound including an electron-withdrawing group (specifically, a halogen group such as a fluoro group or a cyano group), or the like can be used, and a substance exhibiting an electron-acceptor property with respect to the first substance may be selected from such substances as appropriate.

As the transition metal oxide or the oxide of metal belonging to Group 4 to Group 8 of the periodic table that can be used as the second substance, vanadium oxide, niobium oxide, tantalum oxide, chromium oxide, molybdenum oxide, tungsten oxide, manganese oxide, rhenium oxide, titanium oxide, ruthenium oxide, zirconium oxide, hafnium oxide, and silver oxide are preferable because they exhibit a high acceptor property. Among them, molybdenum oxide is particularly preferable because of its high stability in the air, low hygroscopicity, and high handiness.

As the organic compound including an electron-withdrawing group (a halogen group or a cyano group) that can be used as the second substance, 7,7,8,8-tetracyano-2,3,5,6-tetrafluoroquinodimethane (abbreviation: F$_4$-TCNQ), chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), 2-(7-dicyanomethylene-1,3,4,5,6,8,9,10-octafluoro-7H-pyren-2-ylidene)malononitrile, and the like can be given. A compound in which electron-withdrawing groups are bonded to a condensed aromatic ring having a plurality of hetero atoms, such as HAT-CN, is particularly preferable because it is thermally stable. A [3]radialene derivative including an electron-withdrawing group (in particular, a halogen group such as a fluoro group, or a cyano group) has a very high electron-accepting property and thus is preferable; specifically, α,α',α''-1,2,3-cyclopropanetriylidenetris[4-cyano-2,3,5,6-tetrafluorobenzeneacetonitrile], α,α',α''-1,2,3-cyclopropanetriylidenetris[2,6-dichloro-3,5-difluoro-4-(trifluoromethyl)benzeneacetonitrile], α,α',α''-1,2,3-cyclopropanetriylidenetris[2,3,4,5,6-pentafluorobenzeneacetonitrile], and the like can be given.

Note that the electron-acceptor property of an inorganic compound such as molybdenum oxide tends to be stronger than those of the above-described organic compounds. In a light-emitting device in which the second substance is an organic compound, an increase in the driving voltage and a decrease in the lifetime are likely to occur when the HOMO level of the first substance is deep (e.g., deeper than −5.4 eV); however, the light-emitting device of the present invention also has a characteristic in that such problems are less likely to occur.

The HOMO level of the third substance is preferably higher than or equal to −5.8 eV and lower than or equal to −5.6 eV, in which case hole injection into a light-emitting layer host having a deep HOMO level is performed smoothly. This is particularly important in the case where a blue fluorescent layer is used as the light-emitting layer. For example, in the case where the light-emitting layer contains a host material and a light-emitting material and the light-emitting material exhibits blue fluorescence, the band gap of the host material needs to be wider than that of a blue color, and as a result, the HOMO level thereof tends to be deep. Therefore, it is preferable for hole injection into the light-emitting layer that the HOMO level of the third substance be higher than or equal to −5.8 eV and lower than or equal to −5.6 eV. Note that as such a wide-gap host material, an organic compound having an anthracene skeleton can be given typically.

Note that when the LUMO level of the third substance is higher than or equal to −2.4 eV, preferably higher than or equal to −2.2 eV, loss of electrons from the light-emitting layer can be effectively prevented, leading to an improvement in the emission efficiency. For the same reason, a difference between the LUMO level of the third substance and the LUMO level of the host material is preferably greater than or equal to 0.3 eV, further preferably greater than or equal to 0.5 eV.

In the case where the host material has an anthracene skeleton and a carbazole skeleton, in particular, an anthracene skeleton and a dibenzocarbazole skeleton, the host material has high electron mobility. Therefore, the driving voltage can be reduced while the light-emitting layer tends to have excess electrons correspondingly, and a decrease in the reliability might be caused because of a reduction in the recombination region, loss of electrons from the light-emitting layer, and the like. However, this problem can be overcome because such a third substance described above has a favorable hole-injection property to the light-emitting layer in the light-emitting device of one embodiment of the present invention.

As the third substance, organic compounds represented by a general formula (G1) shown below are preferable. These compounds are compounds that have deep HOMO levels and have not only excellent hole-injection properties to the light-emitting layer but also high durability against electrons. Accordingly, a light-emitting device with favorable reliability can be provided.

[Chemical formulae 6]

(G1)

A—L—B

Note that in the general formula (G1), L represents a substituted or unsubstituted naphthalene-1,4-diyl group or a substituted or unsubstituted naphthalene-1,5-diyl group. The substituted or unsubstituted naphthalene-1,4-diyl group or the substituted or unsubstituted naphthalene-1,5-diyl group can also be represented by a general formula (gL-1) or a general formula (gL-2) shown below.

[Chemical formulae 7]

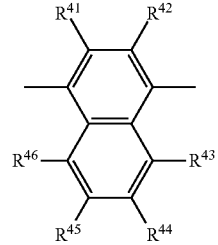

(gL-1)

-continued

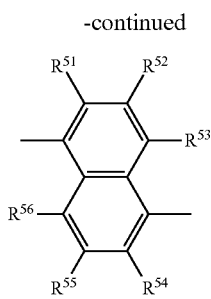

(gL-2)

Note that in the general formula (gL-1), $R^{41}$ to $R^{46}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms in a ring.

In the general formula (gL-2), $R^{51}$ to $R^{56}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms in a ring.

Note that it is preferable that $R^{41}$ to $R^{46}$ or $R^{51}$ to $R^{56}$ be all hydrogen, in which case synthesis is facilitated.

In the general formula (G1), A represents a group represented by a general formula (gA) shown below, and B represents a group represented by a general formula (gB) shown below.

[Chemical formulae 8]

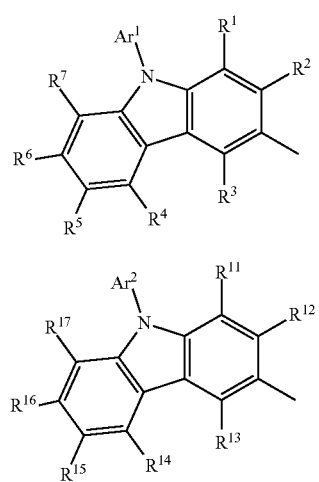

Note that in the general formula (gA), $Ar^1$ represents a substituted or unsubstituted aryl group having 6 to 13 carbon atoms in a ring. Furthermore, $R^1$ to $R^7$ each independently represent any of hydrogen, an alkyl group having 1 to 6 carbon atoms, a cycloalkyl group having 3 to 6 carbon atoms, and a substituted or unsubstituted aryl group having 6 to 25 carbon atoms. Note that $R^1$ and $R^2$, $R^4$ and $R^5$, $R^5$ and $R^6$, and $R^6$ and $R^7$ may be condensed to form benzene rings.

In the general formula (gB), $Ar^2$ represents a substituted or unsubstituted aryl group having 6 to 13 carbon atoms in a ring. Furthermore, $R^{11}$ to $R^{17}$ each independently represent any of hydrogen, an alkyl group having 1 to 6 carbon atoms, a cycloalkyl group having 3 to 6 carbon atoms, and a substituted or unsubstituted aryl group having 6 to 25 carbon atoms. Note that $R^{11}$ and $R^{12}$, $R^{14}$ and $R^{15}$, $R^{15}$ and $R^{16}$, and $R^{16}$ and $R^{17}$ may be condensed to form benzene rings.

$R^1$ to $R^7$, $R^{11}$ to $R^{17}$, $R^{21}$ to $R^{24}$, $R^{25}$ to $R^{28}$, and $R^{31}$ to $R^{38}$ each independently represent hydrogen, an alkyl group having 1 to 6 carbon atoms, a cycloalkyl group having 3 to 6 carbon atoms, or a substituted or unsubstituted aryl group having 6 to 25 carbon atoms; a methyl group, an ethyl group, a propyl group, an isopropyl group, an n-butyl group, a sec-butyl group, an isobutyl group, a tert-butyl group, a pentyl group, a hexyl group, and the like can be given as the alkyl group having 1 to 6 carbon atoms; a cyclopropyl group, a cyclobutyl group, a cyclopentyl group, a cyclohexyl group, and the like can be given as the cycloalkyl group having 3 to 6 carbon atoms; a phenyl group, a biphenyl group, a naphthyl group, a phenanthryl group, an anthryl group, a triphenylenyl group, a fluorenyl group, a 9,9-diphenylfluorenyl group, a 9,9-spirobifluorenyl group, and the like can be given as the substituted or unsubstituted aryl group having 6 to 25 carbon atoms. Note that in order to prevent emergence of an electron-transport property, of those groups described above, a group that does not contain polyacene having three or more rings is preferable.

In the case where the substituted or unsubstituted aryl group having 6 to 25 carbon atoms has a substituent, an alkyl group having 1 to 6 carbon atoms, a cycloalkyl group having 3 to 6 carbon atoms, or an aryl group having 6 to 13 carbon atoms can be used as the substituent. Specific examples of them include a methyl group, an ethyl group, a propyl group, an isopropyl group, a tert-butyl group, a hexyl group, a cyclopropyl group, a cyclohexyl group, a phenyl group, a tolyl group, a naphthyl group, and a biphenyl group.

$R^{41}$ to $R^{46}$ and $R^{51}$ to $R^{56}$ each independently represent hydrogen, an alkyl group having 1 to 6 carbon atoms, a cycloalkyl group having 3 to 6 carbon atoms, or a substituted or unsubstituted aryl group having 6 to 13 carbon atoms in a ring; specifically, a methyl group, an ethyl group, a propyl group, an isopropyl group, a butyl group, a tert-butyl group, a pentyl group, a hexyl group, and the like can be given as the alkyl group having 1 to 6 carbon atoms; a cyclopropyl group, a cyclohexyl group, and the like can be given as the cycloalkyl group having 3 to 6 carbon atoms; a phenyl group, a biphenyl group, a naphthyl group, a phenanthryl group, an anthryl group, a fluorenyl group, and the like can be given as the substituted or unsubstituted aryl group having 6 to 13 carbon atoms in a ring.

In the case where the substituted or unsubstituted aryl group having 6 to 13 carbon atoms in a ring has a substituent, an alkyl group having 1 to 6 carbon atoms, a cycloalkyl group having 3 to 6 carbon atoms, or an aryl group having 6 to 13 carbon atoms can be used as the substituent. Specific examples of them include a methyl group, an ethyl group, a propyl group, an isopropyl group, a tert-butyl group, a hexyl group, a cyclopropyl group, a cyclohexyl group, a phenyl group, a tolyl group, a naphthyl group, and a biphenyl group.

Furthermore, $Ar^1$ and $Ar^2$ each independently represent a substituted or unsubstituted aryl group having 6 to 13 carbon atoms in a ring; specifically, a phenyl group, a naphthyl group, a biphenyl group, a fluorenyl group, a dimethylfluorenyl group, a diphenylfluorenyl group, a tert-butylphenyl group, a tolyl group, a trimethylphenyl group, and the like can be given.

Note that a light-emitting device in which the third substance is 3,3'-(naphthalene-1,4-diyl)bis(9-phenyl-9H-carbazole) or 3,3'-(naphthalene-1,5-diyl)bis(9-phenyl-9H-carbazole) is preferable because of its high emission efficiency.

Note that it is preferable that the third substance, that is, the organic compound having a structure in which at least two substituents including carbazole rings are bonded to a naphthalene ring do not include a triarylamine skeleton in order to prevent the HOMO level from being too shallow.

Note that the hole-transport layer 112 may have a two-layer structure. In that case, the organic compound having the structure in which at least two substituents including carbazole rings are bonded to a naphthalene ring is preferably used in a layer in contact with the light-emitting layer of the two layers. At this time, deterioration of the device can be small when the electron-transport property of the organic compound is small; thus, it is preferable that the organic compound do not have polyacene that has three or more rings in a molecular.

Furthermore, in that case, the other layer on the hole-injection layer side is a layer that contains an organic compound having a hole-transport property, and the organic compound having a hole-transport property is preferably an organic compound the HOMO level of which is higher than or equal to −5.8 eV and lower than or equal to −5.4 eV It is further preferable that the organic compound be the same substance as the first substance.

Embodiment 2

Next, examples of specific structures and materials of the above-described light-emitting device are described. As described above, the light-emitting device of one embodiment of the present invention includes, between the pair of electrodes of the first electrode 101 and the second electrode 102, the EL layer 103 including a plurality of layers; the EL layer 103 includes at least the hole-injection layer 111, the hole-transport layer 112, and the light-emitting layer 113 from the first electrode 101 side.

There is no particular limitation on the other layers included in the EL layer 103, and various layer structures such as a hole-injection layer, a hole-transport layer, an electron-transport layer, an electron-injection layer, a carrier-blocking layer, an exciton-blocking layer, and a charge-generation layer can be employed.

The first electrode 101 is preferably formed using a metal, an alloy, or a conductive compound having a high work function (specifically, 4.0 eV or more), a mixture thereof, or the like. Specifically, for example, indium oxide-tin oxide (ITO: Indium Tin Oxide), indium oxide-tin oxide containing silicon or silicon oxide, indium oxide-zinc oxide, indium oxide containing tungsten oxide and zinc oxide (IWZO), and the like can be given. These conductive metal oxide films are usually formed by a sputtering method but may also be formed by application of a sol-gel method or the like. An example of the formation method is a method in which an indium oxide-zinc oxide film is formed by a sputtering method using a target in which 1 to 20 wt % zinc oxide is added to indium oxide. Indium oxide containing tungsten oxide and zinc oxide (IWZO) can also be formed by a sputtering method using a target containing 0.5 to 5 wt % tungsten oxide and 0.1 to 1 wt % zinc oxide with respect to indium oxide. Alternatively, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), and the like can be given. Graphene can also be used. Note that although the typical substances that have a high work function and are used as a material used for forming the anode are listed above, a composite material of an organic compound having a hole-transport property and a substance exhibiting an electron-accepting property with respect to the organic compound is used for the hole-injection layer 111 of one embodiment of the present invention; thus, an electrode material can be selected regardless of the work function.

In this embodiment, two kinds of stacked-layer structures of the EL layer 103 are described: the structure including the electron-transport layer 114 and the electron-injection layer 115 in addition to the hole-injection layer 111, the hole-transport layer 112, and the light-emitting layer 113 as illustrated in FIG. 1(A); and the structure including the electron-transport layer 114, the electron-injection layer 115, and a charge-generation layer 116 in addition to the hole-injection layer 111, the hole-transport layer 112, and the light-emitting layer 113 as illustrated in FIG. 1(B). Materials forming the layers are specifically described below.

The hole-injection layer 111 is a layer containing the first substance that is an organic compound the HOMO level of which is higher than or equal to −5.8 eV and lower than or equal to −5.4 eV and the second substance that has an electron-acceptor property with respect to the first substance. Although the second substance may be either an inorganic compound or an organic compound in the structure of one embodiment of the present invention, the structure is particularly suitable when the second substance is an organic compound.

The first substance and the second substance are described in Embodiment 1 in detail; thus, repeated description is omitted. Refer to the corresponding description.

The formation of the hole-injection layer 111 can improve the hole-injection property, whereby a light-emitting device having a low driving voltage can be obtained. The organic compound having an electron-acceptor property is an easy-to-use material because evaporation is easy and its film can be easily formed.

The hole-transport layer 112 contains a hole-transport material. The hole-transport material preferably has a hole mobility of $1 \times 10^{-6}$ cm$^2$/Vs or more. In one embodiment of the present invention, as a material of the hole-transport layer, an organic compound having a structure in which at least two substituents including carbazole rings are bonded to a naphthalene ring is used. Note that the organic compound having a structure in which at least two substituents including carbazole rings are bonded to a naphthalene ring is described in detail in Embodiment 1; thus, repeated description is omitted.

The hole-transport layer 112 may have a two-layer structure. In that case, the organic compound having the structure in which at least two substituents including carbazole rings are bonded to a naphthalene ring is preferably used in a layer in contact with the light-emitting layer of the two layers. At this time, deterioration of the device can be small when the electron-transport property of the organic compound is small; thus, it is preferable that the organic compound do not have polyacene that has three or more rings in a molecular.

Furthermore, the other layer is a layer that contains an organic compound having a hole-transport property, and the organic compound having a hole-transport property is preferably an organic compound the HOMO level of which is higher than or equal to −5.8 eV and lower than or equal to −5.4 eV. It is further preferable that the organic compound be the same substance as the first substance.

The light-emitting layer 113 is a layer containing the host material and the light-emitting material. The light-emitting material may be fluorescent substances, phosphorescent substances, substances exhibiting thermally activated delayed fluorescence (TADF), or other light-emitting materials. Furthermore, it may be a single layer or be formed of a plurality of layers including different light-emitting materials. Note that one embodiment of the present invention is more preferably used in the case where the light-emitting layer 113 is a layer that exhibits fluorescence, specifically, a layer that exhibits blue fluorescence.

Examples of a material that can be used as a fluorescent substance in the light-emitting layer 113 are as follows. Fluorescent substances other than those given below can also be used.

For example, 5,6-bis[4-(10-phenyl-9-anthryl)phenyl]-2, 2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-diphenyl-N,N-bis[4-(9-phenyl-9H-fluoren-9-yl)phenyl]pyrene-1,6-diamine (abbreviation: 1,6FLPAPrn), N,N'-bis(3-methylphenyl)-N,N-bis[3-(9-phenyl-9H-fluoren-9-yl)phenyl]-pyrene-1,6-diamine (abbreviation: 1,6mMemFLPAPrn), N,N'-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis[N,N,N-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N,N-triphenyl-1,4-phenylenediamine (abbreviation: 2DPAPPA), N,N,N',N',N'',N'',N''', N''''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N,N-triphenyl-1,4-phenylenediamine (abbreviation: 2DPAPA), N-[9,10-bis(1,1'-biphenyl-2-yl)-2-anthryl]-N,N,N-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[i]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and N,N'-diphenyl-N,N'-(1,6-pyrene-diyl)bis[(6-phenylbenzo [b]naphtho[1,2-d]furan)-8-amine] (abbreviation: 1,6BnfAPrn-03) can be given. In particular, a condensed aromatic diamine compound typified by a pyrenediamine compound such as 1,6FLPAPrn, 1,6mMemFLPAPrn, and 1,6BnfAPrn-03 is preferable because of its high hole-trapping property, high emission efficiency, and high reliability.

Examples of a material that can be used as a phosphorescent substance in the light-emitting layer 113 are as follows.

An organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium (III) (abbreviation: [Ir(mpptz-dmp)$_3$]), tris(5-methyl-3,4-diphenyl-4H-1,2,4-triazolato)iridium(III) (abbreviation: [Ir (Mptz)$_3$]), or tris[4-(3-biphenyl)-5-isopropyl-3-phenyl-4H-1,2,4-triazolato]iridium(III) (abbreviation: [Ir(iPrptz-3b)$_3$]), an organometallic iridium complex having a 1H-triazole skeleton, such as tris[3-methyl-1-(2-methylphenyl)-5-phenyl-1H-1,2,4-triazolato]iridium(III) (abbreviation: [Ir (Mptz1-mp)$_3$]) or tris(1-methyl-5-phenyl-3-propyl-1H-1,2, 4-triazolato)iridium(III) (abbreviation: [Ir(Prptz1-Me)$_3$]), an organometallic iridium complex having an imidazole skeleton, such as fac-tris[1-(2,6-diisopropylphenyl)-2-phenyl-1H-imidazole]iridium(III) (abbreviation: [Ir(iPrpmi)$_3$]) or tris[3-(2,6-dimethylphenyl)-7-methylimidazo[1,2-f] phenanthridinato]iridium(III) (abbreviation: [Ir(dmpimpt-Me)$_3$]), and an organometallic iridium complex in which a phenylpyridine derivative having an electron-withdrawing group is a ligand, such as bis[2-(4',6'-difluorophenyl)pyridinato-N,C$^{2'}$]iridium(III)tetrakis(1-pyrazolyl)borate (abbreviation: FIr6), bis[2-(4',6'-difluorophenyl)pyridinato-N,C$^{2'}$] iridium(III)picolinate (abbreviation: FIrpic), bis{2-[3',5'-bis (trifluoromethyl)phenyl]pyridinato-N,C$^{2'}$}iridium(III) picolinate (abbreviation: [Ir(CF$_3$ppy)$_2$(pic)]), or bis[2-(4',6'-difluorophenyl)pyridinato-N,C$^{2'}$]iridium(III)acetylacetonate (abbreviation: FIracac) can be given. These are compounds exhibiting blue phosphorescence, and are compounds having an emission peak at 440 nm to 520 nm.

Furthermore, an organometallic iridium complex having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(t-Buppm)$_3$]), (acetylacetonato)bis(6-methyl-4-phenylpyrimidinato)iridium(III) (abbreviation: [Ir(mppm)$_2$ (acac)]), (acetylacetonato)bis(6-tert-butyl-4-phenylpyrimidinato)iridium(III) (abbreviation: [Ir (tBuppm)$_2$ (acac)]), (acetylacetonato)bis[6-(2-norbornyl)-4-phenylpyrimidinato]iridium(III) (abbreviation: [Ir(nbppm)$_2$ (acac)]), (acetylacetonato)bis[5-methyl-6-(2-methylphenyl)-4-phenylpyrimidinato]iridium(III) (abbreviation: [Ir(mpmppm)$_2$(acac)]), or (acetylacetonato) bis(4,6-diphenylpyrimidinato)iridium(III) (abbreviation: [Ir (dppm)$_2$(acac)]), an organometallic iridium complex having a pyrazine skeleton, such as (acetylacetonato)bis(3,5-dimethyl-2-phenylpyrazinato)iridium(III) (abbreviation: [Ir (mppr-Me)$_2$(acac)]) or (acetylacetonato)bis(5-isopropyl-3-methyl-2-phenylpyrazinato)iridium(III) (abbreviation: [Ir (mppr-iPr)$_2$(acac)]), an organometallic iridium complex having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III)acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo [h]quinolinato)iridium(III) (abbreviation: [Ir(bzq)$_3$]), tris(2- phenylquinolinato-N,C$^{2'}$)iridium(III) (abbreviation: [Ir(pq)$_3$]), or bis(2-phenylquinolinato-N,C$^{2'}$)iridium(III) acetylacetonate (abbreviation: [Ir(pq)$_2$(acac)]), and a rare earth metal complex such as tris(acetylacetonato) (monophenanthroline)terbium(III) (abbreviation: [Tb(acac)$_3$ (Phen)]) can be given. These are mainly compounds exhibiting green phosphorescence, and have an emission peak at 500 nm to 600 nm. Note that an organometallic iridium complex having a pyrimidine skeleton is particularly preferable because of its distinctively high reliability and emission efficiency.

Furthermore, an organometallic iridium complex having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), or bis[4,6-di(naphthalen-1-yl)pyrimidinato](dipivaloylmethanato)iridium(III) (abbreviation: [Ir(d1npm)$_2$(dpm)]), an organometallic iridium complex having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), or (acetylacetonato)bis[2,3-bis(4-fluorophenyl)quinoxalinato]iridium(III) (abbreviation: [Ir(Fdpq)$_2$(acac)]), an organometallic iridium complex having a pyridine skeleton, such as tris(1-phenylisoquinolinato-N,C$^{2'}$)iridium(III) (abbreviation: [Ir(piq)$_3$]) or bis(1-phenylisoquinolinato-N,C$^{2'}$)iridium(III)acetylacetonate (abbreviation: [Ir(piq)$_2$(acac)]), a platinum complex such as 2,3,7,8,12,13,17,18-octaethyl-21H,23H-porphyrin platinum(II) (abbreviation: PtOEP), and a rare earth metal complex such as tris(1,3-diphenyl-1,3-propanedionato) (monophenanthroline)europium(III) (abbreviation: [Eu(DBM)$_3$(Phen)]) or tris[1-(2-thenoyl)-3,3,3-trifluoroacetonato](monophenanthroline)europium(III) (abbreviation: [Eu(TTA)$_3$(Phen)]) can be given. These are compounds exhibiting red phosphorescence, and have an emission peak at 600 nm to 700 nm. Furthermore, from the organometallic iridium complex having a pyrazine skeleton, red light emission with favorable chromaticity can be obtained.

Besides the above-described phosphorescent compounds, other known phosphorescent materials may be selected and used.

As the TADF material, a fullerene, a derivative thereof, an acridine, a derivative thereof, an eosin derivative, or the like can be used. Other examples include a metal-containing porphyrin containing magnesium (Mg), zinc (Zn), cadmium (Cd), tin (Sn), platinum (Pt), indium (In), palladium (Pd), or the like. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$(OEP)), which are represented by the following structural formulae.

[Chemical formulae 9]

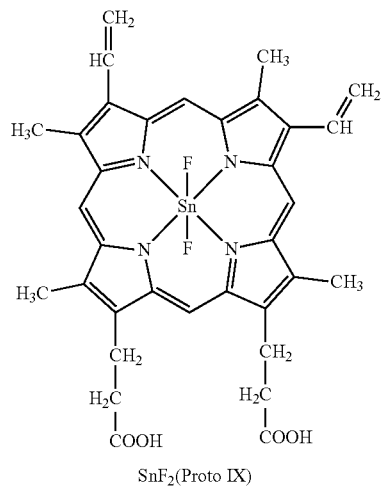

SnF$_2$(Proto IX)

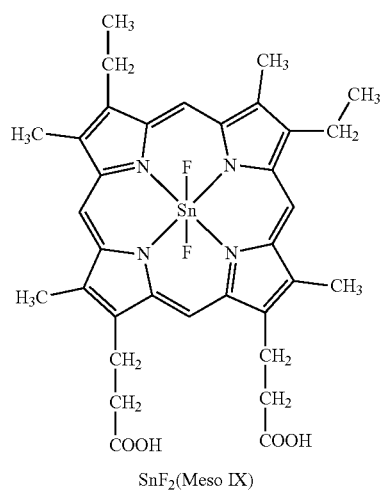

SnF$_2$(Meso IX)

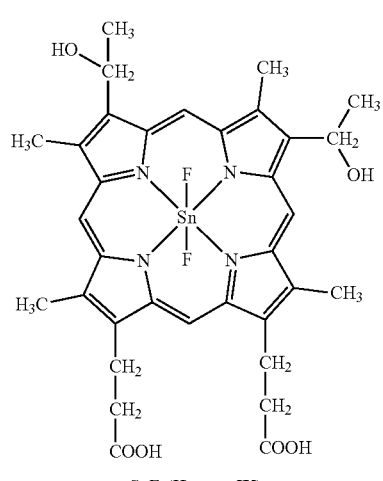

SnF$_2$(Hemato IX)

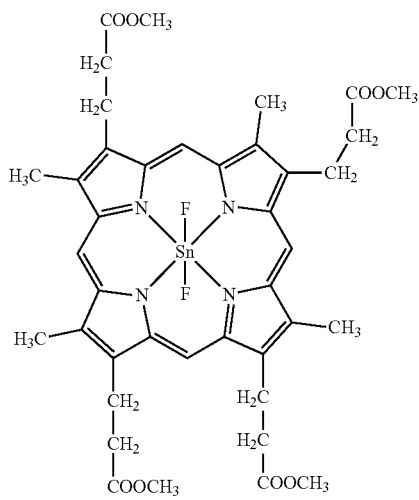

SnF₂(Copro III-4Me)

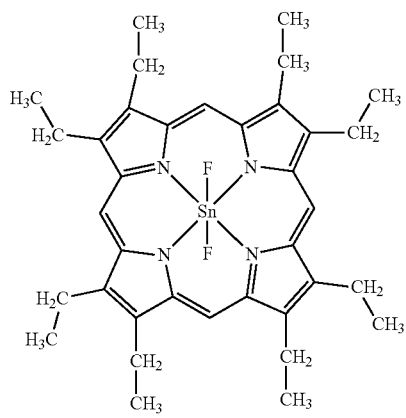

SnF₂(OEP)

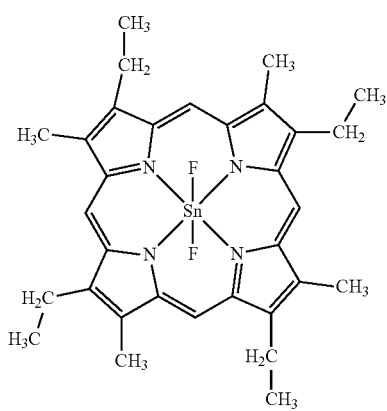

SnF₂(Etio I)

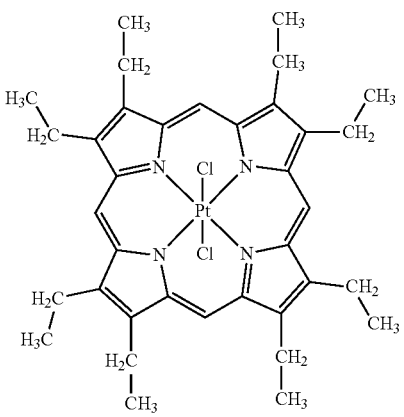

PtCl₂OEP

Alternatively, a heterocyclic compound having both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 9-[4-(4,6-diphenyl-1,3,5-triazin-2-yl)phenyl]-9'-phenyl-9H,9'H-3,3'-bicarbazole (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. The heterocyclic compound is preferable because of having both a high electron-transport property and a high hole-transport property owing to a π-electron rich heteroaromatic ring and a π-electron deficient heteroaromatic ring. Note that a substance in which the π-electron rich heteroaromatic ring and the π-electron deficient heteroaromatic ring are directly bonded to each other is particularly preferable because the donor property of the π-electron rich heteroaromatic ring and the acceptor property of the π-electron deficient heteroaromatic ring are both increased and the energy difference between the S1 level and the T1 level becomes small, so that thermally activated delayed fluorescence can be obtained with high efficiency. Note that an aromatic ring to which an electron-withdrawing group such as a cyano group is bonded may be used instead of the π-electron deficient heteroaromatic ring.

[Chemical formulae 10]
PIC-TRZ
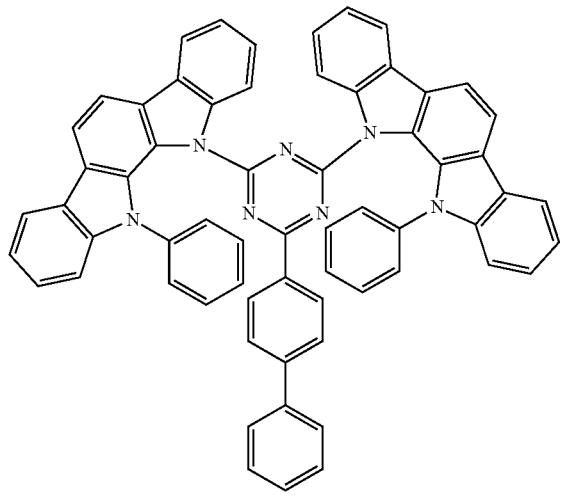
PCCzPTzn
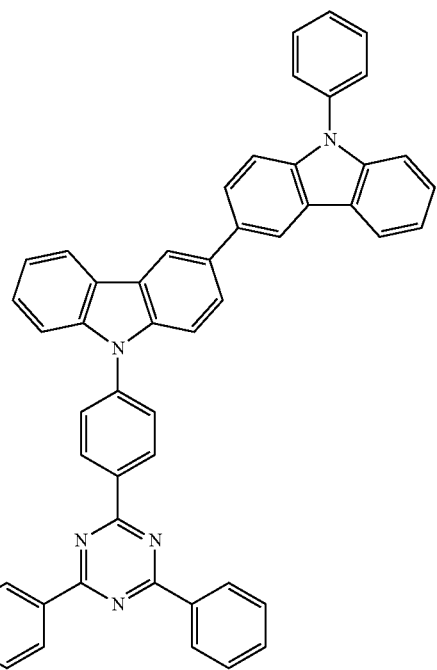
PCCzTzn
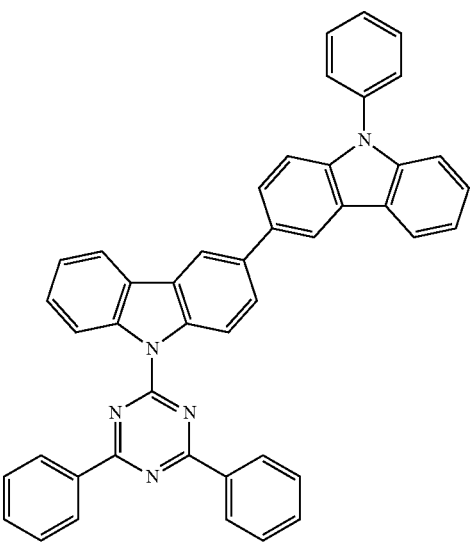
PXZ-TRZ
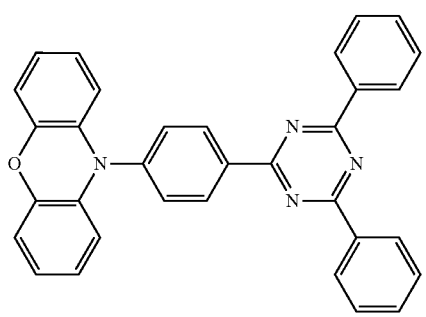
PPZ-3TPT
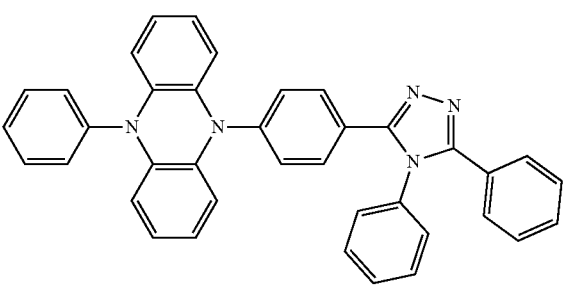
ACRXTN
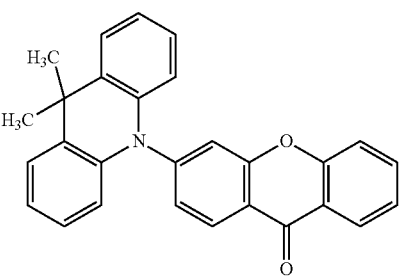

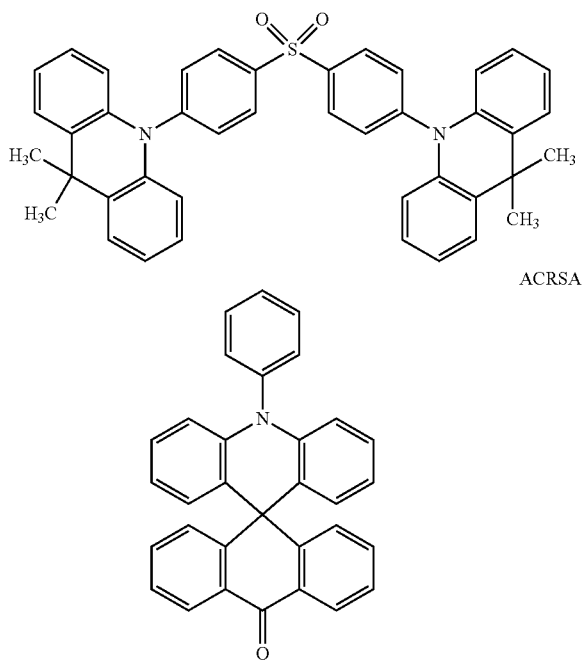

DMAC-DPS

ACRSA

As the host material in the light-emitting layer, a variety of carrier-transport materials such as a material having an electron-transport property and a material having a hole-transport property can be used.

As a material having a hole-transport property, a compound having an aromatic amine skeleton, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)-triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]-spiro-9,9'-bifluoren-2-amine (abbreviation: PCBASF), a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP), a compound having a thiophene skeleton, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV), and a compound having a furan skeleton, such as 4,4',4''-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II) can be given. Among the above, the compound having an aromatic amine skeleton and the compound having a carbazole skeleton are preferable because these have favorable reliability, have high hole-transport properties, and contribute to a reduction in driving voltage.

As the material having an electron-transport property, for example, a metal complex such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ), a heterocyclic compound having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II), a heterocyclic compound having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), or 4,6-bis[3-(4-dibenzothienyl)phenyl]pyrimidine (abbreviation: 4,6mDBTP2Pm-II), and a heterocyclic compound having a pyridine skeleton, such as 3,5-bis[3-(9H-carbazol-9-yl)phenyl]pyridine (abbreviation: 35DCzPPy) or 1,3,5-tri[3-(3-pyridyl)-phenyl]benzene (abbreviation: TmPyPB) can be given. Among the above, the heterocyclic compound having a diazine skeleton and the heterocyclic compound having a pyridine skeleton have favorable reliability and thus are preferable. In particular, the heterocyclic compound having a diazine (pyrimidine or pyrazine) skeleton has a high electron-transport property and contributes to a reduction in driving voltage.

In the case where a fluorescent substance is used as the light-emitting material, a material having an anthracene skeleton is suitable for the host material. The use of a substance having an anthracene skeleton as a host material for a fluorescent substance makes it possible to achieve a light-emitting layer with favorable emission efficiency and durability. As the substance having an anthracene skeleton that is used as the host material, a substance having a diphenylanthracene skeleton, in particular, a substance having a 9,10-diphenylanthracene skeleton, is preferable because of its chemical stability. The host material preferably has a carbazole skeleton because the hole-injection and hole-transport properties are improved; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material having a dibenzocarbazole skeleton is preferable because its HOMO level is shallower than that of carbazole by approximately 0.1 eV so that holes enter the host material easily, the hole-transport property is improved, and the heat resistance is increased. Accordingly, a substance that has both a 9,10-diphenylanthracene skeleton and a carbazole skeleton (or a benzocarbazole skeleton or a dibenzocarbazole skeleton) is further preferable as the host material. Note that in terms of the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)-biphenyl-4'-yl}-anthracene (abbreviation: FLPPA). In particular, CzPA, cgDBCzPA, 2mBnfPPA, and PCzPA are preferably selected because they exhibit favorable characteristics.

Note that a host material may be a material of a mixture of a plurality of kinds of substances; in the case of using a mixed host material, it is preferable to mix a material having an electron-transport property with a material having a hole-transport property. When the material having an electron-transport property is mixed with the material having a hole-transport property, the transport property of the light-emitting layer 113 can be easily adjusted and a recombination region can be easily controlled. The ratio of the content of the material having a hole-transport property to the content of the material having an electron-transport property may be the material having a hole-transport property: the material having an electron-transport property=1:9 to 9:1.

An exciplex may be formed by these mixed materials. A combination is preferably selected so as to form an exciplex that exhibits light emission overlapping with the wavelength of a lowest-energy-side absorption band of a light-emitting material, because energy can be transferred smoothly and light emission can be efficiently obtained. The use of the structure is preferable because the driving voltage is also be reduced.

The electron-transport layer 114 is a layer containing a substance having an electron-transport property. As the substance having an electron-transport property, it is possible to use any of the above-listed substances having electron-transport properties that can be used as the host material.

As the electron-injection layer 115, a layer containing an alkali metal, an alkaline earth metal, or a compound thereof, such as lithium fluoride (LiF), cesium fluoride (CsF), or calcium fluoride (CaF$_2$), may be provided between the electron-transport layer 114 and the second electrode 102. For example, an electride or a layer that is formed using a substance having an electron-transport property and that includes an alkali metal, an alkaline earth metal, or a compound thereof can be used as the electron-injection layer 115. Examples of the electride include a substance in which electrons are added at high concentration to a mixed oxide of calcium and aluminum.

Instead of the electron-injection layer 115, the charge-generation layer 116 may be provided. The charge-generation layer 116 refers to a layer capable of injecting holes into a layer in contact therewith on the cathode side and injecting electrons into a layer in contact therewith on the anode side when supplied with a potential. The charge-generation layer 116 includes at least a P-type layer 117. The P-type layer 117 is preferably formed using the composite materials given above as the material that can form the hole-injection layer 111. The P-type layer 117 may be formed by stacking a film containing the above acceptor material as a material included in the composite material and a film containing the above hole-transport material. When a potential is applied to the P-type layer 117, electrons are injected into the electron-transport layer 114 and holes are injected into the second electrode 102 that is a cathode; thus, the light-emitting device operates.

Note that one or both of an electron-relay layer 118 and an electron-injection buffer layer 119 are preferably provided in the charge-generation layer 116 in addition to the P-type layer 117.

The electron-relay layer 118 contains at least a substance having an electron-transport property and has a function of preventing an interaction between the electron-injection buffer layer 119 and the P-type layer 117 to transfer electrons smoothly. The LUMO level of the substance having an electron-transport property contained in the electron-relay layer 118 is preferably between the LUMO level of an acceptor substance in the P-type layer 117 and the LUMO level of a substance contained in a layer of the electron-transport layer 114 in contact with the charge-generation layer 116. A specific energy level of the LUMO level of the substance having an electron-transport property used for the electron-relay layer 118 may be higher than or equal to −5.0 eV, preferably higher than or equal to −5.0 eV and lower than or equal to −3.0 eV. Note that as the substance having an electron-transport property used for the electron-relay layer 118, a phthalocyanine-based material or a metal complex having a metal-oxygen bond and an aromatic ligand is preferably used.

For the electron-injection buffer layer 119, a substance having a high electron-injection property, such as an alkali metal, an alkaline earth metal, a rare earth metal, or a compound thereof (an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)), can be used.

In the case where the electron-injection buffer layer 119 is formed so as to contain the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound thereof (an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)). Note that as the substance having an electron-transport property, a material similar to the above-described material forming the electron-transport layer 114 can be used for the formation.

As a substance forming the second electrode 102, a metal, an alloy, an electrically conductive compound, or a mixture thereof having a low work function (specifically, 3.8 eV or less) or the like can be used. As specific examples of such a cathode material, elements belonging to Group 1 or Group 2 of the periodic table, such as alkali metals, e.g., lithium (Li) and cesium (Cs)), magnesium (Mg), calcium (Ca), and strontium (Sr), alloys containing these (MgAg and AlLi), rare earth metals such as europium (Eu) and ytterbium (Yb), alloys containing these rare earth metals, and the like can be given. However, when the electron-injection layer is provided between the second electrode 102 and the electron-transport layer, as the second electrode 102, a variety of conductive materials such as Al, Ag, ITO, or indium oxide-tin oxide containing silicon or silicon oxide can be used regardless of their work functions. Films of these conductive materials can be formed by a dry process such as a vacuum evaporation method or a sputtering method, an inkjet method, a spin coating method, or the like. Alternatively, the films may be formed by a wet process using a sol-gel method or a wet process using a paste of a metal material.

Various methods can be used as a method for forming the EL layer 103 regardless of whether it is a dry process or a wet process. For example, a vacuum evaporation method, a gravure printing method, an offset printing method, a screen printing method, an ink-jet method, a spin coating method, or the like may be used.

Different deposition methods may be used to form the electrodes or the layers described above.

The structure of the layers provided between the first electrode 101 and the second electrode 102 is not limited to the above-described structure. However, a structure is preferable in which a light-emitting region where holes and electrons recombine is provided at a position away from the first electrode 101 and the second electrode 102 so as to prevent quenching caused by the proximity of the light-emitting region and a metal used for electrodes and carrier-injection layers.

Furthermore, in order to inhibit energy transfer from an exciton generated in the light-emitting layer, it is preferable to form the hole-transport layer and the electron-transport layer that are in contact with the light-emitting layer 113, particularly a carrier-transport layer closer to the recombination region in the light-emitting layer 113, using the light-emitting material of the light-emitting layer or a substance having a wider band gap than the light-emitting material included in the light-emitting layer.

Next, an embodiment of a light-emitting device with a structure where a plurality of light-emitting units is stacked (also referred to as a stacked-type device or a tandem device) will be described with reference to FIG. 1(C). This light-emitting device is a light-emitting device including a plurality of light-emitting units between an anode and a cathode. One light-emitting unit has substantially the same structure as that of the EL layer 103, which is illustrated in FIG. 1(A). In other words, the light-emitting device illustrated in FIG. 1(C) can be called a light-emitting device including a plurality of light-emitting units, and the light-emitting device illustrated in FIG. 1(A) or FIG. 1(B) can be called a light-emitting device including one light-emitting unit.

Figure 1C:
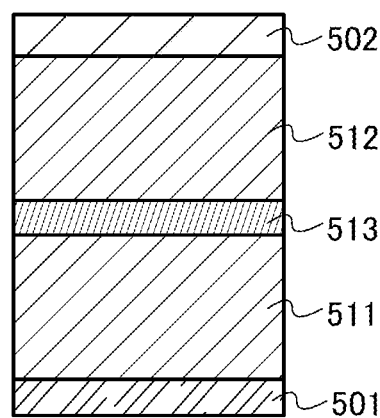

In FIG. 1(C), a first light-emitting unit 511 and a second light-emitting unit 512 are stacked between an anode 501 and a cathode 502, and a charge-generation layer 513 is provided between the first light-emitting unit 511 and the second light-emitting unit 512. The anode 501 and the cathode 502 correspond, respectively, to the first electrode 101 and the second electrode 102 in FIG. 1(A), and the same substance as what is given in the description for FIG. 1(A) can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied to the anode 501 and the cathode 502. That is, in FIG. 1(C), any layer can be used as the charge-generation layer 513 as long as the layer injects electrons into the first light-emitting unit 511 and injects holes into the second light-emitting unit 512 in the case where a voltage is applied such that the potential of the anode is higher than that of the cathode.

The charge-generation layer 513 is preferably formed with a structure similar to that of the charge-generation layer 116 described with reference to FIG. 1(B). A composite material of an organic compound and a metal oxide has an excellent carrier-injection property and an excellent carrier-transport property; thus, low-voltage driving and low-current driving can be achieved. Note that in the case where the anode-side surface of a light-emitting unit is in contact with the charge-generation layer 513, the charge-generation layer 513 can also serve as a hole-injection layer of the light-emitting unit; therefore, a hole-injection layer is not necessarily provided in the light-emitting unit.

In the case where the electron-injection buffer layer 119 is provided in the charge-generation layer 513, the electron-injection buffer layer 119 serves as an electron-injection layer in the light-emitting unit on the anode side; therefore, an electron-injection layer is not necessarily formed in the light-emitting unit on the anode side.

The light-emitting device having two light-emitting units is described with reference to FIG. 1(C); however, the same can also be applied to a light-emitting device in which three or more light-emitting units are stacked. With a plurality of light-emitting units partitioned by the charge-generation layer 513 between a pair of electrodes as in the light-emitting element according to this embodiment, it is possible to achieve an element that can emit light with the current density kept low and has a longer lifetime. Moreover, a light-emitting device that can be driven at a low voltage and has low power consumption can be achieved.

Furthermore, when emission colors of the light-emitting units are different, light emission of a desired color can be obtained from the light-emitting device as a whole. For example, in a light-emitting device having two light-emitting units, emission colors of red and green are obtained in the first light-emitting unit and an emission color of blue is obtained in the second light-emitting unit, whereby a light-emitting device that emits white light as the whole light-emitting device can be obtained.

The above-described layers and electrodes such as the EL layer 103, the first light-emitting unit 511, the second light-emitting unit 512, and the charge-generation layer can be formed by a method such as an evaporation method (including a vacuum evaporation method), a droplet discharge method (also referred to as an ink-jet method), a coating method, or a gravure printing method. Those may include a low molecular material, a middle molecular material (including an oligomer and a dendrimer), or a high molecular material.

Embodiment 3

In this embodiment, a light-emitting apparatus using the light-emitting device described in Embodiment 1 and Embodiment 2 will be described.

In this embodiment, a light-emitting apparatus fabricated using the light-emitting device described in Embodiment 1 and Embodiment 2 will be described with reference to FIG. 2. Note that FIG. 2(A) is a top view illustrating the light-emitting apparatus, and FIG. 2(B) is a cross-sectional view taken along A-B and C-D in FIG. 2(A). This light-emitting apparatus includes a driver circuit portion (source line driver circuit) 601, a pixel portion 602, and a driver circuit portion (gate line driver circuit) 603, which are for controlling light emission of a light-emitting device and are illustrated with dotted lines. Furthermore, 604 denotes a sealing substrate, 605 denotes a sealant, and the inside surrounded by the sealant 605 is a space 607.

Note that a lead wiring 608 is a wiring for transmitting signals to be input to the source line driver circuit 601 and the gate line driver circuit 603 and receiving a video signal, a clock signal, a start signal, a reset signal, and the like from an FPC (flexible printed circuit) 609 serving as an external input terminal. Although only the FPC is illustrated here, a printed wiring board (PWB) may be attached to this FPC. The light-emitting apparatus in this specification includes not only the light-emitting apparatus itself but also the apparatus provided with the FPC or the PWB.

Next, a cross-sectional structure will be described with reference to FIG. 2(B). The driver circuit portion and the pixel portion are formed over an element substrate 610. Here, the source line driver circuit 601, which is the driver circuit portion, and one pixel of the pixel portion 602 are illustrated.

The element substrate 610 may be fabricated using a substrate containing glass, quartz, an organic resin, a metal, an alloy, a semiconductor, or the like, or a plastic substrate formed of FRP (Fiber Reinforced Plastic), PVF (polyvinyl fluoride), polyester, acrylic, or the like.

The structure of transistors used in pixels and driver circuits is not particularly limited. For example, an inverted staggered transistor or a staggered transistor may be used. Furthermore, top-gate transistors or bottom-gate transistors may be used. A semiconductor material used for the transistors is not particularly limited, and for example, silicon, germanium, silicon carbide, gallium nitride, or the like can be used. Alternatively, an oxide semiconductor containing at least one of indium, gallium, and zinc, such as In—Ga—Zn-based metal oxide, may be used.

There is no particular limitation on the crystallinity of a semiconductor material used for the transistors, and any of an amorphous semiconductor or a semiconductor having crystallinity (a microcrystalline semiconductor, a polycrystalline semiconductor, a single-crystal semiconductor, and a semiconductor partly including crystal regions) may be used. A semiconductor having crystallinity is preferably used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. The use of an oxide semiconductor material having a wider band gap than silicon can reduce the off-state current of the transistors.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such a material as the semiconductor layer makes it possible to achieve a highly reliable transistor in which a change in the electrical characteristics is reduced.

Charge accumulated in a capacitor through a transistor including the above-described semiconductor layer can be retained for a long time because of the low off-state current of the transistor. The use of such a transistor in pixels allows a driver circuit to stop while the gray level of an image displayed on each display region is maintained. As a result, an electronic device with significantly reduced power consumption can be achieved.

For stable characteristics of the transistor or the like, a base film is preferably provided. The base film can be formed to be a single-layer or a stacked-layer using an inorganic insulating film such as a silicon oxide film, a silicon nitride film, a silicon oxynitride film, or a silicon nitride oxide film. The base film can be formed by a sputtering method, a CVD (Chemical Vapor Deposition) method (e.g., a plasma CVD method, a thermal CVD method, or an MOCVD (Metal Organic CVD) method), an ALD (Atomic Layer Deposition) method, a coating method, a printing method, or the like. Note that the base film is not necessarily provided when not needed.

Note that an FET 623 is illustrated as a transistor formed in the driver circuit portion 601. The driver circuit can be formed using various circuits such as a CMOS circuit, a PMOS circuit, and an NMOS circuit. Although a driver-integrated type in which the driver circuit is formed over the substrate is described in this embodiment, the driver circuit is not necessarily formed over the substrate and can be formed outside.

The pixel portion 602 is formed with a plurality of pixels including a switching FET 611, a current control FET 612, and a first electrode 613 electrically connected to a drain of the current control FET 612; however, without being limited thereto, a pixel portion in which three or more FETs and a capacitor are combined may be employed.

Note that an insulator 614 is formed to cover an end portion of the first electrode 613. The insulator 614 can be formed using a positive photosensitive acrylic resin film here.

In order to improve the coverage with an EL layer or the like to be formed later, the insulator 614 is formed so as to have a curved surface with curvature at its upper end portion or lower end portion. For example, in the case where positive photosensitive acrylic is used as a material for the insulator 614, only the upper end portion of the insulator 614 preferably has a curved surface with a curvature radius (0.2 μm to 3 μm). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material with a high work function is desirably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stacked layer of titanium nitride film and a film containing aluminum as its main component, a three-layer structure of a titanium nitride film, a film containing aluminum as its main component, and a titanium nitride film, or the like can be used. Note that the stacked-layer structure achieves low wiring resistance, a favorable ohmic contact, and a function as an anode.

The EL layer 616 is formed by any of a variety of methods such as an evaporation method using an evaporation mask, an inkjet method, and a spin coating method. The EL layer 616 has the structure described in Embodiment 1 and Embodiment 2. Alternatively, a material included in the EL layer 616 may be a low molecular compound or a high molecular compound (including an oligomer or a dendrimer).

As a material used for the second electrode 617, which is formed over the EL layer 616 and functions as a cathode, a material with a low work function (e.g., Al, Mg, Li, Ca, or an alloy or a compound thereof (e.g., MgAg, MgIn, or AlLi)) is preferably used. Note that in the case where light generated in the EL layer 616 passes through the second electrode 617, it is preferable to use, for the second electrode 617, a stacked layer of a thin metal film and a transparent conductive film (e.g., ITO, indium oxide containing zinc oxide at 2 wt % to 20 wt %, indium tin oxide containing silicon, or zinc oxide (ZnO)).

Note that a light-emitting device is formed with the first electrode 613, the EL layer 616, and the second electrode 617. The light-emitting device is the light-emitting device described in Embodiment 1 and Embodiment 2. A plurality of light-emitting devices are formed in the pixel portion, and the light-emitting apparatus of this embodiment may include both the light-emitting device described in Embodiment 1 and Embodiment 2 and a light-emitting device having a different structure.

The sealing substrate 604 and the element substrate 610 are attached to each other using the sealant 605, so that a structure is employed in which a light-emitting device 618 is provided in the space 607 surrounded by the element substrate 610, the sealing substrate 604, and the sealant 605. The space 607 is filled with a filler; it is filled with an inert gas (e.g., nitrogen or argon) in some cases, and filled with the sealant in some cases. The structure of the sealing substrate in which a recessed portion is formed and a desiccant is provided is preferable because deterioration due to the influence of moisture can be inhibited.

Note that an epoxy-based resin or glass frit is preferably used for the sealant 605. Furthermore, these materials are preferably materials that transmit moisture or oxygen as little as possible. As the material used for the sealing substrate 604, in addition to a glass substrate and a quartz substrate, a plastic substrate formed of FRP (Fiber Reinforced Plastics), PVF (polyvinyl fluoride), polyester, acrylic, or the like can be used.

Although not illustrated in FIG. 2, a protective film may be provided over the second electrode. The protective film may be formed using an organic resin film or an inorganic insulating film. The protective film may be formed so as to cover an exposed portion of the sealant 605. The protective film may be provided so as to cover surfaces and side surfaces of the pair of substrates and exposed side surfaces of a sealing layer, an insulating layer, and the like.

For the protective film, a material that is less likely transmit an impurity such as water. Thus, diffusion of an impurity such as water from the outside into the inside can be effectively inhibited.

As a material included in the protective film, an oxide, a nitride, a fluoride, a sulfide, a ternary compound, a metal, a polymer, or the like can be used; for example, it is possible to use a material containing aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide; a material containing aluminum nitride, hafnium nitride, silicon nitride, tantalum nitride, titanium nitride, niobium nitride, molybdenum nitride, zirconium nitride, gallium nitride; a material containing a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method that enables favorable step coverage. One such method is an atomic layer deposition (ALD) method. A material that can be formed by an ALD method is preferably used for the protective film. With the use of an ALD method, a dense protective film with reduced defects such as cracks and pinholes or with a uniform thickness can be formed. Furthermore, damage caused to a process member in forming the protective film can be reduced.

By an ALD method, a uniform protective film with few defects can be formed even on a surface with a complex uneven shape or upper, side, and lower surfaces of a touch panel.

As described above, the light-emitting apparatus fabricated using the light-emitting device described in Embodiment 1 and Embodiment 2 can be obtained.

For the light-emitting apparatus in this embodiment, the light-emitting device described in Embodiment 1 and Embodiment 2 is used and thus a light-emitting apparatus having favorable characteristics can be obtained. Specifically, since the light-emitting device described in Embodiment 1 and Embodiment 2 is a light-emitting device having a long lifetime, the light-emitting apparatus can have high reliability. Since the light-emitting apparatus using the light-emitting device described in Embodiment 1 and Embodiment 2 has high emission efficiency, the light-emitting apparatus with a low power consumption can be obtained.

FIG. 3 illustrates examples of a light-emitting apparatus in which full color display is achieved by formation of a light-emitting device exhibiting white light emission and provision of coloring layers (color filters) and the like. FIG. 3(A) illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of the light-emitting devices, a partition 1025, an EL layer 1028, a second electrode 1029 of the light-emitting devices, a sealing substrate 1031, a sealant 1032, and the like.

In FIG. 3(A), coloring layers (a red coloring layer 1034R, a green coloring layer 1034G, and a blue coloring layer 1034B) are provided on a transparent base material 1033. A black layer (black matrix) 1035 may be additionally provided. The transparent base material 1033 provided with the coloring layers and the black matrix is positioned and fixed to the substrate 1001. Note that the coloring layers and the black matrix 1035 are covered with an overcoat layer 1036. In FIG. 3(A), a light-emitting layer from which light is emitted to the outside without passing through the coloring layer and light-emitting layers from which light is emitted to the outside, passing through the coloring layers of the respective colors are shown. Since light that does not pass through the coloring layer is white and light that passes through the coloring layer is red, green, or blue, an image can be expressed by pixels of the four colors.

FIG. 3(B) illustrates an example in which the coloring layers (the red coloring layer 1034R, the green coloring layer 1034G, and the blue coloring layer 1034B) are formed between the gate insulating film 1003 and the first interlayer insulating film 1020. The coloring layers may be provided between the substrate 1001 and the sealing substrate 1031 in this manner.

Figure 4:
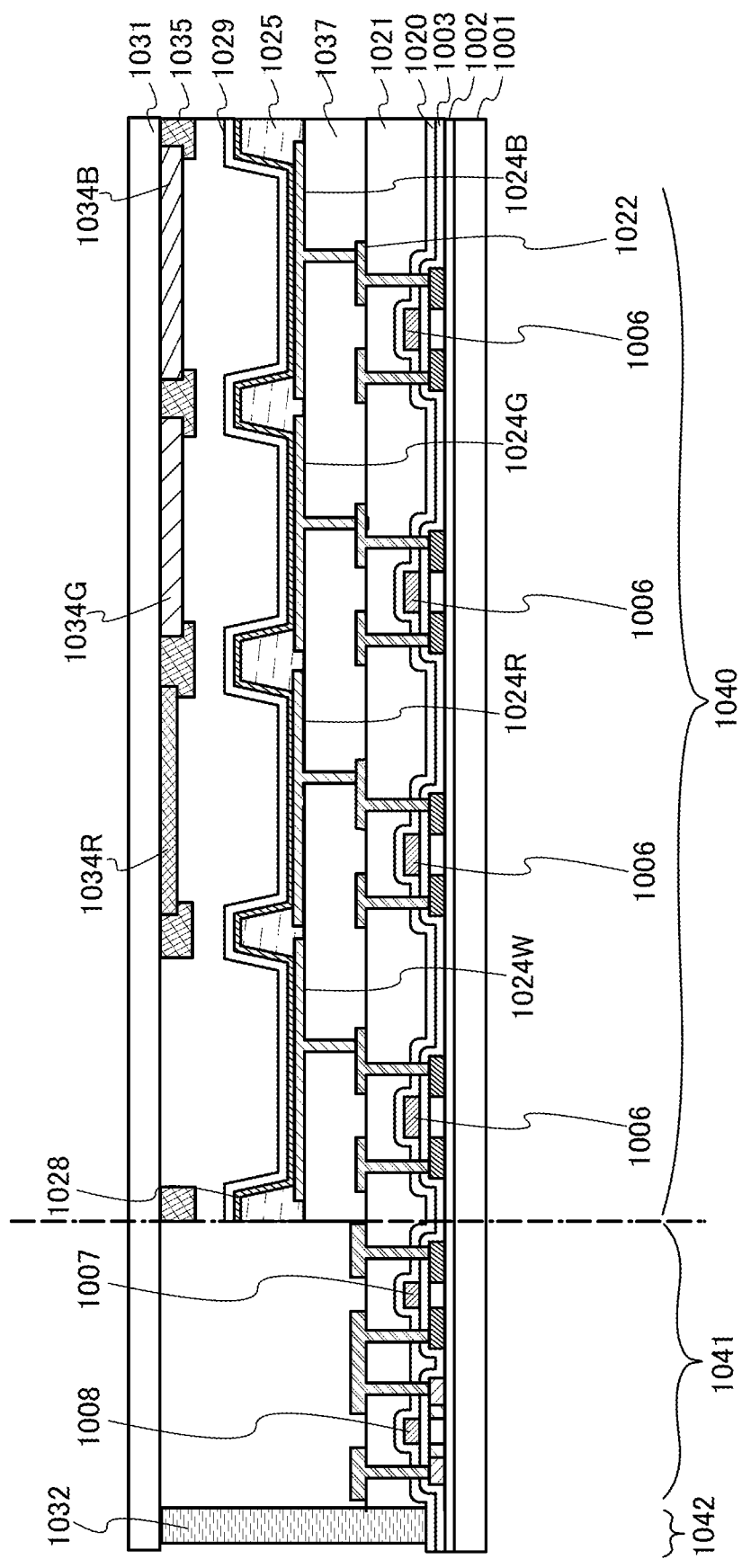
FIG. 4 is a schematic diagram of an active matrix light-emitting apparatus.

The above-described light-emitting apparatus is a light-emitting apparatus having a structure in which light is extracted to the substrate 1001 side where the FETs are formed (a bottom-mission type), but may be a light-emitting apparatus having a structure in which light emission is extracted to the sealing substrate 1031 side (a top-emission type). FIG. 4 illustrates a cross-sectional view of a top-emission light-emitting apparatus. In this case, a substrate that does not transmit light can be used as the substrate 1001. The top-emission light-emitting apparatus is formed in a manner similar to that of the bottom-emission light-emitting apparatus until a connection electrode which connects the FET and the anode of the light-emitting device is formed. Then, a third interlayer insulating film 1037 is formed to cover an electrode 1022. This insulating film may have a planarization function. The third interlayer insulating film 1037 can be formed using a material similar to that for the second interlayer insulating film or using any other known materials.

The first electrodes 1024W, 1024R, 1024G, and 1024B of the light-emitting elements are each an anode here, but may each be a cathode. Furthermore, in the case of the top-emission light-emitting apparatus illustrated in FIG. 4, the first electrodes are preferably reflective electrodes. The structure of the EL layer 1028 is such a structure as described as that of the EL layer 103 in Embodiment 1 and Embodiment 2, and an element structure with which white light emission can be obtained.

In the case of such a top-emission structure as in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix 1035 may be covered with the overcoat layer 1036. Note that a light-transmitting substrate is used as the sealing substrate 1031. Although an example in which full color display is performed using four colors of red, green, blue, and white is shown here, there is no particular limitation and full color display may be performed using four colors of red, yellow, green, and blue or three colors of red, green, and blue.

In the top-emission-type light-emitting apparatus, a microcavity structure can be favorably employed. A light-emitting device with a microcavity structure can be obtained with the use of a reflective electrode as the first electrode and a semi-transmissive and semi-reflective electrode as the second electrode. The light-emitting device with a microcavity structure includes at least an EL layer between the reflective electrode and the semi-transmissive and semi-reflective electrode, which includes at least a light-emitting layer serving as a light-emitting region.

Note that the reflective electrode is a film having a visible light reflectivity of 40% to 100%, preferably 70% to 100%, and a resistivity of $1 \times 10^{-2}$ Ωcm or lower. In addition, the semi-transmissive and semi-reflective electrode is a film having a visible light reflectivity of 20% to 80%, preferably 40% to 70%, and a resistivity of $1 \times 10^{-2}$ Ωcm or lower.

Light emitted from the light-emitting layer included in the EL layer is reflected and resonated by the reflective electrode and the semi-transmissive and semi-reflective electrode.

In the light-emitting device, by changing thicknesses of the transparent conductive film, the above-described composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light); therefore, the optical path length between the reflective electrode and the light-emitting layer is preferably adjusted to $(2n-1)\lambda/4$ (n is a natural number of 1 or larger and $\lambda$ is a wavelength of light emission to be amplified). By adjusting the optical path length, the phases of the first reflected light and the first incident light can be aligned with each other and the light emitted from the light-emitting layer can be further amplified.

Note that in the above structure, the EL layer may have a structure including a plurality of light-emitting layers or may have a structure including a single light-emitting layer. The tandem light-emitting device described above may be combined with a plurality of EL layers; for example, a light-emitting device may have a structure in which a plurality of EL layers are provided, a charge-generation layer is provided between the EL layers, and each EL layer includes a plurality of light-emitting layers or a single light-emitting layer.

With the microcavity structure, emission intensity with a specific wavelength in the front direction can be increased, whereby power consumption can be reduced. Note that in the case of a light-emitting apparatus which displays images with subpixels of four colors, red, yellow, green, and blue, the light-emitting apparatus can have favorable characteristics because a microcavity structure suitable for wavelengths of the corresponding color is employed in each subpixel, in addition to the effect of an improvement in luminance awing to yellow light emission.

For the light-emitting apparatus in this embodiment, the light-emitting device described in Embodiment 1 and Embodiment 2 is used and thus a light-emitting apparatus having favorable characteristics can be obtained. Specifically, since the light-emitting device described in Embodiment 1 and Embodiment 2 is a light-emitting device having a long lifetime, the light-emitting apparatus can have high reliability. Since the light-emitting apparatus using the light-emitting device described in Embodiment 1 and Embodiment 2 has high emission efficiency, the light-emitting apparatus with a low power consumption can be obtained.

Figure 5A:
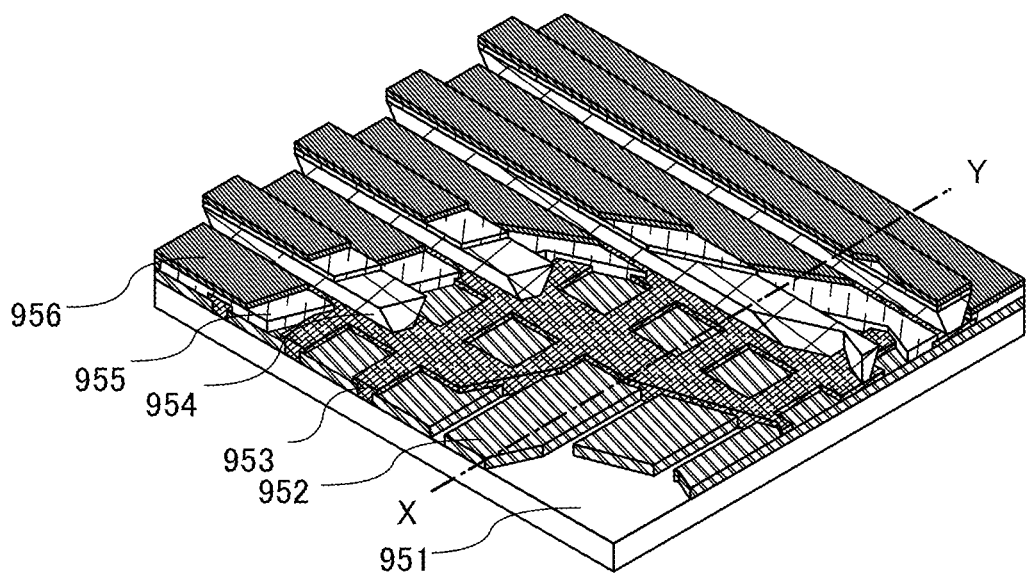
FIGS. 5A and 5B are conceptual diagrams of a passive matrix light-emitting apparatus.
Figure 5B:
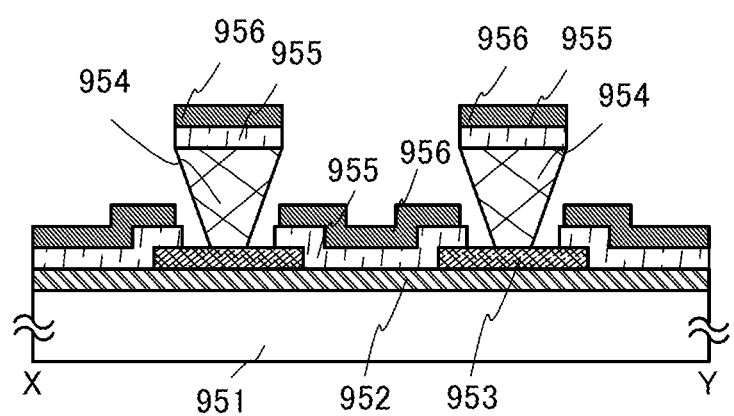

The active matrix light-emitting apparatus is described above, whereas a passive matrix light-emitting apparatus is described below. FIG. 5 illustrates a passive matrix light-emitting apparatus fabricated using the present invention. Note that FIG. 5(A) is a perspective view illustrating the light-emitting apparatus, and FIG. 5(B) is a cross-sectional view taken along X-Y in FIG. 5(A). In FIG. 5, over a substrate 951, an EL layer 955 is provided between an electrode 952 and an electrode 956. An end portion of the electrode 952 is covered with an insulating layer 953. A partition layer 954 is provided over the insulating layer 953. Sidewalls of the partition layer 954 are aslope such that the distance between one sidewall and the other sidewall is gradually narrowed toward the surface of the substrate. That is, a cross section in the short side direction of the partition layer 954 is a trapezoidal shape, and the lower side (the side facing the same direction as the plane direction of the insulating layer 953 and touching the insulating layer 953) is shorter than the upper side (the side facing the same direction as the plane direction of the insulating layer 953, and not touching the insulating layer 953). By providing the partition layer 954 in this manner, defects of the light-emitting element due to static charge or the like can be prevented. The passive-matrix light-emitting apparatus also uses the light-emitting device described in Embodiment 1 and Embodiment 2; thus, the light-emitting apparatus can have favorable reliability or low power consumption.

Since many minute light-emitting devices arranged in a matrix can each be controlled in the light-emitting apparatus described above, the light-emitting apparatus can be suitably used as a display device for displaying images.

This embodiment can be freely combined with any of the other embodiments.

Embodiment 4

Figure 6A:
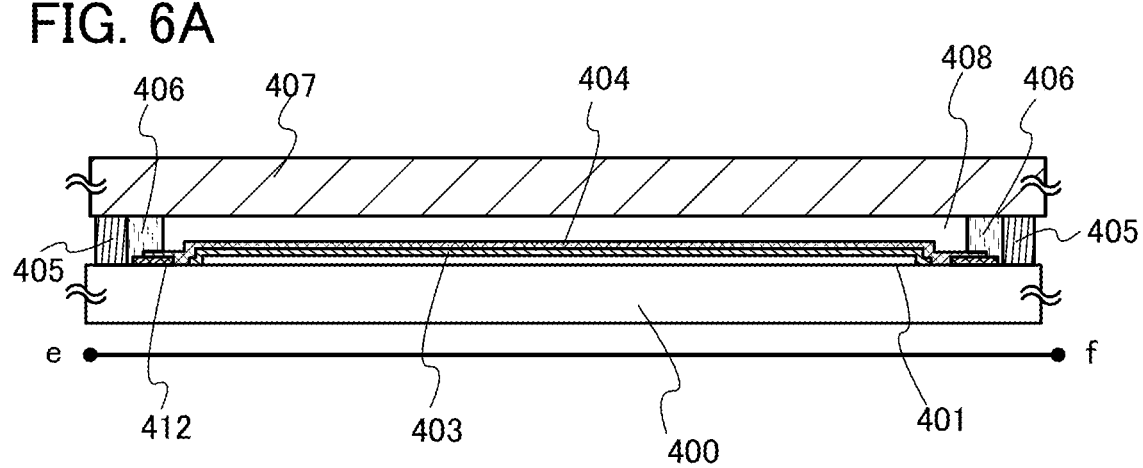
FIGS. 6A and 6B are diagrams illustrating a lighting device.
Figure 6B:
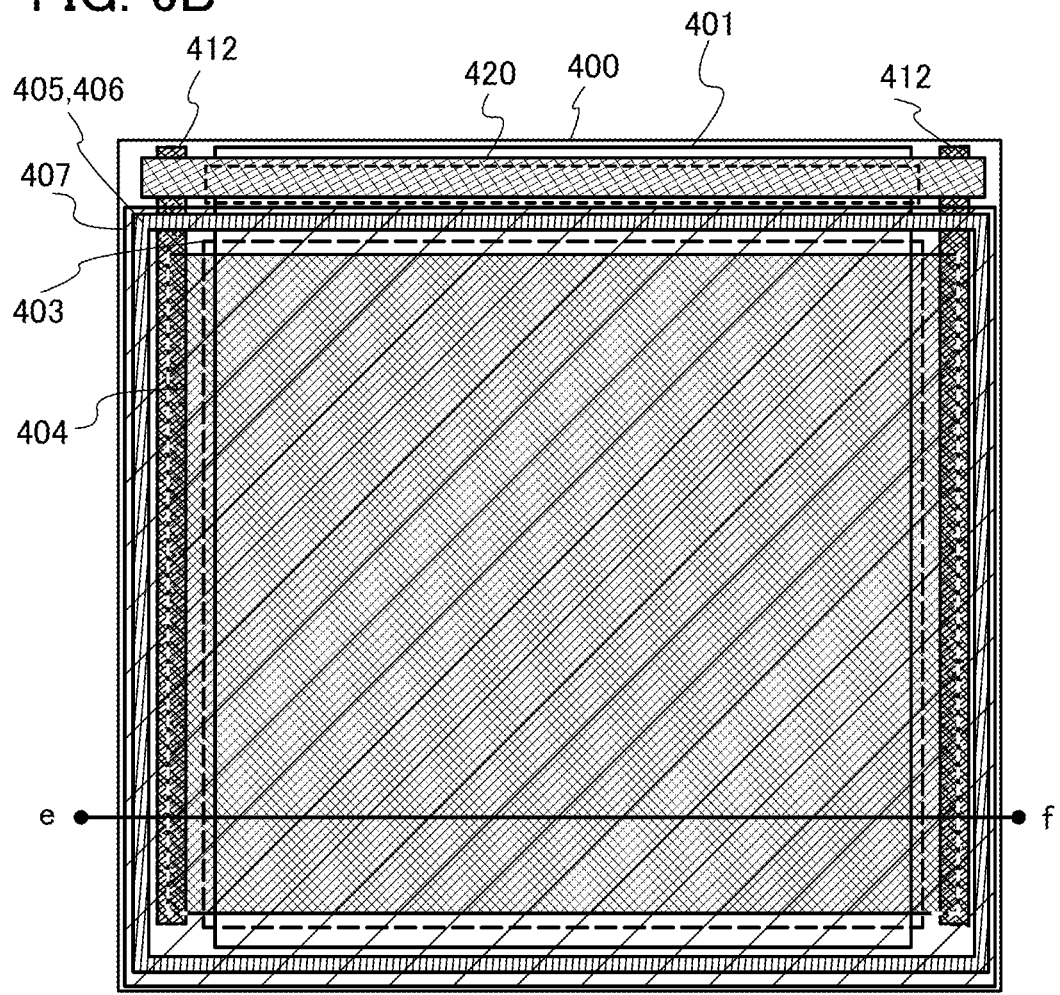

In this embodiment, an example in which the light-emitting device described in Embodiment 1 and Embodiment 2 is used for a lighting device will be described with reference to FIG. 6. FIG. 6(B) is a top view of the lighting device, and FIG. 6(A) is a cross-sectional view taken along e-f in FIG. 6(B).

In the lighting device in this embodiment, a first electrode 401 is formed over a substrate 400 which is a support and has a light-transmitting property. The first electrode 401 corresponds to the first electrode 101 in Embodiment 2. In the case where light emission is extracted from the first electrode 401 side, the first electrode 401 is formed with a material having a light-transmitting property.

A pad 412 for supplying a voltage to a second electrode 404 is formed over the substrate 400.

An EL layer 403 is formed over the first electrode 401. The EL layer 403 has a structure corresponding to that of the EL layer 103 in Embodiment 1 and Embodiment 2, or the structure in which the light-emitting units 511 and 512 are combined with the charge-generation layer 513. Note that for these structures, the corresponding description can be referred to.

The second electrode 404 is formed to cover the EL layer 403. The second electrode 404 corresponds to the second electrode 102 in Embodiment 2. In the case where light-emission is extracted from the first electrode 401 side, the second electrode 404 is formed with a material having high reflectivity. The second electrode 404 is supplied with a voltage when connected to the pad 412.

As described above, the lighting device described in this embodiment includes a light-emitting device including the first electrode 401, the EL layer 403, and the second electrode 404. Since the light-emitting device is a light-emitting device with high emission efficiency, the lighting device in this embodiment can be a lighting device with low power consumption.

The substrate 400 over which the light-emitting device having the above structure is formed is fixed to a sealing substrate 407 with sealants 405 and 406 and sealing is performed, whereby the lighting device is completed. It is possible to use only either the sealant 405 or 406. In addition, the inner sealant 406 (not illustrated in FIG. 6(B)) can be mixed with a desiccant, which enables moisture to be adsorbed, resulting in improved reliability.

When parts of the pad 412 and the first electrode 401 are provided to extend to the outside of the sealants 405 and 406, those can serve as external input terminals. An IC chip 420 mounted with a converter or the like may be provided over the external input terminals.

The lighting device described in this embodiment uses the light-emitting device described in Embodiment 1 and Embodiment 2 as an EL device; thus, the light-emitting apparatus can have favorable reliability. Furthermore, the light-emitting apparatus can have low power consumption.

Embodiment 5

In this embodiment, examples of electronic devices each partly including the light-emitting device described in Embodiment 1 and Embodiment 2 are described. The light-emitting device described in Embodiment 1 and Embodiment 2 is a light-emitting device having a favorable lifetime and favorable reliability. As a result, the electronic devices described in this embodiment can be electronic devices each including a light-emitting portion with favorable reliability.

Examples of electronic devices to which the light-emitting device is applied include a television devices (also referred to as TV or television receivers), monitors for computers and the like, cameras such as digital cameras and digital video cameras, digital photo frames, mobile phones (also referred to as portable telephones or portable telephone devices), portable game machines, portable information terminals, audio playback devices, and large game machines such as pin-ball machines. Specific examples of these electronic devices are shown below.

FIG. 7(A) illustrates an example of a television device. In the television device, a display portion 7103 is incorporated in a housing 7101. Here, a structure in which the housing 7101 is supported by a stand 7105 is shown. Images can be displayed on the display portion 7103, and the light-emitting devices described in Embodiment 1 and Embodiment 2 are arranged in a matrix in the display portion 7103.

The television device can be operated with an operation switch of the housing 7101 or a separate remote controller 7110. With operation keys 7109 of the remote controller 7110, channels and volume can be operated and images displayed on the display portion 7103 can be operated. Furthermore, a structure may be employed in which the remote controller 7110 is provided with a display portion 7107 for displaying data output from the remote controller 7110.

Note that the television device has a structure of including a receiver, a modem, and the like. With the use of the receiver, a general television broadcast can be received, and moreover, when the television device is connected to a communication network with or without a wire via the modem, one-way (from a sender to a receiver) or two-way (between a sender and a receiver or between receivers) data communication can be performed.

FIG. 7(B1) is a computer which includes a main body 7201, a housing 7202, a display portion 7203, a keyboard 7204, an external connection port 7205, a pointing device 7206, and the like. Note that this computer is fabricated using the light-emitting devices described in Embodiment 1 and Embodiment 2 arranged in a matrix in the display portion 7203. The computer in FIG. 7(B1) may be such a mode as illustrated in FIG. 7(B2). The computer in FIG. 7(B2) is provided with a second display portion 7210 instead of the keyboard 7204 and the pointing device 7206. The second display portion 7210 is of a touch-panel type, and input can be performed by operating display for input displayed on the second display portion 7210 with a finger or a dedicated pen. The second display portion 7210 can also display images other than the display for input. The display portion 7203 may also be a touch panel. Connecting the two screens with a hinge can prevent troubles such as a crack in or damage to the screens caused when the computer is stored or carried.

FIG. 7(C) illustrates an example of a portable terminal. A mobile phone includes operation buttons 7403, an external connection port 7404, a speaker 7405, a microphone 7406, and the like in addition to a display portion 7402 incorporated in a housing 7401. Note that a mobile phone 7400 includes the display portion 7402 which is fabricated by arranging the light-emitting devices described in Embodiment 1 and Embodiment 2 in a matrix.

The portable terminal illustrated in FIG. 7(C) may have a structure in which information can be input by touching the display portion 7402 with a finger or the like. In this case, operations such as making a call and creating an e-mail can be performed by touching the display portion 7402 with a finger or the like.

The display portion 7402 has mainly three screen modes. The first one is a display mode mainly for displaying images, and the second one is an input mode mainly for inputting data such as text. The third one is a display+input mode in which two modes of the display mode and the input mode are combined.

For example, in the case of making a call or creating an e-mail, a text input mode mainly for inputting text is selected for the display portion 7402 so that an operation of inputting text displayed on the screen may be performed. In this case, it is preferable to display a keyboard or number buttons on almost the entire screen of the display portion 7402.

When a sensing device including a sensor for sensing inclination, such as a gyroscope sensor or an acceleration sensor, is provided inside the portable terminal, screen display of the display portion 7402 can be automatically changed by determining the orientation of the portable terminal (vertically or horizontally).

The screen modes are changed by touching the display portion 7402 or operating the operation buttons 7403 of the housing 7401. Alternatively, the screen modes can be changed depending on the kind of image displayed on the display portion 7402. For example, when a signal of an image displayed on the display portion is moving image data, the screen mode is changed to the display mode, and when the signal is text data, the screen mode is changed to the input mode.

Moreover, in the input mode, when input by the touch operation of the display portion 7402 is not performed for a certain period while a signal sensed by an optical sensor in the display portion 7402 is sensed, the screen mode may be controlled so as to be changed from the input mode to the display mode.

The display portion 7402 can also function as an image sensor. For example, an image of a palm print, a fingerprint, or the like is taken when the display portion 7402 is touched with the palm or the finger, whereby personal authentication can be performed. Furthermore, by using a backlight which emits near-infrared light or a sensing light source which emits near-infrared light in the display portion, an image of a finger vein, a palm vein, or the like can be taken.

Note that the structures described in this embodiment can be combined with the structures described in any of Embodiment 1 to Embodiment 4 as appropriate.

As described above, the application range of the light-emitting apparatus including the light-emitting device described in Embodiment 1 and Embodiment 2 is wide so that this light-emitting apparatus can be applied to electronic devices in a variety of fields. With the use of the light-emitting device described in Embodiment 1 and Embodiment 2, an electronic device with high reliability can be obtained.

Figure 8A:
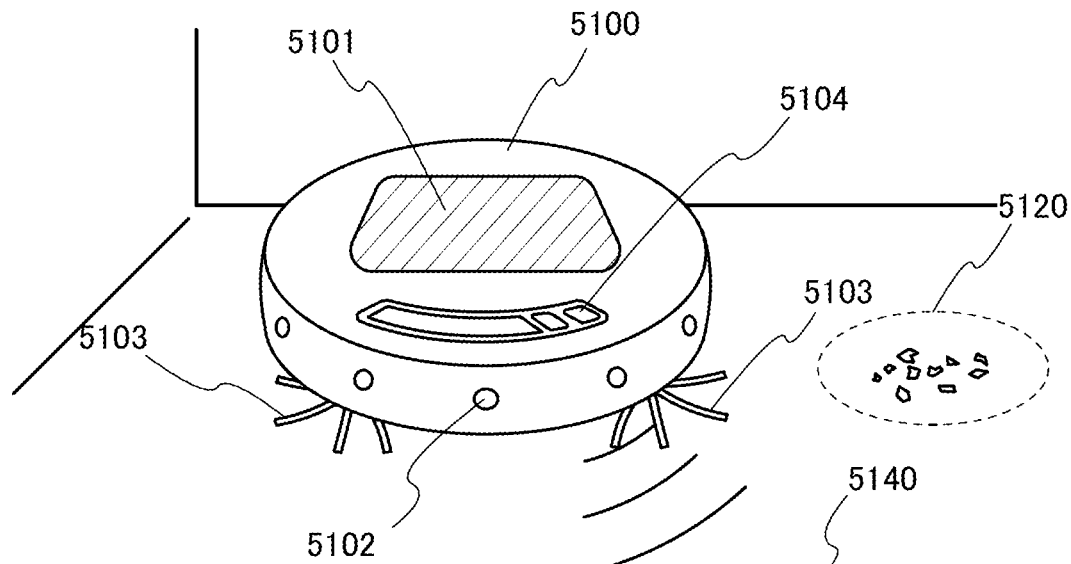
FIGS. 8A-8C are diagrams illustrating electronic devices.

FIG. 8(A) is a schematic view illustrating an example of a cleaning robot.

A cleaning robot 5100 includes a display 5101 placed on its top surface, a plurality of cameras 5102 placed on its side surface, a brush 5103, and operation buttons 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. In addition, the cleaning robot 5100 has a wireless communication means.

The cleaning robot 5100 is self-propelled, detects dust 5120, and sucks up the dust through the inlet provided on the bottom surface.

The cleaning robot 5100 can judge whether there is an obstacle such as a wall, furniture, or a step by analyzing images taken by the cameras 5102. When an object that is likely to be caught in the brush 5103, such as a wire, is detected by image analysis, the rotation of the brush 5103 can be stopped.

The display 5101 can display the remaining capacity of a battery, the amount of vacuumed dust, and the like. The display 5101 may display a path on which the cleaning robot 5100 has run. The display 5101 may be a touch panel, and the operation buttons 5104 may be provided on the display 5101.

The cleaning robot 5100 can communicate with a portable electronic device 5140 such as a smartphone. The portable electronic device 5140 can display images taken by the cameras 5102. Accordingly, an owner of the cleaning robot 5100 can monitor the room even from the outside. The display on the display 5101 can be checked by the portable electronic device 5140 such as a smartphone.

The light-emitting apparatus of one embodiment of the present invention can be used for the display 5101.

Figure 8B:
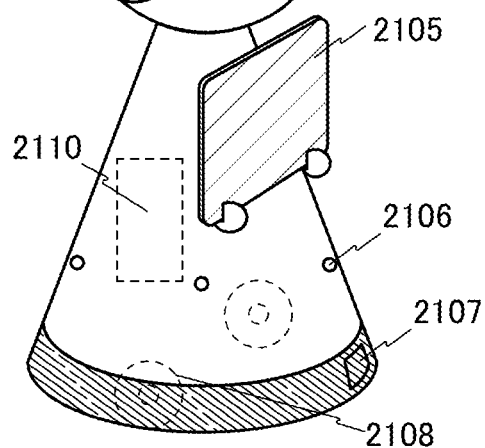

A robot 2100 illustrated in FIG. 8(B) includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect the presence of an obstacle in the direction where the robot 2100 advances with the moving mechanism 2108. The robot 2100 can move safely by recognizing the surroundings with the upper camera 2103, the lower camera 2106, and the obstacle sensor 2107. The light-emitting apparatus of one embodiment of the present invention can be used for the display 2105.

Figure 8C:
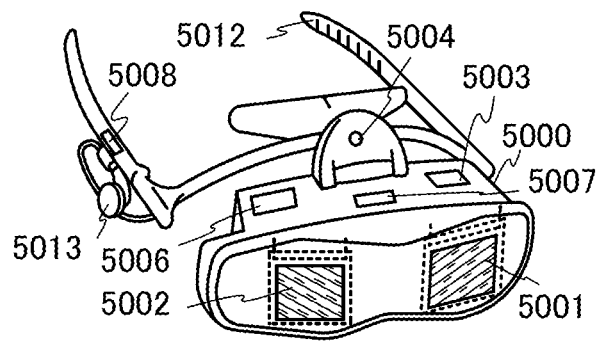

FIG. 8(C) shows an example of a goggle-type display. The goggle-type display includes, for example, a housing 5000, a display portion 5001, a speaker 5003, an LED lamp 5004, an operation keys 5005 (including a power switch or an operation switch), a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared ray), a microphone 5008, a second display portion 5002, a support 5012, and an earphone 5013.

The light-emitting apparatus of one embodiment of the present invention can be used for the display portion 5001 and the second display portion 5002.

Figure 9:
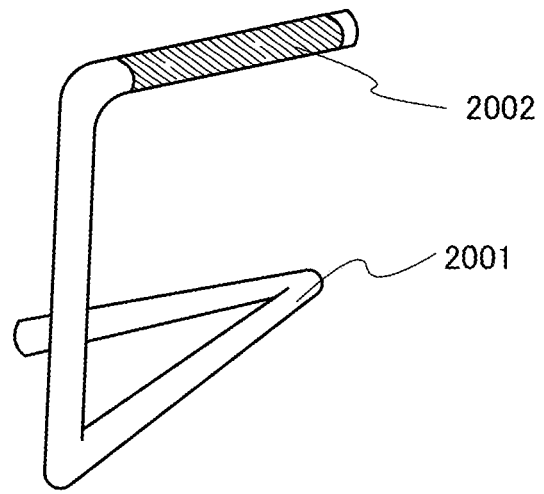
FIG. 9 is a diagram illustrating a lighting device.

FIG. 9 illustrates an example in which the light-emitting device described in Embodiment 1 and Embodiment 2 is used for a table lamp which is a lighting device. The table lamp illustrated in FIG. 9 includes a housing 2001 and a light source 2002, and the lighting device described in Embodiment 3 may be used for the light source 2002.

Figure 10:
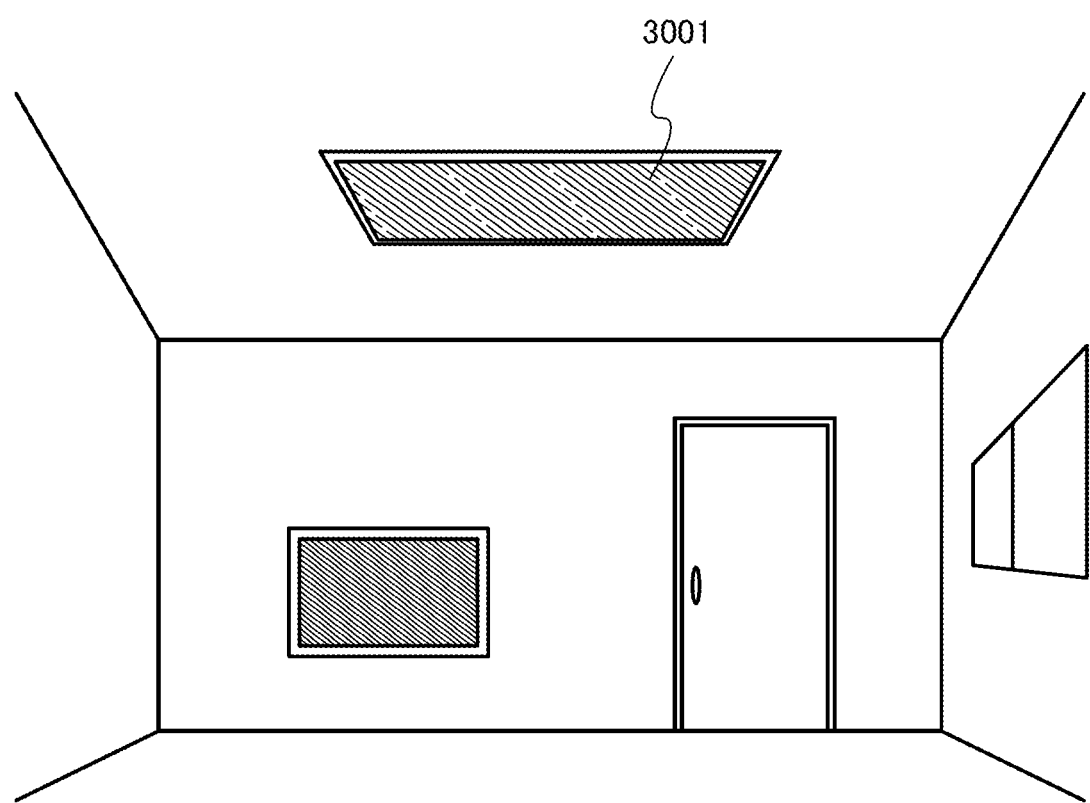
FIG. 10 is a diagram illustrating a lighting device.

FIG. 10 illustrates an example in which the light-emitting device described in Embodiment 1 and Embodiment 2 is used for an indoor lighting device 3001. Since the light-emitting device described in Embodiment 1 and Embodiment 2 is a light-emitting device having high reliability, the lighting device can have high reliability. Furthermore, the light-emitting device described in Embodiment 1 and Embodiment 2 can have a larger area, and thus can be used for a large-area lighting device. Furthermore, the light-emitting device described in Embodiment 1 and Embodiment 2 is thin, and thus can be used for a lighting device having a reduced thickness.

Figure 11:
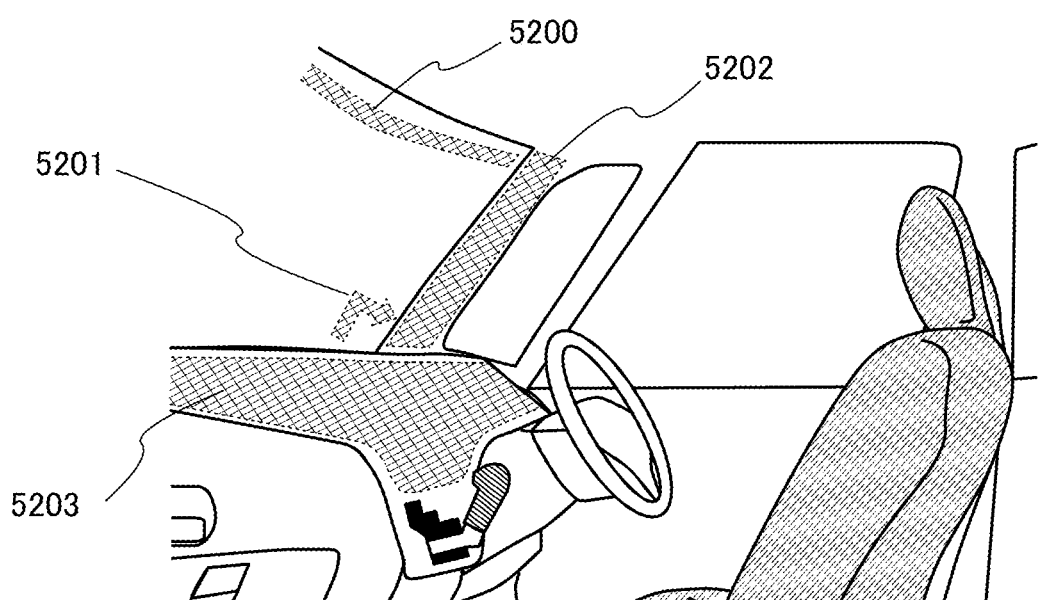
FIG. 11 is a diagram illustrating in-vehicle display devices and lighting devices.

The light-emitting device described in Embodiment 1 and Embodiment 2 can also be incorporated in an automobile windshield or an automobile dashboard. FIG. 11 illustrates one mode in which the light-emitting device described in Embodiment 1 and Embodiment 2 is used for a windshield and a dashboard of an automobile. A display region 5200 to a display region 5203 are each a display region provided using the light-emitting device described in Embodiment 1 and Embodiment 2.

The display region 5200 and the display region 5201 are display devices provided in the automobile windshield, in which the light-emitting devices described in Embodiment 1 and Embodiment 2 are incorporated. When the light-emitting devices described in Embodiment 1 and Embodiment 2 are fabricated using electrodes having light-transmitting properties as a first electrode and a second electrode, what is called see-through display devices, through which the opposite side can be seen, can be obtained. See-through display devices can be provided without hindering the vision even when being provided in the automobile windshield. Note that in the case where a driving transistor or the like is provided, a transistor having a light-transmitting property, such as an organic transistor using an organic semiconductor material or a transistor using an oxide semiconductor, is preferably used.

The display region 5202 is a display device provided in a pillar portion, in which the light-emitting devices described in Embodiment 1 and Embodiment 2 are incorporated. The display region 5202 can compensate for the view hindered by the pillar by displaying an image taken by an imaging means provided on the car body. Similarly, the display region 5203 provided in the dashboard portion can compensate for the view hindered by the car body by displaying an image taken by an imaging means provided on the outside of the automobile. Thus, blind areas can be compensated for and the safety can be enhanced. Showing an image so as to compensate for the area that cannot be seen makes it possible to confirm safety more naturally and comfortably.

The display region 5203 can provide a variety of kinds of information by displaying navigation data, a speedometer, a tachometer, a mileage, a fuel meter, a gearshift state, air-condition setting, and the like. The content or layout of the display can be changed freely in accordance with the preference of a user. Note that such information can also be provided on the display region 5200 to the display region 5202. The display region 5200 to the display region 5203 can also be used as lighting devices.

Figure 12A:
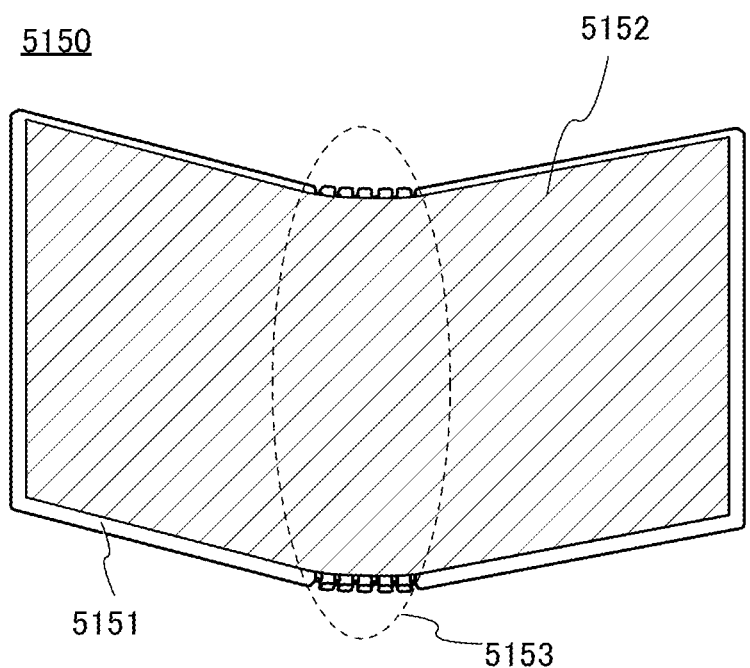
FIGS. 12A and 12B are diagrams illustrating an electronic device.
Figure 12B:
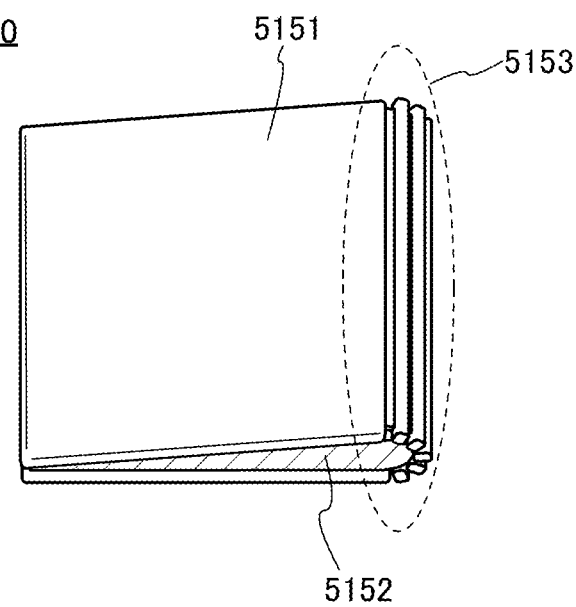

FIGS. 12(A) and 12(B) illustrate a foldable portable information terminal 5150. The foldable portable information terminal 5150 includes a housing 5151, a display region 5152, and a bend portion 5153. FIG. 12(A) illustrates the portable information terminal 5150 that is opened. FIG. 12(B) illustrates the portable information terminal 5150 that is folded. The portable information terminal 5150 is compact in size and has excellent portability when folded, despite its large display region 5152.

The display region 5152 can be folded in half with the bend portion 5153. The bend portion 5153 includes a flexible member and a plurality of supporting members, and when the display region is folded, the flexible member expands and the bend portion 5153 has a radius of curvature of 2 mm or more, preferably 3 mm or more.

Note that the display region 5152 may be a touch panel (an input/output device) including a touch sensor (an input device). The light-emitting apparatus of one embodiment of the present invention can be used for the display region 5152.

Figure 13A:
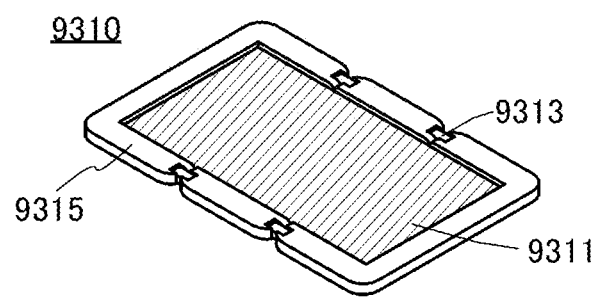
FIGS. 13A-13C are diagrams illustrating an electronic device.
Figure 13B:
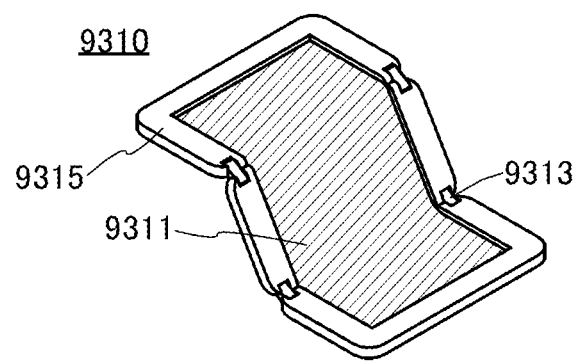
Figure 13C:
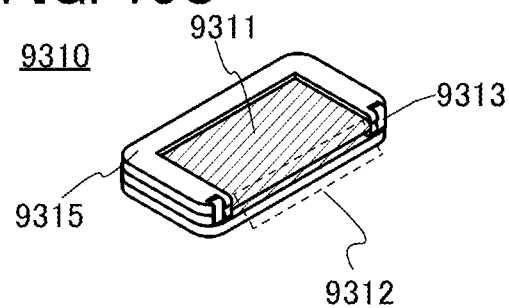

FIGS. 13(A) to 13(C) illustrate a foldable portable information terminal 9310. FIG. 13(A) illustrates the portable information terminal 9310 that is opened. FIG. 13(B) illustrates the portable information terminal 9310 which is in the state of being changed from one of an opened state and a folded state to the other. FIG. 13(C) illustrates the portable information terminal 9310 that is folded. The portable information terminal 9310 is excellent in portability when folded, and is excellent in display browsability when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. A light-emitting apparatus of one embodiment of the present invention can be used for the display panel 9311. A display region 9312 in the display panel 9311 is a display region that is positioned at a side surface of the portable information terminal 9310 which is folded. On the display region 9312, information icons, file shortcuts of frequently used applications or programs, and the like can be displayed, and confirmation of information and start of an application can be smoothly performed.

EXAMPLE

Device Example 1

In this example, a light-emitting device 1 of one embodiment of the present invention and a comparative light-emitting device 1 will be described. The structural formulae of organic compounds used in the light-emitting device 1 and the comparative light-emitting device 1 are shown below.

[Chemical formulae 11]

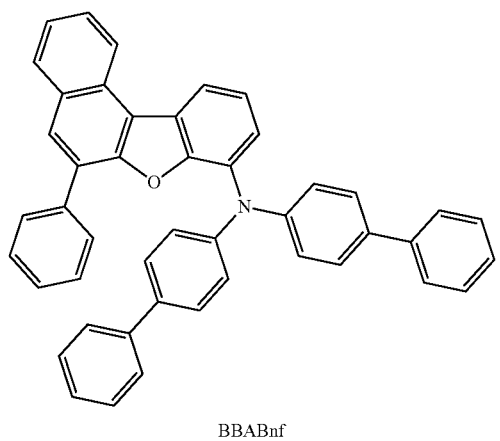

(i)

BBABnf

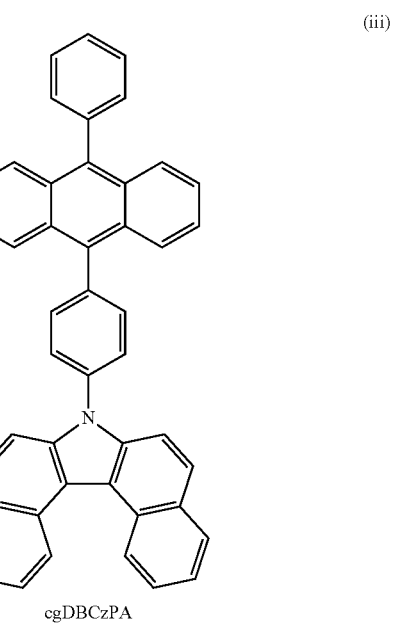

(iii)

cgDBCzPA

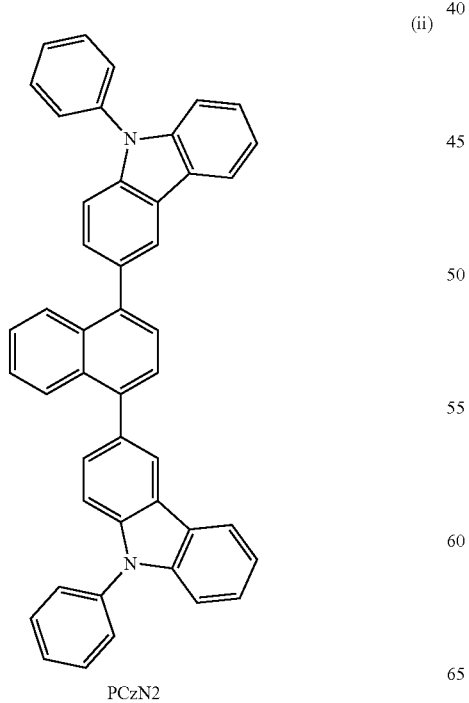

(ii)

PCzN2

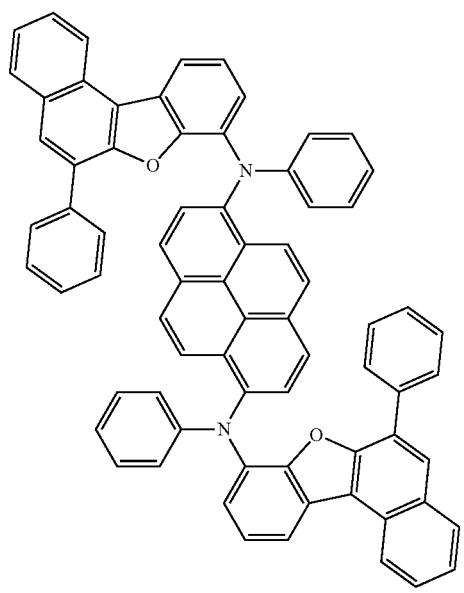

(iv)

1,6BnfAPrn-03

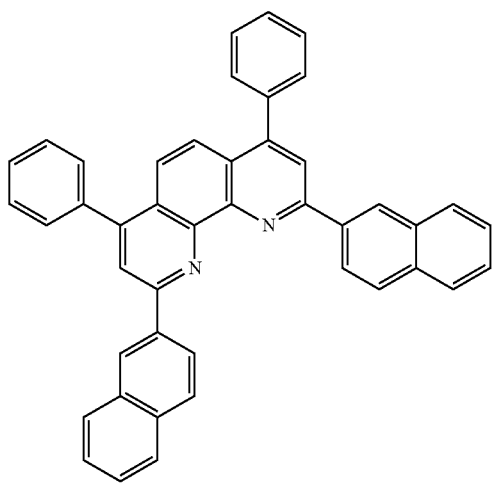

NBPhen

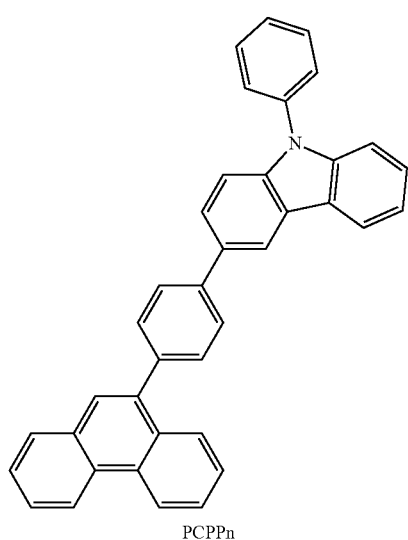

PCPPn (Fabricating Method of Light-Emitting Device 1)

First, a film of indium tin oxide containing silicon oxide (ITSO) was formed over a glass substrate by a sputtering method, so that the first electrode 101 was formed. Note that the thickness was 70 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate provided with the first electrode 101 was fixed to a substrate holder provided in the vacuum evaporation apparatus such that the side on which the first electrode 101 was formed faced downward, and then N,N-bis(4-biphenyl)-6-phenylbenzo[b]naphtho[1,2-d]furan-8-amine (abbreviation: BBABnf) represented by the structural formula (i) and NDP-9 (produced by Analysis Atelier Corporation, material serial No. 1S20170124) were deposited by co-evaporation to a thickness of 10 nm on the first electrode 101 at a weight ratio of 1:0.1 (=BBABnf:NDP-9) by an evaporation method using resistance heating, whereby the hole-injection layer 111 was formed.

Subsequently, over the hole-injection layer 111, BBABnf was deposited as a first hole-transport layer 112-1 by evaporation to a thickness of 20 nm, and then 3,3'-(naphthalene-1,4-diyl)bis(9-phenyl-9H-carbazole) (abbreviation: PCzN2) represented by the structural formula (ii) was deposited as a second hole-transport layer 112-2 by evaporation to a thickness of 10 nm, whereby the hole-transport layer 112 was formed.

Then, 7-[4-(10-phenyl-9-anthryl)phenyl]-7H-dibenzo[c,g]carbazole (abbreviation: cgDBCzPA) represented by the structural formula (iii) and N,N-(pyrene-1,6-diyl)bis[(6,N-diphenylbenzo[b]naphtho[1,2-d]furan)-8-amine] (abbreviation: 1,6BnfAPrn-03) represented by the structural formula (iv) were deposited to a thickness of 25 nm by co-evaporation at a weight ratio of 1:0.03 (=cgDBCzPA:1,6BnfAPrn-03), whereby the light-emitting layer 113 was formed.

After that, over the light-emitting layer 113, cgDBCzPA was deposited by evaporation to a thickness of 15 nm, and then 2,9-bis(naphthalen-2-yl)-4,7-diphenyl-1,10-phenanthroline (abbreviation: NBPhen) represented by the structural formula (v) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the second electrode 102, whereby the light-emitting device 1 of this example was fabricated.

(Fabricating Method of Comparative Light-Emitting Device 1)

The comparative light-emitting device 1 was fabricated in a manner similar to that of the light-emitting device 1 except that PCzN2 used in the second hole-transport layer 112-2 of the light-emitting device 1 was replaced with 3-[4-(9-phenanthryl)-phenyl]-9-phenyl-9H-carbazole (abbreviation: PCPPn) represented by the structural formula (vi).

The device structures of the light-emitting device 1 and the comparative light-emitting device 1 are listed in the following table.

TABLE 1

| | Hole-injection layer | Hole-transport layer | | Light-emitting layer | Electron-transport layer | | Electron-injection layer |
|---|---|---|---|---|---|---|---|
| | | 1 | 2 | | | | |
| | 10 nm | 20 nm | 10 nm | 25 nm | 15 nm | 10 nm | 1 nm |
| Light-emitting device 1 | BBABnf:NDP-9 | BBABnf | PCzN2 | cgDBCzPA:1,6BnfAPrn-03 | cgDBCzPA | NBPhen | LiF |

TABLE 1-continued

| | Hole-injection layer | Hole-transport layer | | Light-emitting layer | Electron-transport layer | | Electron-injection layer |
|---|---|---|---|---|---|---|---|
| | | 1 | 2 | | | | |
| | 10 nm | 20 nm | 10 nm | 25 nm | 15 nm | 10 nm | 1 nm |
| Comparative light-emitting device 1 | (1:0.1) | | PCPPn | (1:0.03) | | | |

The light-emitting device 1 and the comparative light-emitting device 1 were each subjected to sealing with a glass substrate (a sealant was applied to surround the device, followed by UV treatment and one-hour heat treatment at 80° C. at the time of sealing) in a glove box in a nitrogen atmosphere so that the light-emitting device is not exposed to the air, and then initial characteristics and reliabilities of these light-emitting devices were measured. Note that the measurement was performed at room temperature.

Figure 14:
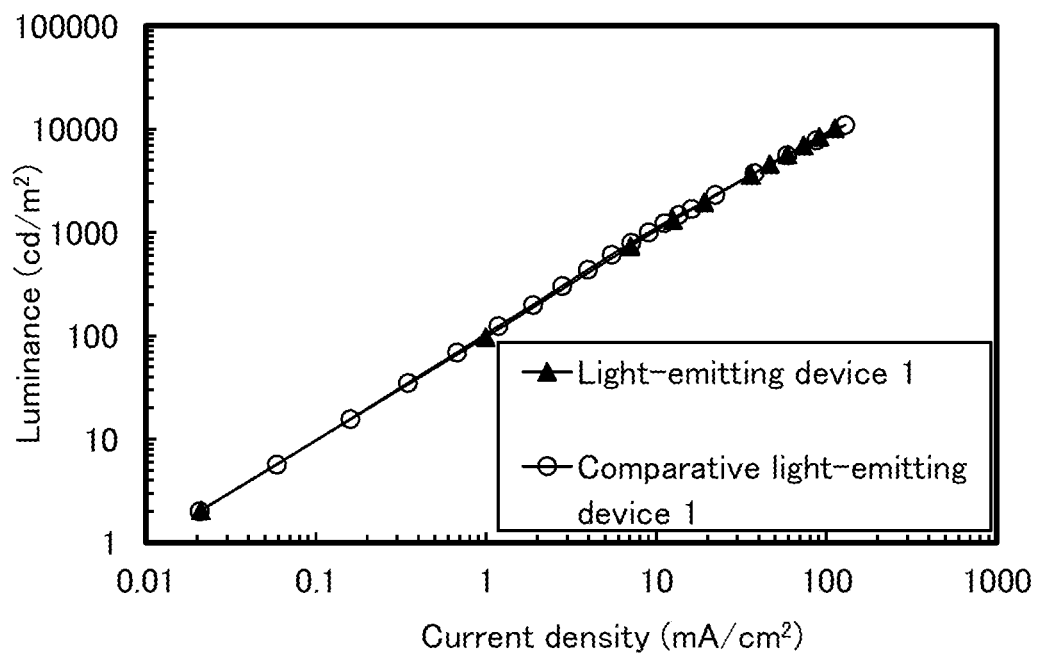
FIG. 14 is luminance-current density characteristics of a light-emitting device 1 and a comparative light-emitting device 1.
Figure 15:
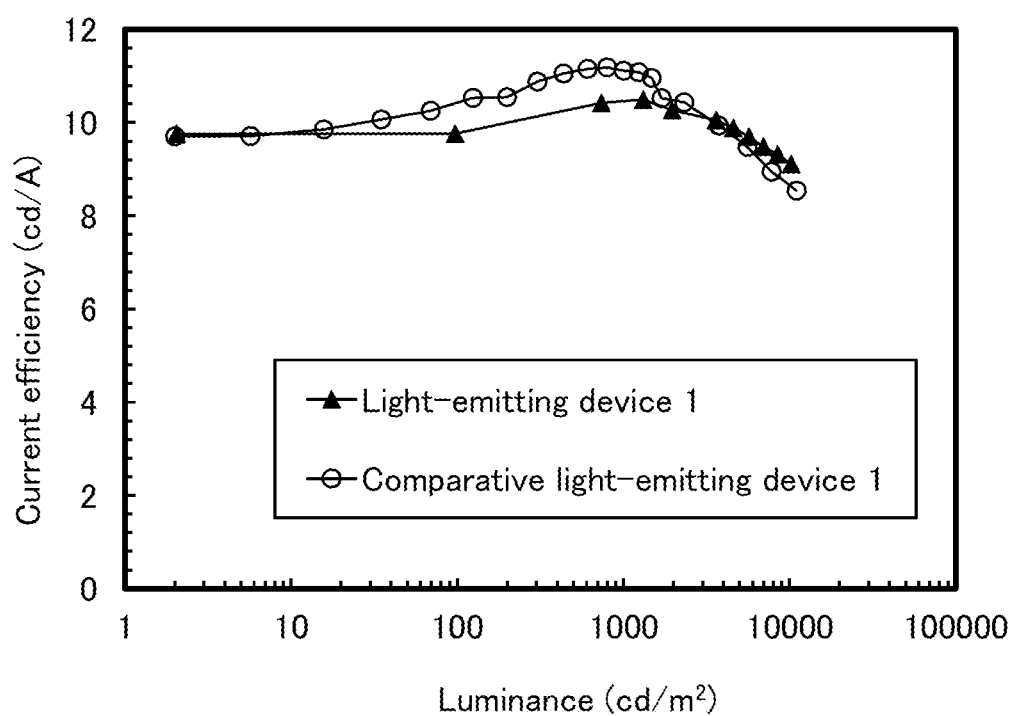
FIG. 15 is current efficiency-luminance characteristics of the light-emitting device 1 and the comparative light-emitting device 1.
Figure 16:
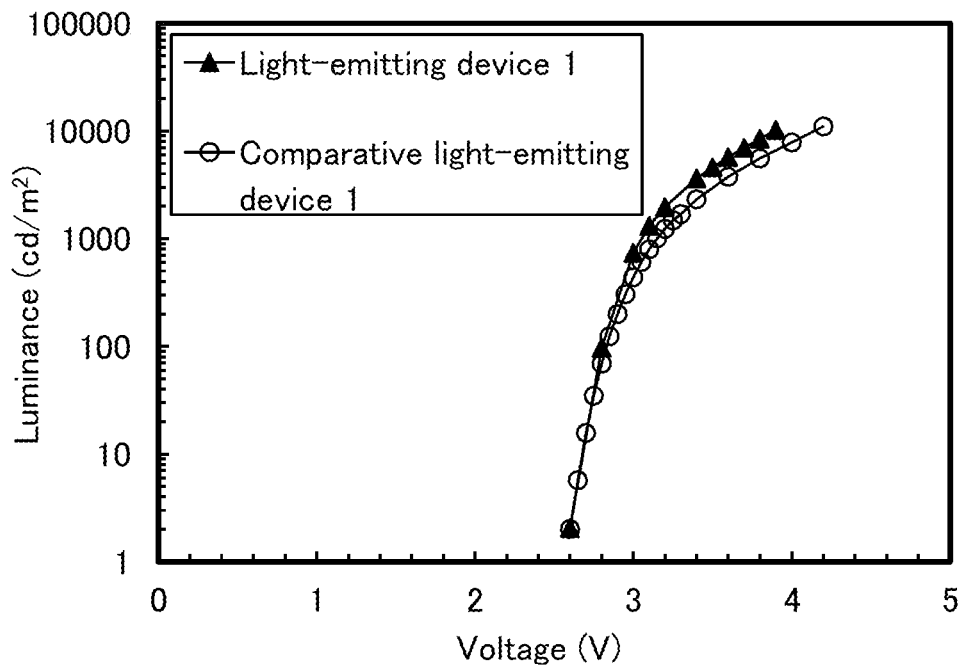
FIG. 16 is luminance-voltage characteristics of the light-emitting device 1 and the comparative light-emitting device 1.
Figure 17:
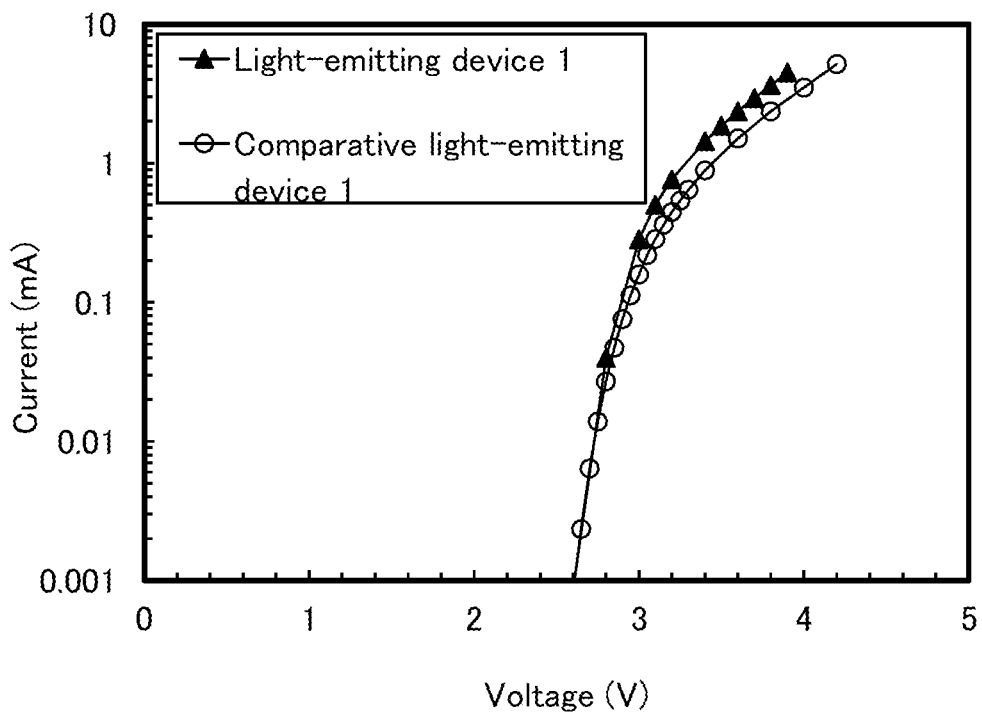
FIG. 17 is current-voltage characteristics of the light-emitting element 1 and the comparative light-emitting element 1.
Figure 18:
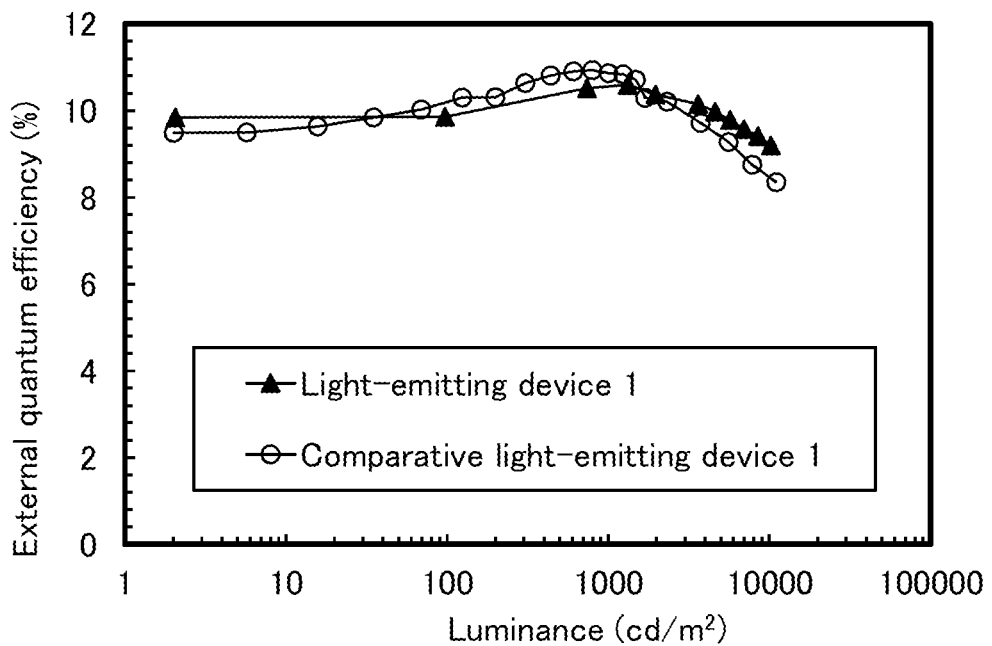
FIG. 18 is external quantum efficiency-luminance characteristics of the light-emitting device 1 and the comparative light-emitting device 1.
Figure 19:
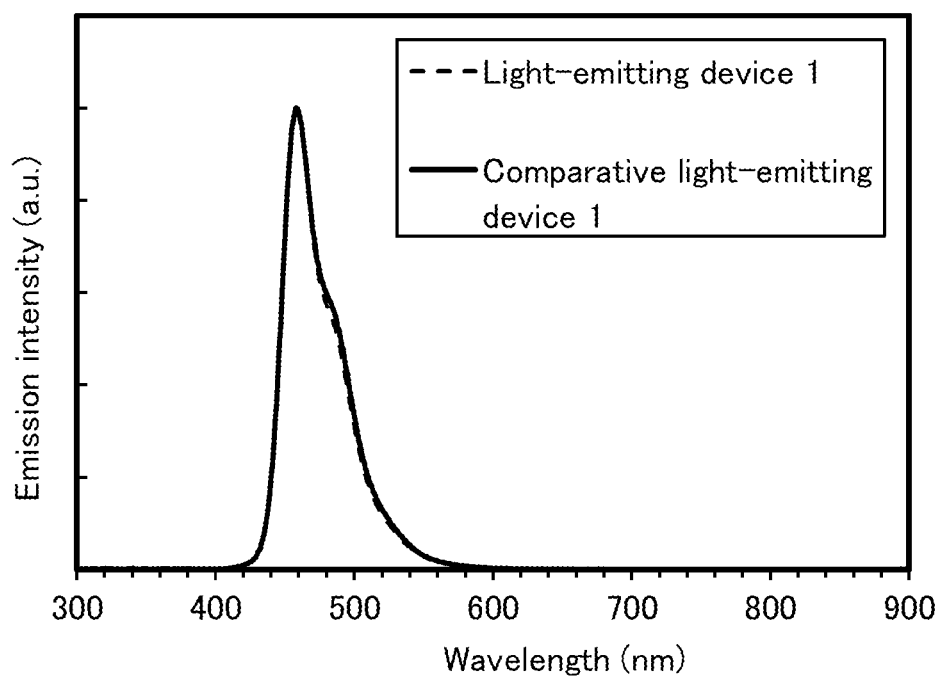
FIG. 19 is emission spectra of the light-emitting device 1 and the comparative light-emitting device 1.

Luminance-current density characteristics of the light-emitting device 1 and the comparative light-emitting device 1 are shown in FIG. 14, current efficiency-luminance characteristics thereof are shown in FIG. 15, luminance-voltage characteristics thereof are shown in FIG. 16, current-voltage characteristics thereof are shown in FIG. 17, external quantum efficiency-luminance characteristics thereof are shown in FIG. 18, and emission spectra thereof are shown in FIG. 19. In addition, Table 2 shows the main characteristics of the light-emitting devices at around 1000 cd/m².

TABLE 2

| | Voltage (V) | Current (mA) | Current density (mA/cm²) | Chromaticity x | Chromaticity y | Current efficiency (cd/A) | External quantum efficiency (%) |
|---|---|---|---|---|---|---|---|
| Light-emitting device 1 | 3.0 | 0.28 | 7.1 | 0.14 | 0.12 | 10.4 | 10.5 |
| Comparative light-emitting device 1 | 3.2 | 0.36 | 9.0 | 0.14 | 0.13 | 11.1 | 10.9 |

It was found from FIG. 14 to FIG. 19 and Table 2 that the light-emitting device 1, which is one embodiment of the present invention, was a favorable blue light-emitting device in which the driving voltage was low and the characteristics such as the emission efficiency were equivalent to those of the comparative light-emitting device 1.

Figure 20:
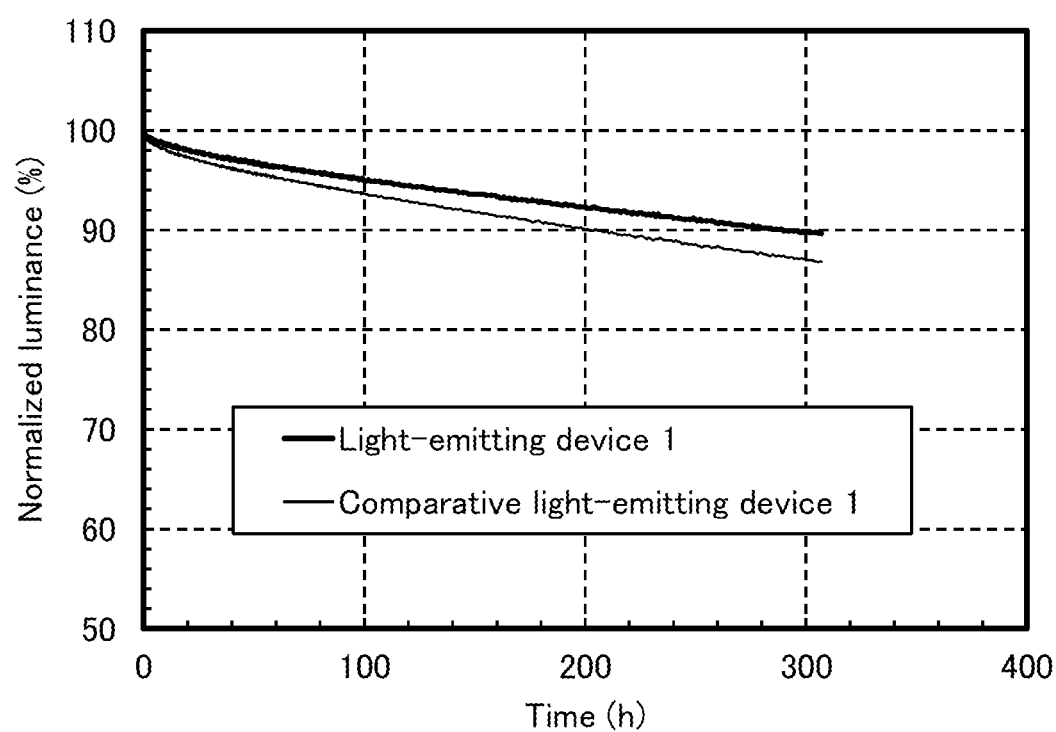
FIG. 20 is normalized luminance-temporal change characteristics of the light-emitting device 1 and the comparative light-emitting device 1.

FIG. 20 is a graph showing a change in luminance over driving time at a current density of 50 mA/cm². As shown in FIG. 20, the light-emitting device 1, which is a light-emitting device of one embodiment of the present invention, was found to be a light-emitting device with favorable lifetime with a small reduction in luminance over the accumulated driving time.

Device Example 2

In this example, a light-emitting device 2 of one embodiment of the present invention and a comparative light-emitting device 2 will be described. The structural formulae of organic compounds used in the light-emitting device 2 and the comparative light-emitting device 2 are shown below.

[Chemical formulae 12]

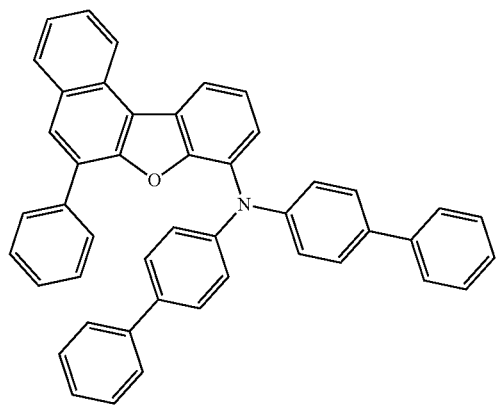

(i)

BBABnf

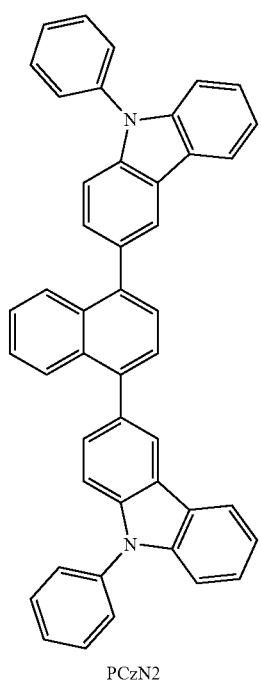
PCzN2
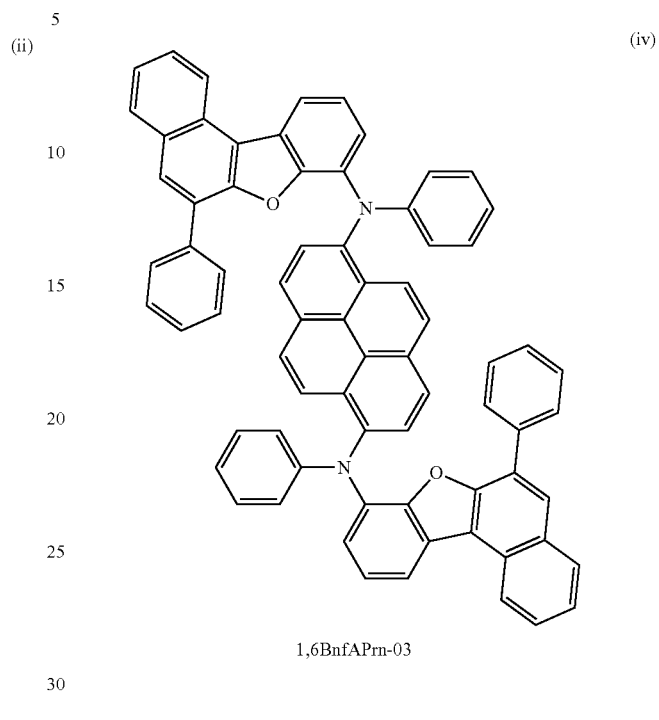
1,6BnfAPrn-03
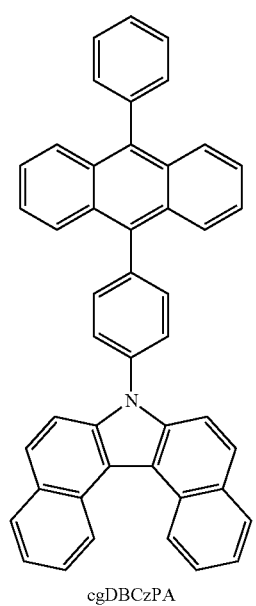
cgDBCzPA
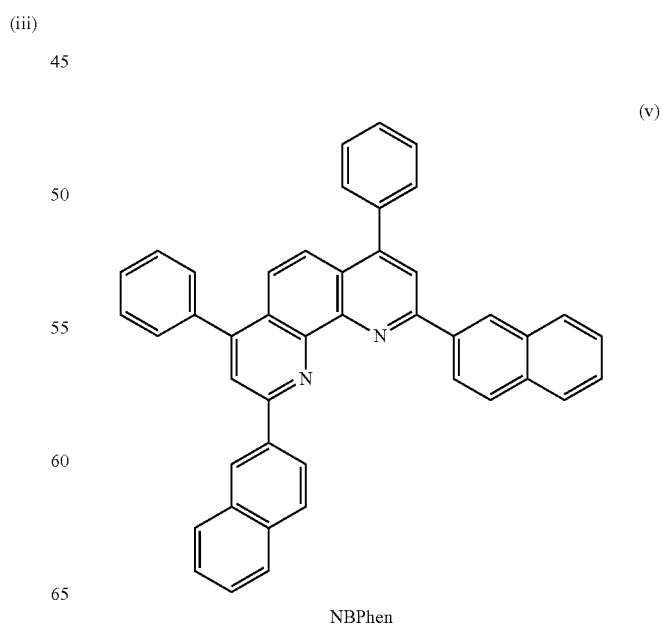
NBPhen -continued (vi)

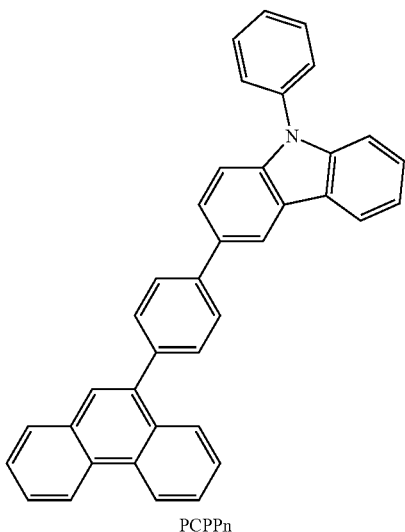

PCPPn (Fabricating Method of Light-Emitting Device 2)

First, a film of indium tin oxide containing silicon oxide (ITSO) was formed over a glass substrate by a sputtering method, so that the first electrode 101 was formed. Note that the thickness was 70 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate provided with the first electrode 101 was fixed to a substrate holder provided in the vacuum evaporation apparatus such that the side on which the first electrode 101 was formed faced downward, and then N,N-bis(4-biphenyl)-6-phenylbenzo[b]naphtho[1,2-d]furan-8-amine (abbreviation: BBABnf) represented by Structural formula (i) shown above and NDP-9 (produced by Analysis Atelier Corporation, material serial No. 1S20170124) were deposited by co-evaporation to a thickness of 10 nm on the first electrode 101 at a weight ratio of 1:0.1 (=BBABnf: NDP-9) by an evaporation method using resistance heating, whereby the hole-injection layer 111 was formed.

Subsequently, over the hole-injection layer 111, 3,3'-(naphthalene-1,4-diyl)bis(9-phenyl-9H-carbazole) (abbreviation: PCzN2) represented by the structural formula (ii) was deposited by evaporation to a thickness of 30 nm, whereby the hole-transport layer 112 was formed.

Then, 7-[4-(10-phenyl-9-anthryl)phenyl]-7H-dibenzo[c,g]carbazole (abbreviation: cgDBCzPA) represented by the structural formula (iii) and N,N-(pyrene-1,6-diyl)bis[(6,N-diphenylbenzo[b]naphtho[1,2-d]furan)-8-amine] (abbreviation: 1,6BnfAPrn-03) represented by the structural formula (iv) were deposited to a thickness of 25 nm by co-evaporation at a weight ratio of 1:0.03 (=cgDBCzPA:1,6BnfAPrn-03), whereby the light-emitting layer 113 was formed.

After that, over the light-emitting layer 113, cgDBCzPA was deposited by evaporation to a thickness of 15 nm, and then 2,9-bis(naphthalen-2-yl)-4,7-diphenyl-1,10-phenanthroline (abbreviation: NBPhen) represented by the structural formula (v) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the second electrode 102, whereby the light-emitting device 2 of this example was fabricated.

(Fabricating Method of Comparative Light-Emitting Device 2) The comparative light-emitting device 2 was fabricated in a manner similar to that of the light-emitting device 2 except that PCzN2 used in the hole-transport layer 112 of the light-emitting device 2 was replaced with 3-[4-(9-phenanthryl)-phenyl]-9-phenyl-9H-carbazole (abbreviation: PCPPn) represented by the structural formula (vi).

The device structures of the light-emitting device 2 and the comparative light-emitting device 2 are listed in the following table.

TABLE 3

| | Hole-injection layer | Hole-transport layer | Light-emitting layer | Electron-transport layer | | Electron-injection layer |
|---|---|---|---|---|---|---|
| | 10 nm | 30 nm | 25 nm | 15 nm | 10 nm | 1 nm |
| Light-emitting device 2 | BBABnf: NDP-9 (1:0.1) | PCzN2 | cgDBCzPA: 1,6BnfAPrn-03 (1:0.03) | cgDBCzPA | NBPhen | LiF |
| Comparative light-emitting device 2 | | PCPPn | | | | |

The light-emitting device 2 and the comparative light-emitting device 2 were each subjected to sealing with a glass substrate (a sealant was applied to surround the device, followed by UV treatment and one-hour heat treatment at 80° C. at the time of sealing) in a glove box in a nitrogen atmosphere so that the light-emitting device is not exposed to the air, and then initial characteristics and reliabilities of these light-emitting devices were measured. Note that the measurement was performed at room temperature.

Figure 21:
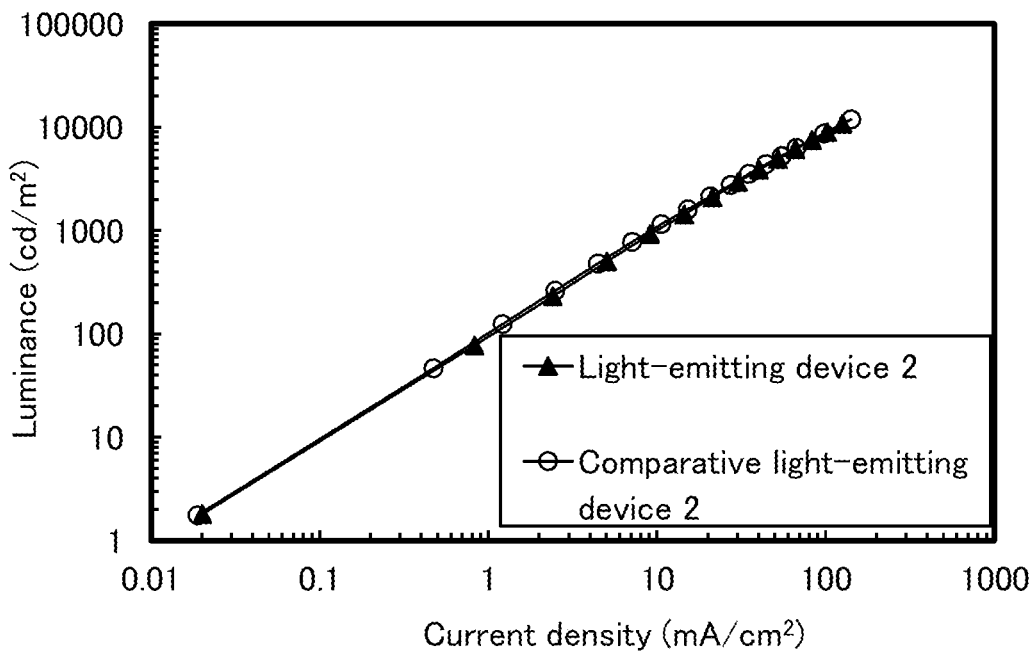
FIG. 21 is luminance-current density characteristics of a light-emitting device 2 and a comparative light-emitting device 2.
Figure 22:
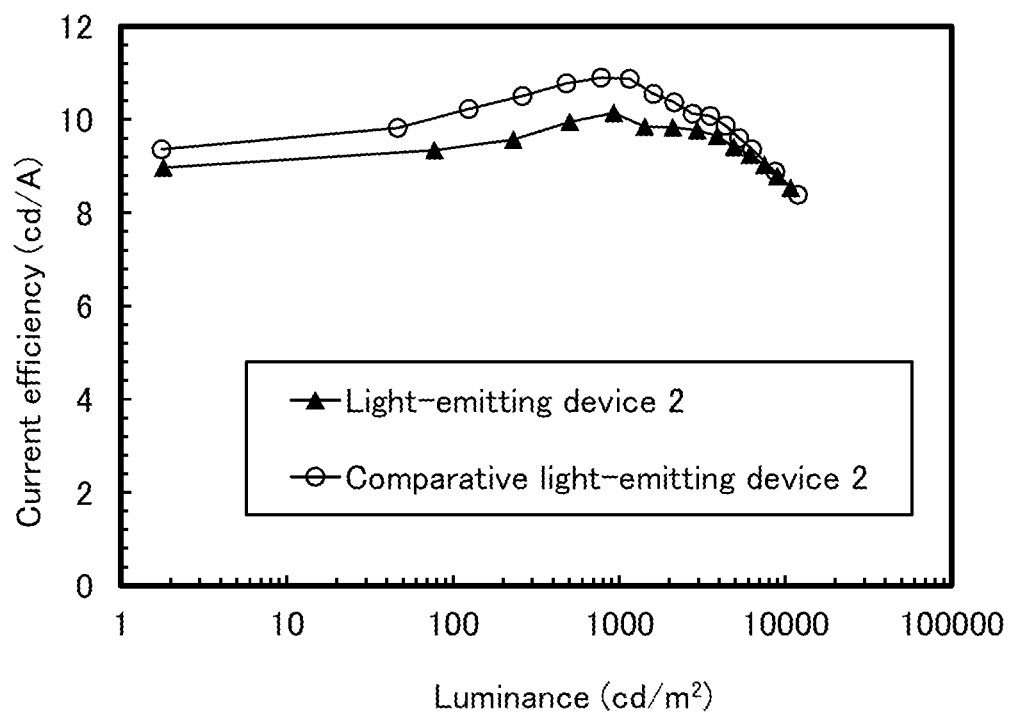
FIG. 22 is current efficiency-luminance characteristics of the light-emitting device 2 and the comparative light-emitting device 2.
Figure 23:
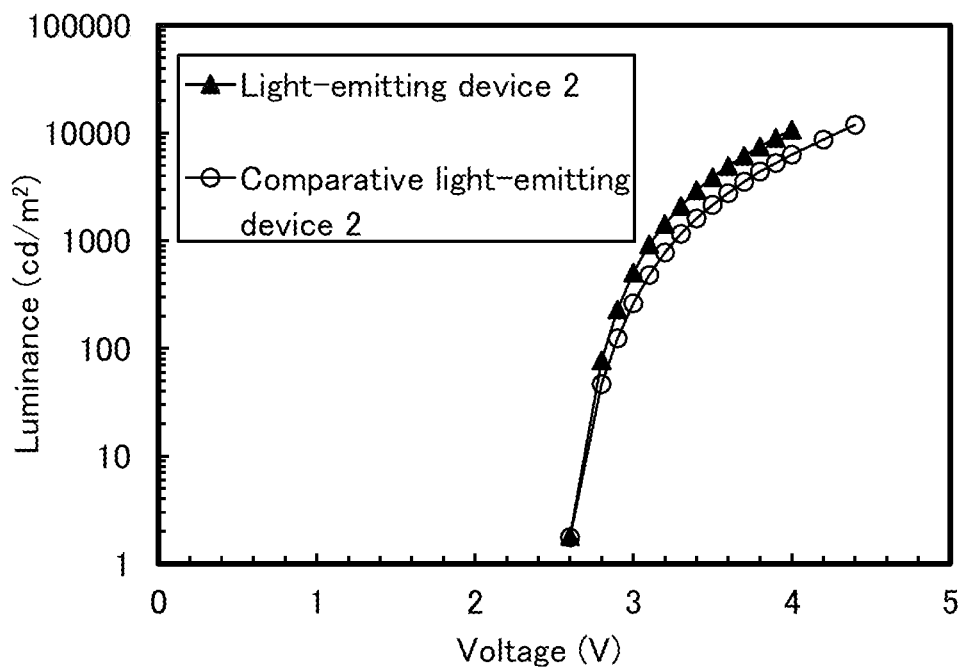
FIG. 23 is luminance-voltage characteristics of the light-emitting device 2 and the comparative light-emitting device 2.
Figure 24:
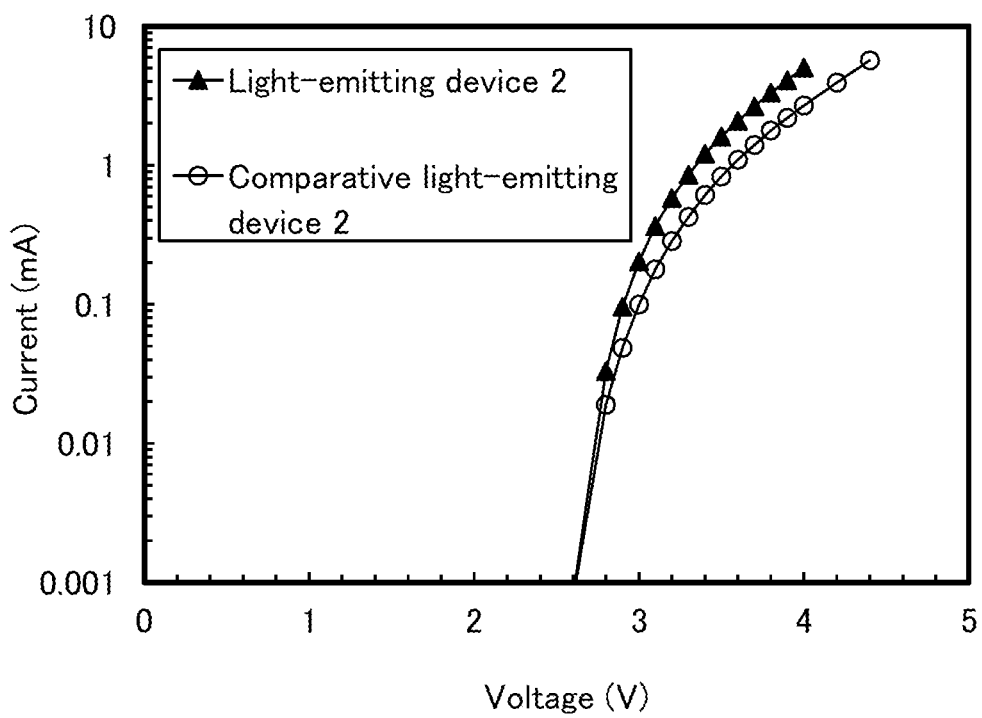
FIG. 24 is current-voltage characteristics of the light-emitting element 2 and the comparative light-emitting element 2.
Figure 25:
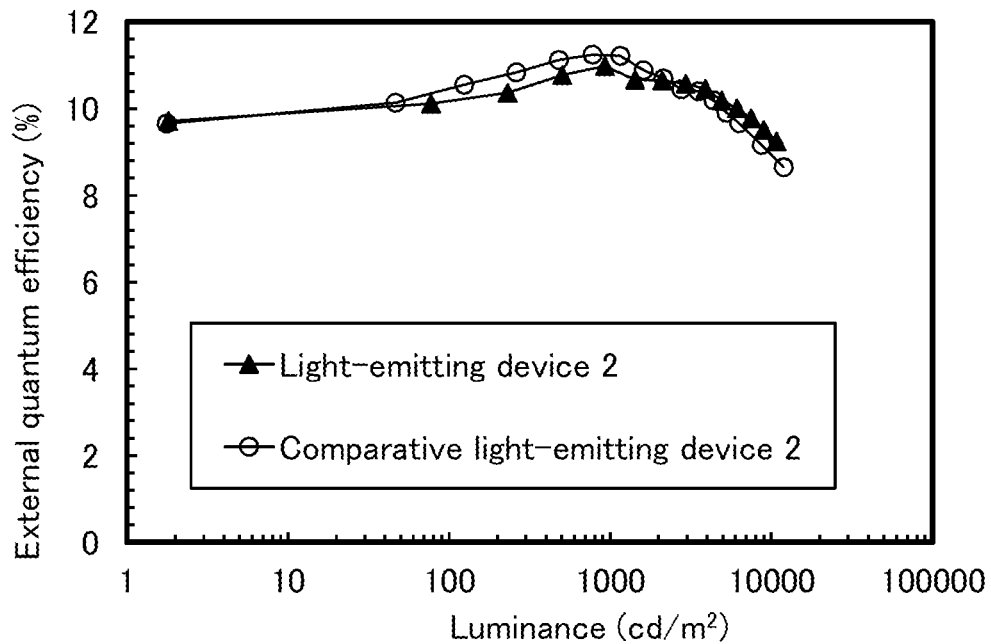
FIG. 25 is external quantum efficiency-luminance characteristics of the light-emitting device 2 and the comparative light-emitting device 2.
Figure 26:
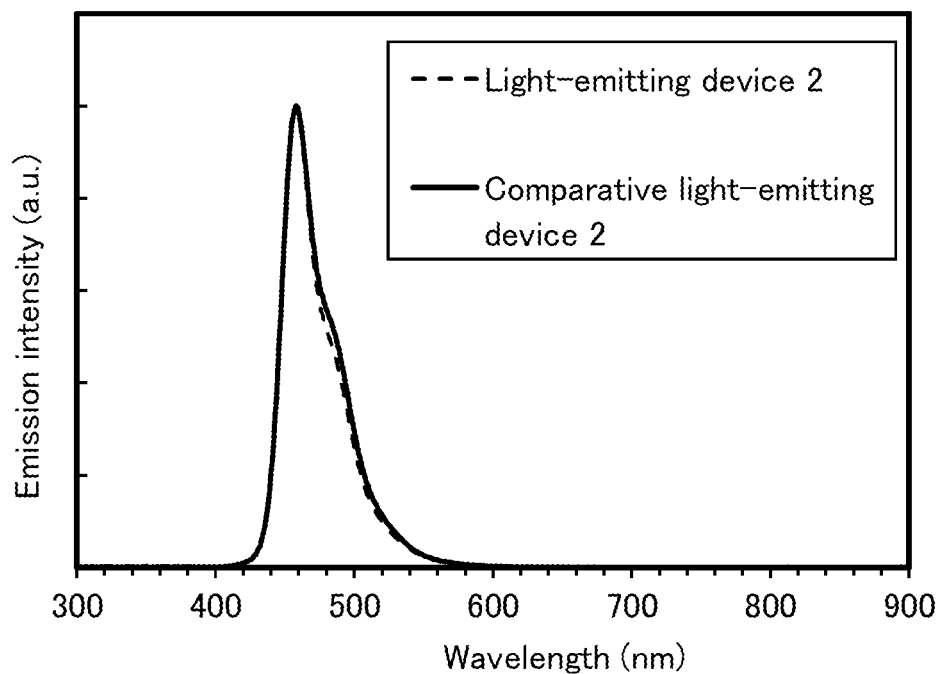
FIG. 26 is emission spectra of the light-emitting device 2 and the comparative light-emitting device 2.

Luminance-current density characteristics of the light-emitting device 2 and the comparative light-emitting device 2 are shown in FIG. 21, current efficiency-luminance characteristics thereof are shown in FIG. 22, luminance-voltage characteristics thereof are shown in FIG. 23, current-voltage characteristics thereof are shown in FIG. 24, external quantum efficiency-luminance characteristics thereof are shown in FIG. 25, and emission spectra thereof are shown in FIG. 26. In addition, Table 4 shows the main characteristics of the light-emitting devices at around 1000 cd/m².

TABLE 4

|  | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting device 2 | 3.1 | 0.37 | 9.1 | 0.14 | 0.11 | 10.1 | 11.0 |
| Comparative light-emitting device 2 | 3.3 | 0.43 | 10.6 | 0.14 | 0.12 | 10.9 | 11.2 |

It was found from FIG. 21 to FIG. 25 and Table 4 that the light-emitting device 2, which is one embodiment of the present invention, was a favorable blue light-emitting device in which the driving voltage was low and the characteristics such as the emission efficiency were equivalent to those of the comparative light-emitting device 2.

Figure 27:
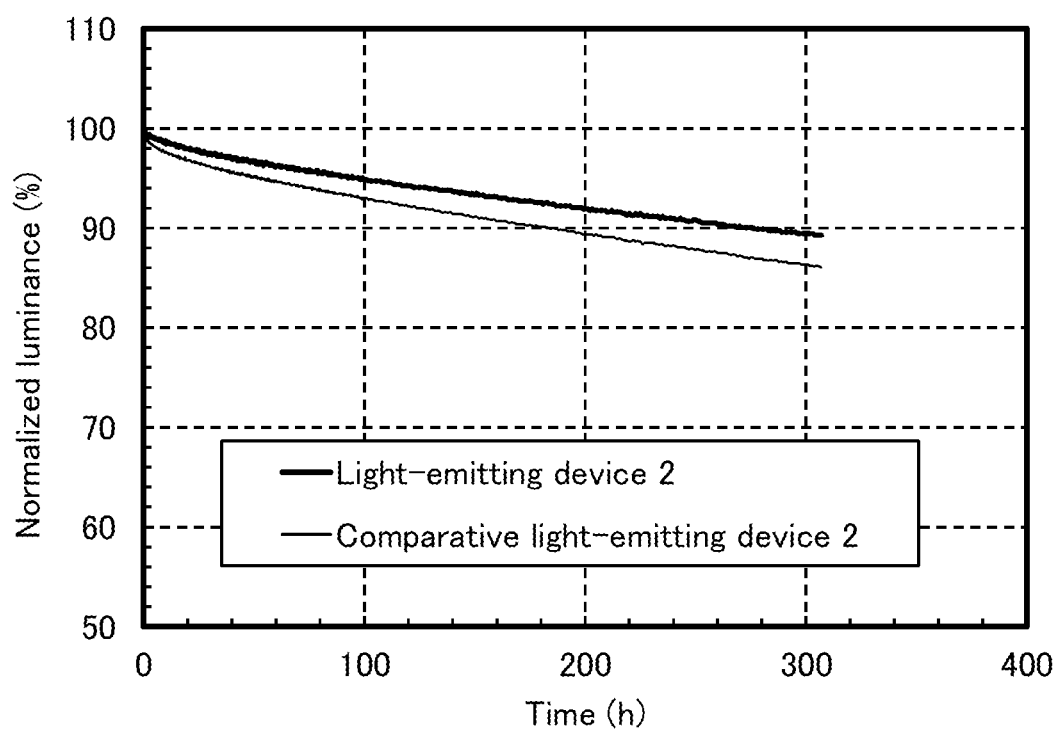
FIG. 27 is normalized luminance-temporal change characteristics of the light-emitting device 2 and the comparative light-emitting device 2.

FIG. 27 is a graph showing a change in luminance over driving time at a current density of 50 mA/cm$^2$. As shown in FIG. 27, the light-emitting device 2, which is a light-emitting device of one embodiment of the present invention, was found to be a light-emitting device with favorable lifetime with a small reduction in luminance over the accumulated driving time.

Device Example 3

In this example, a light-emitting device 3 of one embodiment of the present invention and a comparative light-emitting device 3 will be described. The structural formulae of organic compounds used in the light-emitting device 3 and the comparative light-emitting device 3 are shown below.

[Chemical formulae 13]

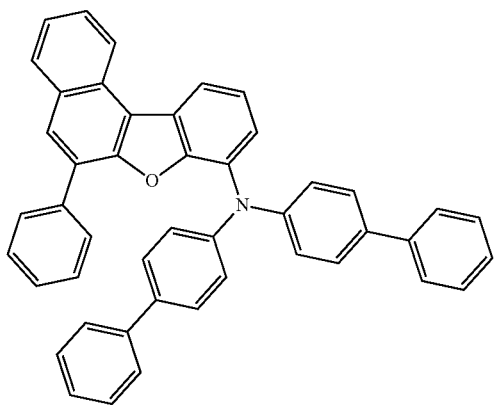

BBABnf (i)

-continued

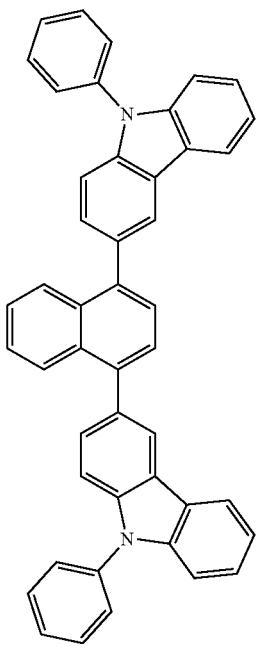

PCzN2 (ii)

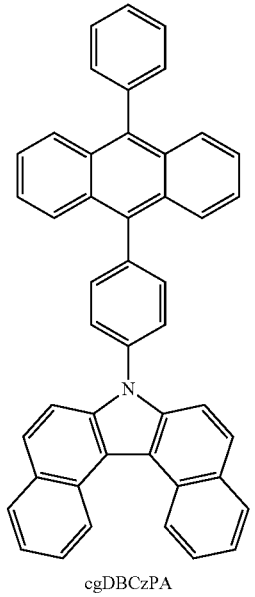

cgDBCzPA (iii)

-continued

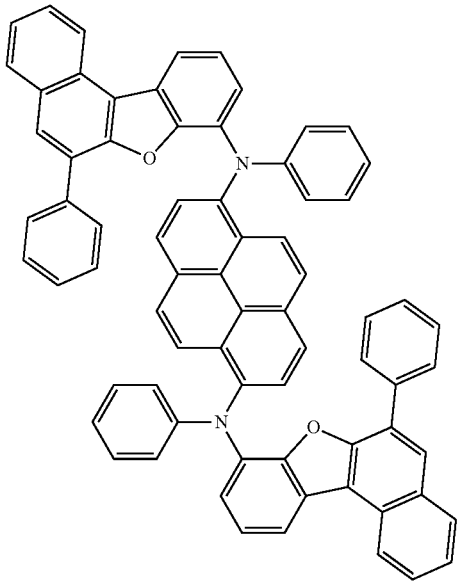

1,6BnfAPrn-03

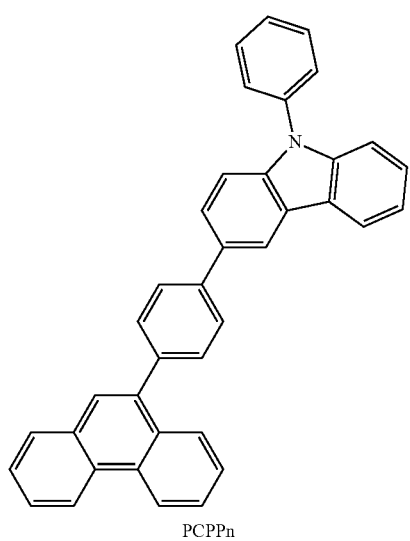

PCPPn

-continued

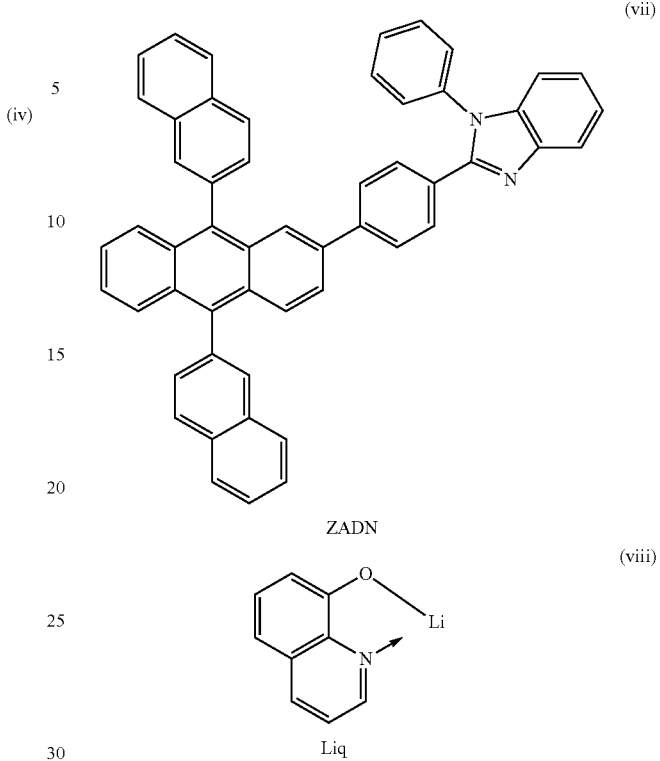

ZADN

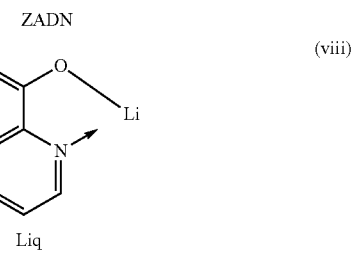

Liq (Fabricating Method of Light-Emitting Device 3)

First, a film of indium tin oxide containing silicon oxide (ITSO) was formed over a glass substrate by a sputtering method, so that the first electrode 101 was formed. Note that the thickness was 70 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate provided with the first electrode 101 was fixed to a substrate holder provided in the vacuum evaporation apparatus such that the side on which the first electrode 101 was formed faced downward, and then N,N-bis(4-biphenyl)-6-phenylbenzo[b]naphtho[1,2-d]furan-8-amine (abbreviation: BBABnf) represented by Structural formula (i) shown above and NDP-9 (produced by Analysis Atelier Corporation, material serial No. 1520170124) were deposited by co-evaporation to a thickness of 10 nm on the first electrode 101 at a weight ratio of 1:0.1 (=BBABnf: NDP-9) by an evaporation method using resistance heating, whereby the hole-injection layer 111 was formed.

Subsequently, over the hole-injection layer 111, BBABnf was deposited as the first hole-transport layer 112-1 by evaporation to a thickness of 20 nm, and then 3,3'-(naphthalene-1,4-diyl)bis(9-phenyl-9H-carbazole) (abbreviation: PCzN2) represented by the structural formula (ii) was deposited as the second hole-transport layer 112-2 by evaporation to a thickness of 10 nm, whereby the hole-transport layer 112 was formed.

Then, 7-[4-(10-phenyl-9-anthryl)phenyl]-7H-dibenzo[c,g]carbazole (abbreviation: cgDBCzPA) represented by the structural formula (iii) and N,N-(pyrene-1,6-diyl)bis[(6,N-diphenylbenzo[b]naphtho[1,2-d]furan)-8-amine] (abbreviation: 1,6BnfAPrn-03) represented by the structural formula (iv) were deposited to a thickness of 25 nm by co-evaporation at a weight ratio of 1:0.03 (=cgDBCzPA:1,6BnfAPrn-03), whereby the light-emitting layer 113 was formed.

Then, over the light-emitting layer 113, 2-{4-[9,10-di(naphthalen-2-yl)-2-anthryl]-1-phenyl-1H-benzoimidazole (abbreviation: ZADN) represented by the structural formula (vii) and 8-hydroxyquinolinolato-lithium (abbreviation: Liq) represented by the structural formula (viii) were deposited by evaporation to a thickness of 25 nm at a weight ratio of 1:1 (=ZADN:Liq), whereby the electron-transport layer 114 was formed.

After the formation of the electron-transport layer 114, Liq was deposited by evaporation to a thickness of 1 nm to form the electron-injection layer 115, and then aluminum was deposited by evaporation to a thickness of 200 nm to form the second electrode 102, whereby the light-emitting device 3 of this example was fabricated.

(Fabricating Method of Comparative Light-Emitting Device 3)

The comparative light-emitting device 3 was fabricated in a manner similar to that of the light-emitting device 3 except that PCzN2 used in the hole-transport layer 112 of the light-emitting device 3 was replaced with 3-[4-(9-phenanthryl)-phenyl]-9-phenyl-9H-carbazole (abbreviation: PCPPn) represented by the structural formula (vi).

The device structures of the light-emitting device 3 and the comparative light-emitting device 3 are listed in the following table.

TABLE 5

| | Hole-injection layer | Hole-transport layer | | Light-emitting layer | Electron-transport layer | Electron-injection layer |
|---|---|---|---|---|---|---|
| | | 1 | 2 | | | |
| | 10 nm | 20 nm | 10 nm | 25 nm | 25 nm | 1 nm |
| Light-emitting device 3 | BBABnf: NDP-9 (1:0.1) | BBABnf | PCzN2 | cgDBCzPA: 1,6BnfAPrn-03 (1:0.03) | ZADN:Liq (1:1) | Liq |
| Comparative light-emitting device 3 | | | PCPPn | | | |

The light-emitting device 3 and the comparative light-emitting device 3 were each subjected to sealing with a glass substrate (a sealant was applied to surround the device, followed by UV treatment and one-hour heat treatment at 80° C. at the time of sealing) in a glove box in a nitrogen atmosphere so that the light-emitting device is not exposed to the air, and then initial characteristics and reliabilities of these light-emitting devices were measured. Note that the measurement was performed at room temperature.

Figure 28:
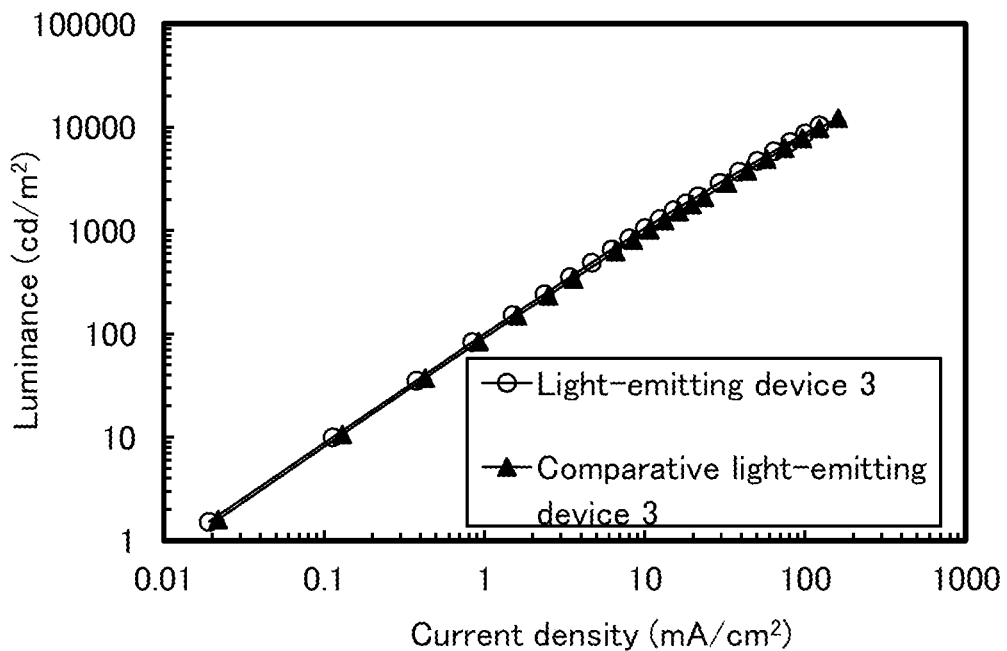
FIG. 28 is luminance-current density characteristics of a light-emitting device 3 and a comparative light-emitting device 3.
Figure 29:
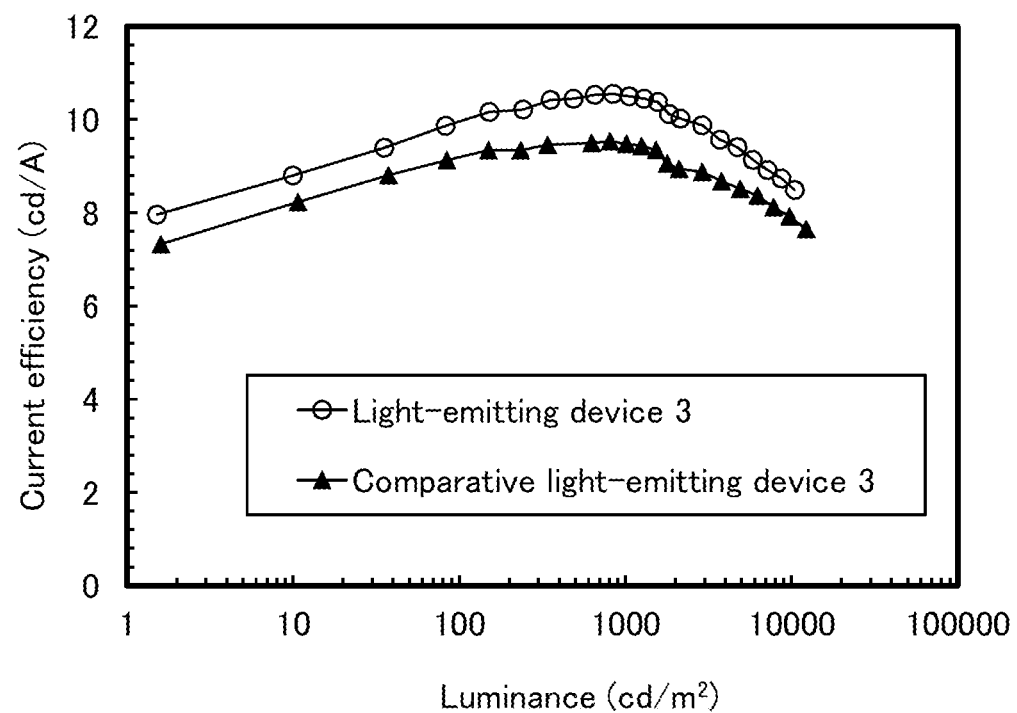
FIG. 29 is current efficiency-luminance characteristics of the light-emitting device 3 and the comparative light-emitting device 3.
Figure 30:
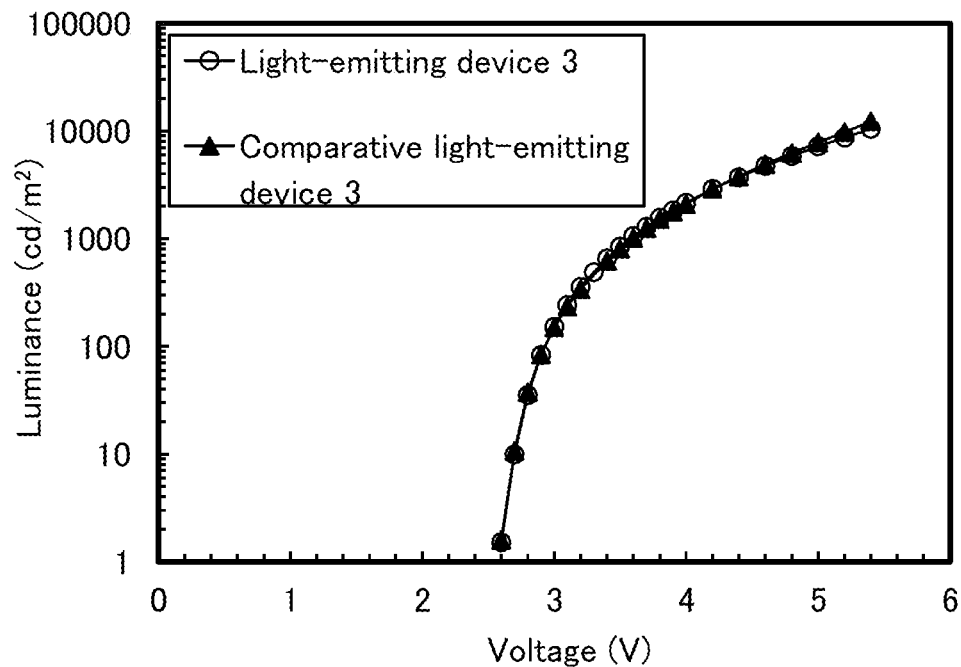
FIG. 30 is luminance-voltage characteristics of the light-emitting device 3 and the comparative light-emitting device 3.
Figure 31:
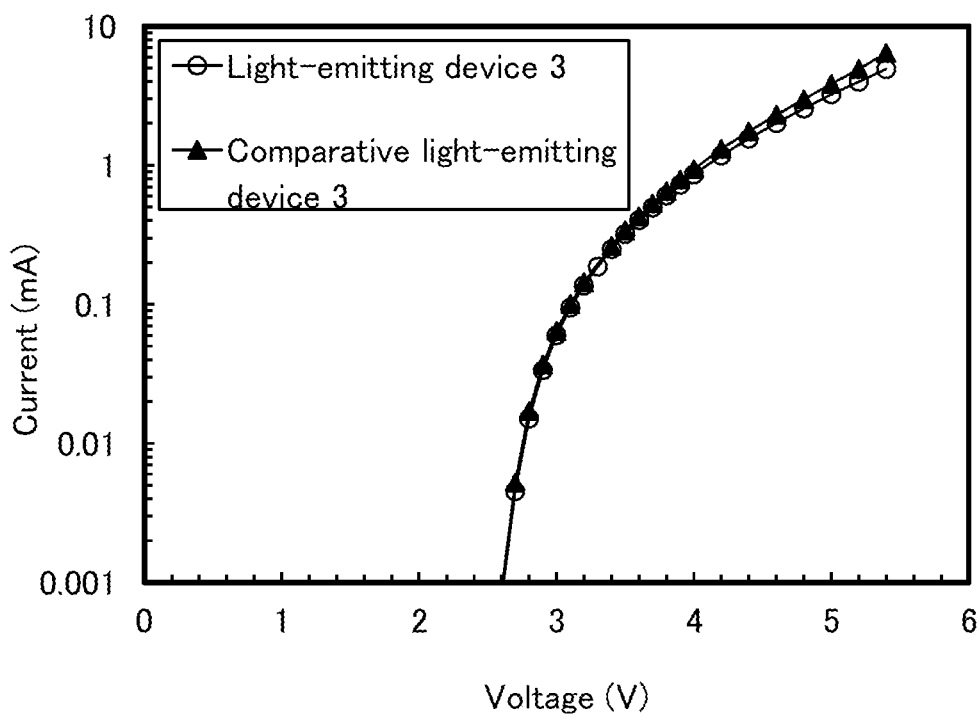
FIG. 31 is current-voltage characteristics of the light-emitting element 3 and the comparative light-emitting element 3.
Figure 32:
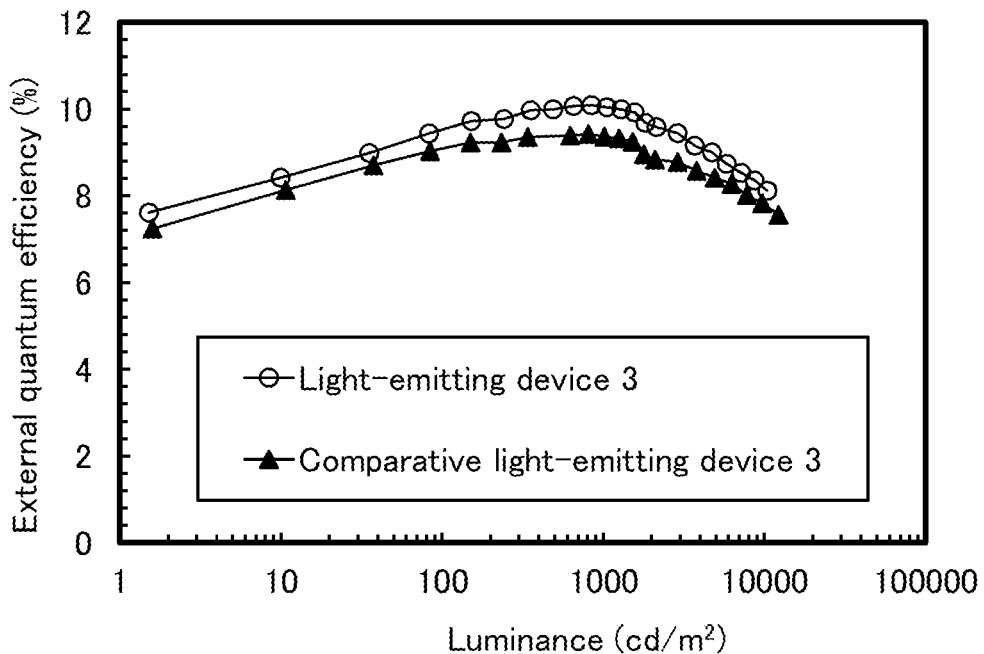
FIG. 32 is external quantum efficiency-luminance characteristics of the light-emitting device 3 and the comparative light-emitting device 3.
Figure 33:
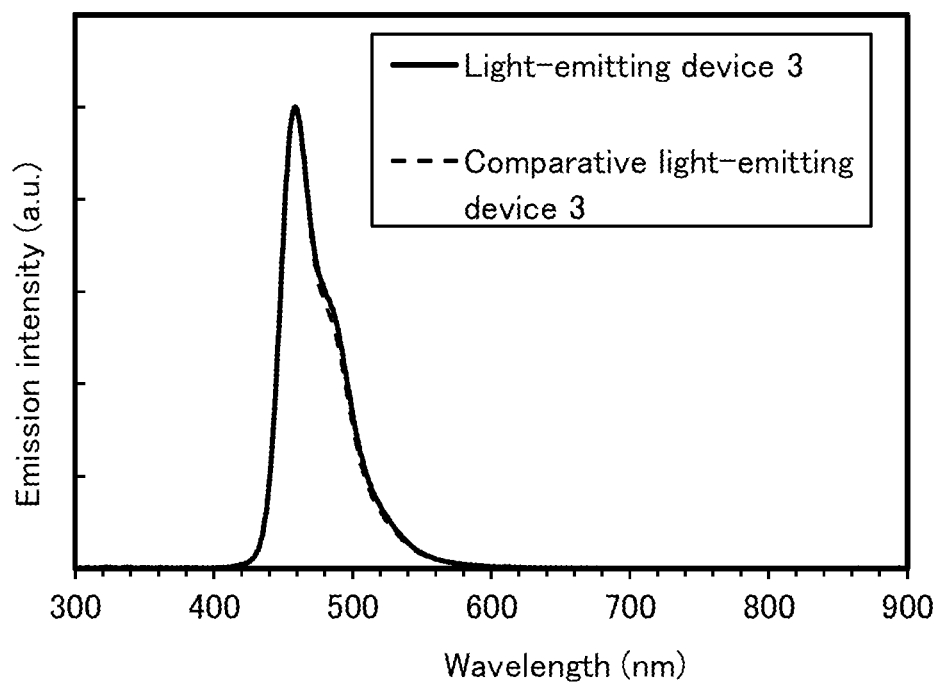
FIG. 33 is emission spectra of the light-emitting device 3 and the comparative light-emitting device 3.

Luminance-current density characteristics of the light-emitting device 3 and the comparative light-emitting device 3 are shown in FIG. 28, current efficiency-luminance characteristics thereof are shown in FIG. 29, luminance-voltage characteristics thereof are shown in FIG. 30, current-voltage characteristics thereof are shown in FIG. 31, external quantum efficiency-luminance characteristics thereof are shown in FIG. 32, and emission spectra thereof are shown in FIG. 33. In addition, Table 6 shows the main characteristics of the light-emitting devices at around 1000 cd/m$^2$.

TABLE 6

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting device 3 | 3.6 | 0.43 | 10.7 | 0.14 | 0.13 | 9.5 | 9.4 |
| Comparative light-emitting device 3 | 3.6 | 0.40 | 10.0 | 0.14 | 0.13 | 10.5 | 10.0 |

It was found from FIG. 28 to FIG. 32 and Table 6 that the light-emitting device 3, which is one embodiment of the present invention, was a favorable blue light-emitting device in which the driving voltage was low and the characteristics such as the emission efficiency were equivalent to those of the comparative light-emitting device 3.

Figure 34:
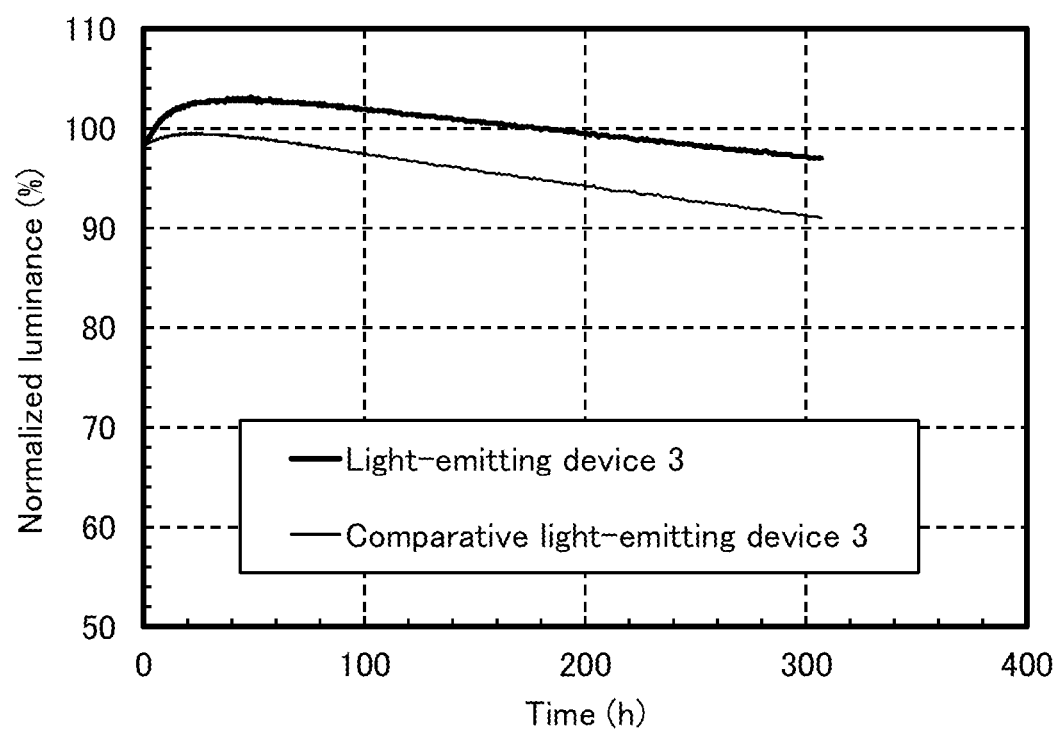
FIG. 34 is normalized luminance-temporal change characteristics of the light-emitting device 3 and the comparative light-emitting device 3.

FIG. 34 is a graph showing a change in luminance over driving time at a current density of 50 mA/cm$^2$. As shown in FIG. 34, the light-emitting device 3, which is a light-emitting device of one embodiment of the present invention, kept 97% or more of the initial luminance even when 300 hours have passed, and thus was found to be a light-emitting device with a favorable lifetime and an extremely small reduction in the luminance over the accumulated driving time.

Device Example 4

In this example, a light-emitting device 4 of one embodiment of the present invention and a comparative light-emitting device 4 will be described. The structural formulae of organic compounds used in the light-emitting device 4 and the comparative light-emitting device 4 are shown below.

[Chemical formulae 14]
(i)
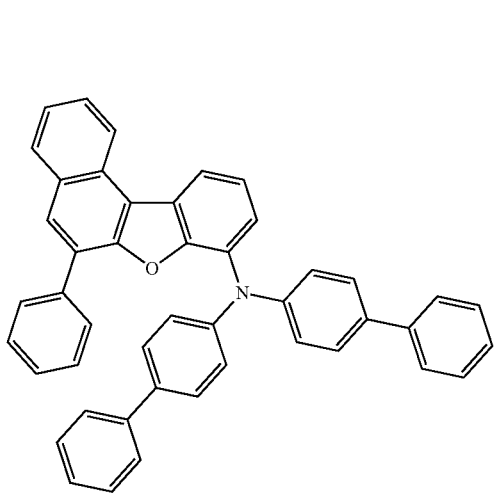
BBABnf
(ii)
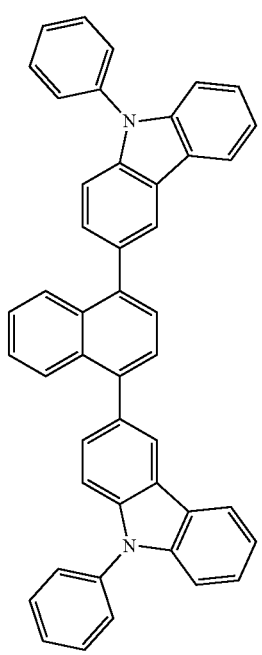
PCzN2
(iii)
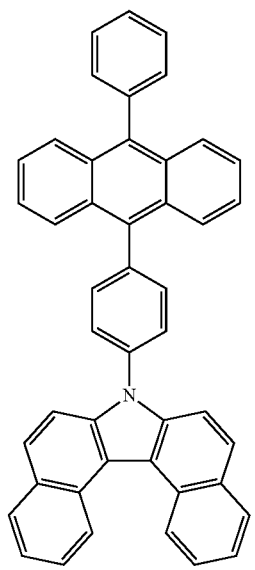
cgDBCzPA
(iv)
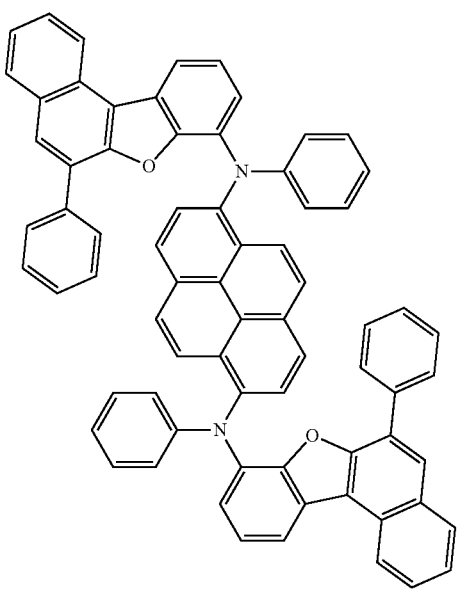
1,6BnfAPrn-03

-continued

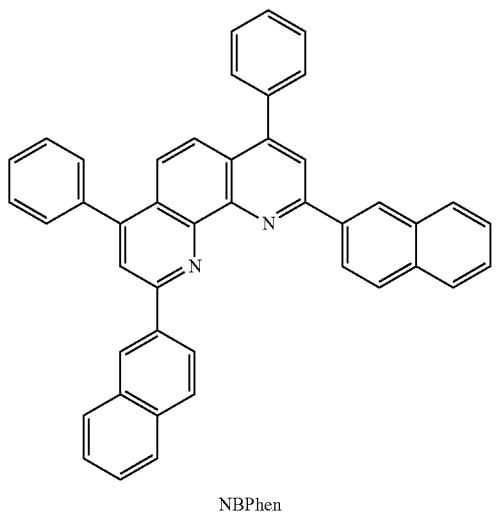

(v)

NBPhen

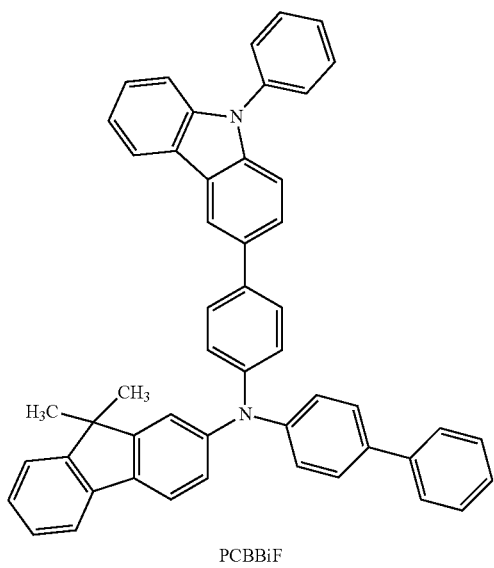

(ix)

PCBBiF (Fabricating Method of Light-Emitting Device 4)

First, a film of indium tin oxide containing silicon oxide (ITSO) was formed over a glass substrate by a sputtering method, so that the first electrode 101 was formed. Note that the thickness was 70 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate provided with the first electrode 101 was fixed to a substrate holder provided in the vacuum evaporation apparatus such that the side on which the first electrode 101 was formed faced downward, and then N,N-bis(4-biphenyl)-6-phenylbenzo[b]naphtho[1,2-d]furan-8-amine (abbreviation: BBABnf) represented by Structural formula (i) shown above and NDP-9 (produced by Analysis Atelier Corporation, material serial No. 1S20170124) were deposited by co-evaporation to a thickness of 10 nm on the first electrode 101 at a weight ratio of 1:0.1 (=BBABnf: NDP-9) by an evaporation method using resistance heating, whereby the hole-injection layer 111 was formed.

Subsequently, over the hole-injection layer 111, BBABnf was deposited as the first hole-transport layer 112-1 by evaporation to a thickness of 20 nm, and then 3,3'-(naphthalene-1,4-diyl)bis(9-phenyl-9H-carbazole) (abbreviation: PCzN2) represented by the structural formula (ii) was deposited as the second hole-transport layer 112-2 by evaporation to a thickness of 10 nm, whereby the hole-transport layer 112 was formed.

Then, 7-[4-(10-phenyl-9-anthryl)phenyl]-7H-dibenzo[c,g]carbazole (abbreviation: cgDBCzPA) represented by the structural formula (iii) and N,N-(pyrene-1,6-diyl)bis[(6,N-diphenylbenzo[b]naphtho[1,2-d]furan)-8-amine] (abbreviation: 1,6BnfAPrn-03) represented by the structural formula (iv) were deposited to a thickness of 25 nm by co-evaporation at a weight ratio of 1:0.03 (=cgDBCzPA:1,6BnfAPrn-03), whereby the light-emitting layer 113 was formed.

After that, over the light-emitting layer 113, cgDBCzPA was deposited by evaporation to a thickness of 15 nm, and then 2,9-bis(naphthalen-2-yl)-4,7-diphenyl-1,10-phenanthroline (abbreviation: NBPhen) represented by the structural formula (v) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the second electrode 102, whereby the light-emitting device 4 of this example was fabricated.

(Fabricating Method of Comparative Light-Emitting Device 4) The comparative light-emitting device 4 was fabricated in a manner similar to that of the light-emitting device 4 except that BBABnf used in the hole-injection layer 111 and the first hole-transport layer 112-1 of the light-emitting device 4 was replaced with N-(1,1'-biphenyl-4-yl)-9,9-dimethyl-N-[4-(9-phenyl-9H-carbazol-3-yl)phenyl]-9H-fluoren-2-amine (abbreviation:PCBBiF) represented by the structural formula (ix).

The device structures of the light-emitting device 4 and the comparative light-emitting device 4 are listed in the following table.

TABLE 7

| | Hole-injection layer | Hole-transport layer | | Light-emitting layer | Electron-transport layer | | Electron-injection layer |
|---|---|---|---|---|---|---|---|
| | | 1 | 2 | | | | |
| | 10 nm | 20 nm | 10 nm | 25 nm | 15 nm | 10 nm | 1 nm |
| Light-emitting device 4 | BBABnf:NDP-9 (1:0.1) | BBABnf | PCzN2 | cgDBCzPA:1,6BnfAPrn-03 (1:0.03) | cgDBCzPA | NBPhen | LiF |
| Comparative light-emitting device 4 | PCBBiF:NDP-9 (1:0.1) | PCBBiF | | | | | |

The light-emitting device 4 and the comparative light-emitting device 4 were each subjected to sealing with a glass substrate (a sealant was applied to surround the device, followed by UV treatment and one-hour heat treatment at 80° C. at the time of sealing) in a glove box in a nitrogen atmosphere so that the light-emitting device is not exposed to the air, and then initial characteristics and reliabilities of these light-emitting devices were measured. Note that the measurement was performed at room temperature.

Figure 35:
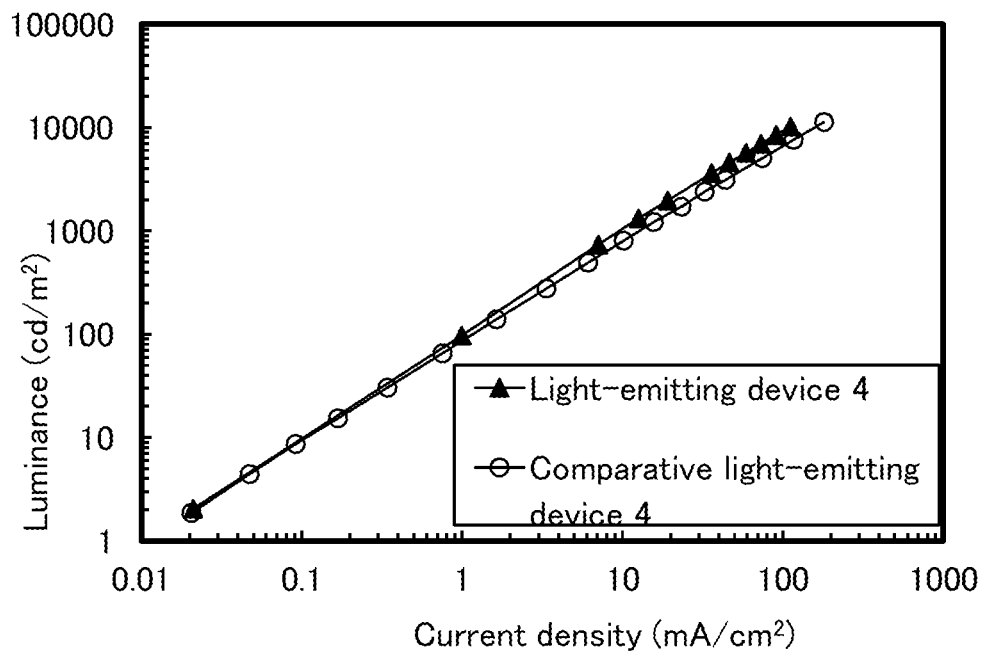
FIG. 35 is luminance-current density characteristics of a light-emitting device 4 and a comparative light-emitting device 4.
Figure 36:
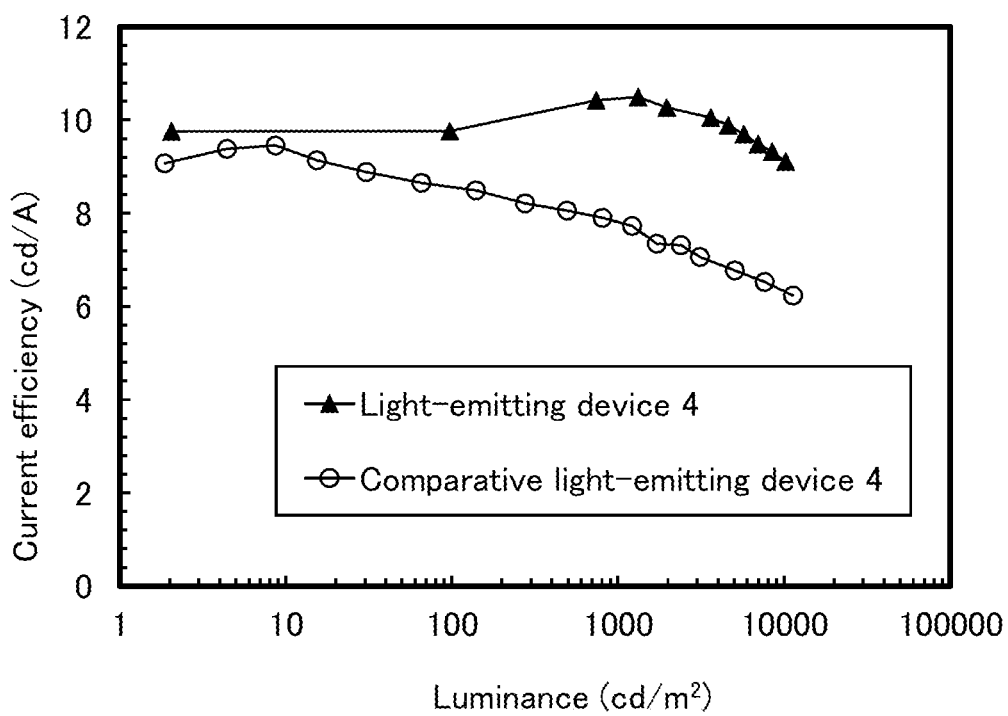
FIG. 36 is current efficiency-luminance characteristics of the light-emitting device 4 and the comparative light-emitting device 4.
Figure 37:
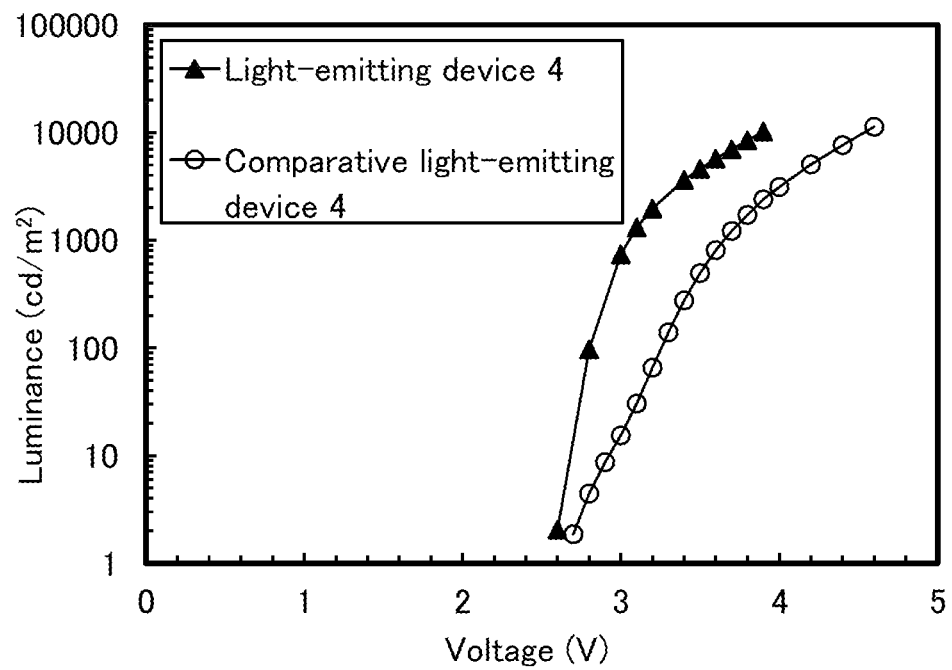
FIG. 37 is luminance-voltage characteristics of the light-emitting device 4 and the comparative light-emitting device 4.
Figure 38:
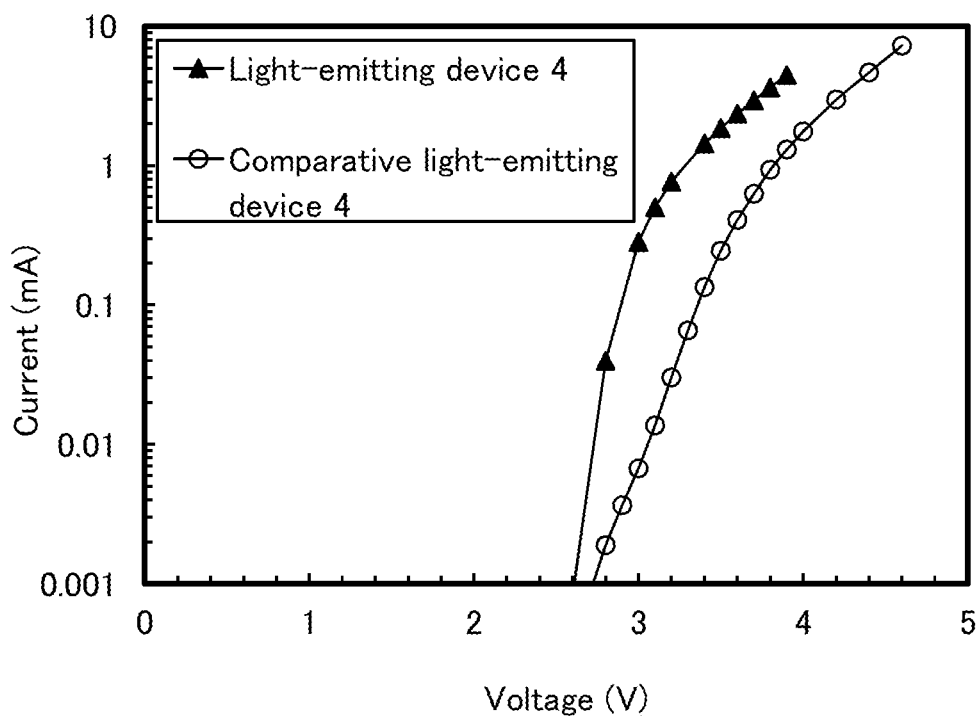
FIG. 38 is current-voltage characteristics of the light-emitting element 4 and the comparative light-emitting element 4.
Figure 39:
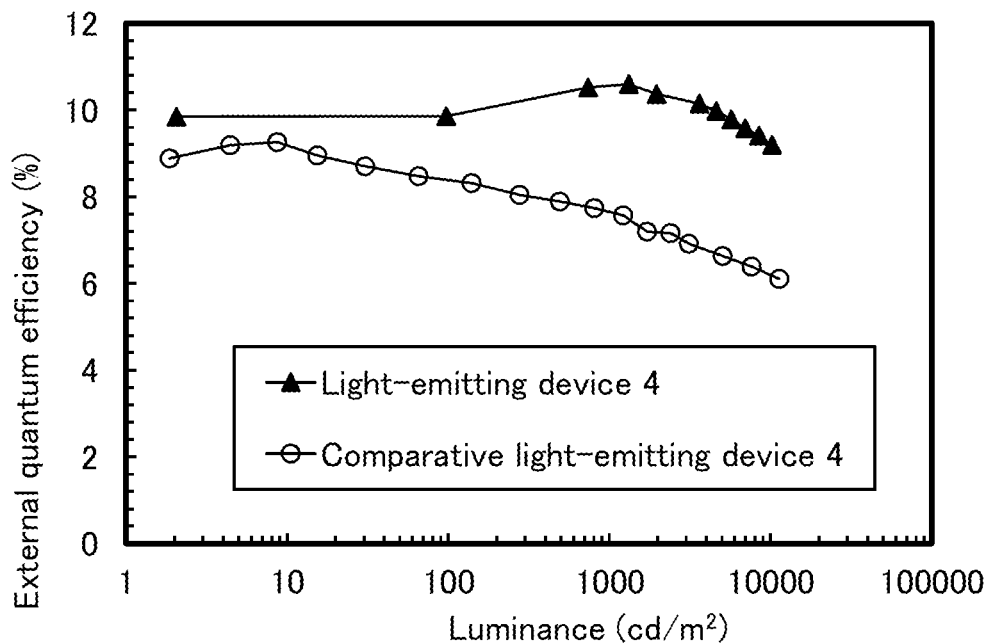
FIG. 39 is external quantum efficiency-luminance characteristics of the light-emitting device 4 and the comparative light-emitting device 4.
Figure 40:
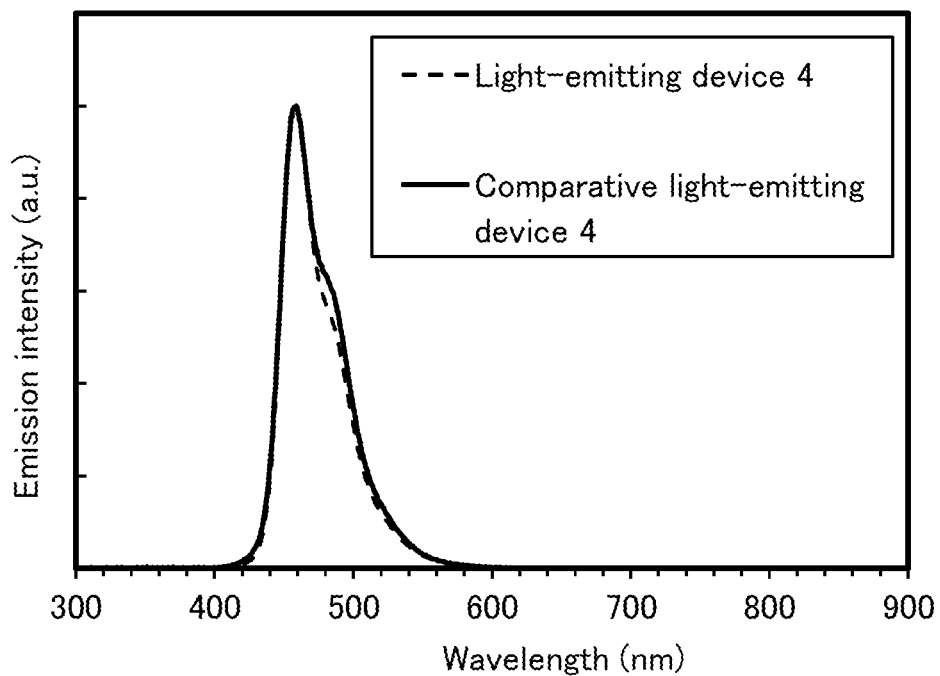
FIG. 40 is emission spectra of the light-emitting device 4 and the comparative light-emitting device 4.

Luminance-current density characteristics of the light-emitting device 4 and the comparative light-emitting device 4 are shown in FIG. 35, current efficiency-luminance characteristics thereof are shown in FIG. 36, luminance-voltage characteristics thereof are shown in FIG. 37, current-voltage characteristics thereof are shown in FIG. 38, external quantum efficiency-luminance characteristics thereof are shown in FIG. 39, and emission spectra thereof are shown in FIG. 40. In addition, Table 8 shows the main characteristics of the light-emitting devices at around 1000 cd/m².

TABLE 8

| | Voltage (V) | Current (mA) | Current density (mA/cm²) | Chromaticity x | Chromaticity y | Current efficiency (cd/A) | External quantum efficiency (%) |
|---|---|---|---|---|---|---|---|
| Light-emitting device 4 | 3.0 | 0.28 | 7.1 | 0.14 | 0.12 | 10.4 | 10.5 |
| Comparative light-emitting device 4 | 3.6 | 0.41 | 10.2 | 0.14 | 0.13 | 7.9 | 7.7 |

According to FIG. 35 to FIG. 39 and Table 8, since the light-emitting device 4, which is one embodiment of the present invention, uses the hole-transport material that has a deeper HOMO level than that of the comparative light-emitting device 4, holes can be injected also into the hole-transport material having a deep HOMO level, such as PCzN2, without any barrier. Thus, it was found that it is a blue light-emitting device that has low driving voltage and favorable emission efficiency.

Figure 41:
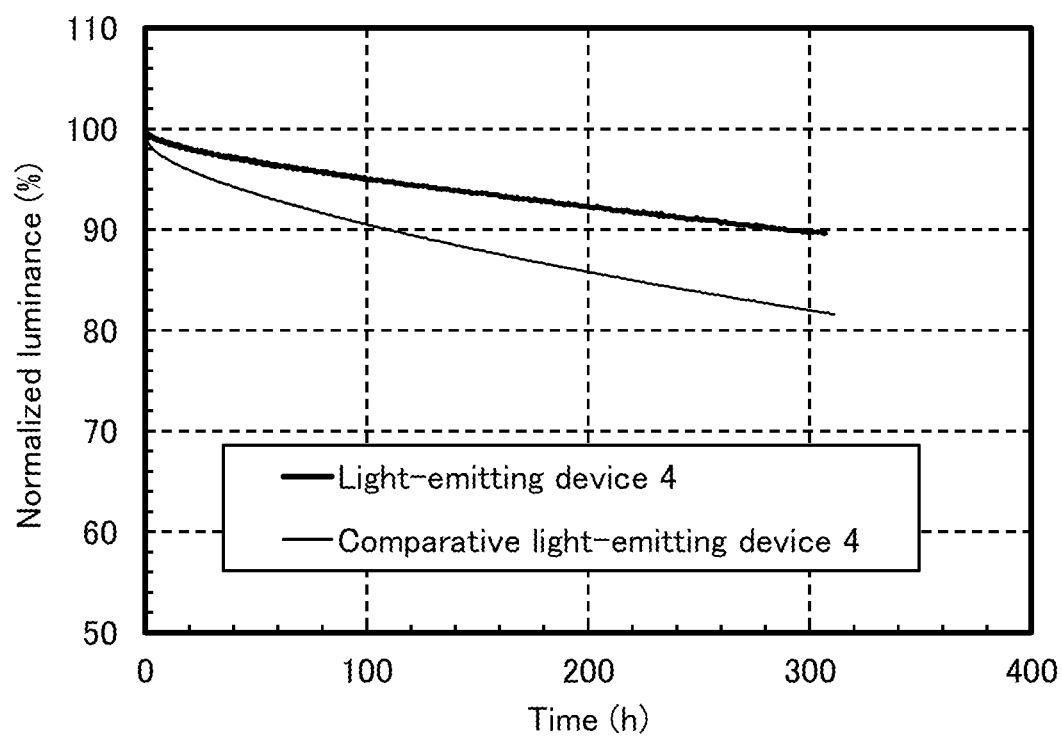
FIG. 41 is normalized luminance-temporal change characteristics of the light-emitting device 4 and the comparative light-emitting device 4.

FIG. 41 is a graph showing a change in luminance over driving time at a current density of 50 mA/cm². As shown in FIG. 41, the light-emitting device 4, which is a light-emitting device of one embodiment of the present invention, was found to be a light-emitting device with a favorable lifetime with a small reduction in luminance over the accumulated driving time.

Device Example 5

In this example, light-emitting devices of one embodiment of the present invention will be described. The structural formulae of organic compounds used in the light-emitting devices of this example are shown below.

[Chemical formulae 15]

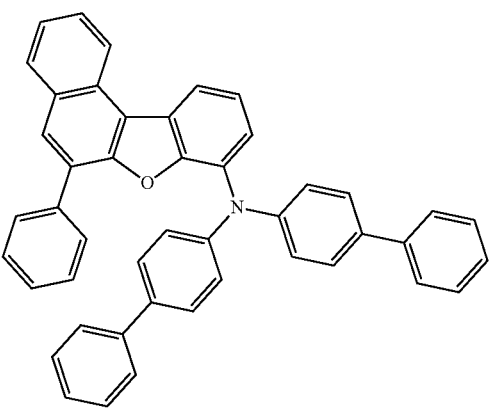

(i)

BBABnf (ii)

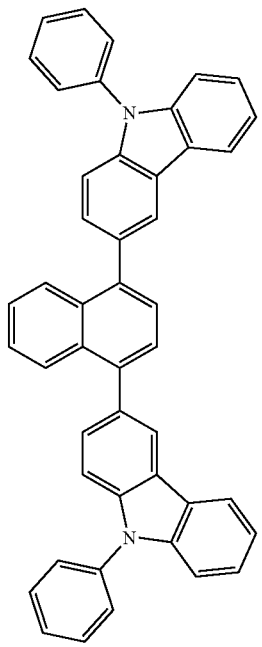

PCzN2

(iii)

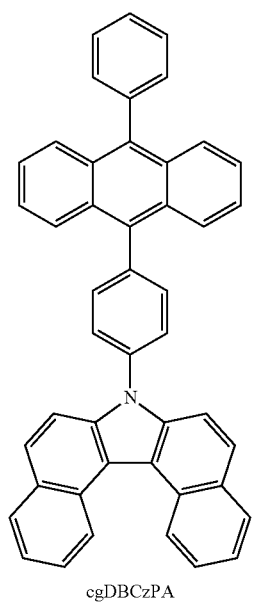

cgDBCzPA (iv)

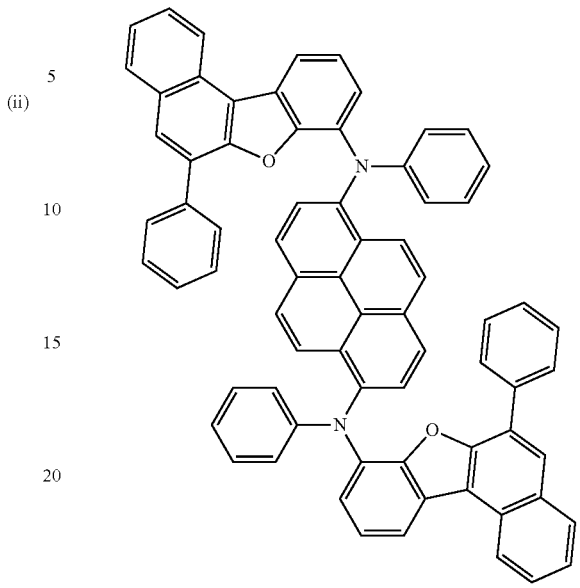

1,6BnfAPrn-03

(v)

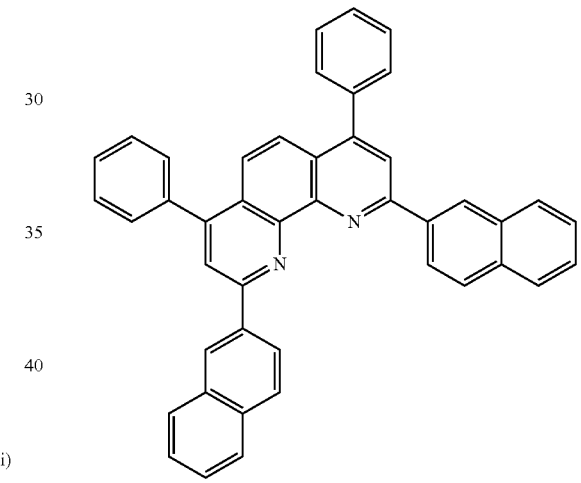

NBPhen (Fabricating Method of Light-Emitting Device 30)

First, a film of indium tin oxide containing silicon oxide (ITSO) was formed over a glass substrate by a sputtering method, so that the first electrode 101 was formed. Note that the thickness was 110 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate provided with the first electrode 101 was fixed to a substrate holder provided in the vacuum evaporation apparatus such that the side on which the first electrode 101 was formed faced downward, and then N,N- bis(4-biphenyl)-6-phenylbenzo[b]naphtho[1,2-d]furan-8-amine (abbreviation: BBABnf) represented by Structural formula (i) shown above and NDP-9 (produced by Analysis Atelier Corporation, material serial No. 1S20170124) were deposited by co-evaporation to a thickness of 10 nm on the first electrode 101 at a weight ratio of 1:0.1 (=BBABnf: NDP-9) by an evaporation method using resistance heating, whereby the hole-injection layer 111 was formed.

Subsequently, over the hole-injection layer 111, BBABnf was deposited as the first hole-transport layer 112-1 by evaporation to a thickness of 10 nm, and then 3,3'-(naphthalene-1,4-diyl)bis(9-phenyl-9H-carbazole) (abbreviation: PCzN2) represented by the structural formula (ii) was deposited as the second hole-transport layer 112-2 by evaporation to a thickness of 30 nm, whereby the hole-transport layer 112 was formed.

Then, 7-[4-(10-phenyl-9-anthryl)phenyl]-7H-dibenzo[c,g]carbazole (abbreviation: cgDBCzPA) represented by the structural formula (iii) and N,N-(pyrene-1,6-diyl)bis[(6,N-diphenylbenzo[b]naphtho[1,2-d]furan)-8-amine] (abbreviation: 1,6BnfAPrn-03) represented by the structural formula (iv) were deposited to a thickness of 25 nm by co-evaporation at a weight ratio of 1:0.03 (=cgDBCzPA:1,6BnfAPrn-03), whereby the light-emitting layer 113 was formed.

After that, over the light-emitting layer 113, cgDBCzPA was deposited by evaporation to a thickness of 15 nm, and then 2,9-bis(naphthalen-2-yl)-4,7-diphenyl-1,10-phenanthroline (abbreviation: NBPhen) represented by the structural formula (v) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the second electrode 102, whereby a light-emitting device 30 of this example was fabricated.

(Fabricating Method of Light-Emitting Device 50) A light-emitting device 50 was fabricated in a manner similar to that of the light-emitting device 30 except that the thickness of the second hole-transport layer 112-2 in the light-emitting device 30 was 50 nm.

(Fabricating Method of Light-Emitting Device 70)

A light-emitting device 70 was fabricated in a manner similar to that of the light-emitting element 30 except that the thickness of the second hole-transport layer 112-2 in the light-emitting device 30 was 70 nm.

(Fabricating Method of Light-Emitting Device 80)

A light-emitting device 80 was fabricated in a manner similar to that of the light-emitting element 30 except that the thickness of the second hole-transport layer 112-2 in the light-emitting device 30 was 80 nm.

(Fabricating Method of Light-Emitting Device 90)

A light-emitting device 90 was fabricated in a manner similar to that of the light-emitting element 30 except that the thickness of the second hole-transport layer 112-2 in the light-emitting device 30 was 90 nm.

(Fabricating Method of Light-Emitting Device 100)

A light-emitting device 100 was fabricated in a manner similar to that of the light-emitting element 30 except that the thickness of the second hole-transport layer 112-2 in the light-emitting device 30 was 100 nm.

(Fabricating Method of Light-Emitting Device 110)

A light-emitting device 110 was fabricated in a manner similar to that of the light-emitting element 30 except that the thickness of the second hole-transport layer 112-2 in the light-emitting device 30 was 110 nm.

(Fabricating Method of Light-Emitting Device 130)

A light-emitting device 130 was fabricated in a manner similar to that of the light-emitting element 30 except that the thickness of the second hole-transport layer 112-2 in the light-emitting device 30 was 130 nm.

The light-emitting device 30 to the light-emitting device 130 were each subjected to sealing with a glass substrate (a sealant was applied to surround the device, followed by UV treatment and one-hour heat treatment at 80° C. at the time of sealing) in a glove box in a nitrogen atmosphere so that the light-emitting device is not exposed to the air, and then the reliabilities of these light-emitting devices were measured. Note that the measurement was performed at room temperature.

Figure 42:
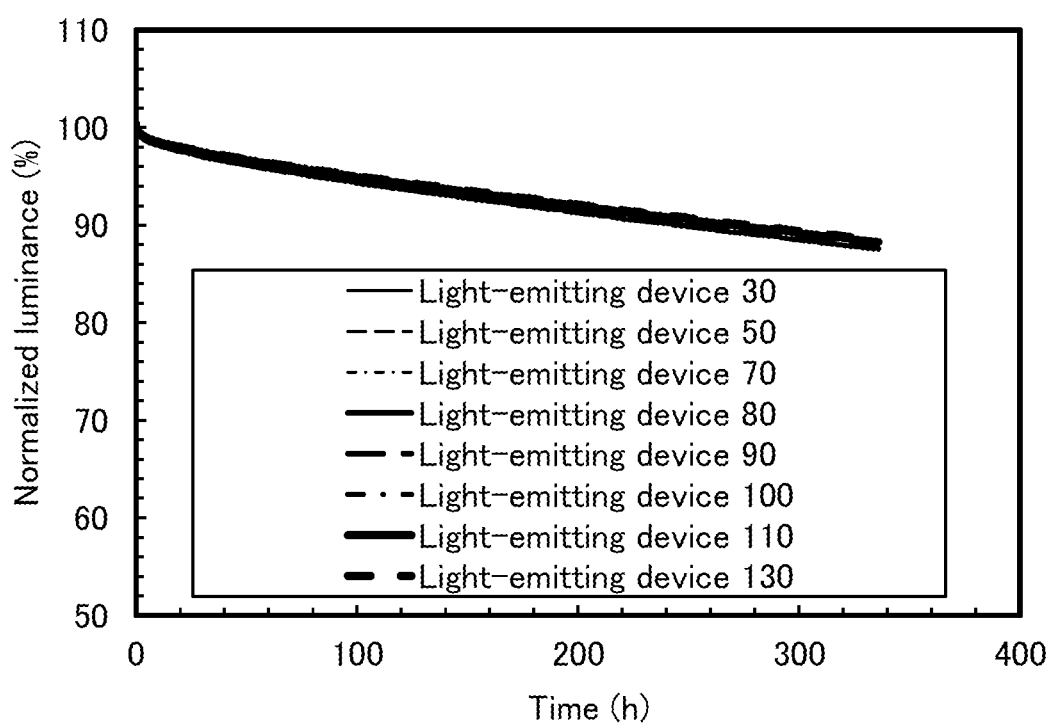
FIG. 42 is normalized luminance-temporal change characteristics of light-emitting devices and comparative light-emitting devices.

FIG. 42 is a graph showing a change in luminance over driving time of the light-emitting device 30 to the light-emitting device 130 at a current density of 50 mA/cm². As shown in FIG. 42, it was found that the light-emitting device of one embodiment of the present invention was a light-emitting device the lifetime of which was not influenced by an increase in the thickness of the second hole-transport layer 112-2. Thus, it was found that the light-emitting device of the present invention was a light-emitting device in which the optical path was able to be easily adjusted by changing the thickness of the second hole-transport layer 112-2.

Synthesis Example 1

In this synthesis example, a method for synthesizing 4-[4'-(carbazol-9-yl)biphenyl-4-yl]-4',4''-diphenyltriphenylamine (abbreviation: YGTBi1BP), a substance that can be used as the organic compound of the hole-injection layer 111 in the light-emitting device of one embodiment of the present invention, will be described in detail. The structural formula of YGTBi1BP is shown below.

[Chemical formula 16]

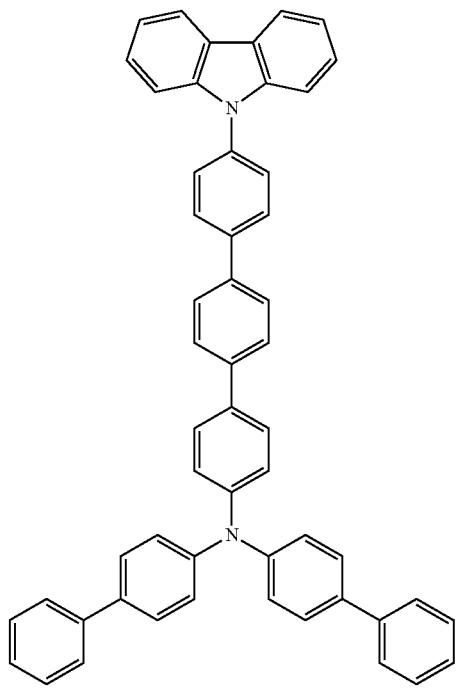

After 10 g (20 mmol) of N,N-di(4-biphenyl)-4-(4,4,5,5-tetramethyl-1,3,2-dioxaborolane-2-yl)aniline, 8.0 g (20 mmol) of 9-(4'-bromobiphenyl-4-yl)carbazole, 0.12 g (0.40 mmol) of tri(ortho-tolyl)phosphine, 30 mL of an aqueous solution of potassium carbonate (potassium carbonate 5.5 g, 40 mmol), 120 mL of toluene, and 40 mL of ethanol were put into a 200 mL three-neck flask equipped with a reflux pipe and mixed and the mixture was degassed under reduced pressure, the air in the system was replaced with nitrogen. This mixture was heated at 60° C., and 44 mg (0.20 mmol) of palladium(II) acetate was added to the mixture. The mixture was stirred at 90° C. for 6 hours. The obtained mixture was subjected to suction filtration. Water was added to the obtained filtrate to separate an aqueous layer and an organic layer, and the aqueous layer was subjected to extraction with toluene. The obtained extracted solution and the organic layer were combined, washed with water and a saturated saline solution, and dried with magnesium sulfate. This mixture was subjected to gravity filtration and the obtained filtrate was concentrated to give a pale brown solid. This solid was purified by high performance liquid chromatography (HPLC) (mobile phase: chloroform) to give 10 g of a target pale yellow solid in a yield of 70%.

By a train sublimation method, 10 g of the obtained solid was sublimated and purified. In the sublimation purification, the solid was heated at 365° C. for 15 hours under a pressure of 3.4 Pa with a flow of argon at 15 mL/min. After the sublimation purification, 8.7 g of a target pale yellow solid was obtained at a collection rate of 87%. The synthesis scheme of this synthesis is shown below.

[Chemical formula 17]

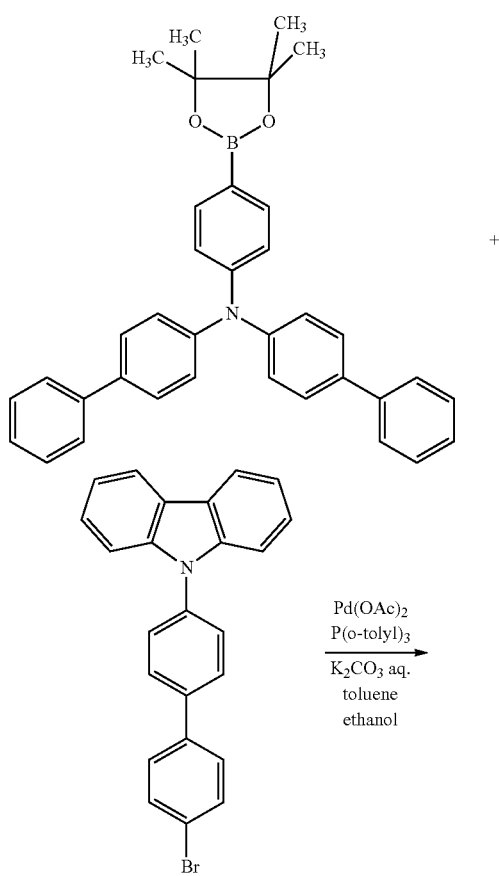

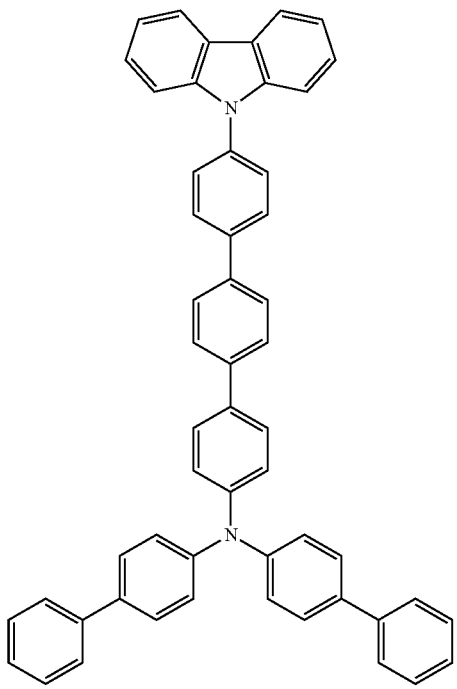

Figure 43A:
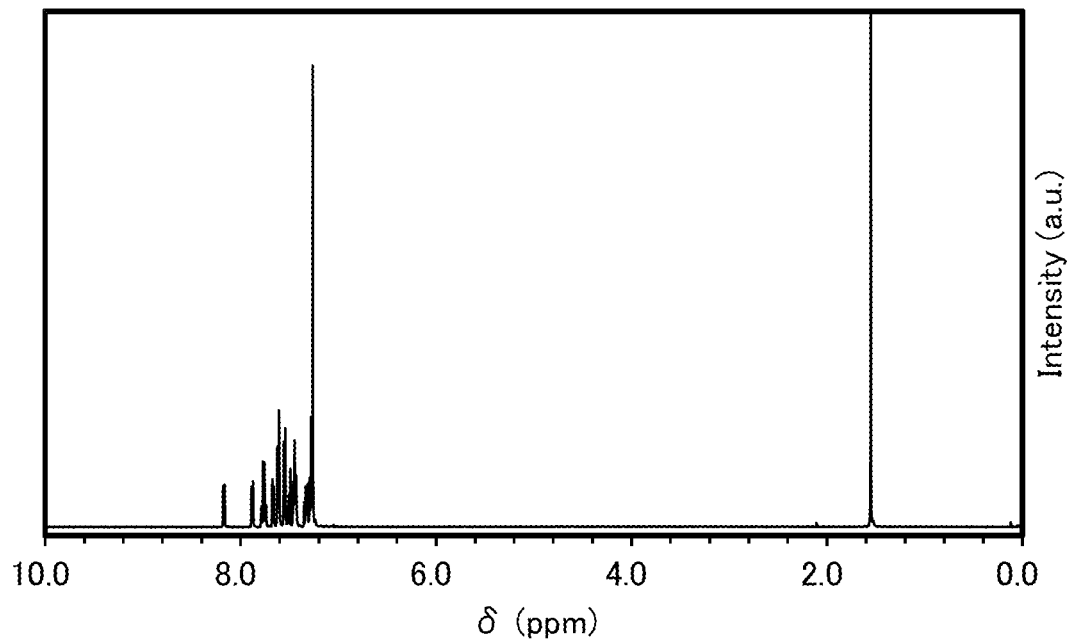
FIGS. 43A and 43B are $^1$H NMR charts of YGTBi1BP.
Figure 43B:
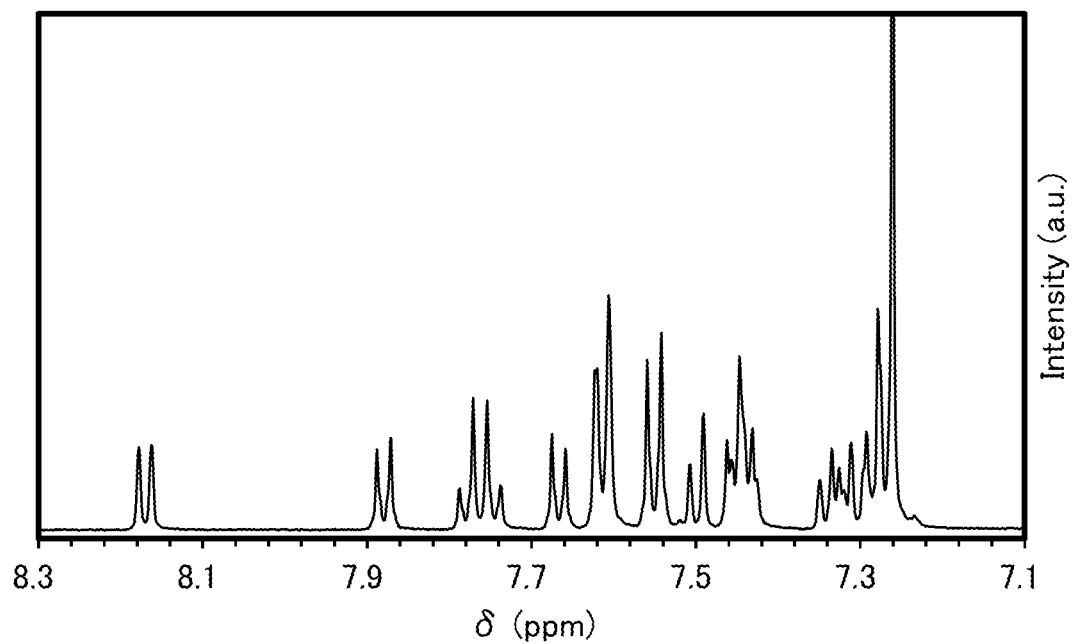

The numeric data of $^1$H-NMR of the obtained solid are shown below and $^1$H NMR charts are shown in FIGS. 43(A) and 43(B). Note that FIG. 43(B) is a chart showing an enlarged view of the range of 7.1 ppm to 8.3 ppm in FIG. 43(A). These indicate that YGTBi1BP was obtained in this synthesis example.

$^1$H NMR (chloroform-d, 500 MHz): δ=8.17 (d, J=7.5 Hz, 2H), 7.88 (d, J=8.5 Hz, 2H), 7.78 (d, J=, 8.0 Hz, 2H), 7.74 (d, J=8.0 Hz, 2H), 7.66 (d, J=8.0 Hz, 2H), 7.62-7.61 (m, 6H), 7.55 (d, J=8.5 Hz, 4H), 7.50 (d, J=8.0 Hz, 2H), 7.46-7.43 (m, 6H), 7.35-7.28 (m, 10H).

Next, the ultraviolet-visible absorption spectra (hereinafter, simply referred to as "absorption spectra") and emission spectra of a toluene solution and a solid thin film of YGTBi1BP were measured. The solid thin film was formed over a quartz substrate by a vacuum evaporation method. For the measurement of the absorption spectra, UV-visible spectrophotometers (solution: V-550 manufactured by JASCO Corporation, thin film: U-4100 manufactured by Hitachi High-Technologies Corporation) were used. Note that the absorption spectrum of the solution was calculated by subtracting the absorption spectrum measured by putting only toluene in a quartz cell, and the absorption spectrum of the thin film was calculated from an absorbance ($-\log_{10}$[% T/(100-% R)]) obtained from a transmittance and a reflectance of the substrate and the thin film. Note that % T represents transmittance and % R represents reflectance. The emission spectra were measured using a fluorescence spectrophotometer (FS920 manufactured by Hamamatsu Photonics K.K.).

Figure 44:
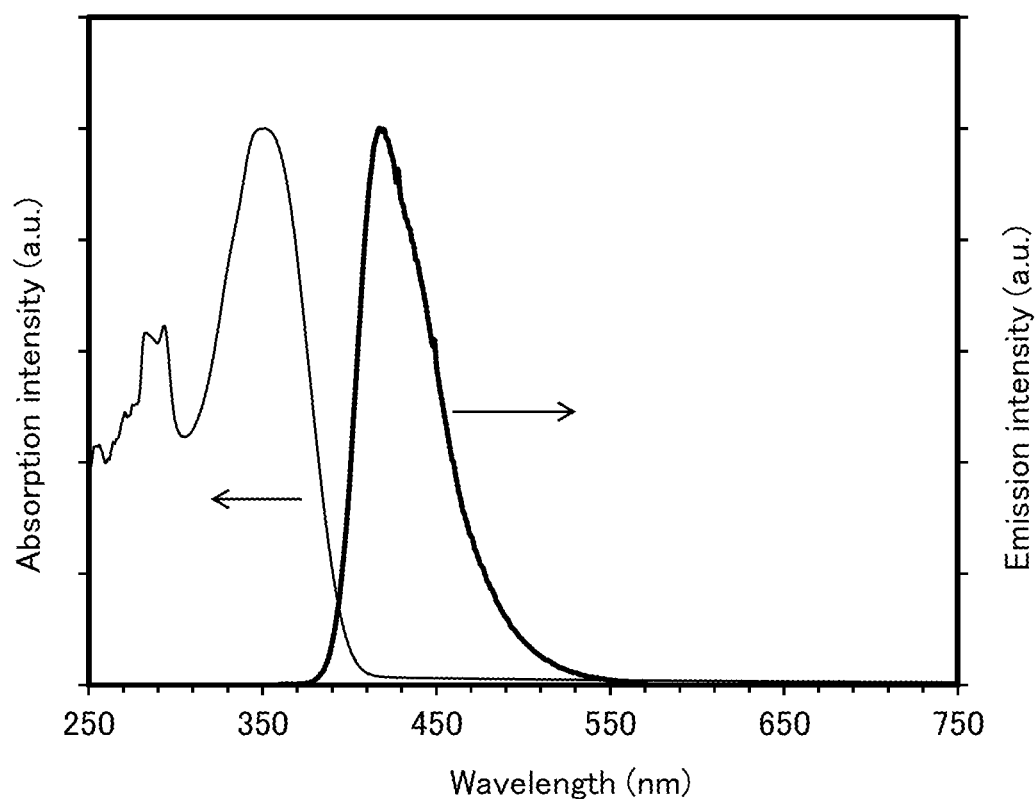
FIG. 44 is an absorption spectrum and an emission spectrum of YGTBi1BP in a toluene solution.
Figure 45:
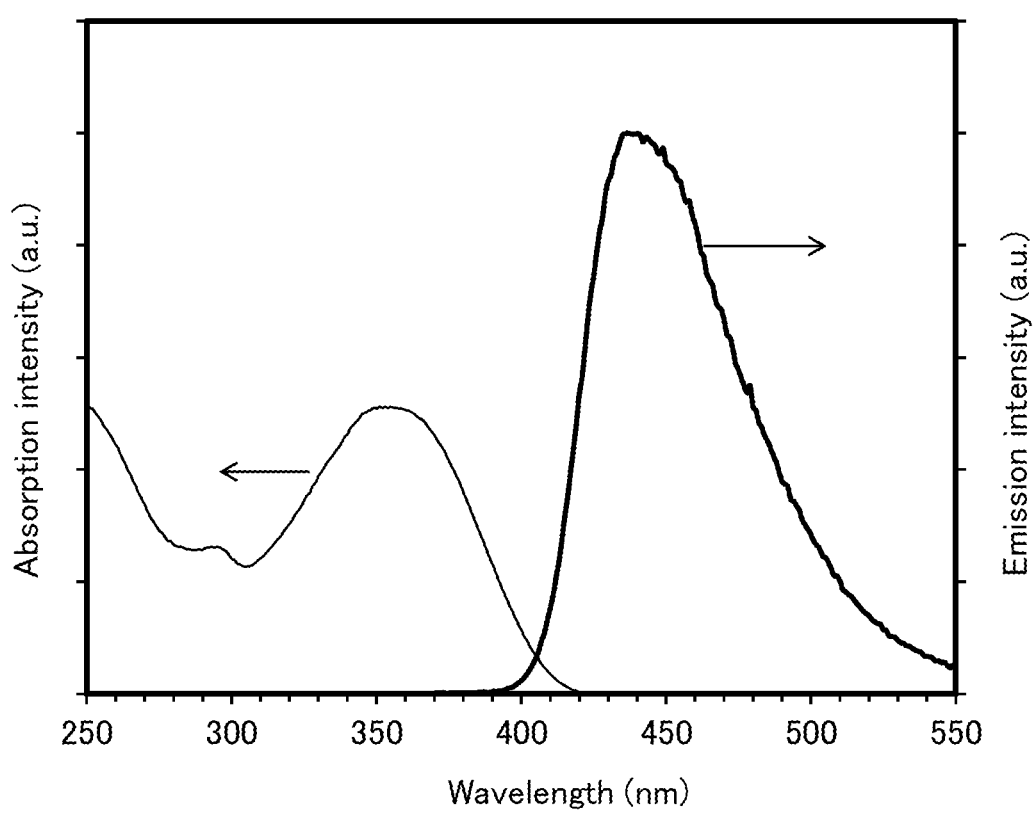
FIG. 45 is an absorption spectrum and an emission spectrum of YGTBi1BP in a thin film state.

FIG. 44 shows the obtained measurement results of the absorption spectrum and the emission spectrum of the toluene solution. FIG. 45 shows the measurement results of the absorption spectrum and the emission spectrum of the solid thin film.

According to the results of FIG. 44, the toluene solution of YGTBi1BP exhibited an absorption peak at around 351 nm and an emission wavelength peak at 417 nm (excitation wavelength: 350 nm). According to the results of FIG. 45, the solid thin film of YGTBi1BP exhibited absorption peaks at around 356 nm, 296 nm, and 245 nm and an emission wavelength peak at around 437 nm (excitation wavelength: 360 nm).

The HOMO level and the LUMO level of YGTBi1BP were calculated on the basis of a cyclic voltammetry (CV) measurement. The calculation method is shown below.

An electrochemical analyzer (ALS model 600A or 600C, manufactured by BAS Inc.) was used as a measurement apparatus. To prepare a solution for the CV measurement, dehydrated dimethylformamide (DMF) (produced by Sigma-Aldrich Inc., 99.8%, catalog No. 22705-6) was used as a solvent, tetra-n-butylammonium perchlorate (n-Bu$_4$NClO$_4$) (produced by Tokyo Chemical Industry Co., Ltd., catalog No. T0836) as a supporting electrolyte was dissolved at a concentration of 100 mmol/L, and the object to be measured was also dissolved at a concentration of 2 mmol/L.

A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag+ electrode (RE7 reference electrode for non-aqueous solvent, manufactured by BAS Inc.) was used as a reference electrode. Note that the measurement was performed at room temperature (20° C. to 25° C.).

In addition, the scan speed in the CV measurement was fixed to 0.1 V/sec, and an oxidation potential Ea [V] and a reduction potential Ec [V] with respect to the reference electrode were measured. Ea was an intermediate potential of an oxidation-reduction wave, and Ec was an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]−4.94−Ea and LUMO level [eV]−4.94−Ec.

As a result, the HOMO level of YGTBi1BP was found to be −5.47 eV Furthermore, the LUMO level was found to be −2.34 eV.

When CV measurement was repeated 100 times and the peak intensities of an oxidation-reduction wave at the 100th cycle and an oxidation-reduction wave at the first cycle were compared, 83% was kept in the Ea measurement and 83% was kept in the Ec measurement, which showed that YGTBi1BP was an organic compound having extremely high resistance to oxidation and reduction.

Note that YGTBi1BP can be synthesized under conditions similar to those of the above synthesis scheme, in which the borane compound is replaced with 4'-bromotri(4-biphenylyl)amine and halide is replaced with 4-(9H-carbazol-9-yl)phenylboronic acid, as shown in the following synthesis scheme.

[Chemical formula 18]

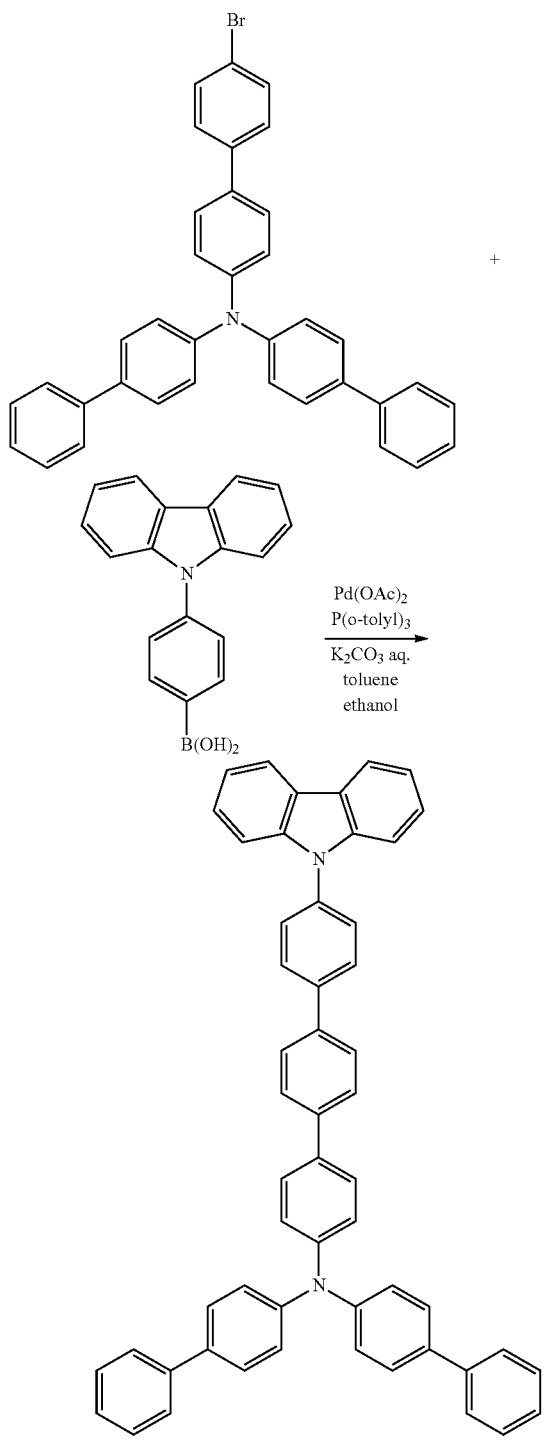

Synthesis Example 2

In this synthesis example, a method for synthesizing 4-[4'-(carbazol-9-yl)biphenyl-4-yl]-4'-(2-naphthyl)-4''-phenyltriphenylamine (abbreviation: YGTBiβNB), a substance that can be used as the organic compound of the hole-injection layer 111 in the light-emitting device of one embodiment of the present invention, will be described. The structural formula of YGTBiβNB is shown below.

[Chemical formula 19]

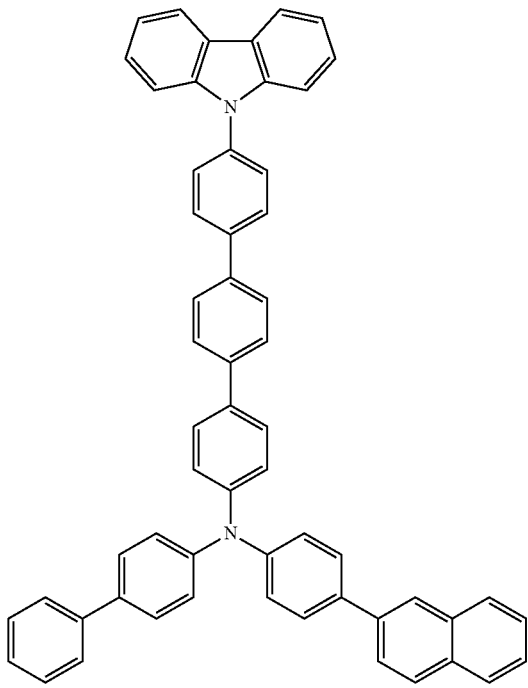

Step 1: Synthesis of N-[4-(4,4,5,5-tetramethyl-1,3,2-dioxaborolane-2-yl)phenyl]-(1,1'-biphenyl)-4-amine>

Into a 200 mL three-neck flask equipped with a reflux pipe were put 6.4 g (20 mmol) of N-(4-bromophenyl)-4-biphenylamine, 5.1 g (20 mmol) of bis(pinacolato)diboron, 3.9 g (40 mmol) of potassium acetate, and 100 mL of 1,4-dioxane, the mixture was degassed under reduced pressure, and then the air in the system was replaced with nitrogen. To the obtained mixture was added 0.16 g (0.20 mmol) of [1,1'-bis(diphenylphosphino)ferrocene]palladium(II) dichloride dichloromethane adduct, and the resulting mixture was refluxed for 7 hours. Water was added to the obtained mixture to separate an aqueous layer and an organic layer, and then the aqueous layer was subjected to extraction with toluene. The obtained extracted solution and the organic layer were combined, washed with water and a saturated saline solution, and dried with magnesium sulfate. This mixture was subjected to gravity filtration and the obtained filtrate was concentrated to give a brown solid. The obtained solid was recrystallized with ethanol to give 3.2 g of a pale brown solid in a yield of 43%. The synthesis scheme of Step 1 is shown below.

[Chemical formula 20]

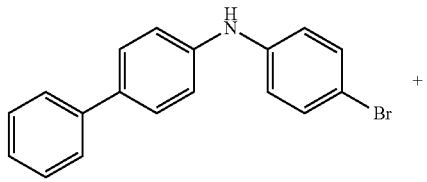

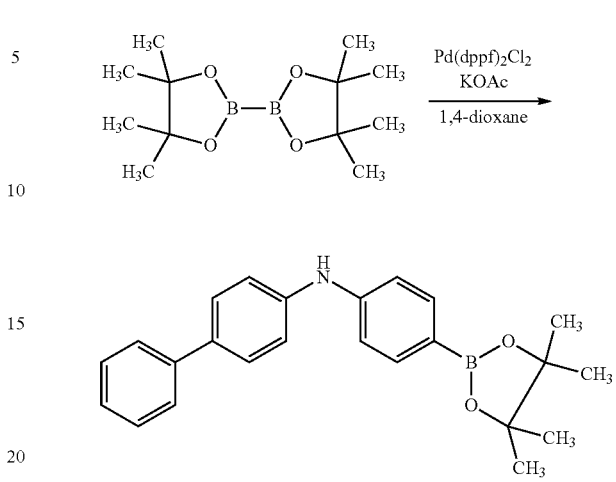

The numeric data of $^1$H NMR of the obtained solid are shown below. These indicate that N-[4-(4,4,5,5-tetramethyl-1,3,2-dioxaborolan-2-yl)phenyl]-(1,1'-biphenyl)-4-amine, which was the target compound, was obtained in this synthesis step.

$^1$H NMR (chloroform-d, 500 MHz): δ=7.72 (d, J=9.0 Hz, 2H), 7.57 (d, J=8.0 Hz, 2H), 7.53 (d, J=8.5 Hz, 2H), 7.42 (t, J=7.5 Hz, 2H), 7.31 (t, J=7.5 Hz, 1H), 7.20 (d, J=8.5 Hz, 2H), 7.06 (d, J=8.5 Hz, 2H), 5.93 (s, 1H), 1.34 (s, 12H).

Step 2: Synthesis of 4-[4'-(Carbazol-9-Yl)Biphenyl-4-Yl]-4'-Biphenylamine

Into a 200 mL three-neck flask equipped with a reflux pipe were put 3.2 g (8.6 mmol) of N-[4-(4,4,5,5-tetramethyl-1,3,2-dioxaborolan-2-yl)phenyl]-(1,1'-biphenyl)-4-amine, which was obtained in Step 1, 3.4 g (8.6 mmol) of 9-(4'-bromo-4-biphenylyl)carbazole, 52 mg (0.17 mmol) of tri(ortho-tolyl)phosphine, 10 mL of an aqueous solution of potassium carbonate (2.0 mol/L), 60 mL of toluene, and 25 mL of ethanol, the mixture was degassed under reduced pressure, and then the air in the system was replaced with nitrogen. To the obtained mixture was added 24 mg (0.11 mmol) of palladium(II) acetate, and the mixture was refluxed for 11 hours. After the reflux, the precipitated solid was collected by suction filtration and the obtained sold was washed with toluene, ethanol, and water to give 4.6 g of a target gray solid in a yield of 93%. The synthesis scheme of Step 2 is shown below.

[Chemical formula 21]

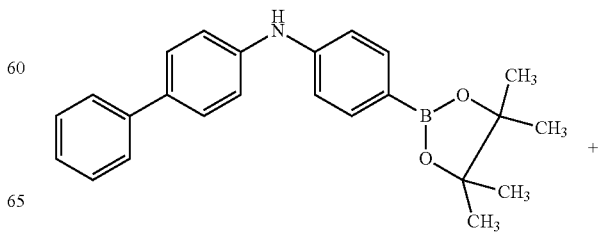

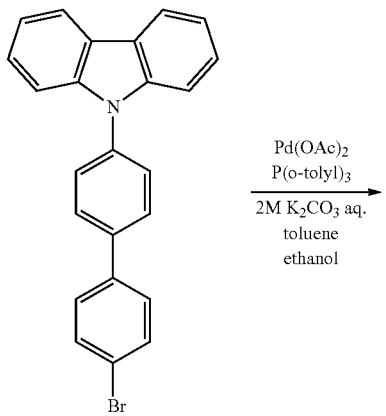

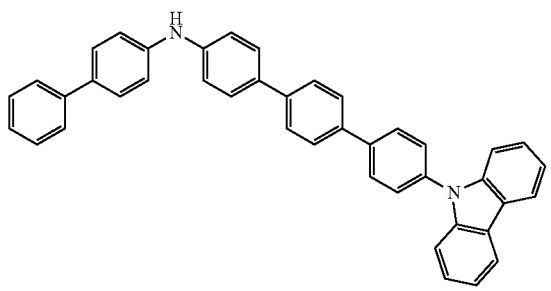

Figure 46A:
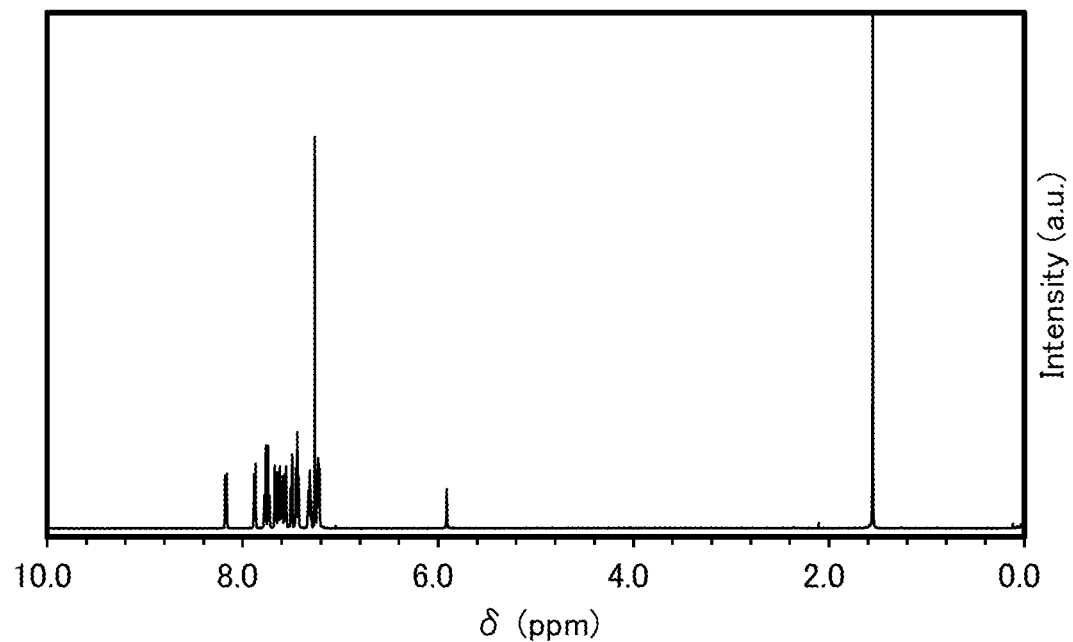
FIGS. 46A and 46B are $^1$H NMR charts of 4-[4'-(carbazol-9-yl)biphenyl-4-yl]-4'-biphenylamine.
Figure 46B:
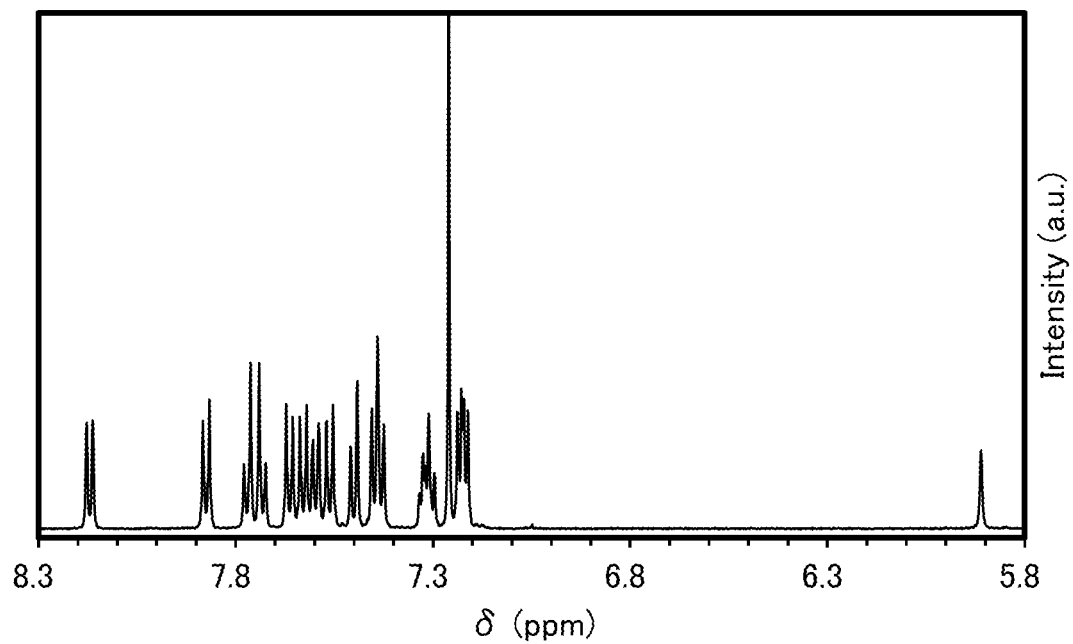

The numeric data of ¹H-NMR of the obtained solid are shown below and ¹H-NMR charts are shown in FIGS. 46(A) and 46(B). Note that FIG. 46(B) is a chart showing an enlarged view of the range of 5.8 ppm to 8.3 ppm in FIG. 46(A). These indicate that 4-[4'-(carbazol-9-yl)biphenyl-4-yl]-4'-biphenylamine, which was the target compound, was obtained in this synthesis step.

¹H NMR (chloroform-d, 500 MHz): δ=8.17 (d, J=7.5 Hz, 2H), 7.87 (d, J=8.5 Hz, 2H), 7.75 (dd, J=9.5, 8.0 Hz, 4H), 7.66 (d, J=8.0 Hz, 2H), 7.63 (d, J=8.5 Hz, 2H), 7.59 (d, J=7.0 Hz, 2H), 7.56 (d, J=8.0 Hz, 4H), 7.50 (d, J=8.5 Hz, 2H), 7.45-7.42 (m, 4H), 7.33-7.29 (m, 3H), 7.24-7.21 (m, 4H), 5.91 (s, 1H).

Step 3: Synthesis of 4-[4'-(carbazol-9-yl)biphenyl-4-yl]-4'-(2-naphthyl)-4''-phenyltriphenylamine (abbreviation: YGTBiβNB)

Into a 200 mL three-neck flask equipped with a reflux pipe were put 0.85 g (1.5 mmol) of 4-[4'-(carbazol-9-yl)biphenyl-4-yl]-4'-biphenylamine, which was obtained in Step 2, 0.43 g (1.5 mmol) of 2-(4-bromophenyl)naphthalene, 11 mg (30 μmol) of di-tert-butyl(1-methyl-2,2-diphenylcyclopropyl)phosphine (product name: cBRIDP (registered trademark)), 0.29 g (3.0 mmol) of sodium tert-butoxide, and 100 mL of toluene, the mixture was degassed under reduced pressure, and then the air in the system was replaced with nitrogen. To the obtained mixture was added 8 mg (15 μmol) of bis(dibenzylideneacetone)palladium(0), and the mixture was refluxed for 8 hours. Water was added to the obtained mixture to separate an aqueous layer and an organic layer, and then the aqueous layer was subjected to extraction with toluene. The obtained extracted solution and the organic layer were combined, washed with water and a saturated saline solution, and dried with magnesium sulfate. This mixture was subjected to gravity filtration and the obtained filtrate was concentrated to give 0.83 g of a brown solid. The synthesis scheme of Step 3 is shown below.

[Chemical formula 22]

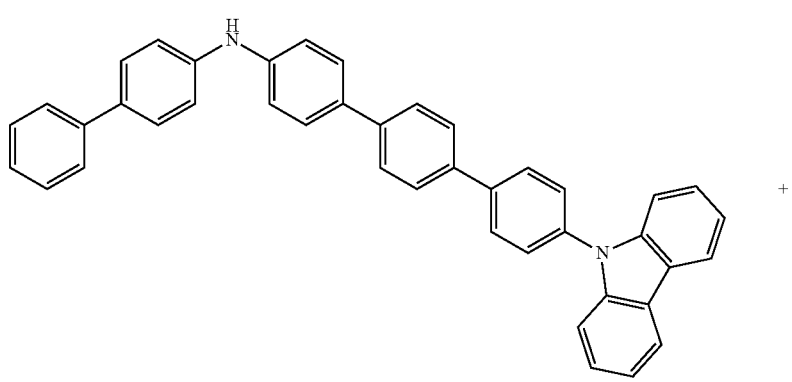

+

-continued

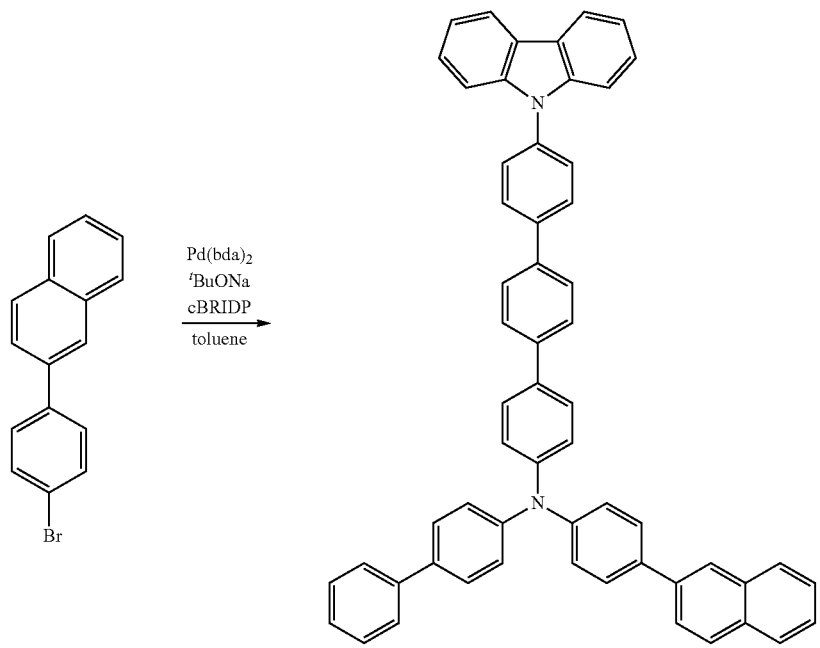

By a train sublimation method, 0.83 g of the obtained solid was sublimated and purified. In the sublimation purification, the solid was heated at 345° C. for 15 hours under a pressure of 3.8 Pa with a flow of argon at 15 mL/min. After the sublimation purification, 0.49 g of a target pale yellow solid was obtained at a collection rate of 59%.

Figure 47A:
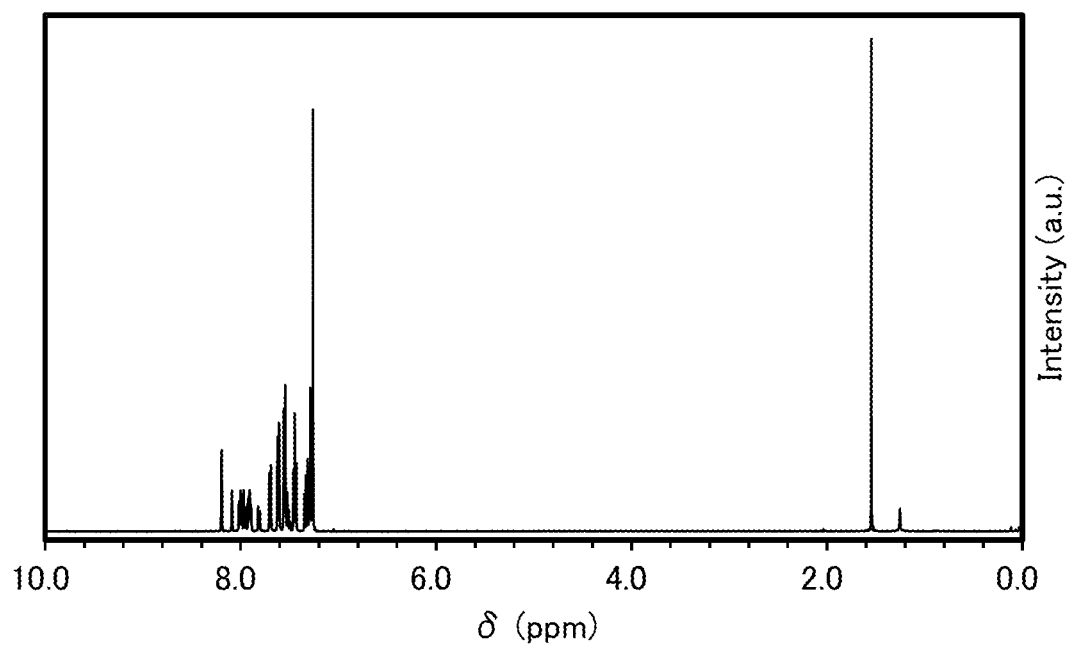
FIGS. 47A and 47B are $^1$H NMR charts of YGTBiβNB.
Figure 47B:
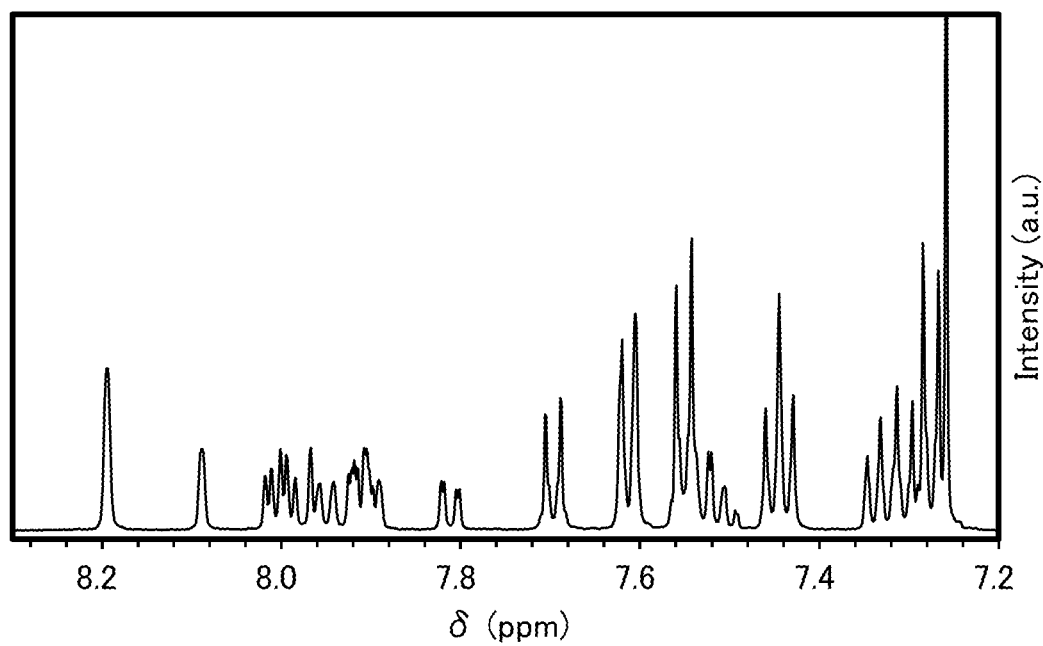

The numeric data of $^1$H NMR of the obtained solid are shown below and $^1$H NMR charts are shown in FIGS. 47(A) and 47(B). Note that FIG. 47(B) is a chart showing an enlarged view of the range of 7.2 ppm to 8.3 ppm in FIG. 47(A). These indicate that YGTBiβNB, which was the target compound, was obtained in this synthesis example.

$^1$H NMR (chloroform-d, 500 MHz): δ=8.17 (d, J=8.0 Hz, 2H), 8.05 (d, J=1.0 Hz, 1H), 7.93-7.86 (m, 5H), 7.79-7.75 (m, 5H), 7.67 (t, J=8.0 Hz, 4H), 7.63-7.61 (m, 4H), 7.56 (d, J=8.5 Hz, 2H), 7.52-7.42 (m, 8H), 7.35-7.28 (m, 9H).

Next, absorption spectra and emission spectra of a toluene solution and a solid thin film of YGTBiβNB were measured. The measurement method, apparatus, and conditions are the same as those of Synthesis example 1; therefore, repeated description will be omitted.

Figure 48:
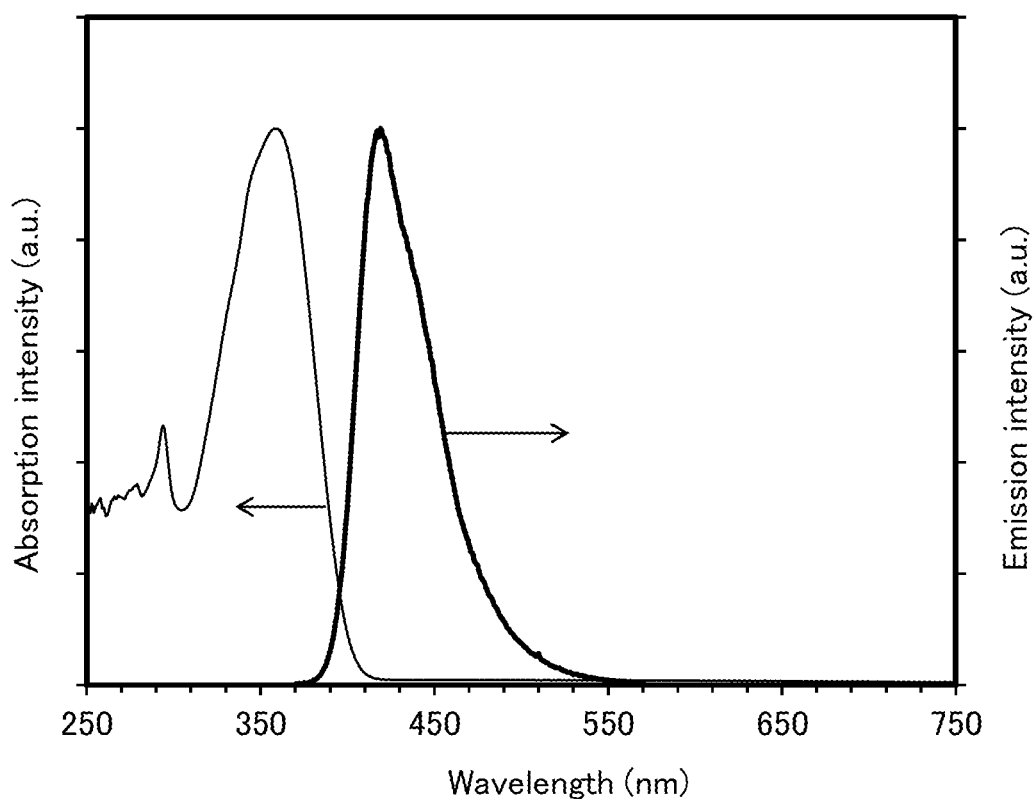
FIG. 48 is an absorption spectrum and an emission spectrum of YGTBiβNB in a toluene solution.
Figure 49:
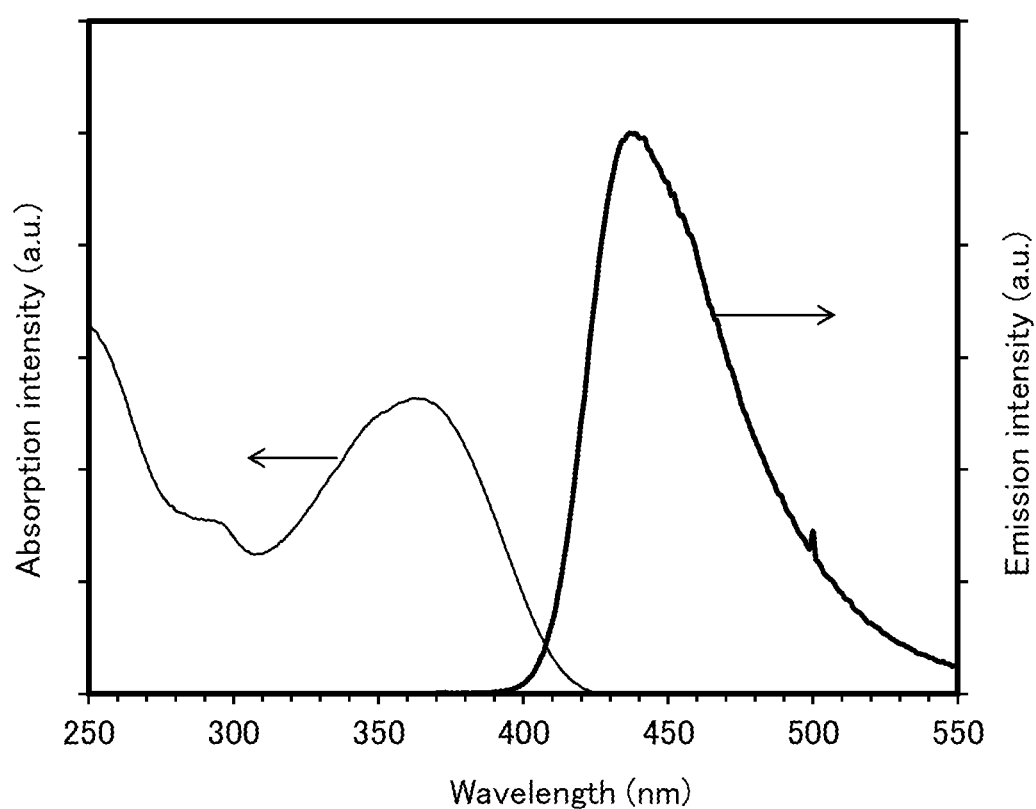
FIG. 49 is an absorption spectrum and an emission spectrum of YGTBiβNB in a thin film state.

FIG. 48 shows the obtained measurement results of the absorption spectrum and the emission spectrum of the toluene solution. FIG. 49 shows the measurement results of the absorption spectrum and the emission spectrum of the solid thin film.

According to the results of FIG. 48, the toluene solution of YGTBiβNB exhibited an absorption peak at around 359 nm and an emission wavelength peak at 419 nm (excitation wavelength: 350 nm). According to the results of FIG. 49, the solid thin film of YGTBiβNB exhibited absorption peaks at around 365 nm, 295 nm, and 245 nm and an emission wavelength peak at around 437 nm (excitation wavelength: 360 nm).

The HOMO level and the LUMO level of YGTBiβNB were calculated on the basis of a cyclic voltammetry (CV) measurement. The calculation method is similar to that described in Synthesis example 1.

As a result, the HOMO level of YGTBiβNB was found to be −5.47 eV. Furthermore, the LUMO level was found to be −2.35 eV.

When CV measurement was repeated 100 times and the peak intensities of an oxidation-reduction wave at the 100th cycle and an oxidation-reduction wave at the first cycle were compared, 85% of the peak intensity was kept in the Ea measurement and 95% of the peak intensity was kept in the Ec measurement, which showed that YGTBiβNB had extremely high resistance to oxidation and reduction.

Synthesis Example 3

In this synthesis example, a method for synthesizing 4,4'-diphenyl-4''-(9-phenyl-9H-fluoren-9-yl)triphenylamine (abbreviation: BBAFLP), a substance that can be used as the organic compound of the hole-injection layer 111 in the light-emitting device of one embodiment of the present invention, will be described. The structure of BBAFLP is shown below.

[Chemical formula 23]

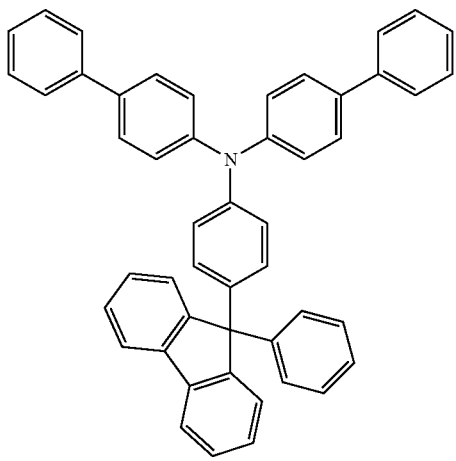

Into a 100 mL three-neck flask were put 1.62 g (5.03 mmol) of bis(4-biphenylyl)amine, 2.00 g (5.03 mmol) of 9-(4-bromophenyl)-9-phenylfluoren, 0.97 g (10.1 mmol) of sodium tert-butoxide, 29 mg (0.050 mmol) of bis(dibenzylideneacetone)palladium(0), 31 mg (0.10 mmol) of tris(o-tolyl)phosphine, and 25 mL of toluene. The mixture was degassed by being stirred while the pressure was reduced, and the air in the flask was replaced with nitrogen. This mixture was stirred under a nitrogen stream at 110° C. for 5.5 hours. After this mixture was cooled to room temperature, 25 ml of toluene was added, heating was performed again so that the precipitated solid was dissolved, and purification was performed with Celite/alumina/Florisil/Celite. The obtained filtrate was concentrated, and then recrystallization with ethyl acetate was performed to give 2.61 g of a target white solid in a yield of 81%. The synthesis scheme of the above synthesis method is shown below.

[Chemical formula 24]

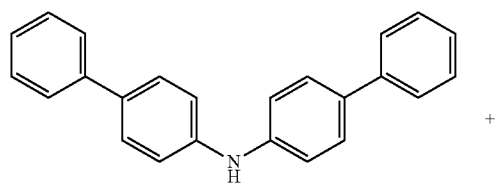

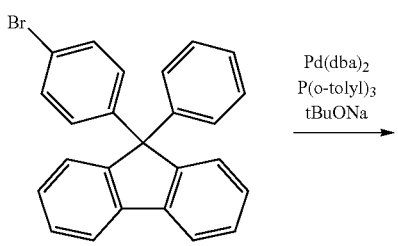

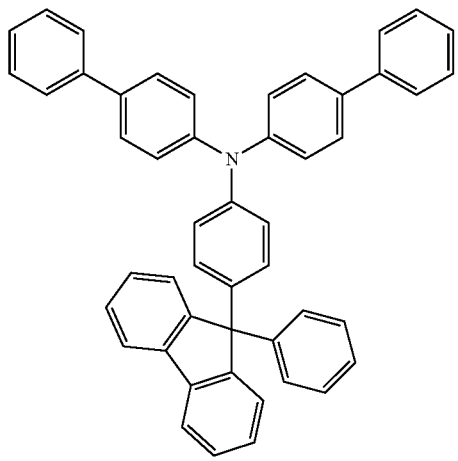

By the train sublimation method, 2.53 g of the obtained white solid was sublimated and purified. The sublimation purification was performed by heating at 275° C. under the conditions where the pressure was 2.4 Pa and the argon flow rate was 10 mL/min. After the purification by sublimation, 1.29 g of a white solid of BBAFLP was obtained at a collection rate of 51%.

Figure 50A:
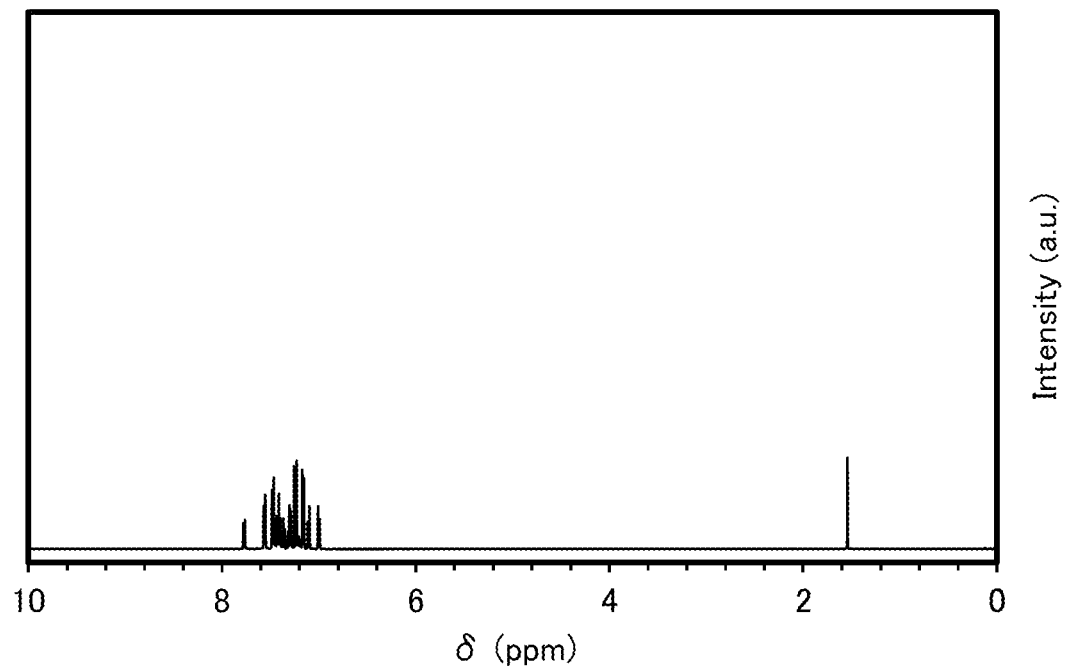
FIGS. 50A and 50B are $^1$H NMR charts of BBAFLP.
Figure 50B:
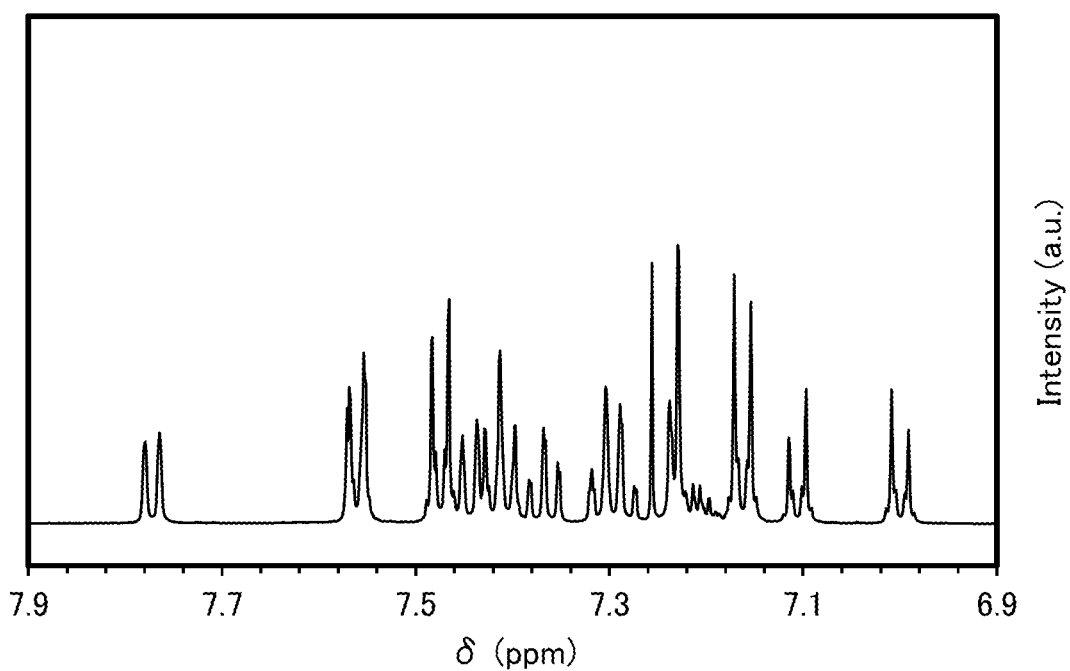

Analysis results by nuclear magnetic resonance spectroscopy (H NMR) of the obtained white solid are shown below. In addition, $^1$H NMR charts are shown in FIGS. 50(A) and 50(B). Note that FIG. 50(B) is a chart showing an enlarged view of the range of 6.9 ppm to 7.9 ppm in FIG. 50(A). The results show that BBAFLP was obtained in this synthesis example.

$^1$H NMR (CDCl$_3$, 500 MHz): δ=7.00 (d, J=8.6 Hz, 2H), δ=7.11 (d, J=9.2 Hz, 2H), δ=7.16 (d, J=8.6 Hz, 4H), δ=7.20-7.24 (m, 5H), δ=7.29 (q, J=13.2 Hz, 7.5 Hz, 4H), δ=7.37 (ddd, J=7.5 Hz, 1.1 Hz, 2H), δ=7.41-7.49 (m, 10H), δ=7.56 (d, J=8.1 Hz, 4H), δ=7.77 (d, J=7.5 Hz, 2H).

Synthesis Example 4

In this synthesis example, a method for synthesizing 4-[4-(9-phenyl-9H-fluoren-9-yl)phenyl]-4',4''-diphenyltriphenylamine (abbreviation: BBAFLBi), a substance that can be used as the organic compound of the hole-injection layer 111 in the light-emitting device of one embodiment of the present invention, will be described. Note that the structural formula of BBAFLBi is shown below.

Step 1: Synthesis of 4-(9-phenyl-9H-fluoren-9-yl)Phenylboronic Acid

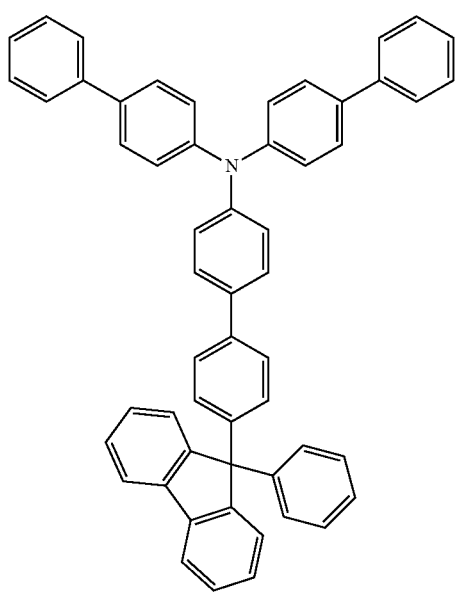

Into a 500 mL three-neck flask was put 15.89 g (40 mmol) of 9-(4-bromophenyl)-9-phenyl-9H-fluorene, the mixture was degassed under reduced pressure, and the air in the flask was replaced with nitrogen. In the flask, 200 ml of dehydrated tetrahydrofuran (abbreviation: THF) was added. After the mixture was cooled to approximately −78° C. while being stirred, 30 mL (48 mmol) of an n-butyllithium hexane solution at 1.59 mol/L was dripped to the mixture, and then the temperature of the mixture was raised to −40° C. and stirred for 1 hour. After that, 50 ml of dehydrated THE was added and the mixture was cooled to approximately −78° C. again, and then 6.4 ml (57 mmol) of trimethylborate was dripped. The temperature of the mixture was raised to room temperature and stirred for 16 hours. Then, 25 ml of water and 30 ml of iN hydrochloric acid were added to the solution, the solution was stirred, an organic layer and an aqueous layer were separated, and the obtained organic layer was washed with 100 ml of a saturated solution of sodium bicarbonate once and washed with 100 ml of a saturated saline solution once. After the washing, the solution was dried with magnesium sulfate, concentrated, and recrystallized with toluene to give 10.1 g of a white solid in a yield of 70%. The synthesis scheme of Step 1 is shown below.

[Chemical formula 26]

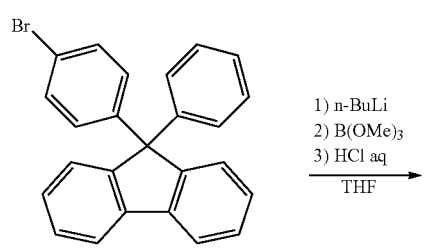

Step 2: Synthesis of BBAFLBi

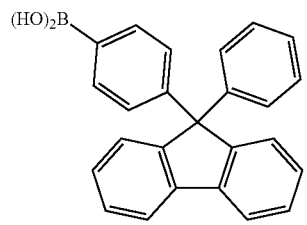

Into a 200 mL three-neck flask were added 2.53 g (7 mmol) of 4-(9-phenyl-9H-fluoren-9-yl)phenylboronic acid, 3.34 g (7 mmol) of 4-bromo-4',4"-diphenyltriphenylamine, 2.90 g (7 mmol) of potassium carbonate, 70 mL of toluene, 12.5 mL of ethanol, and 10.5 mL of water. The mixture was degassed by being stirred while the pressure was reduced, and the air in the flask was replaced with nitrogen. To this mixture were added 15.7 mg (0.07 mmol) of palladium acetate and 42.2 mg (0.07 mmol) of tris(o-tolyl)phosphine, and stirring was performed under a nitrogen stream at 85° C. for 6 hours. After the mixture was cooled to room temperature, the precipitated solid was separated by filtration, the obtained solution (filtrate) was washed with 100 ml of water twice and washed with 50 ml of saturated brine once, and then, moisture was removed with magnesium sulfate. The obtained solid and the solid precipitated after the reaction and separated by filtration were combined, 300 ml of toluene was added, heating was performed so that the solid was dissolved, and purification was performed with Celite/alumina/Florisil/Celite. The obtained filtrate was concentrated, ethanol was added, and recrystallization was performed to give 4.54 g of a white solid in a yield of 89%. The synthesis scheme of Step 2 is shown below.

[Chemical formula 27]

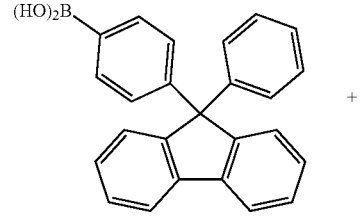

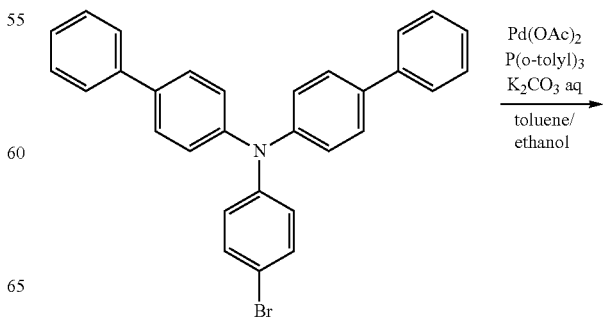

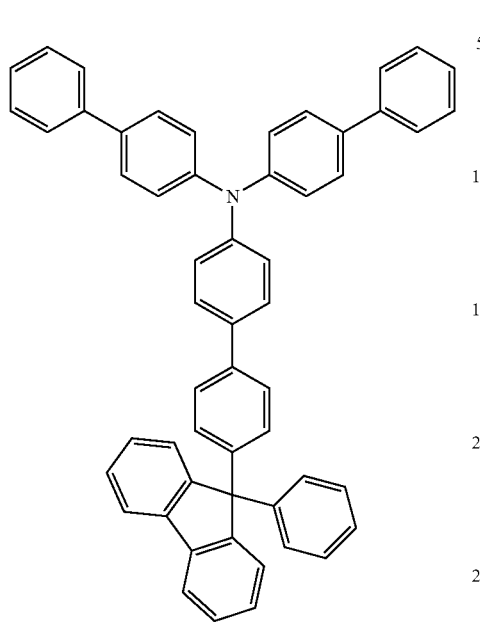

By the train sublimation method, 4.39 g of the obtained white solid was sublimated and purified. The sublimation purification was performed by heating at 320° C. under the conditions where the pressure was 3.5 Pa and the argon flow rate was 15 mL/min. After the purification by sublimation, 2.73 g of a white solid of BBAFLBi was obtained at a collection rate of 62%.

Analysis results by nuclear magnetic resonance spectroscopy ($^1$H NMR) of the obtained white solid are shown below. In addition, $^1$H NMR charts are shown in FIGS. 51(A) and 51(B). Note that FIG. 51(B) is a chart showing an enlarged view of the range of 6.9 ppm to 7.9 ppm in FIG. 51(A). The results show that BBAFLBi was obtained in this synthesis example.

$^1$H NMR (CDCl$_3$, 500 MHz): δ=7.17-7.28 (m, 13H), δ=7.31 (dd, J=12.6 Hz, 7.4 Hz, 4H), δ=7.37 (dd, J=7.5 Hz, 1.1 Hz, 4H), δ=7.40-7.47 (m, 10H), δ=7.51 (d, J=8.6 Hz, 4H) δ=7.58 (d, J=8.1 Hz, 4H) 6=7.78 (d, J=7.4 Hz, 2H).

Synthesis Example 5

In this synthesis example, a method for synthesizing 4,4'-diphenyl-3"-(9-phenylfluoren-9-yl)triphenylamine (abbreviation: mBBAFLP), a substance that can be used as the organic compound of the hole-injection layer 111 in the light-emitting device of one embodiment of the present invention, will be described. Note that the structure of mBBAFLP is shown below.

[Chemical formula 28]

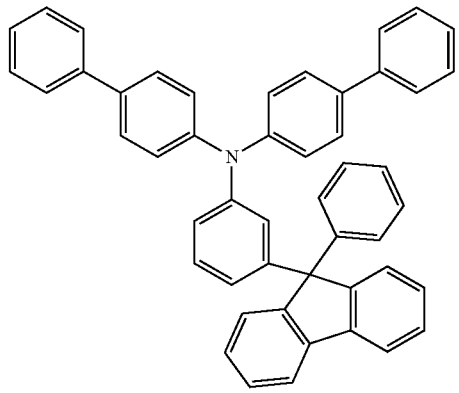

Into a 300 mL three-neck flask were put 2.67 g (8.31 mmol) of bis(4-biphenylyl)amine, 3.00 g (7.55 mmol) of 9-(3-bromophenyl)-9-phenylfluoren, 1.88 g (16.8 mmol) of sodium tert-butoxide, and 40 mL of toluene. The mixture was degassed by being stirred while the pressure was reduced, and the air in the flask was replaced with nitrogen. To this mixture were added 0.2 mL of tri-tert-butylphosphine (10 wt % hexane solution) and 45 mg (0.078 mmol) of bis(dibenzylideneacetone)palladium(0) and then, stirring was performed for 3 hours at 110° C. under a nitrogen stream. After the stirring, the mixture was cooled to room temperature, and a solid was separated by filtration. The obtained filtrate was subjected to suction filtration through Celite and Florisil. The filtrate was concentrated, ethanol was added, and recrystallization was performed. The obtained white crystal was purified by silica gel column chromatography (developing solvent: toluene) to give 4.58 g of a target white solid in a yield of 95%. The synthesis scheme of the above synthesis method is shown below.

[Chemical formula 29]

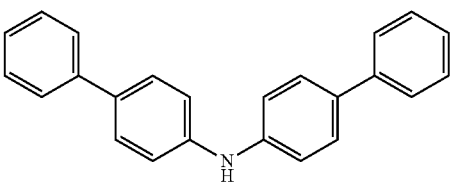

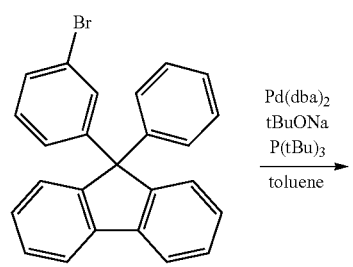

-continued

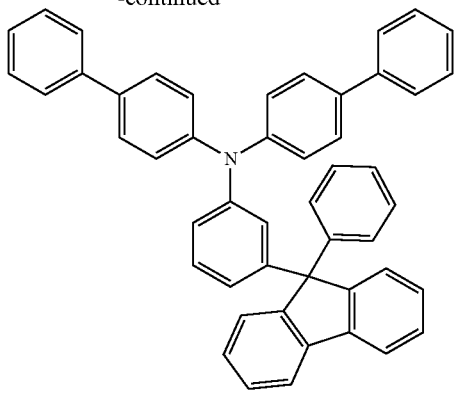

By the train sublimation method, 2.00 g of the obtained white solid was sublimated and purified. The sublimation purification was performed by heating at 270° C. under the conditions where the pressure was 2.9 Pa and the argon flow rate was 5 mL/min. After the purification by sublimation, 1.87 g of a white solid of mBBAFLP was obtained at a collection rate of 94%.

Figure 52A:
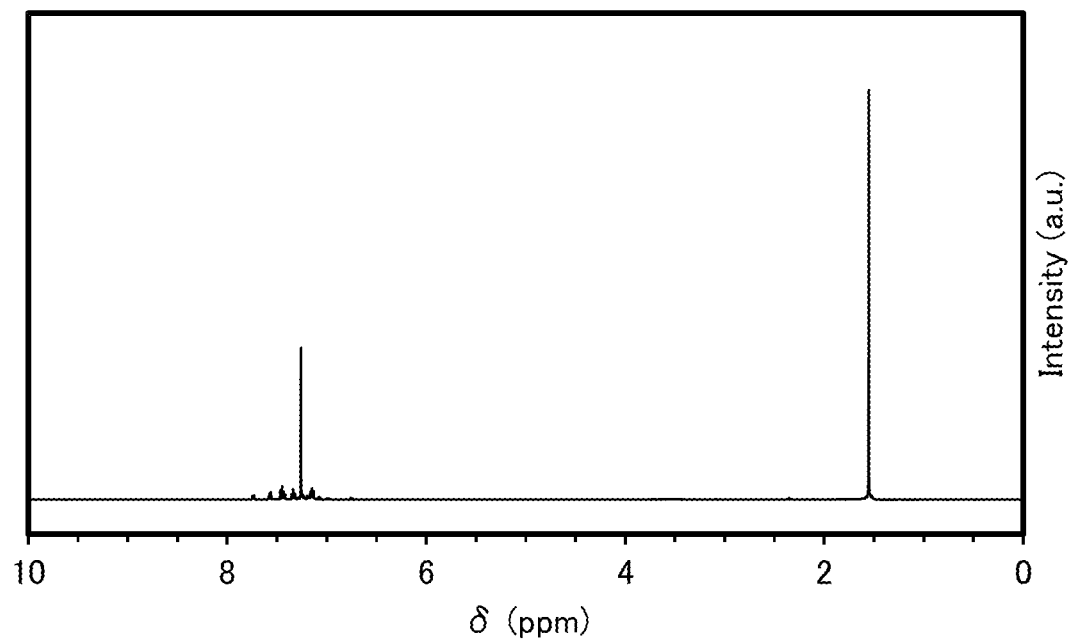
FIGS. 52A and 52B are $^1$H NMR charts of mBBAFLP.
Figure 52B:
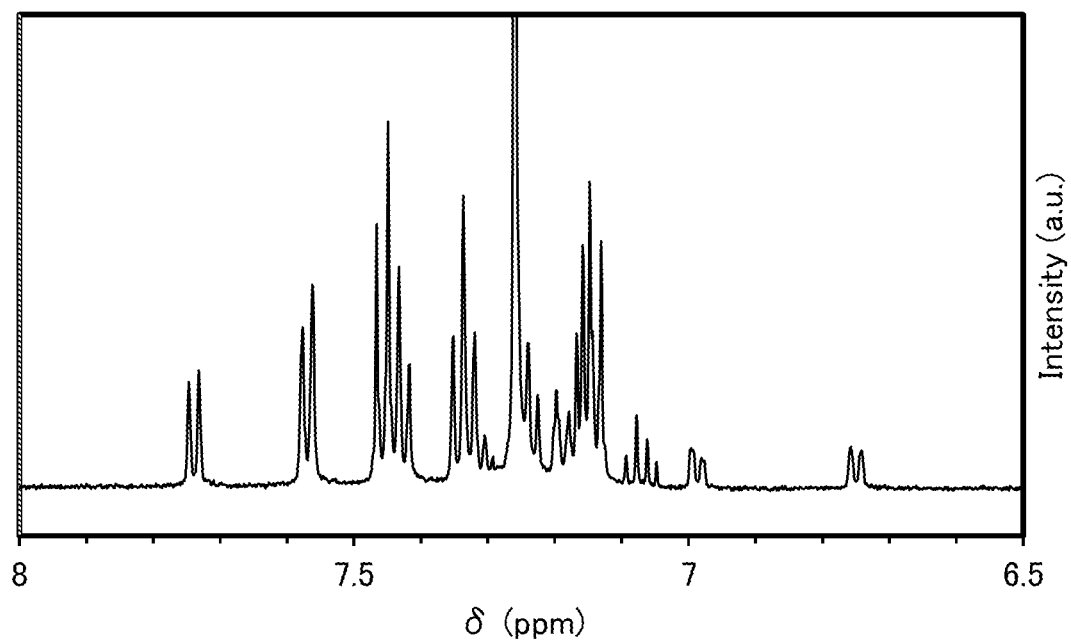

Analysis results by nuclear magnetic resonance spectroscopy (1H NMR) of the obtained white solid are shown below. In addition, 1H NMR charts are shown in FIGS. 52(A) and 52(B). Note that FIG. 52(B) is a chart showing an enlarged view of the range of 6.5 ppm to 8.0 ppm in FIG. 52(A). The results show that mBBAFLP was obtained in this synthesis example.

1H NMR (CDCl$_3$, 500 MHz): δ=6.75 (d, J=8.0 Hz, 1H), 6=6.99 (d, J=7.0 Hz, 1H), δ=7.07 (q, J=7.7 Hz, 11H), δ=7.13-7.20 (m, 111H), δ=7.23 (d, J=7.5 Hz, 1H) 6=7.34 (t, J=8.0 Hz, 6H), δ=7.42 (s, 1H), δ=7.45 (t, J=8.3 Hz, 7H), δ=7.57 (d, J=7.5, 4H), δ=7.74 (d, J=7.5, 2H).

Synthesis Example 6

In this synthesis example, a method for synthesizing 4-[3-(9-phenyl-9H-fluoren-9-yl)phenyl]-4',4''-diphenyltriphenylamine (abbreviation: mpBBAFLBi), a substance that can be used as the organic compound of the hole-injection layer 111 in the light-emitting device of one embodiment of the present invention, will be described. Note that the structural formula of mpBBAFLBi is shown below.

[Chemical formula 30]

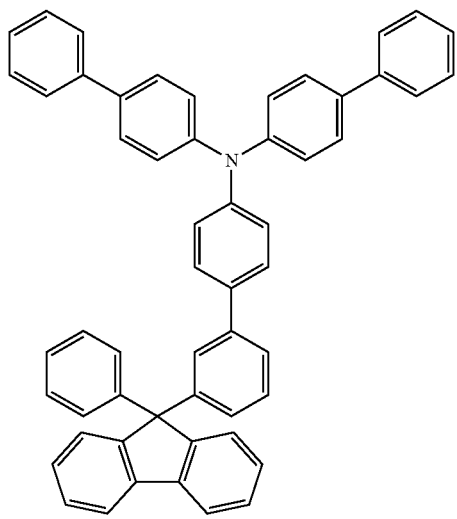

Into a 200 mL three-neck flask were added 2.0 g (5.0 mmol) of 9-(3-bromophenyl)-9-phenyl-9H-fluorene, 2.6 g (5.0 mmol) of 2-{4-[di(4-biphenylyl)amino]phenyl}-4,4,5,5-tetramethyl-1,3,2-dioxaborolan, 30 mg (0.10 mmol) of tri(ortho-tolyl)phosphine, and 2.8 g (20 mmol) of potassium carbonate, and the air in the flask was replaced with nitrogen. To the mixture were added 15 mL of toluene, 10 mL of ethanol, and 10 mL of water, and the mixture was degassed by being stirred under reduced pressure. To this mixture was added 11 mg (0.050 mmol) of palladium(II) acetate and the mixture was stirred at 80° C. under a nitrogen stream for 2 hours.

After the stirring, the mixture was subjected to suction filtration, whereby a solid was collected. The solid was dissolved in heated toluene and subjected to suction filtration through Celite, alumina, and Florisil. A solid obtained by concentration of the filtrate was recrystallized with toluene to give 2.7 g of a target white solid in a yield of 74%. The synthesis scheme of the above synthesis method is shown below.

[Chemical formula 31]

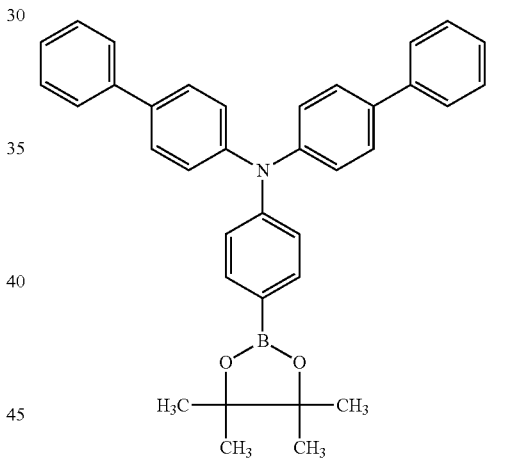

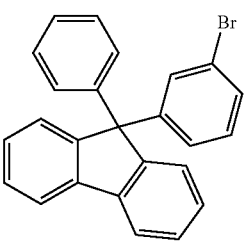

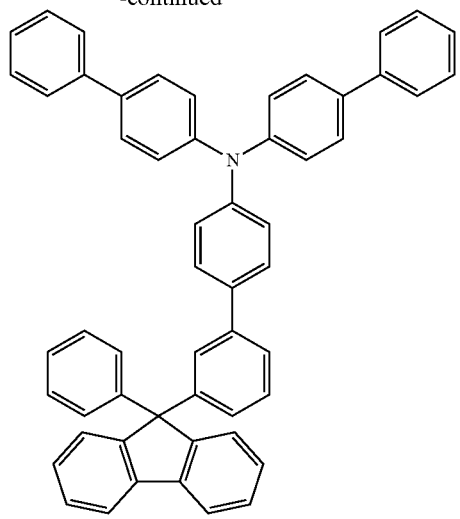

By the train sublimation method, 2.6 g of the obtained white solid was sublimated and purified. The sublimation purification was performed by heating the white solid at 280° C. under the conditions where the pressure was 3.5 Pa and the argon flow rate was 5.0 mL/min. After the purification by sublimation, 2.3 g of a pale yellow solid was obtained at a collection rate of 88%.

Figure 53A:
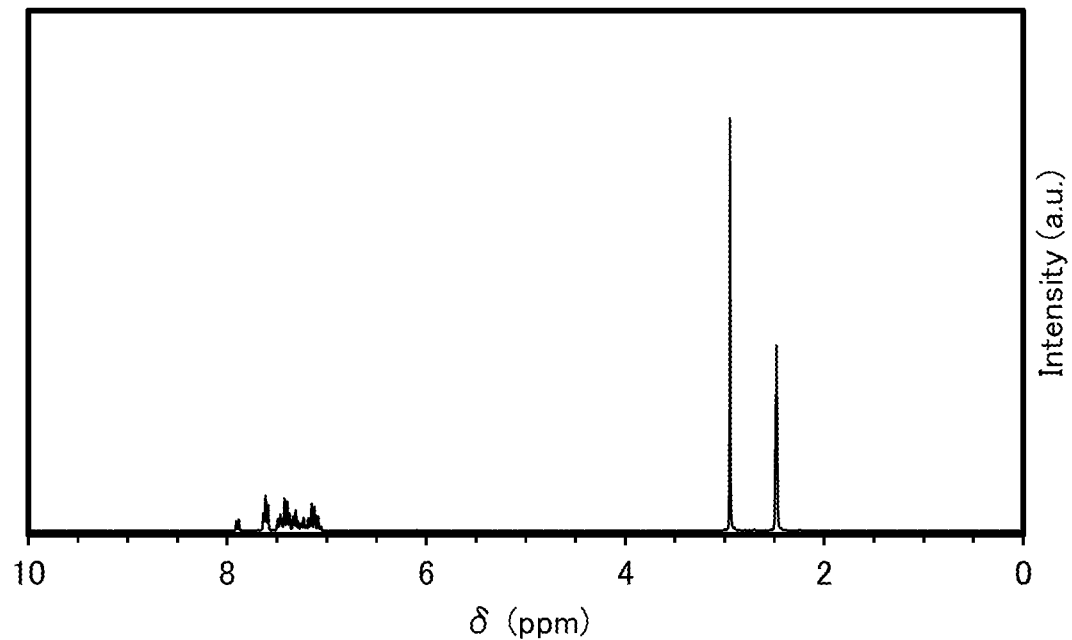
FIGS. 53A and 53B are $^1$H NMR charts of mpBBAFLBi.
Figure 53B:
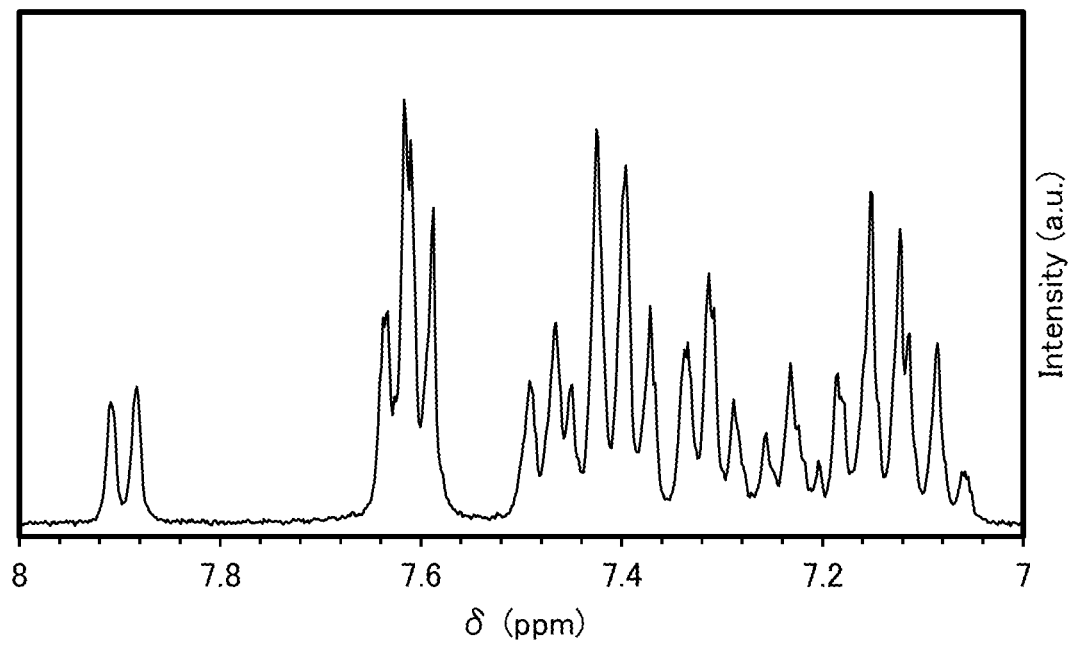

Analysis results by nuclear magnetic resonance ($^1$H NMR) spectroscopy of the obtained pale yellow solid are shown below. In addition, $^1$H NMR charts are shown in FIGS. 53(A) and 53(B). Note that FIG. 53(B) is a chart showing an enlarged view of the range of 7.0 ppm to 8.0 ppm in FIG. 53(A). The results show that mpBBAFLBi was obtained in this synthesis example.

$^1$H NMR (DMSO, 300 MHz): δ=7.06-7.49 (m, 29H), 7.59-7.64 (m, 8H), 7.90 (d, J=7.8 Hz, 2H)

Next, absorption spectra and emission spectra of a toluene solution and a solid thin film of mpBBAFLBi were measured. Note that the measurement method, apparatus, and conditions are the same as those of Synthesis example 1; therefore, repeated description will be omitted.

Figure 54:
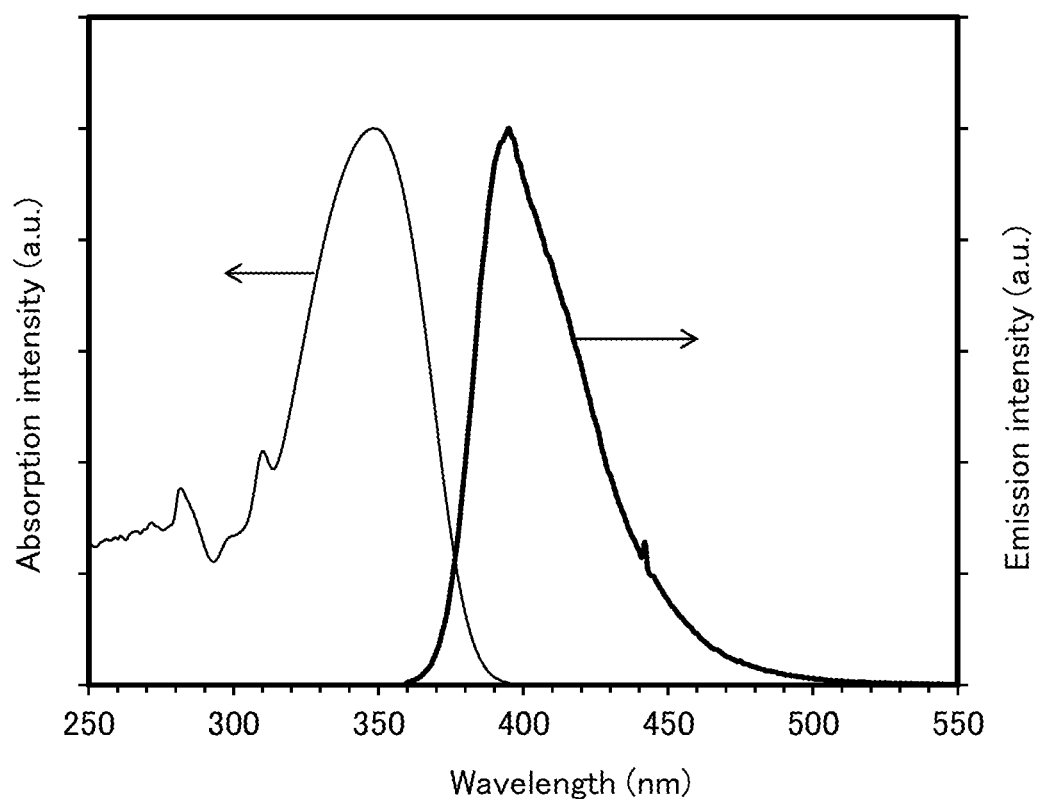
FIG. 54 is an absorption spectrum and an emission spectrum of mpBBAFLBi in a toluene solution.
Figure 55:
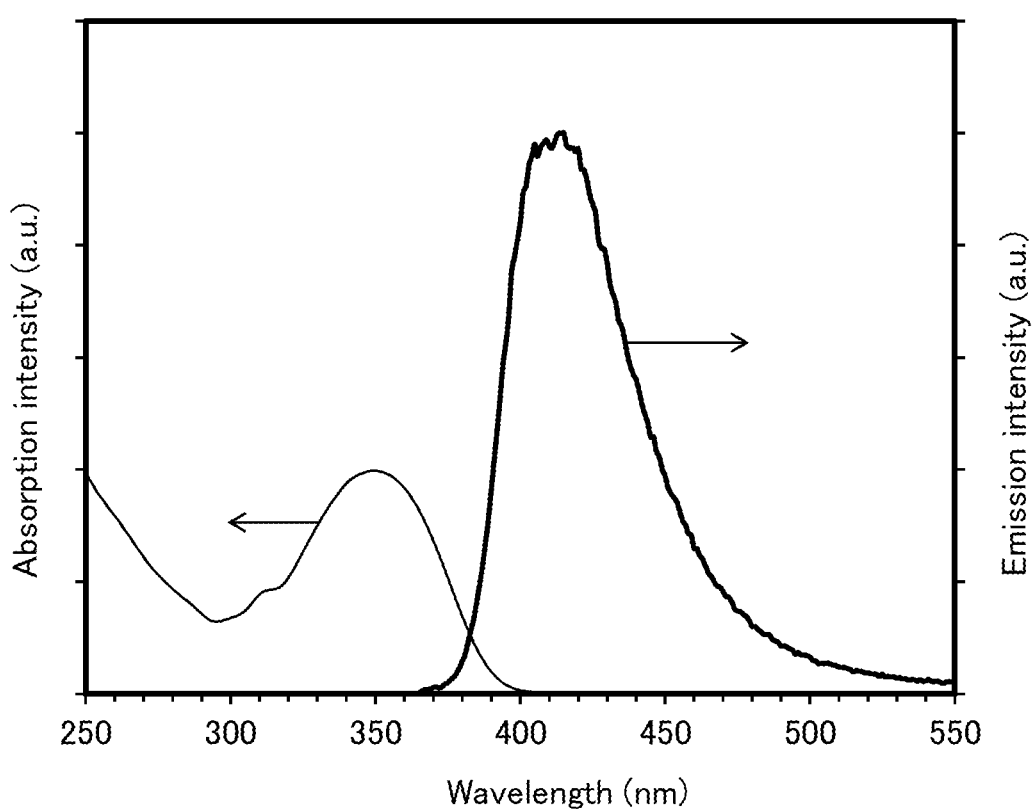
FIG. 55 is an absorption spectrum and an emission spectrum of mpBBAFLBi in a thin film state.

FIG. 54 shows the obtained measurement results of the absorption spectrum and the emission spectrum of the toluene solution. FIG. 55 shows the measurement results of the absorption spectrum and the emission spectrum of the solid thin film.

According to the results of FIG. 54, the toluene solution of mpBBAFLBi exhibited an absorption peak at around 348 nm and an emission wavelength peak at 394 nm (excitation wavelength: 353 nm). According to the results of FIG. 55, the solid thin film of mpBBAFLBi exhibited absorption peaks at around 352 nm and 313 nm and an emission wavelength peak at around 414 nm (excitation wavelength: 355 nm).

The HOMO level and the LUMO level of mpBBAFLBi were calculated on the basis of a cyclic voltammetry (CV) measurement. The calculation method is similar to that described in Synthesis example 1.

As a result, the HOMO level of mpBBAFLBi was found to be −5.49 eV. Furthermore, the LUMO level was found to be −2.12 eV.

When CV measurement was repeated 100 times and the peak intensities of an oxidation-reduction wave at the 100th cycle and an oxidation-reduction wave at the first cycle were compared, 85% was kept in the Ea measurement and 93% was kept in the Ec measurement, which showed that mpBBAFLBi was an organic compound having extremely high resistance to oxidation and reduction.

Synthesis Example 7

In this synthesis example, a method for synthesizing 4-(4-biphenylyl)-4'-(2-naphthyl)-4''-phenyltriphenylamine (abbreviation: TPBiAβNB), a substance that can be used as the organic compound of the hole-injection layer 111 in the light-emitting device of one embodiment of the present invention, will be described. The structural formula of TPBiAβNB is shown below.

[Chemical formula 32]

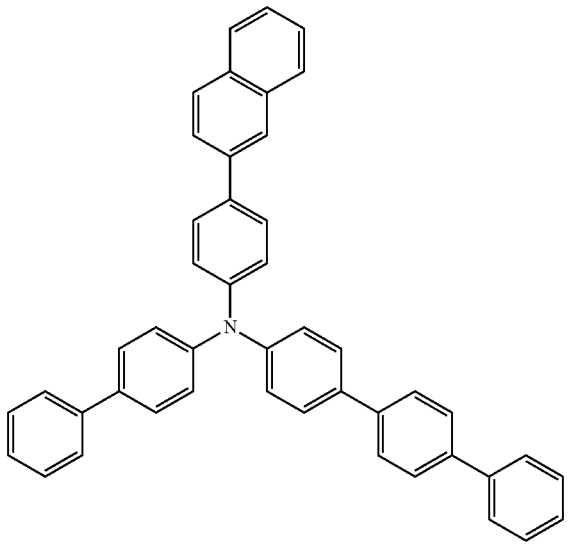

Into a 200 mL three-neck flask equipped with a reflux pipe were added 3.2 g (10 mmol) of N-(4-bromophenyl)-4-biphenylamine, 2.5 g (10 mmol) of 4-biphenylboronic acid, 61 mg (0.20 mmol) of tri(ortho-tolyl)phosphine, 10 mL of an aqueous solution of potassium carbonate (2.0 mol/L), 70 mL of toluene, and 30 mL of ethanol, the mixture was degassed under reduced pressure, and then the air of the system was replaced with nitrogen. To the obtained mixture was added 22 mg (0.10 mol) of palladium(II) acetate, and the resulting mixture was refluxed for 3 hours. After the stirring, the precipitated solid was collected by suction filtration and the obtained solid was washed with toluene, ethanol, and water to give 2.69 g of a brown solid was obtained in a yield of 86%. The synthesis scheme of Step 1 is shown below.

[Chemical formula 33]

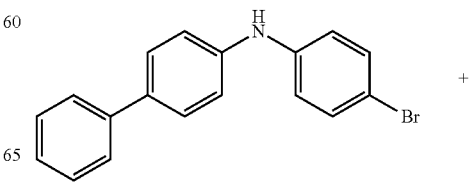

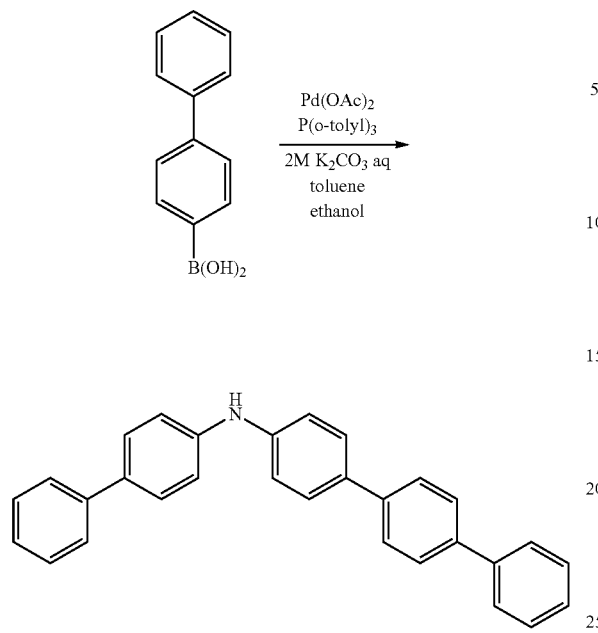

Step 2: Synthesis of 4-(4-biphenylyl)-4'-(2-naphthyl)-4''-phenyltriphenylamine (Abbreviation: TPBiAβNB)

Into a 200 mL three-neck flask equipped with a reflux pipe were put 1.5 g (2.7 mmol) of N-(1,1'-biphenyl)-4-yl-(1,1': 4',1''-terphenyl)-4-4-amine, which was obtained in Step 1, 0.75 g (2.7 mmol) of 2-(4-bromophenyl)naphthalene, 18 mg (0.053 mmol) of di-tert-butyl(1-methyl-2,2-diphenylcyclopropyl)phosphine, 0.51 g (5.3 mmol) of sodium tert-butoxide, and 100 mL of toluene, the mixture was degassed under reduced pressure, and then the air in the system was replaced with nitrogen. To the obtained mixture was added 15 mg (0.027 mmol) of bis(dibenzylideneacetone)palladium(0) was added, and the mixture was refluxed for 8 hours. Water was added to the obtained mixture to separate an aqueous layer and an organic layer, and then the aqueous layer was subjected to extraction with toluene. The obtained extracted solution and the organic layer were combined, washed with water and a saturated saline solution, and dried with magnesium sulfate. This mixture was subjected to gravity filtration and the obtained filtrate was concentrated to give 1.1 g of a brown solid. The synthesis scheme of Step 2 is shown below.

[Chemical formula 34]

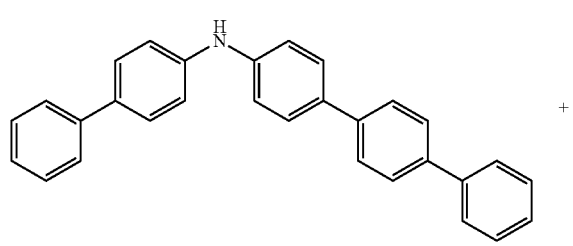

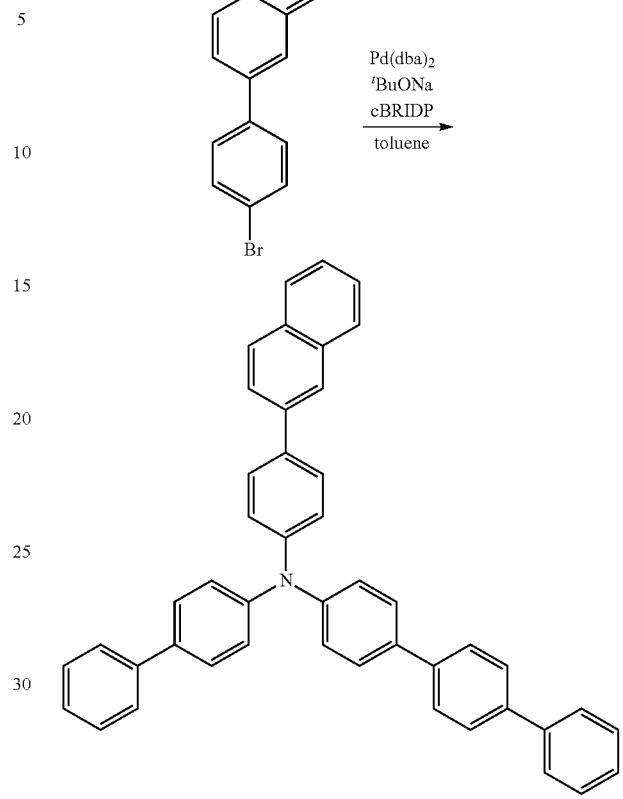

By a train sublimation method, 1.1 g of the obtained solid was sublimated and purified. In the sublimation purification, the solid was heated at 300° C. for 15 hours under a pressure of 3.7 Pa with a flow of argon at 15 mL/min. After the sublimation purification, 620 mg of a target pale yellow solid was obtained at a collection rate of 56%.

Figure 56A:
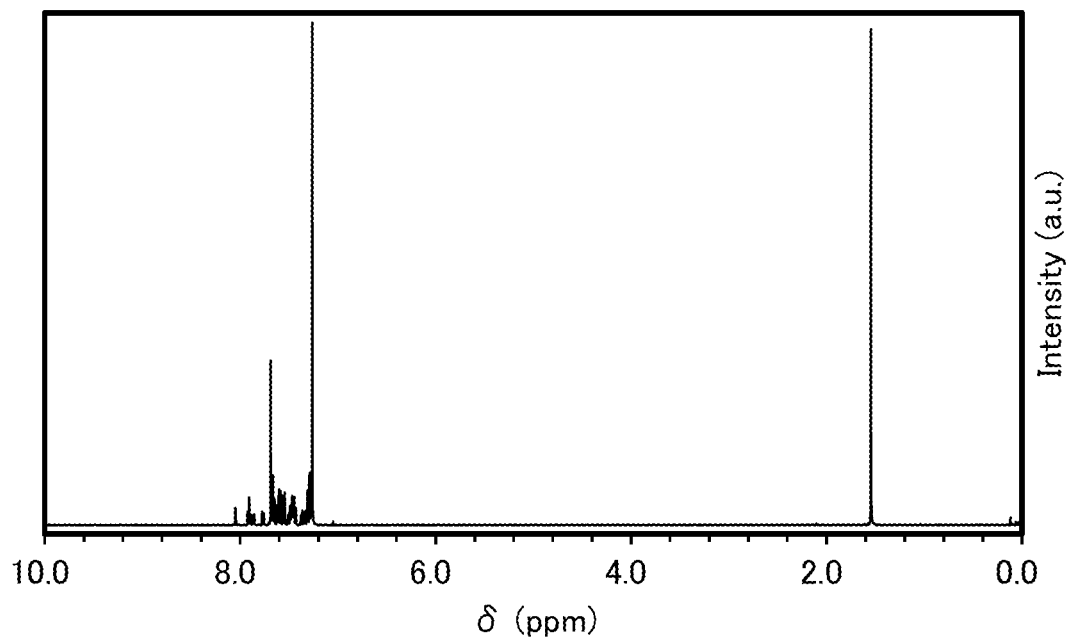
FIGS. 56A and 56B are ¹H NMR charts of TPBiAβNB.
Figure 56B:
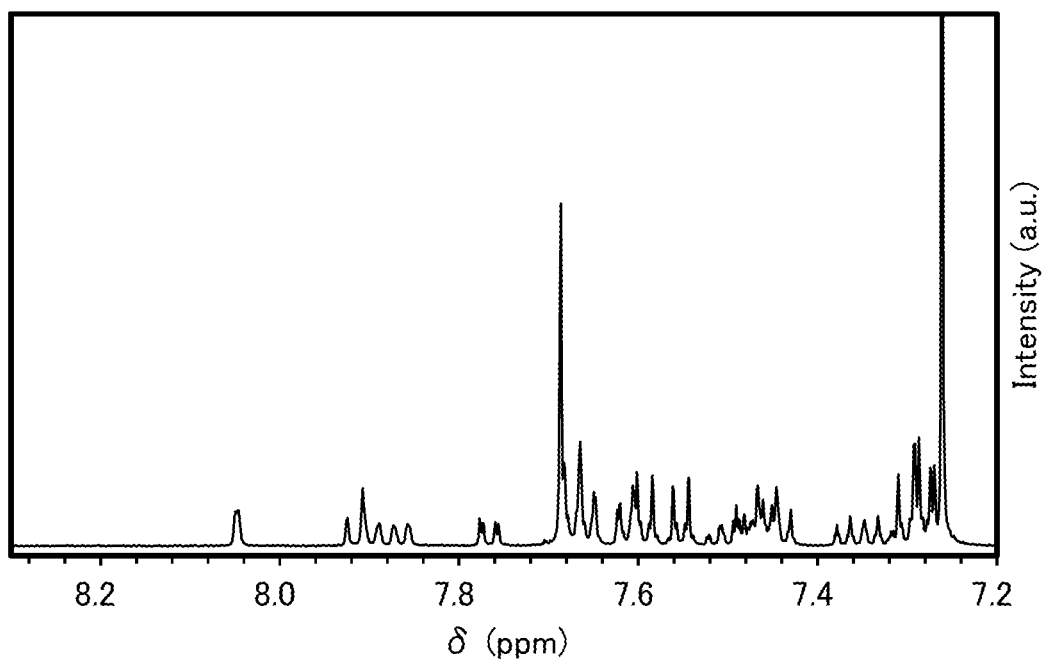

The numeric data of the obtained solid are shown below and $^1$H NMR charts are shown in FIGS. 56(A) and 56(B). Note that FIG. 56(B) is a chart showing an enlarged view of the range of 7.2 ppm to 8.3 ppm in FIG. 56(A). These indicate that TPBiAβNB, which was the target compound, was obtained in this synthesis example.

$^1$H NMR (chloroform-d, 500 MHz): δ=8.04 (d, J=1.5 Hz, 1H), 7.91 (d, J=8.5 Hz, 1H), 7.89 (d, J=9.5 Hz, 1H), 7.86 (d, J=8.0 Hz, 1H), 7.77 (dd, J=4.0 Hz, 1.5 Hz, 1H), 7.70-7.65 (m, 8H), 7.62-7.58 (m, 4H), 7.55 (d, J=9.0 Hz, 2H), 7.52-7.43 (m, 6H), 7.38-7.27 (m, 8H)

Next, absorption spectra and emission spectra of a toluene solution and a solid thin film of TPBiAβNB were measured. The measurement method, apparatus, and conditions are the same as those of Synthesis example 1; therefore, repeated description will be omitted.

Figure 57:
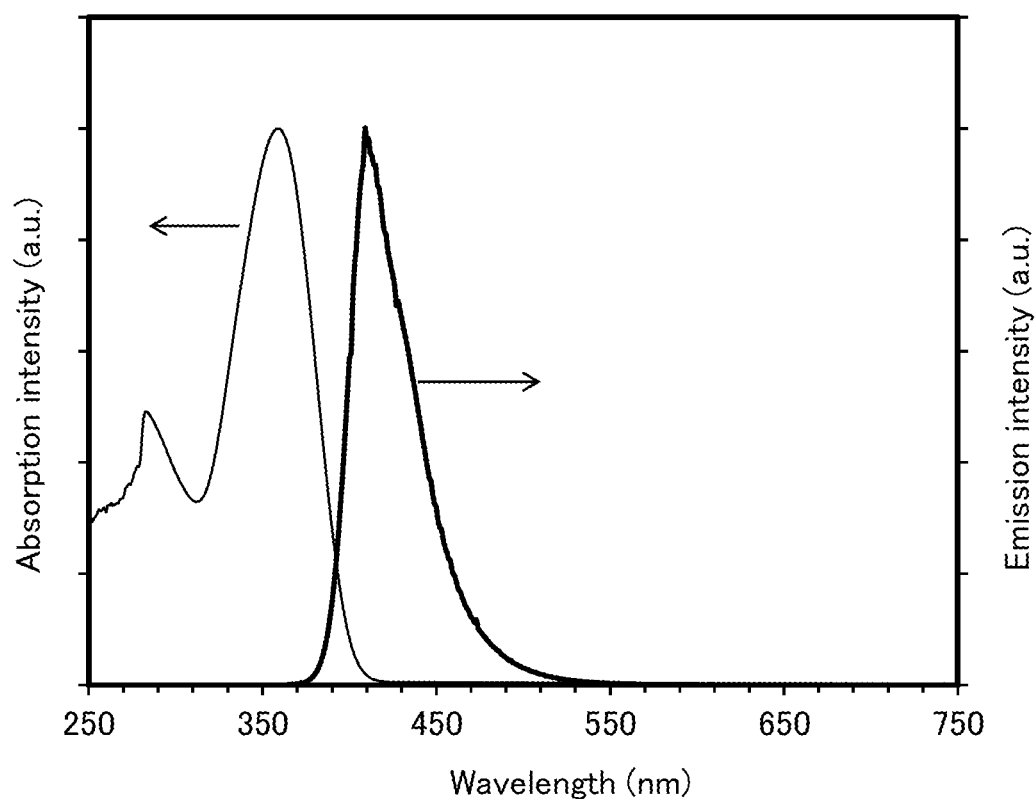
FIG. 57 is an absorption spectrum and an emission spectrum of TPBiAβNB in a toluene solution.
Figure 58:
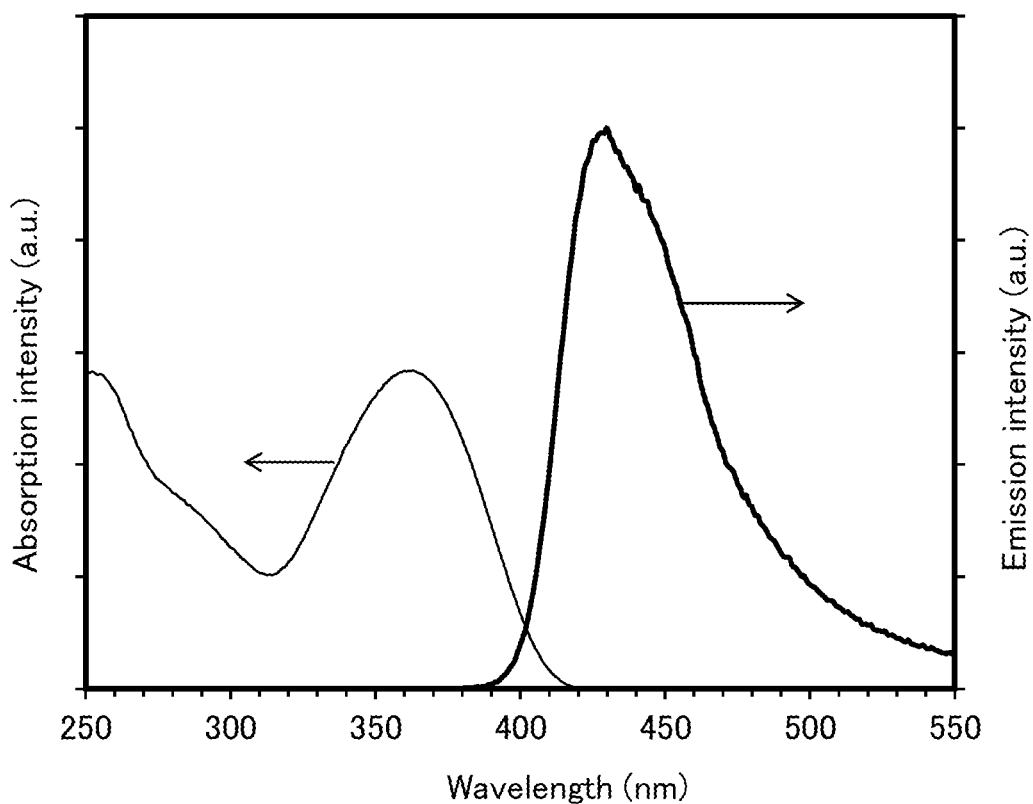
FIG. 58 is an absorption spectrum and an emission spectrum of TPBiAβNB in a thin film state.

FIG. 57 shows the obtained measurement results of the absorption spectrum and the emission spectrum of the toluene solution. FIG. 58 shows the measurement results of the absorption spectrum and the emission spectrum of the solid thin film.

According to the results of FIG. 57, the toluene solution of TPBiAβNB exhibited an absorption peak at around 357 nm and an emission wavelength peak at 409 nm (excitation wavelength: 357 nm). According to the results of FIG. 58, the solid thin film of TPBiAβNB exhibited absorption peaks at around 364 nm, 280 nm, and 253 nm and an emission wavelength peak at around 430 nm (excitation wavelength: 370 nm).

The HOMO level and the LUMO level of TPBiAβNB were calculated on the basis of a cyclic voltammetry (CV) measurement. The calculation method is similar to that described in Synthesis example 1.

As a result, the HOMO level of TPBiAβNB was found to be −5.47 eV, and the LUMO level was found to be −2.29 eV.

When CV measurement was repeated 100 times and the peak intensities of an oxidation-reduction wave at the 100th cycle and an oxidation-reduction wave at the first cycle were compared, 89% of the peak intensity was kept in the Ea measurement and 98% of the peak intensity was kept in the Ec measurement, which showed that TPBiAβNB had extremely high resistance to oxidation and reduction.

Synthesis Example 8

In this synthesis example, a method for synthesizing 4-(4-biphenylyl)-4'-{4-(2-naphthyl)phenyl}-4"-phenyltriphenylamine (abbreviation: TPBiAβNBi), a substance that can be used as the organic compound of the hole-injection layer 111 in the light-emitting device of one embodiment of the present invention, will be described. The structural formula of TPBiAβNBi is shown below.

[Chemical formula 35]

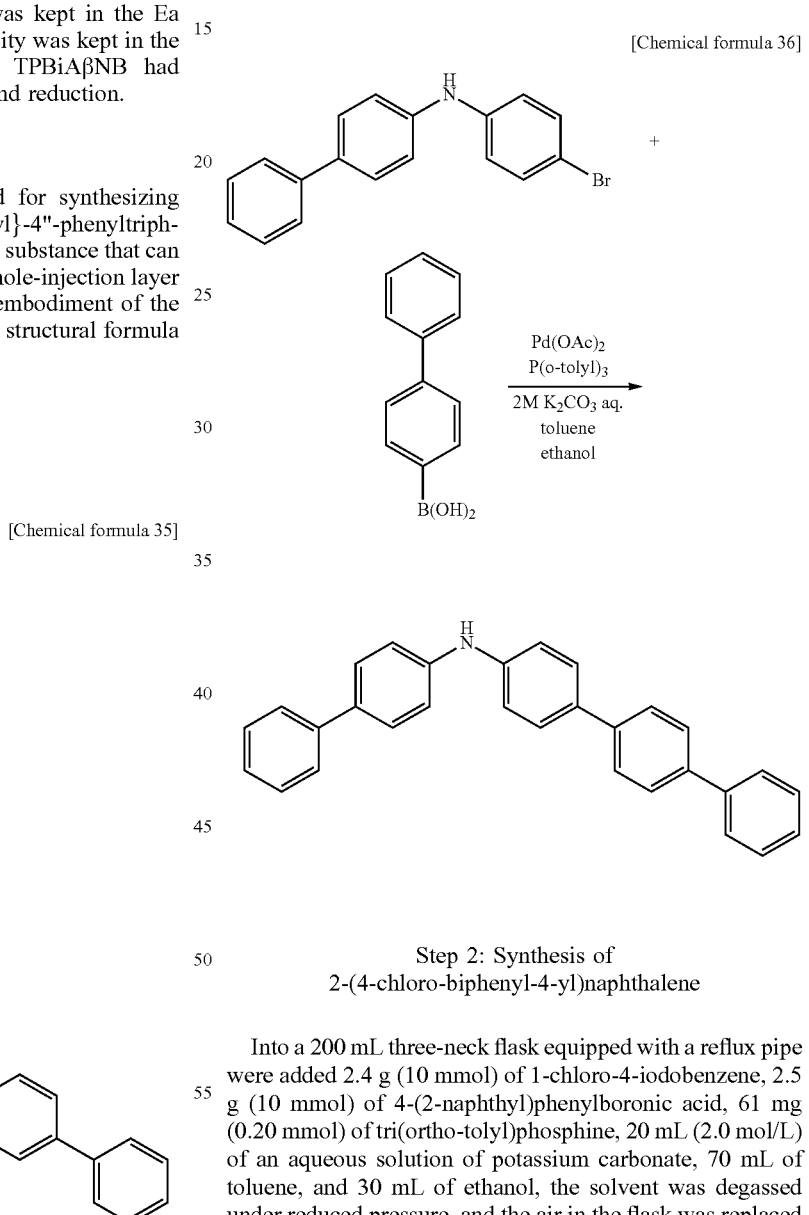

Step 1: Synthesis of N-(1,1'-biphenyl)-4-yl-(1,1':4', 1"-terphenyl)-4-4-amine

Into a 200 mL three-neck flask equipped with a reflux pipe were added 2.4 g (7.4 mmol) of N-(4-bromophenyl)-4-biphenylamine, 1.5 g (7.4 mmol) of 4-biphenylboronic acid, 47 mg (0.15 mmol) of tri(ortho-tolyl)phosphine, 7 mL (2.0 mol/L) of an aqueous solution of potassium carbonate, 60 mL of toluene, and 20 mL of ethanol, the mixture was degassed under reduced pressure, and then the air in the system was replaced with nitrogen. To the obtained mixture was added 16 mg (74 μmol) of palladium(II) acetate, and the mixture was refluxed for 3 hours. After the stirring, the precipitated solid was collected by suction filtration and the obtained solid was washed with toluene, ethanol, and water to give 2.94 g of a target gray solid in a yield of 99% or higher. The synthesis scheme of Step 2 is shown below.

[Chemical formula 36]

Step 2: Synthesis of 2-(4-chloro-biphenyl-4-yl)naphthalene

Into a 200 mL three-neck flask equipped with a reflux pipe were added 2.4 g (10 mmol) of 1-chloro-4-iodobenzene, 2.5 g (10 mmol) of 4-(2-naphthyl)phenylboronic acid, 61 mg (0.20 mmol) of tri(ortho-tolyl)phosphine, 20 mL (2.0 mol/L) of an aqueous solution of potassium carbonate, 70 mL of toluene, and 30 mL of ethanol, the solvent was degassed under reduced pressure, and the air in the flask was replaced with nitrogen. After heating at 60° C., 22 mg (0.10 mmol) of palladium(II) acetate was added, and reaction was caused by stirring at 50° C. for 3 hours. After the stirring, the precipitated solid was collected by suction filtration and washed with toluene, water, and ethanol to give 2.7 g of a brown solid in a yield of 86%. The synthesis scheme of Step 2 is shown below.

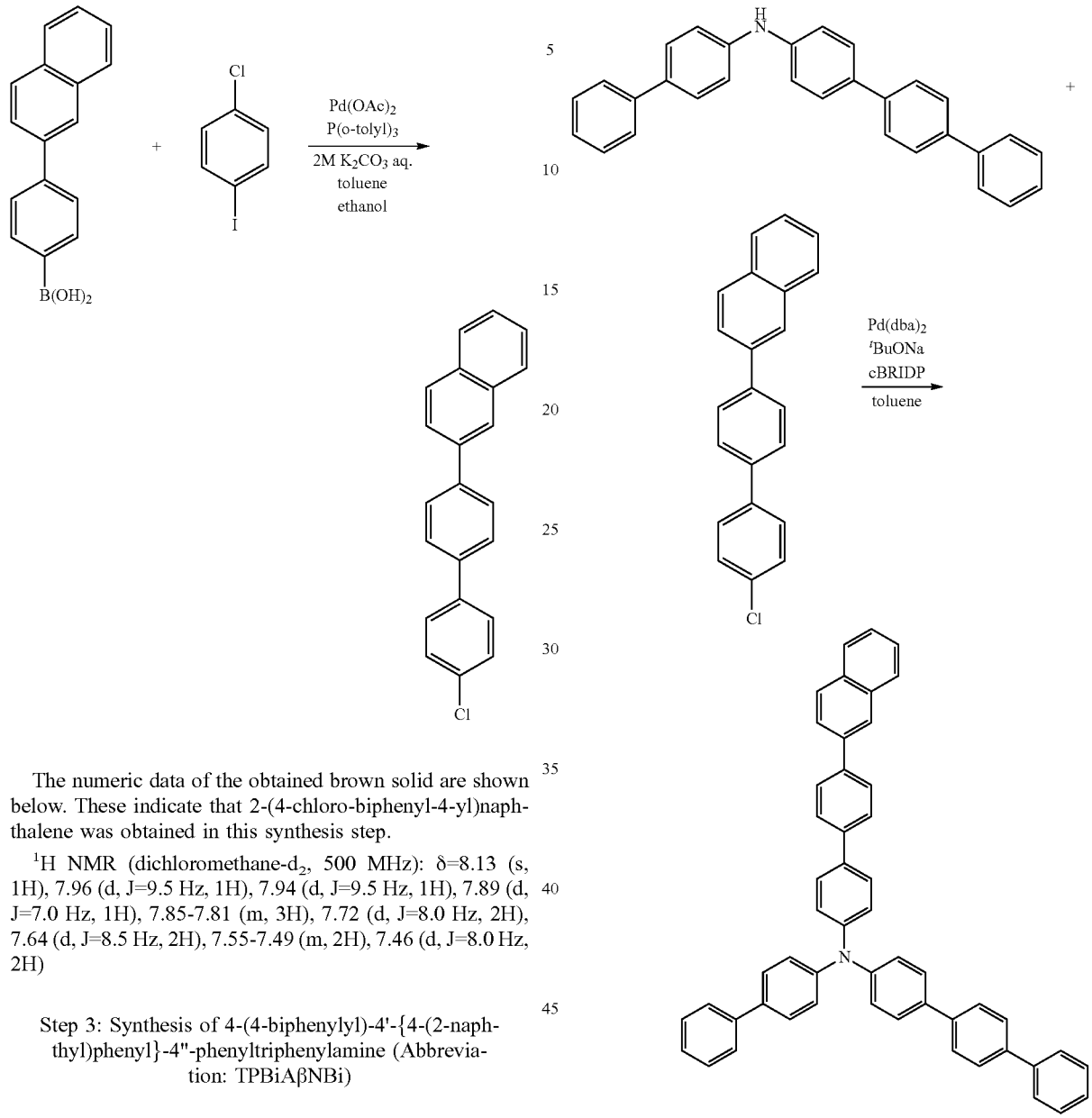

[Chemical formula 37]

[Chemical formula 38]

The numeric data of the obtained brown solid are shown below. These indicate that 2-(4-chloro-biphenyl-4-yl)naphthalene was obtained in this synthesis step.

$^1$H NMR (dichloromethane-$d_2$, 500 MHz): δ=8.13 (s, 1H), 7.96 (d, J=9.5 Hz, 1H), 7.94 (d, J=9.5 Hz, 1H), 7.89 (d, J=7.0 Hz, 1H), 7.85-7.81 (m, 3H), 7.72 (d, J=8.0 Hz, 2H), 7.64 (d, J=8.5 Hz, 2H), 7.55-7.49 (m, 2H), 7.46 (d, J=8.0 Hz, 2H)

Step 3: Synthesis of 4-(4-biphenylyl)-4'-{4-(2-naphthyl)phenyl}-4''-phenyltriphenylamine (Abbreviation: TPBiAβNBi)

Into a 200 mL three-neck flask equipped with a reflux pipe were put 2.94 g (7.4 mmol) of N-(1,1'-biphenyl)-4-yl-(1,1': 4',1''-terphenyl)-4-4-amine, which was obtained in Step 1, 2.32 g (7.4 mmol) of 2-(4-chloro-biphenyl-4-yl)naphthalene, which was obtained in Step 2, 52 mg (0.15 mmol) of di-tert-butyl(1-methyl-2,2-diphenylcyclopropyl)phosphine (product name: cBRIDP (registered trademark)), 1.4 g (15 mmol) of sodium tert-butoxide, and 140 mL of xylene, the mixture was degassed under reduced pressure, and then the air in the system was replaced with nitrogen. To the obtained mixture was added 43 mg (74 µmol) of bis(dibenzylideneacetone)palladium(0), and the mixture was refluxed for 5 hours. After stirring, the precipitated solid was collected by suction filtration and washing with toluene, water, and ethanol was performed to give 3.8 g of a gray solid. The synthesis scheme of Step 3 is shown below.

By a train sublimation method, 3.8 g of the obtained solid was sublimated and purified. In the purification by sublimation, the solid was heated at 335° C. under a pressure of 3.8 Pa for 15 hours with a flow of argon at 15 mL/min. After the sublimation purification, 2.8 g of a target pale yellow solid was obtained at a collection rate of 74%.

Figure 59A:
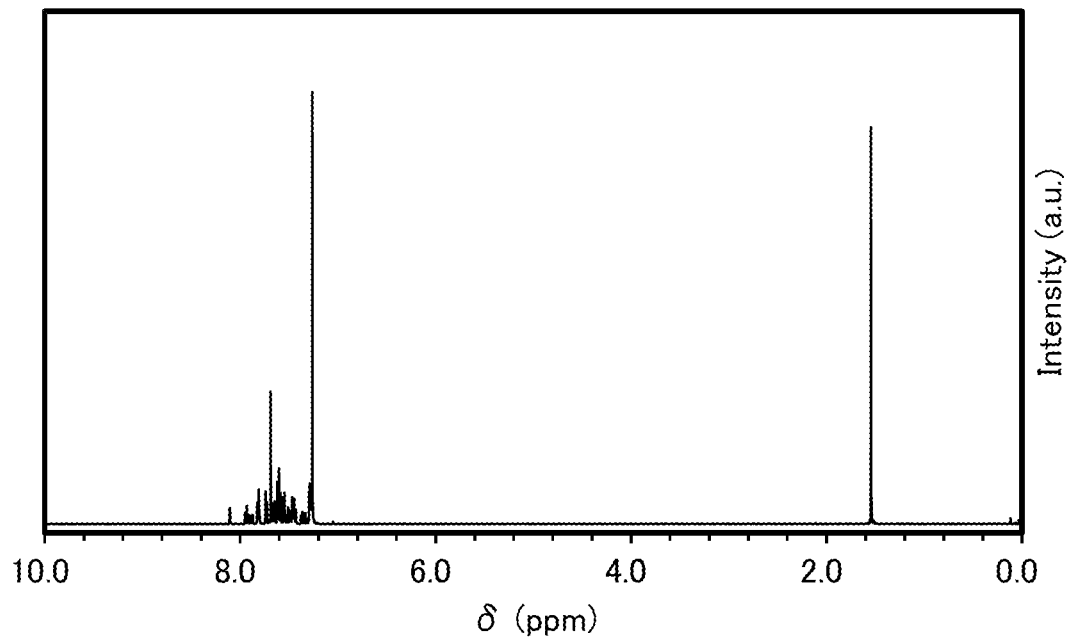
FIGS. 59A and 59B are ¹H NMR charts of TPBiAβNBi.
Figure 59B:
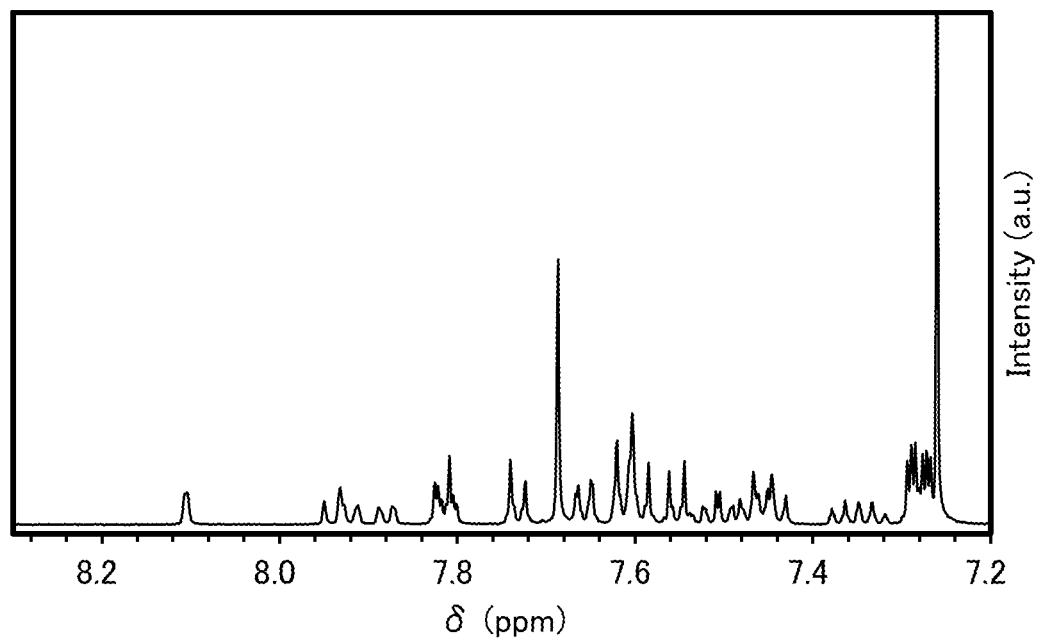

The numeric data of the obtained solid are shown below and $^1$H NMR charts are shown in FIGS. 59(A) and 59(B). Note that FIG. 59(B) is a chart showing an enlarged view of the range of 7.2 ppm to 8.3 ppm in FIG. 59(A). These indicate that TPBiAβNBi, which was the target compound, was obtained in this synthesis example.

$^1$H NMR (chloroform-d, 500 MHz): δ=8.10 (d, J=1.5 Hz, 1H), 7.94 (d, J=9.0 Hz, 1H), 7.92 (d, J=7.5 Hz, 1H), 7.88 (d, J=7.5 Hz, 1H), 7.82-7.80 (m, 3H), 7.73 (d, J=8.5 Hz, 2H), 7.68 (s, 4H), 7.66 (d, J=7.0 Hz, 2H), 7.62-7.58 (m, 6H), 7.55

(d, J=8.5 Hz, 2H), 7.52-7.43 (m, 6H), 7.36 (t, J=7.0 Hz, 1H), 7.33 (t, J=7.0 Hz, 1H), 7.29-7.27 (m, 6H)

Next, absorption spectra and emission spectra of a toluene solution and a solid thin film of TPBiAβNBi were measured. The measurement method, apparatus, and conditions are the same as those of Synthesis example 1; therefore, repeated description will be omitted.

Figure 60:
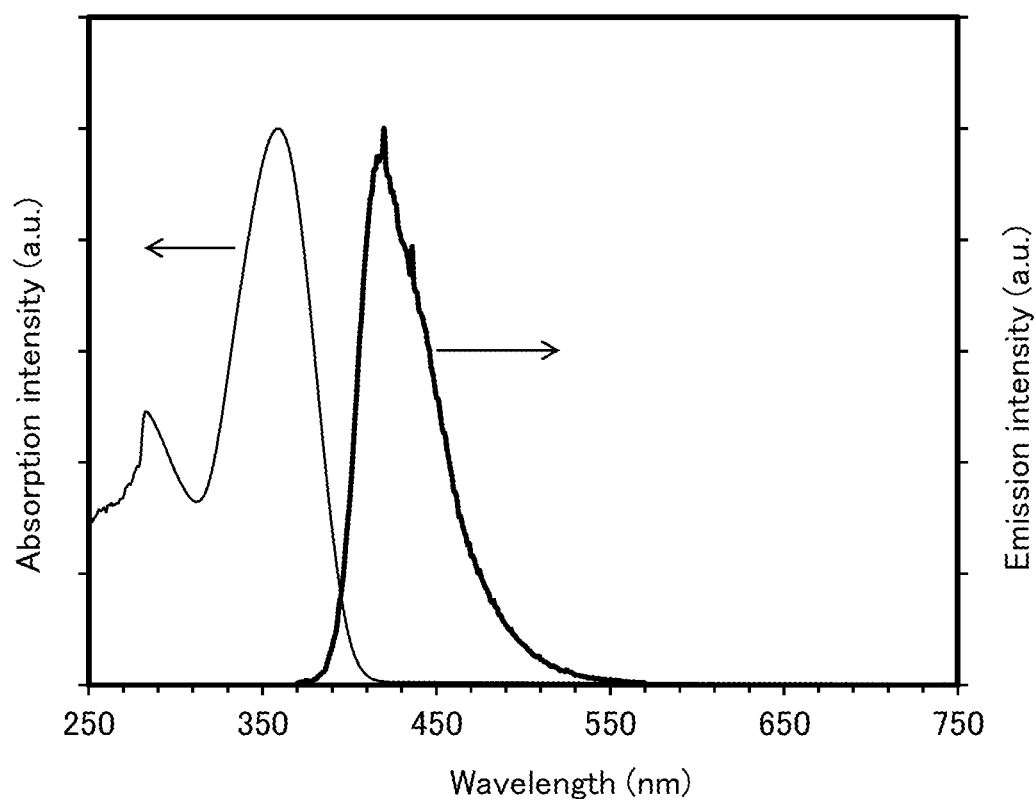
FIG. 60 is an absorption spectrum and an emission spectrum of TPBiAβNBi in a toluene solution.
Figure 61:
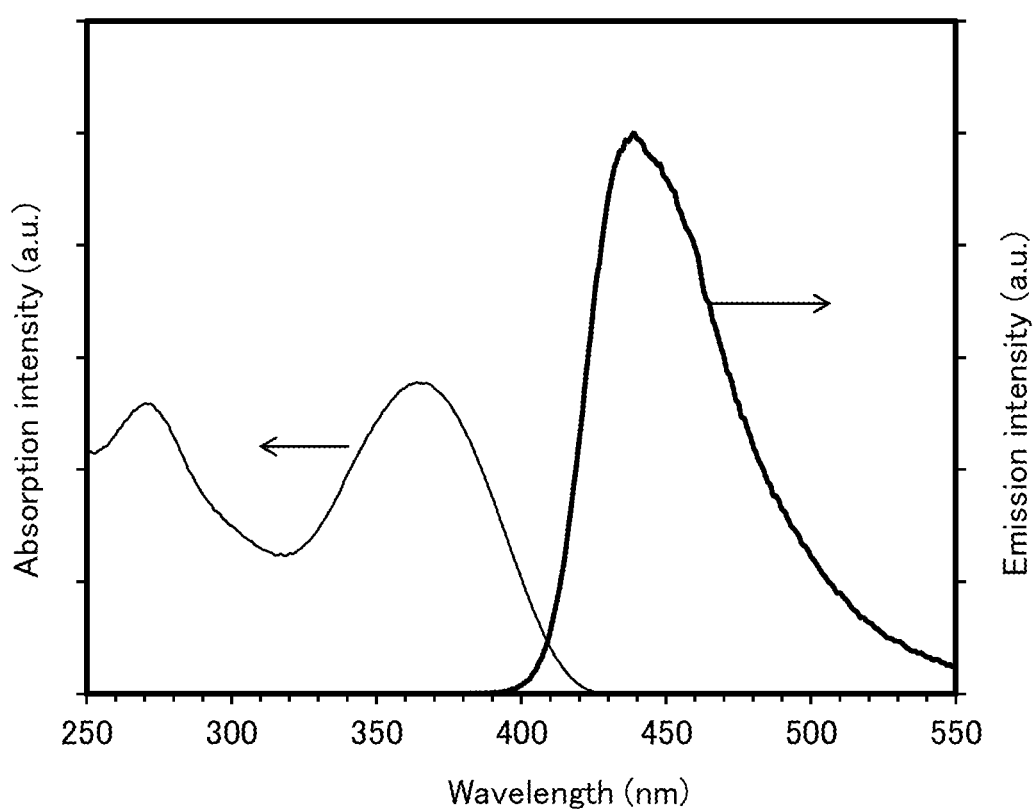
FIG. 61 is an absorption spectrum and an emission spectrum of TPBiAβNBi in a thin film state.

FIG. 60 shows the obtained measurement results of the absorption spectrum and the emission spectrum of the toluene solution. FIG. 61 shows the measurement results of the absorption spectrum and the emission spectrum of the solid thin film.

According to the results of FIG. 60, the toluene solution of TPBiAβNBi exhibited an absorption peak at around 359 nm and an emission wavelength peak at 420 nm (excitation wavelength: 410 nm). According to the results of FIG. 61, the solid thin film of TPBiAβNBi exhibited absorption peaks at around 368 nm, 295 nm, and 272 nm and an emission wavelength peak at around 439 nm (excitation wavelength: 370 nm).

The HOMO level and the LUMO level of TPBiAβNBi were calculated on the basis of a cyclic voltammetry (CV) measurement. The calculation method is similar to that described in Synthesis example 1.

As a result, the HOMO level of TPBiAβNBi was found to be −5.47 eV, and the LUMO level was found to be −2.38 eV.

When CV measurement was repeated 100 times and the peak intensities of an oxidation-reduction wave at the 100th cycle and an oxidation-reduction wave at the first cycle were compared, 83% of the peak intensity was kept in the Ea measurement and 95% of the peak intensity was kept in the Ec measurement, which showed that TPBiAβNBi had extremely high resistance to oxidation and reduction.

Synthesis Example 9

In this synthesis example, a method for synthesizing 4,4'-diphenyl-4"-(7-phenyl)naphthyl-2-yltriphenylamine (abbreviation: BBAPβNB-03), a substance that can be used as the organic compound of the hole-injection layer 111 in the light-emitting device of one embodiment of the present invention, will be described. The structural formula of BBAPβNB-03 is shown below.

[Chemical formula 39]

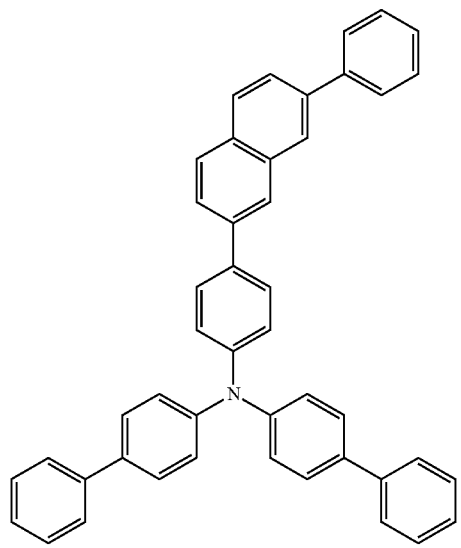

Step 1: Synthesis of 7-bromo-2-phenylnaphthalene

Into a 200 mL three-neck flask equipped with a reflux pipe were added 3.8 g (13 mmol) of 2,7-dibromonaphthalene, 2.3 g (13 mmol) of phenylboronic acid, 81 mg (27 μmol) of tri(ortho-tolyl)phosphine, 65 mL of toluene, 30 mL of ethanol, and 15 mL of a 2M aqueous solution of potassium carbonate (2.0 mmol/L), the mixture was degassed under reduced pressure, and then the air in the system was replaced with nitrogen. After that, 30 mg (0.13 mmol) of palladium acetate was added, and stirring was performed at room temperature for 3 hours. A solid precipitated in the obtained reaction mixture was removed by suction filtration. Water was added to the obtained filtrate to separate an aqueous layer and an organic layer, and then the aqueous layer was subjected to extraction with toluene. The obtained extracted solution and the organic layer were combined, washed with water and a saturated saline solution, and dried with magnesium sulfate. The obtained mixture was subjected to gravity filtration and then concentrated, and the obtained residue was purified by high performance liquid chromatography (mobile phase: chloroform). Thus, 2.3 g of a white solid, which was the target compound, was obtained in a yield of 52%. The synthesis scheme of Step 1 is shown below.

[Chemical formula 40]

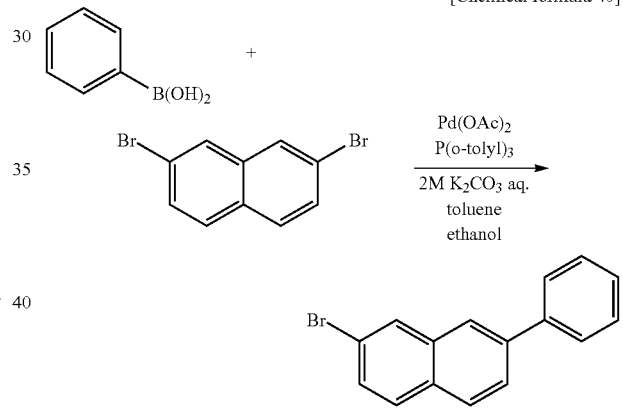

Step 2: Synthesis of 4,4'-diphenyl-4"-(7-phenyl) naphthyl-2-yltriphenylamine (Abbreviation: BBAPβNB-03)

Into a 200 mL three-neck flask equipped with a reflux pipe were put 1.8 g (6.5 mmol) of 7-bromo-2-phenylnaphthalene, which was obtained in Step 1, 3.5 g (6.5 mmol) of N,N-di (4-biphenyl)-4-(4,4,5,5-tetramethyl-1,3,2-dioxaborolan-2-yl)aniline, 40 mg (0.13 mmol) of tri(ortho-tolyl)phosphine, 6.5 mL of an aqueous solution of potassium carbonate (2.0 mol/L), 60 mL of toluene, and 35 mL of ethanol, the mixture was degassed under reduced pressure, and then the air in the system was replaced with nitrogen. To the obtained mixture was added 14 mg (65 μmol) of palladium(II) acetate, and the mixture was refluxed for 4 hours. After stirring, the precipitated solid was removed by suction filtration. Water was added to the obtained filtrate to separate an aqueous layer and an organic layer, and then the aqueous layer was subjected to extraction with toluene. The obtained extracted solution and the organic layer were combined, washed with water and a saturated saline solution, and dried with magnesium sulfate. This mixture was subjected to gravity filtration and the obtained filtrate was concentrated to give 2.1 g of a brown solid. The synthesis scheme of Step 2 is shown below.

By a train sublimation method, 1.9 g of the obtained brown solid was sublimated and purified. In the sublimation purification, the solid was heated at 280° C. under a pressure of 4.1 Pa for 24 hours with a flow of argon at 15 mL/min. After the purification by sublimation, 1.1 g of a target pale yellow solid was obtained at a collection rate of 51%.

Figure 62A:
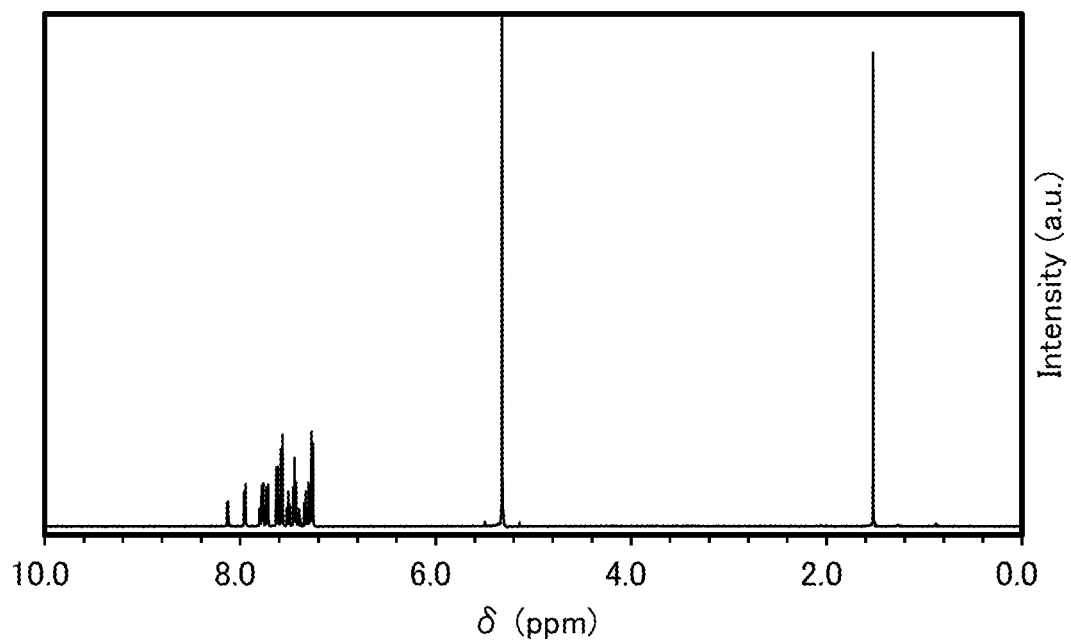
FIGS. 62A and 62B are ¹H NMR charts of BBAPβNB-03.
Figure 62B:
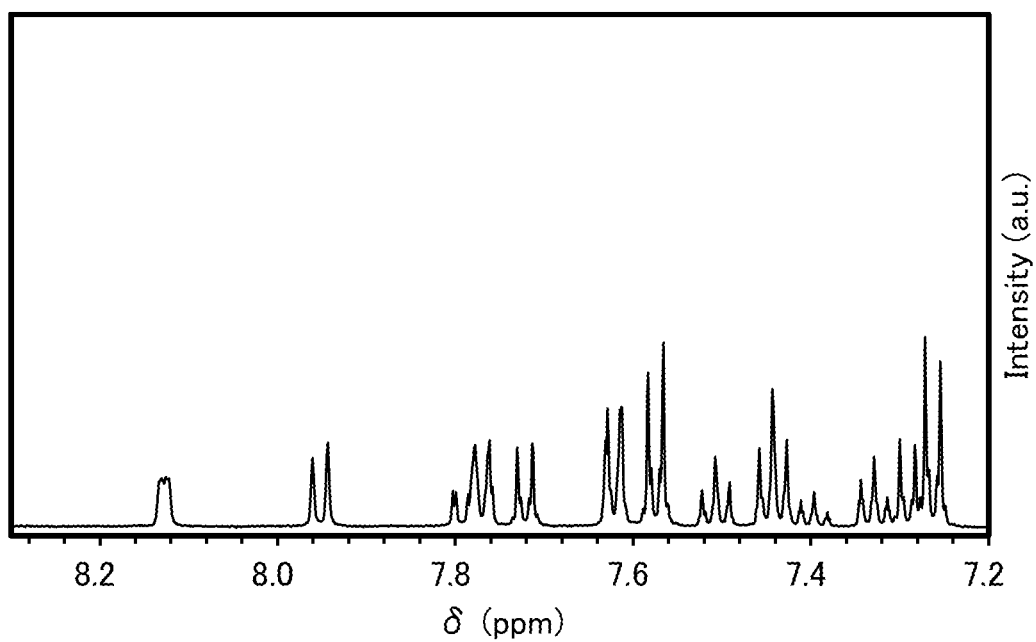

The numeric data of the obtained solid are shown below and $^1$H NMR charts are shown in FIGS. 62(A) and 62(B). Note that FIG. 62(B) is a chart showing an enlarged view of the range of 7.2 ppm to 8.3 ppm in FIG. 62(A). These indicate that BBAPβNB-03, which was the target compound, was obtained in this synthesis example.

$^1$H NMR (dichloromethane-d$_2$, 500 MHz): δ=8.13 (d, J=2.0 Hz, 2H), 7.95 (d, J=8.5 Hz, 2H), 7.80-7.76 (m, 4H), 7.72 (d, J=9.0 Hz, 2H), 7.62 (d, J=8.0 Hz, 4H), 7.57 (d, J=8.5 Hz, 4H), 7.50 (t, J=8.0 Hz, 2H), 7.44 (t, J=8.0 Hz, 4H), 7.40 (t, J=7.5 Hz, 1H), 7.33 (t, J=7.5 Hz, 2H), 7.29 (d, J=8.5 Hz, 2H), 7.26 (d, J=8.5 Hz, 4H).

Next, absorption spectra and emission spectra of a toluene solution and a solid thin film of BBAPβNB-03 were measured. The measurement method, apparatus, and conditions are the same as those of Synthesis example 1; therefore, repeated description will be omitted.

Figure 63:
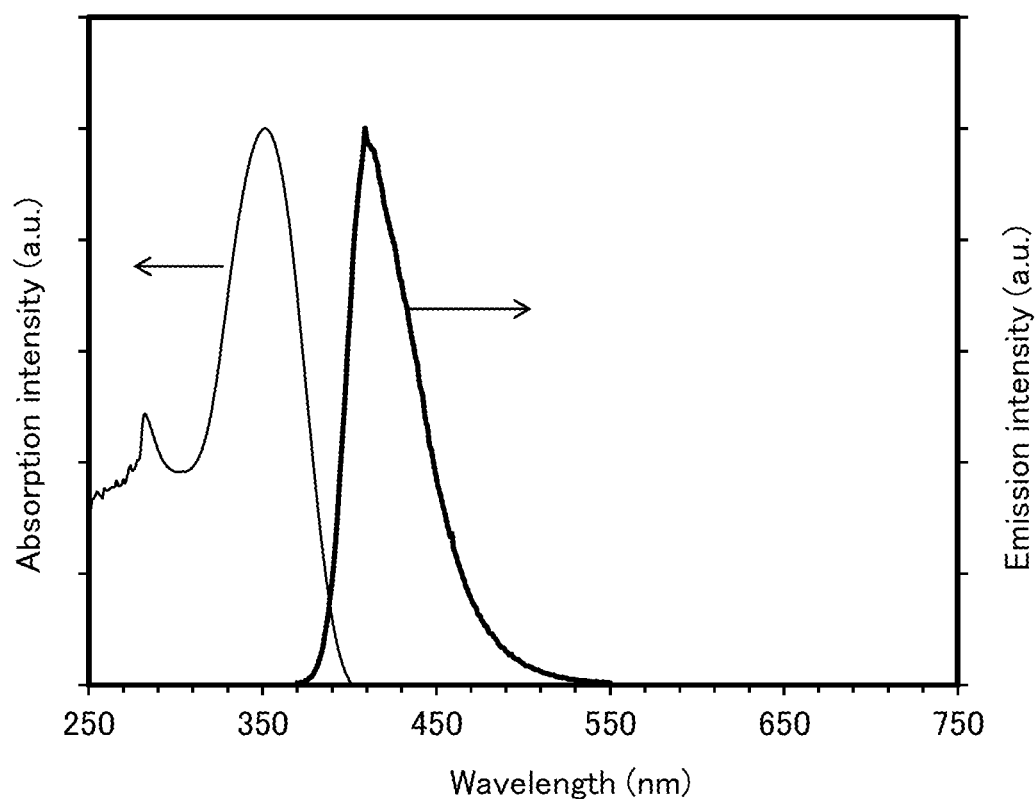
FIG. 63 is an absorption spectrum and an emission spectrum of BBAPβNB-03 in a toluene solution.
Figure 64:
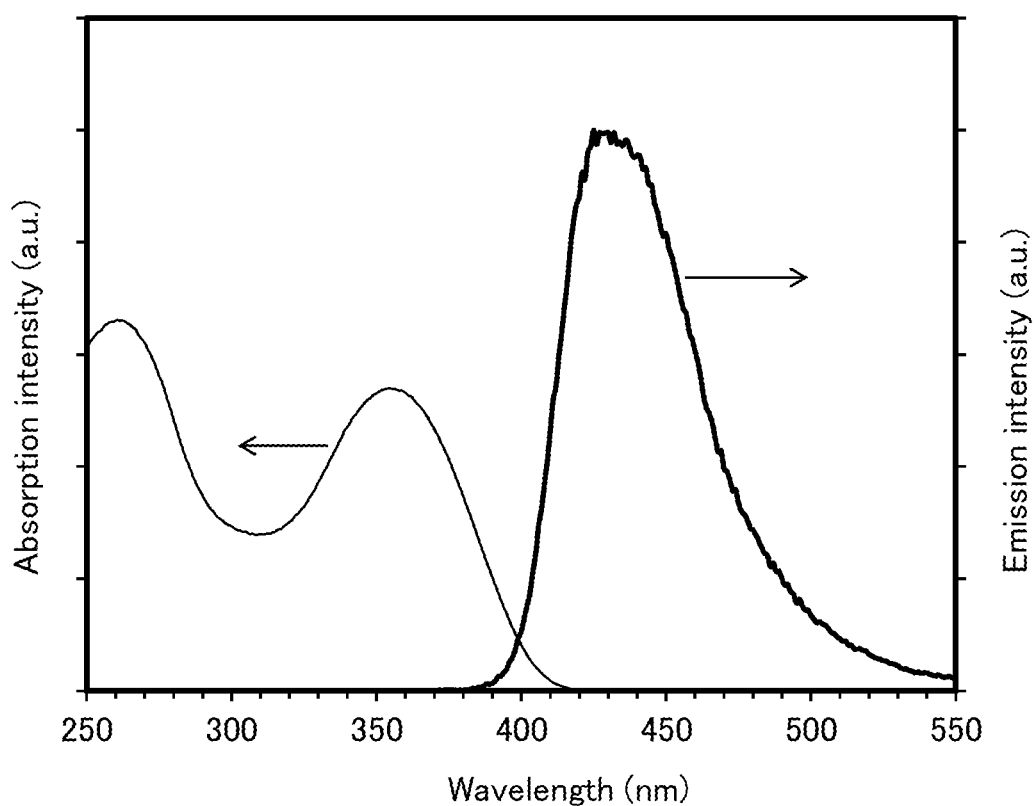
FIG. 64 is an absorption spectrum and an emission spectrum of BBAPβNB-03 in a thin film state.

FIG. 63 shows the obtained measurement results of the absorption spectrum and the emission spectrum of the toluene solution. FIG. 64 shows the measurement results of the absorption spectrum and the emission spectrum of the solid thin film.

According to the results of FIG. 63, the toluene solution of BBAPβNB-03 exhibited an absorption peak at around 352 nm and an emission wavelength peak at 409 nm (excitation wavelength: 352 nm). According to the results of FIG. 64, the solid thin film of BBAPβNB-03 exhibited absorption peaks at around 359 nm, 259 nm, and 211 nm and an emission wavelength peak at around 430 nm (excitation wavelength: 360 nm).

The HOMO level and the LUMO level of BBAPβNB-03 were calculated on the basis of a cyclic voltammetry (CV) measurement. The calculation method is similar to that described in Synthesis example 1.

As a result, the HOMO level of BBAPβNB-03 was found to be −5.47 eV, and the LUMO level was found to be −2.33 eV.

When CV measurement was repeated 100 times and the peak intensities of an oxidation-reduction wave at the 100th cycle and an oxidation-reduction wave at the first cycle were compared, 91% of the peak intensity was kept in the Ea measurement and 85% of the peak intensity was kept in the Ec measurement, which showed that BBAPβNB-03 had extremely high resistance to oxidation and reduction.

Synthesis Example 10

In this synthesis example, a method for synthesizing 4'-[4-(3-phenyl-9H-carbazol-9-yl)phenyl]tris(1,1'-biphenyl-4-yl)amine (abbreviation: YGTBi1BP-02), a substance that can be used as the organic compound of the hole-injection layer 111 in the light-emitting device of one embodiment of the present invention, will be described. The structural formula of YGTBi1BP-02 is shown below.

[Chemical formula 42]

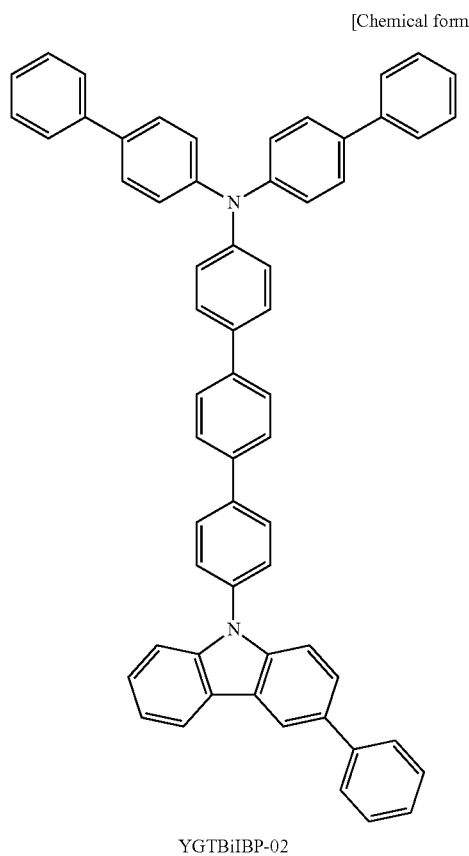

YGTBiIBP-02

Step 1: Synthesis of 4'-(4-chlorophenyl)tris(1,1'-biphenyl-4-yl)amine

Into a 200 mL three-neck flask were put 8.8 g (17 mmol) of 2-{4-[di(4-biphenylyl)amino]phenyl}-4,4,5,5-tetramethyl-1,3,2-dioxaborolane, 4.5 g (17 mmol) of 4-bromo-4'-chlorobiphenyl, 0.15 g (0.50 mmol) of tri(ortho-tolyl)phosphine, 25 mL of an aqueous solution of potassium carbonate (2.0 mmol/L), 128 mL of toluene, and 32 mL of ethanol, the mixture was degassed under reduced pressure, and then the air in the flask was replaced with nitrogen. To the mixture was added 39 mg (0.17 mmol) of palladium(II) acetate, and stirring was performed at 60° C. for 9.5 hours. After the stirring, the precipitated solid was collected by suction filtration, and the obtained solid was washed with toluene, ethanol, and water. The washed solid was dissolved in hot toluene, the obtained solution was filtered through alumina, Florisil (Wako Pure Chemical Industries, Ltd., Catalog No. 066-05265), and Celite (Wako Pure Chemical Industries, Ltd., Catalog No. 537-02305), and the filtrate was cooled, whereby a white solid was precipitated. This white solid was collected by suction filtration to give 6.1 g of a target substance. A single yellow solid obtained by concentration of the filtrate was recrystallized with toluene to give 3.4 g of a white solid. In total, 9.5 g of a white solid was obtained in a yield of 95%. The synthesis scheme of Step 1 is shown below.

[Chemical formula 43]

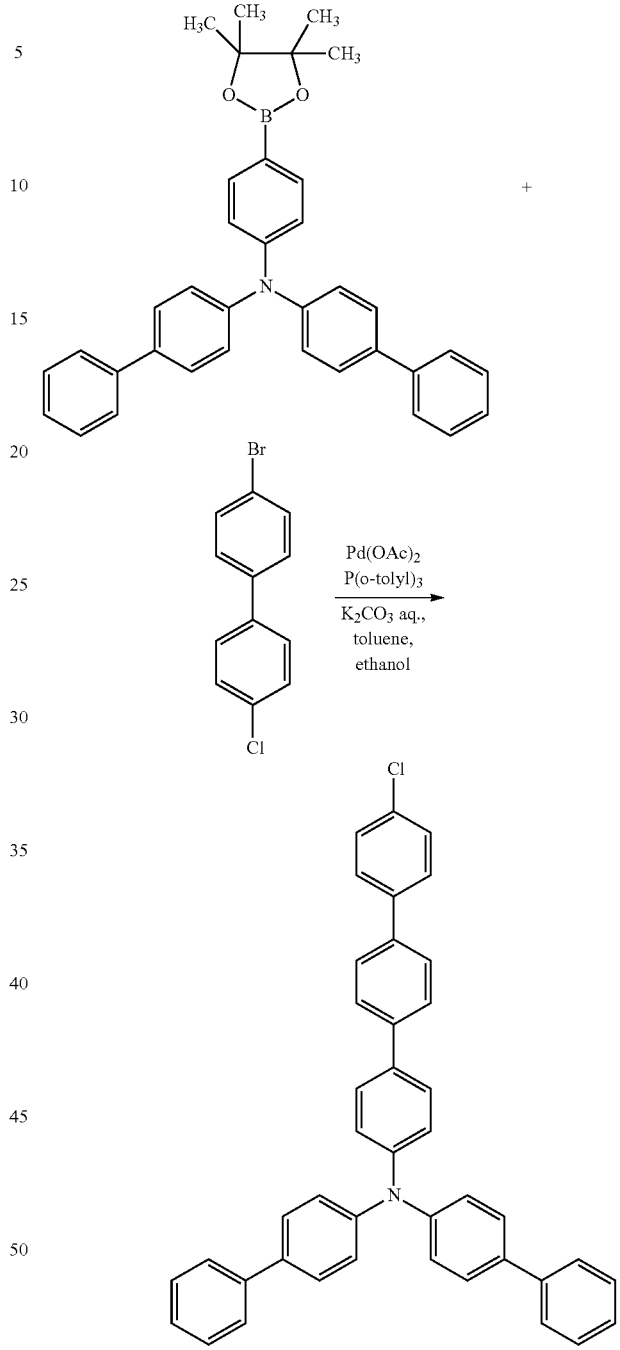

Step 2: Synthesis of 4'-[4-(3-phenyl-9H-carbazol-9-yl)phenyl]tris(1,1'-biphenyl-4-yl)amine (Abbreviation: YGTBi1BP-02)

Into a 200 mL three-neck flask were put 2.0 g (3.4 mmol) of 4'-(4-chlorophenyl)tris(1,1'-biphenyl-4-yl)amine, which was obtained in Step 1, 0.83 g (3.4 mmol) of 3-phenyl-9H-carbazole, 36 mg (0.10 mmol) of di-tert-butyl(2,2-diphenyl-1-methyl-1-cyclopropyl)phosphine (abbreviation: cBRIDP), 0.99 g (10 mmol) of sodium tert butoxide, and 35 mL of mesitylene, the mixture was degassed under reduced pressure, and then the air in the system was replaced with nitrogen. To this mixture was added 21 mg (34 μmol) of bis(dibenzylideneacetone)palladium(II), and the mixture was stirred at 120° C. for 8.5 hours. After the stirring, the raw material was left when reaction was checked with thin layer chromatography; therefore, 37 mg (0.10 mmol) of cBRIDP and 20 mg (33 μmol) of bis(dibenzylideneacetone) palladium(II)) were added to the mixture and then the mixture was heated and stirred at 150° C. for 6 hours. After the heating, toluene and water were added to the obtained mixture, the mixture was stirred, and then an organic layer of the mixture was washed with water and a saturated saline solution. Anhydrous magnesium sulfate was added to the obtained organic layer and drying was performed. This mixture was subjected to gravity filtration and the filtrate was concentrated to give a brown solid. The obtained solid was dissolved in toluene, the solution was filtered through alumina, Florisil (Wako Pure Chemical Industries, Ltd., Catalog No. 066-05265), and Celite (Wako Pure Chemical Industries, Ltd., Catalog No. 537-02305), and the obtained filtrate was concentrated to give a yellow brown solid. The solid was recrystallized with toluene to give 1.9 g of a target yellow solid in a yield of 69%. The synthesis scheme of Step 2 is shown below.

[Chemical formula 44]

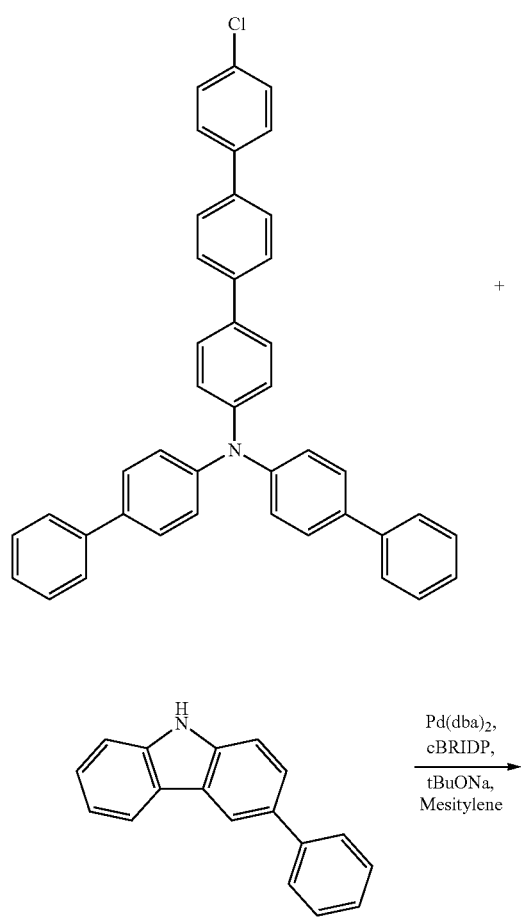

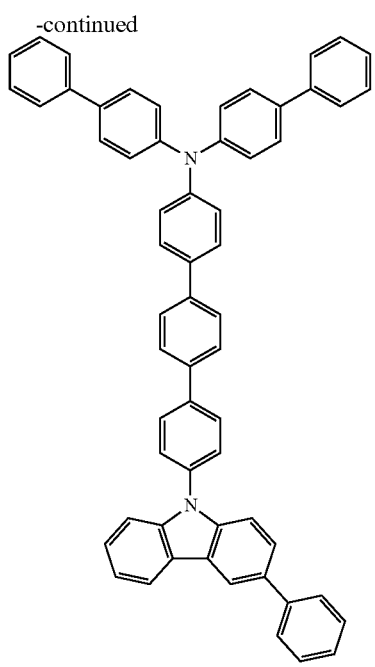

YGTBi1BP-02

Figure 65A:
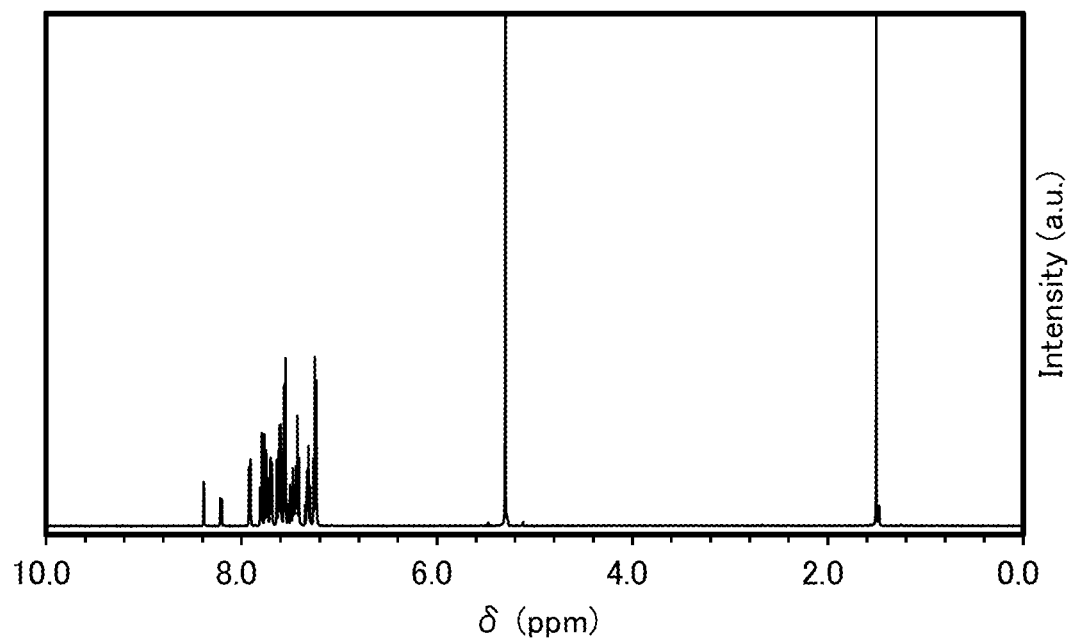
FIGS. 65A and 65B are ¹H NMR charts of YGTBi1BP-02.
Figure 65B:
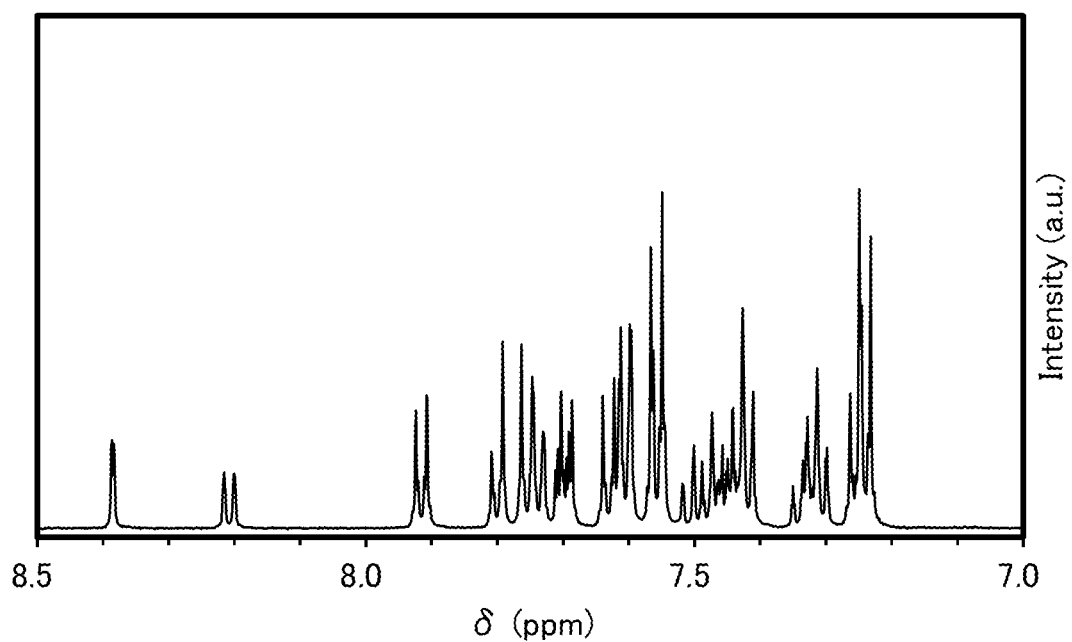

$^1$H-NMR data of the obtained solid are shown in FIG. 65, and the numeric data are shown below. These indicate that 4'-[4-(3-phenyl-9H-carbazol-9-yl)phenyl]tris(1,1'-biphenyl-4-yl)amine (abbreviation: YGTBi1BP-02) was obtained.

$^1$H NMR (dichloromethane-d$_2$, 500 MHz): δ=7.24 (d, J=7.0 Hz, 3H), 7.26 (d, J=7.0 Hz, 3H), 7.30-7.35 (m, 4H), 7.41-7.52 (m, 8H), 7.56 (dt, J1=8.5 Hz, J2=1.5 Hz, 5H), 7.63 (d, J=8.5 Hz, 4H), 7.63 (d, J=8.5 Hz, 2H), 7.69-7.71 (m, 3H), 7.73-7.76 (m, 4H), 7.80 (d, J=8.5 Hz, 2H), 7.92 (dt, J1=8.0 Hz, J2=1.5 Hz, 2H), 8.21 (d, J=7.5 Hz, 1H), 8.39 (sd, J=1.0 Hz, 1H).

Sublimation purification was performed on 1.9 g of the obtained solid. The sublimation purification was performed under the condition of the pressure being $1.9\times10^{-3}$ Pa, by heating the solid to 370° C. After the sublimation purification, 0.74 g of a yellow solid, which was the target compound, was obtained at a collection rate of 40%.

Next, absorption spectra and emission spectra of a toluene solution and a solid thin film of YGTBi1BP-02 were measured. The measurement method, apparatus, and conditions are the same as those of Synthesis example 1; therefore, repeated description will be omitted.

Figure 66:
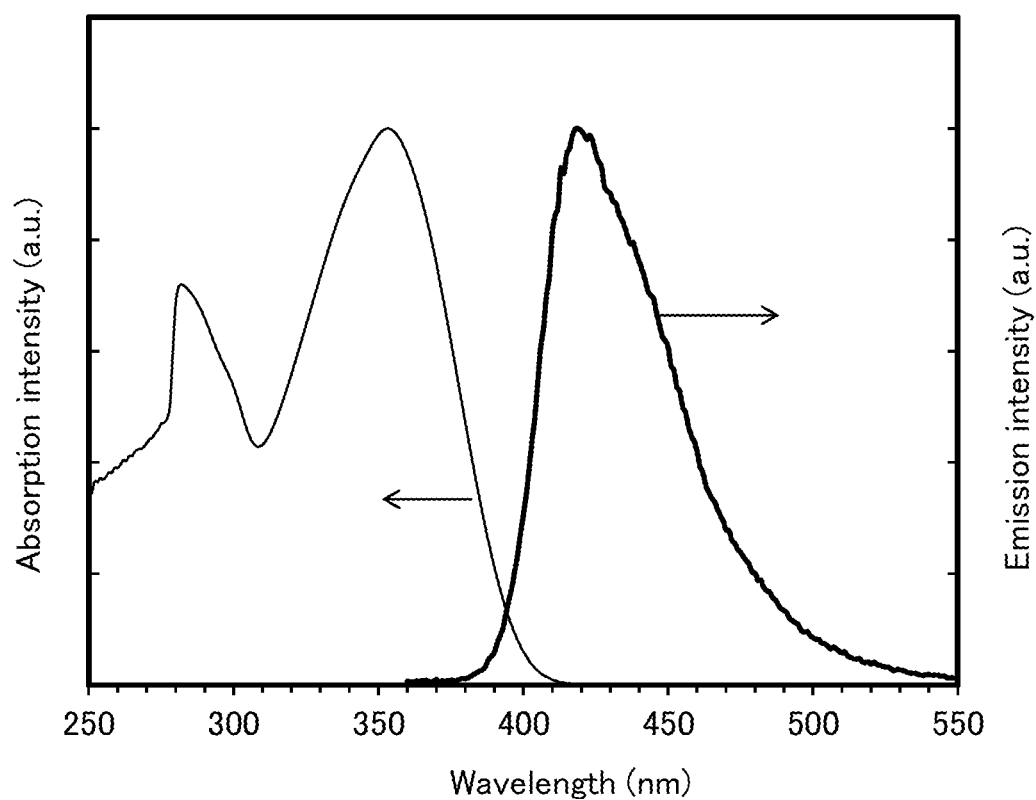
FIG. 66 is an absorption spectrum and an emission spectrum of YGTBi1BP-02 in a toluene solution.
Figure 67:
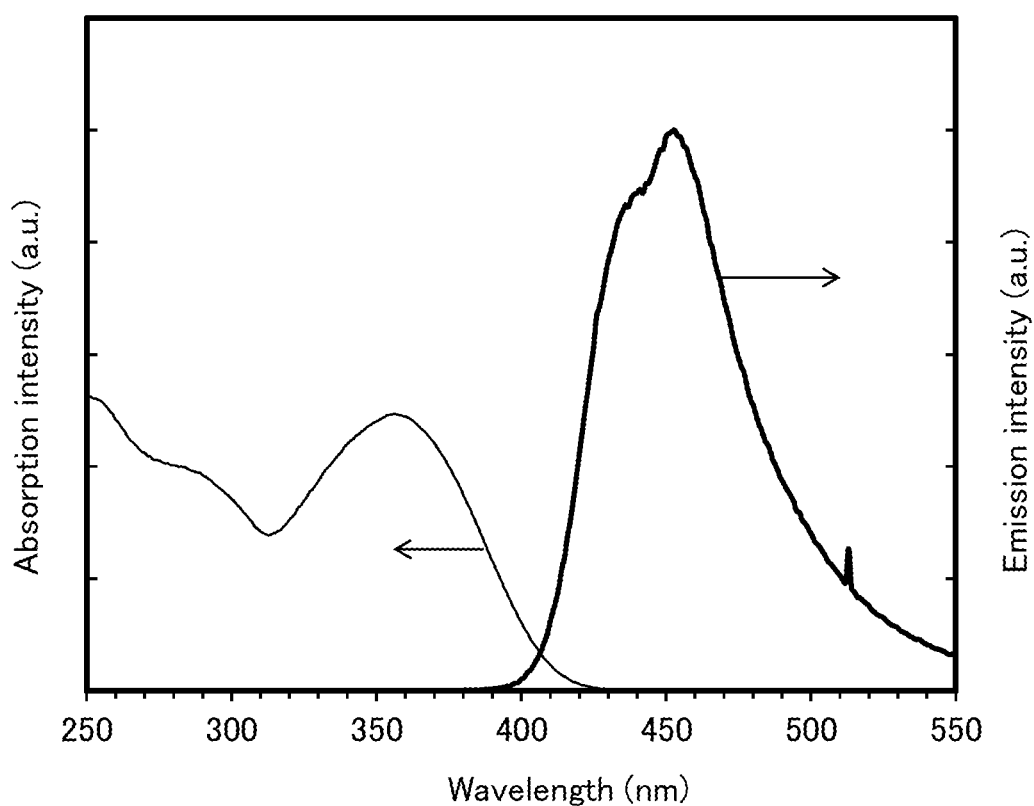
FIG. 67 is an absorption spectrum and an emission spectrum of YGTBi1BP-02 in a thin film state.

FIG. 66 shows the obtained measurement results of the absorption spectrum and the emission spectrum of the toluene solution. FIG. 67 shows the measurement results of the absorption spectrum and the emission spectrum of the solid thin film.

According to the results of FIG. 66, the toluene solution of YGTBi1BP-02 exhibited an absorption peak at around 353 nm and an emission wavelength peak at around 419 nm (excitation wavelength: 353 nm). According to FIG. 67, the solid thin film of YGTBi1BP-02 exhibited absorption peaks at around 356 nm, 290 nm, 251 nm, and 207 nm, and emission wavelength peaks at around 439 nm and 453 nm (excitation wavelength: 370 nm). These results indicate that YGTBi1BP-02 emits blue light and can also be used as a host for a light-emitting substance or a host for a fluorescent substance in the visible region.

The HOMO level and the LUMO level of YGTBi1BP-02 were calculated based on the basis of a cyclic voltammetry (CV) measurement. The calculation method is similar to that described in Synthesis example 1.

As a result, the HOMO level of YGTBi1BP-02 was found to be −5.47 eV, and the LUMO level was found to be −2.35 eV.

When CV measurement was repeated 100 times and the peak intensities of an oxidation-reduction wave at the 100th cycle and an oxidation-reduction wave at the first cycle were compared, 88% of the peak intensity was kept in the Ea measurement and 96% of the peak intensity was kept in the Ec measurement, which showed that YGTBi1BP-02 had extremely high resistance to oxidation and reduction.

Differential scanning calorimetry (DSC) of YGTBi1BP-02 was performed with Pyris1DSC manufactured by PerkinElmer, Inc. The DSC was performed in the following manner: the temperature was raised from −10° C. to 360° C. at a temperature rising rate of 40° C./min and held for three minutes; then, the temperature was decreased to −10° C. at a temperature decreasing rate of 100° C./min and held at −10° C. for three minutes. This operation was performed twice in succession. It was found from the DSC result of the second cycle that the glass transition point of YGTBi1BP-02 was 142° C., that is, YGTBi1BP-02 was a substance with extremely high heat resistance.

Then, thermogravimetry-differential thermal analysis (TG-DTA) of YGTBi1BP-02 was performed. The measurement was performed using a high vacuum differential type differential thermal balance (TG-DTA2410SA, produced by Bruker AXS K.K.). The measurement was performed under atmospheric pressure at a temperature rising rate of 10° C./min under a nitrogen stream (flow rate: 200 mL/min). In the thermogravimetry-differential thermal analysis, the temperature (decomposition temperature) at which the weight obtained by thermogravimetry was reduced by 5% of the weight at the beginning of the measurement was found to be 500° C. or higher, which shows that YGTBi1BP-02 is a substance with high heat resistance.

REFERENCE NUMERALS

101: first electrode, 102: second electrode, 103: EL layer, 111: hole-injection layer, 112: hole-transport layer, 112-1: first hole-transport layer, 112-2: second hole-transport layer, 113: light-emitting layer, 114: electron-transport layer, 115: electron-injection layer, 116: charge-generation layer, 117: P-type layer, 118: electron-relay layer, 119: electron-injection buffer layer, 400: substrate, 401: first electrode, 403: EL layer, 404: second electrode, 405: sealant, 406: sealant, 407: sealing substrate, 412: pad, 420: IC chip, 501: anode, 502: cathode, 511: first light-emitting unit, 512: second light-emitting unit, 513: charge-generation layer, 601: driver circuit portion (source line driver circuit), 602: pixel portion, 603: driver circuit portion (gate line driver circuit), 604: sealing substrate, 605: sealant, 607: space, 608: wiring, 609: FPC (flexible printed circuit), 610: element substrate, 611: switching FET, 612: current control FET, 613: first electrode, 614: insulator, 616: EL layer, 617: second electrode, 618: light-emitting device, 951: substrate, 952: electrode, 953: insulating layer, 954: partition layer, 955: EL layer, 956: electrode, 1001 substrate, 1002 base insulating film, 1003 gate insulating film, 1006 gate electrode, 1007 gate electrode, 1008 gate electrode, 1020 first interlayer insulating film, 1021 second interlayer insulating film, 1022 electrode, 1024W first electrode, 1024R first electrode, 1024G first electrode, 1024B first electrode, 1025 partition, 1028 EL layer, 1029 second electrode, 1031 sealing substrate, 1032 sealant, 1033 transparent base material, 1034R red coloring layer, 1034G green coloring layer, 1034B blue coloring layer, 1035 black matrix, 1036 overcoat layer, 1037 third interlayer insulating film, 1040 pixel portion, 1041 driver circuit portion, 1042 peripheral portion, 2001: housing, 2002: light source, 2100: robot, 2110: arithmetic device, 2101: illuminance sensor, 2102: microphone, 2103: upper camera, 2104: speaker, 2105: display, 2106: lower camera, 2107: obstacle sensor, 2108: moving mechanism, 3001: lighting device, 5000: housing, 5001: display portion, 5002: second display portion, 5003: speaker, 5004: LED lamp, 5005: operation key, 5006: connection terminal, 5007: sensor, 5008: microphone, 5012: support, 5013: earphone, 5100: cleaning robot, 5101: display, 5102: camera, 5103: brush, 5104: operation button, 5150: portable information terminal, 5151: housing, 5152: display region, 5153: bend portion, 5120: dust, 5200: display region, 5201: display region, 5202: display region, 5203: display region, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7210: second display portion, 7401: housing, 7402: display portion, 7403: operation button, 7404: external connection port, 7405: speaker, 7406: microphone, 7400: mobile phone, 9310: portable information terminal, 9311: display panel, 9312: display region, 9313: hinge, 9315: housing.

This application is based on Japanese Patent Application Serial No. 2018-053135 filed with Japan Patent Office on Mar. 20, 2018, the entire contents of which are hereby incorporated herein by reference.

The invention claimed is:

1. A light-emitting device comprising:
   an anode;
   a cathode; and
   a layer comprising an organic compound positioned between the anode and the cathode,
   wherein the layer comprising the organic compound comprises a first layer, a second layer, and a light-emitting layer in order from the anode side,
   wherein the first layer comprises a first substance and a second substance,
   wherein the second layer comprises a third substance,
   wherein the first substance is an organic compound having a HOMO level higher than or equal to −5.8 eV and lower than or equal to −5.4 eV,
   wherein the second substance is a substance having a halogen group or a cyano group, or both a halogen group and a cyano group,
   wherein the third substance is an organic compound, and
   wherein at least two substituents comprising carbazole rings bond to a naphthalene ring in the organic compound of the third substance.

2. The light-emitting device according to claim 1, wherein the first substance is an organic compound comprising an N,N-bis(4-biphenyl)amino group.

3. The light-emitting device according to claim 1, comprising:
   a third layer between the first layer and the second layer,
   wherein the third layer comprises a fourth substance, and
   wherein the fourth substance is an organic compound having a hole-transport property.

4. The light-emitting device according to claim 1, comprising:
a third layer between the first layer and the second layer, wherein the third layer comprises a fourth substance, and
wherein the fourth substance is an organic compound having a HOMO level higher than or equal to −5.8 eV and lower than or equal to −5.4 eV.

5. The light-emitting device according to claim 3, wherein the fourth substance is the same substance as the first substance.

6. A light-emitting device comprising:
an anode;
a cathode; and
a layer comprising an organic compound positioned between the anode and the cathode,
wherein the layer comprising the organic compound comprises a first layer, a second layer, and a light-emitting layer in order from the anode side,
wherein the first layer comprises a first substance and a second substance,
wherein the second layer comprises a third substance,
wherein the first substance is an aromatic amine comprising a substituent comprising a dibenzofuran ring or a dibenzothiophene ring,
wherein the second substance is a substance having a halogen group or a cyano group, or both a halogen group and a cyano group,
wherein the third substance is an organic compound, and
wherein at least two substituents comprising carbazole rings bond to a naphthalene ring in the organic compound of the third substance.

7. The light-emitting device according to claim 6, wherein the first substance is an organic compound comprising an N,N-bis(4-biphenyl)amino group.

8. The light-emitting device according to claim 6, comprising:
a third layer between the first layer and the second layer, wherein the third layer comprises a fourth substance, and
wherein the fourth substance is an organic compound having a hole-transport property.

9. The light-emitting device according to claim 6, comprising:
a third layer between the first layer and the second layer, wherein the third layer comprises a fourth substance, and
wherein the fourth substance is an organic compound having a HOMO level higher than or equal to −5.8 eV and lower than or equal to −5.4 eV.

10. The light-emitting device according to claim 8, wherein the fourth substance is the same substance as the first substance.

11. A light-emitting device comprising:
an anode;
a cathode; and
a layer comprising an organic compound positioned between the anode and the cathode,
wherein the layer comprising the organic compound comprises a first layer, a second layer, and a light-emitting layer in order from the anode side,
wherein the first layer comprises a first substance and a second substance,
wherein the second layer comprises a third substance,
wherein the first substance is an aromatic monoamine comprising a naphthalene ring,
wherein the second substance is a substance having a halogen group or a cyano group, or both a halogen group and a cyano group,
wherein the third substance is an organic compound, and
wherein at least two substituents comprising carbazole rings bond to a naphthalene ring in the organic compound of the third substance.

12. The light-emitting device according to claim 11, wherein the first substance is an organic compound comprising an N,N-bis(4-biphenyl)amino group.

13. The light-emitting device according to claim 11, comprising:
a third layer between the first layer and the second layer, wherein the third layer comprises a fourth substance, and
wherein the fourth substance is an organic compound having a hole-transport property.

14. The light-emitting device according to claim 11, comprising:
a third layer between the first layer and the second layer, wherein the third layer comprises a fourth substance, and
wherein the fourth substance is an organic compound having a HOMO level higher than or equal to −5.8 eV and lower than or equal to −5.4 eV.

15. The light-emitting device according to claim 13, wherein the fourth substance is the same substance as the first substance.

16. A light-emitting device comprising:
an anode;
a cathode; and
a layer comprising an organic compound positioned between the anode and the cathode,
wherein the layer comprising the organic compound comprises a first layer, a second layer, and a light-emitting layer in order from the anode side,
wherein the first layer comprises a first substance and a second substance,
wherein the second layer comprises a third substance,
wherein the first substance is an aromatic monoamine in which a 9-fluorenyl group is bonded to nitrogen through an arylene group,
wherein the second substance is a substance having a halogen group or a cyano group, or both a halogen group and a cyano group,
wherein the third substance is an organic compound, and
wherein at least two substituents comprising carbazole rings bond to a naphthalene ring in the organic compound.

17. The light-emitting device according to claim 16, wherein the first substance is an organic compound comprising an N,N-bis(4-biphenyl)amino group.

18. The light-emitting device according to claim 16, comprising:
a third layer between the first layer and the second layer, wherein the third layer comprises a fourth substance, and
wherein the fourth substance is an organic compound having a hole-transport property.

19. The light-emitting device according to claim 16, comprising:
a third layer between the first layer and the second layer, wherein the third layer comprises a fourth substance, and
wherein the fourth substance is an organic compound having a HOMO level higher than or equal to −5.8 eV and lower than or equal to −5.4 eV.

20. The light-emitting device according to claim 18, wherein the fourth substance is the same substance as the first substance.

* * * * *